(12) United States Patent
Duquenne et al.

(10) Patent No.: US 9,018,382 B2
(45) Date of Patent: Apr. 28, 2015

(54) INDAZOLES

(71) Applicant: GlaxoSmithKline LLC, Wilmington, New Castle, DE (US)

(72) Inventors: Celine Duquenne, Collegeville, PA (US); Neil Johnson, Collegeville, PA (US); Steven D. Knight, Collegeville, PA (US); Louis LaFrance, Collegeville, PA (US); William H. Miller, Collegeville, PA (US); Kenneth Newlander, Collegeville, PA (US); Stuart Romeril, Collegeville, PA (US); Meagan B. Rouse, Collegeville, PA (US); Xinrong Tian, Collegeville, PA (US); Sharad Kumar Verma, Collegeville, PA (US)

(73) Assignee: GlaxoSmithKline LLC, Wilmington, New Castle, DE (US)

( * ) Notice: Subject to any disclaimer, the term of this patent is extended or adjusted under 35 U.S.C. 154(b) by 0 days.

(21) Appl. No.: 14/458,305

(22) Filed: Aug. 13, 2014

(65) Prior Publication Data
US 2014/0350013 A1    Nov. 27, 2014

Related U.S. Application Data

(62) Division of application No. 13/696,436, filed as application No. PCT/US2011/035340 on May 5, 2011, now Pat. No. 8,846,935.

(60) Provisional application No. 61/332,312, filed on May 7, 2010.

(51) Int. Cl.
| *C07D 405/00* | (2006.01) |
| *C07D 401/00* | (2006.01) |
| *C07D 231/56* | (2006.01) |
| *C07D 409/14* | (2006.01) |
| *C07D 401/12* | (2006.01) |
| *C07D 401/14* | (2006.01) |

(52) U.S. Cl.
CPC ............ *C07D 409/14* (2013.01); *C07D 401/12* (2013.01); *C07D 401/14* (2013.01)

(58) Field of Classification Search
USPC .............................. 546/256, 275.7; 548/361.1
See application file for complete search history.

(56) References Cited

U.S. PATENT DOCUMENTS

| 7,709,500 | B2 | 5/2010 | Alcaraz et al. |
| 8,536,179 | B2 | 9/2013 | Miller et al. |
| 8,637,509 | B2 | 1/2014 | Burgess et al. |
| 2009/0012031 | A1 | 1/2009 | Chinnaiyan et al. |

FOREIGN PATENT DOCUMENTS

| WO | WO 00/69826 A1 | 5/2000 |
| WO | WO 2004/112719 A2 | 12/2004 |
| WO | WO 2009/012312 A1 | 1/2009 |
| WO | WO 2010/036213 A1 | 4/2010 |
| WO | WO 2012/118812 A2 | 9/2012 |

OTHER PUBLICATIONS

Verma, et al. ACS Med. Chem. Lett., Article ASAP. DOI: 10.1021/ml3003346 (Web Publn. date: Oct. 19, 2012).

*Primary Examiner* — James O Wilson
*Assistant Examiner* — Oluwafemi Masha
(74) *Attorney, Agent, or Firm* — Duke M. Fitch; John Lemanowicz; William R. Majarian

(57) ABSTRACT

Herein are disclosed indazoles of formula (I)

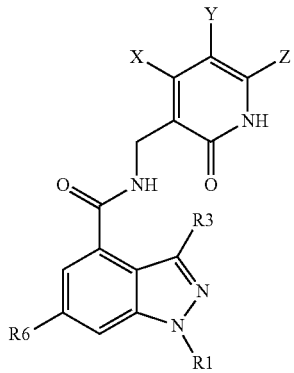

where the various groups are defined herein, and which are useful for treating cancer.

9 Claims, No Drawings

INDAZOLES

FIELD OF THE INVENTION

This invention relates to substituted indazoles which inhibit EZH2 and thus are useful for inhibiting the proliferation of and/or inducing apoptosis in cancer cells.

BACKGROUND OF THE INVENTION

Epigenetic modifications play an important role in the regulation of many cellular processes including cell proliferation, differentiation, and cell survival. Global epigenetic modifications are common in cancer, and include global changes in DNA and/or histone methylation, dysregulation of non-coding RNAs and nucleosome remodeling leading to aberrant activation or inactivation of oncogenes, tumor suppressors and signaling pathways. However, unlike genetic mutations which arise in cancer, these epigenetic changes can be reversed through selective inhibition of the enzymes involved. Several methylases involved in histone or DNA methylation are known to be dysregulated in cancer. Thus, selective inhibitors of particular methylases will be useful in the treatment of proliferative diseases such as cancer.

EZH2 (enhancer of zeste homolog 2; human EZH2 gene: Cardoso, C, et al; *European J of Human Genetics*, Vol. 8, No. 3 Pages 174-180, 2000) is the catalytic subunit of the Polycomb Repressor Complex 2 (PRC2) which functions to silence target genes by tri-methylating lysine 27 of histone H3 (H3K27me3). Histone H3 is one of the five main histone proteins involved in the structure of chromatin in eukaryotic cells. Featuring a main globular domain and a long N-terminal tail, Histones are involved with the structure of the nucleosomes, a 'beads on a string' structure. Histone proteins are highly post-translationally modified however Histone H3 is the most extensively modified of the five histones. The term "Histone H3" alone is purposely ambiguous in that it does not distinguish between sequence variants or modification state. Histone H3 is an important protein in the emerging field of epigenetics, where its sequence variants and variable modification states are thought to play a role in the dynamic and long term regulation of genes.

Increased EZH2 expression has been observed in numerous solid tumors including those of the prostate, breast, skin, bladder, liver, pancreas, head and neck and correlates with cancer aggressiveness, metastasis and poor outcome (Varambally et al., 2002; Kleer et al., 2003; Breuer et al., 2004; Bachmann et al., 2005; Weikert et al., 2005; Sudo et al., 2005; Bachmann et al., 2006). For instance, there is a greater risk of recurrence after prostatectomy in tumors expressing high levels of EZH2, increased metastasis, shorter disease-free survival and increased death in breast cancer patients with high EZH2 levels (Varambally et al., 2002; Kleer et al., 2003). More recently, inactivating mutations in UTX (ubiquitously transcribed tetratricopeptixe repeas X), a H3K27 demethylase which functions in opposition to EZH2, have been identified in multiple solid and hematological tumor types (including renal, glioblastoma, esophageal, breast, colon, non-small cell lung, small cell lung, bladder, multiple myeloma, and chronic myeloid leukemia tumors), and low UTX levels correlate with poor survival in breast cancer suggesting that loss of UTX function leads to increased H3K27me3 and repression of target genes (Wang et al., 2010). Together, these data suggest that increased H3K27me3 levels contribute to cancer aggressiveness in many tumor types and that inhibition of EZH2 activity may provide therapeutic benefit.

Numerous studies have reported that direct knockdown of EZH2 via siRNA or shRNA or indirect loss of EZH2 via treatment with the SAH hydrolase inhibitor 3-deazaneplanocin A (DZNep) decreases cancer cell line proliferation and invasion in vitro and tumor growth in vivo (Gonzalez et al., 2008, GBM 2009). While the precise mechanism by which aberrant EZH2 activity leads to cancer progression is not known, many EZH2 target genes are tumor suppressors suggesting that loss of tumor suppressor function is a key mechanism (refs). In addition, EZH2 overexpression in immortalized or primary epithelial cells promotes anchorage independent growth and invasion and requires EZH2 catalytic activity. (Kleer et al., 2003; Cao et al., 2008).

Thus, there is strong evidence to suggest that inhibition of EZH2 activity decreases cellular proliferation and invasion. Accordingly, compounds that inhibit EZH2 activity would be useful for the treatment of cancer. The indazoles of this invention provide such treatment.

SUMMARY OF THE INVENTION

In a first instance, this invention relates to compounds of formula (I)

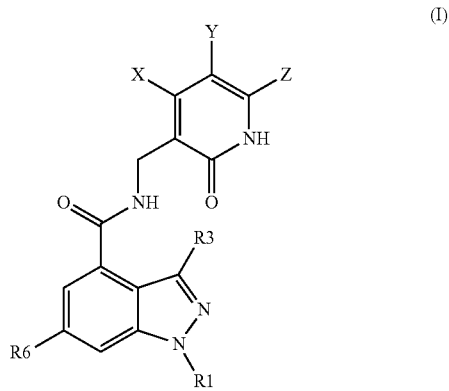

(I)

wherein

X and Z are selected independently from the group consisting of hydrogen, $(C_1-C_8)$alkyl, $(C_2-C_8)$alkenyl, $(C_2-C_8)$alkynyl, unsubstituted or substituted $(C_3-C_8)$cycloalkyl, unsubstituted or substituted $(C_3-C_8)$cycloalkyl-$(C_1-C_8)$alkyl or -$(C_2-C_8)$alkenyl, unsubstituted or substituted $(C_5-C_8)$cycloalkenyl, unsubstituted or substituted $(C_5-C_8)$cycloalkenyl-$(C_1-C_8)$alkyl or -$(C_2-C_8)$alkenyl, $(C_6-C_{10})$bicycloalkyl, unsubstituted or substituted heterocycloalkyl, unsubstituted or substituted heterocycloalkyl-$(C_1-C_8)$alkyl or -$(C_2-C_8)$alkenyl, unsubstituted or substituted aryl, unsubstituted or substituted aryl-$(C_1-C_8)$alkyl or -$(C_2-C_8)$alkenyl, unsubstituted or substituted heteroaryl, unsubstituted or substituted heteroaryl-$(C_1-C_8)$alkyl or -$(C_2-C_8)$alkenyl, halo, cyano, —$COR^a$, —$CO_2R^a$, —$CONR^aR^b$, —$CONR^aNR^aR^b$, —$SR^a$, —$SOR^a$, —$SO_2R^a$, —$SO_2NR^aR^b$, nitro, —$NR^aR^b$, —$NR^aC(O)R^b$, —$NR^aC(O)NR^aR^b$, —$NR^aC(O)OR^a$, —$NR^aSO_2R^b$, —$NR^aSO_2NR^aR^b$, —$NR^aNR^aR^b$, —$NR^aNR^aC(O)R^b$, —$NR^aNR^aC(O)NR^aR^b$, —$NR^aNR^aC(O)OR^a$, —$OR^a$, —$OC(O)R^a$, and —$OC(O)NR^aR^b$;

Y is H or halo;

$R^1$ is $(C_1-C_8)$alkyl, $(C_2-C_8)$alkenyl, $(C_2-C_8)$alkynyl, unsubstituted or substituted $(C_3-C_8)$cycloalkyl, unsubstituted or substituted $(C_3-C_8)$cycloalkyl-$(C_1-C_8)$alkyl or -$(C_2-C_8)$alkenyl, unsubstituted or substituted $(C_5-C_8)$cycloalkenyl, unsubstituted or substituted $(C_5-C_8)$cycloalkenyl-$(C_1-C_8)$ alkyl or -($C_2$-$C_8$)alkenyl, unsubstituted or substituted ($C_6$-$C_{10}$)bicycloalkyl, unsubstituted or substituted heterocycloalkyl or -($C_2$-$C_8$)alkenyl, unsubstituted or substituted heterocycloalkyl-($C_1$-$C_8$)alkyl, unsubstituted or substituted aryl, unsubstituted or substituted aryl-($C_1$-$C_8$)alkyl or -($C_2$-$C_8$)alkenyl, unsubstituted or substituted heteroaryl, unsubstituted or substituted heteroaryl-($C_1$-$C_8$)alkyl or -($C_2$-$C_8$)alkenyl, —$COR^a$, —$CO_2R^a$, —$CONR^aR^b$, —$CONR^aNR^aR^b$;

$R^3$ is hydrogen, ($C_1$-$C_8$)alkyl, cyano, trifluoromethyl, —$NR^aR^b$, or halo;

$R^6$ is selected from the group consisting of hydrogen, halo, ($C_1$-$C_8$)alkyl, ($C_2$-$C_8$)alkenyl, —$B(OH)_2$, substituted or unsubstituted ($C_2$-$C_8$)alkynyl, unsubstituted or substituted ($C_3$-$C_8$)cycloalkyl, unsubstituted or substituted ($C_3$-$C_8$)cycloalkyl-($C_1$-$C_8$)alkyl, unsubstituted or substituted ($C_5$-$C_8$)cycloalkenyl, unsubstituted or substituted ($C_5$-$C_8$)cycloalkenyl-($C_1$-$C_8$)alkyl, ($C_6$-$C_{10}$)bicycloalkyl, unsubstituted or substituted heterocycloalkyl, unsubstituted or substituted heterocycloalkyl-($C_1$-$C_8$)alkyl, unsubstituted or substituted aryl, unsubstituted or substituted aryl-($C_1$-$C_8$)alkyl, unsubstituted or substituted heteroaryl, unsubstituted or substituted heteroaryl-($C_1$-$C_8$)alkyl, cyano, —$COR^a$, —$CO_2R^a$, —$CONR^aR^b$, —$CONR^aNR^aR^b$, —$SR^a$, —$SOR^a$, —$SO_2R^a$, —$SO_2NR^aR^b$, nitro, —$NR^aR^b$, —$NR^aC(O)R^b$, —$NR^aC(O)NR^aR^b$, —$NR^aC(O)OR^a$, —$NR^aSO_2R^b$, —$NR^aSO_2NR^aR^b$, —$NR^aNR^aR^b$, —$NR^aNR^aC(O)R^b$, —$NR^aNR^aC(O)NR^aR^b$, —$NR^aNR^aC(O)OR^a$, —$OR^a$, —$OC(O)R^a$, —$OC(O)NR^aR^b$;

wherein any ($C_1$-$C_8$)alkyl, ($C_2$-$C_8$)alkenyl, ($C_2$-$C_8$)alkynyl, cycloalkyl, cycloalkenyl, bicycloalkyl, heterocycloalkyl, aryl, or heteroaryl group is optionally substituted by 1, 2 or 3 groups independently selected from the group consisting of —$O(C_1$-$C_6)$alkyl$(R^c)_{1-2}$, —$S(C_1$-$C_6)$alkyl$(R^c)_{1-2}$, —$(C_1$-$C_6)$alkyl$(R^c)_{1-2}$, ($C_1$-$C_8$)alkyl-heterocycloalkyl, ($C_3$-$C_8$)cycloalkyl-heterocycloalkyl, halo, ($C_1$-$C_6$)alkyl, ($C_3$-$C_8$)cycloalkyl, ($C_5$-$C_8$)cycloalkenyl, ($C_1$-$C_6$)haloalkyl, cyano, —$COR^a$, —$CO_2R^a$, —$CONR^aR^b$, —$SR^a$, —$SOR^a$, —$SO_2R^a$, —$SO_2NR^aR^b$, nitro, —$NR^aR^b$, —$NR^aC(O)R^b$, —$NR^aC(O)NR^aR^b$, —$NR^aC(O)OR^a$, —$NR^aSO_2R^b$, —$NR^aSO_2NR^aR^b$, —$OR^a$, —$OC(O)R^a$, —$OC(O)NR^aR^b$, heterocycloalkyl, aryl, heteroaryl, aryl($C_1$-$C_4$)alkyl, and heteroaryl($C_1$-$C_4$)alkyl;

wherein any aryl or heteroaryl moiety of said aryl, heteroaryl, aryl($C_1$-$C_4$)alkyl, or heteroaryl($C_1$-$C_4$)alkyl is optionally substituted by 1, 2 or 3 groups independently selected from the group consisting of halo, ($C_1$-$C_6$)alkyl, ($C_3$-$C_8$)cycloalkyl, ($C_5$-$C_8$)cycloalkenyl, ($C_1$-$C_6$)haloalkyl, cyano, —$COR^a$, —$CO_2R^a$, —$CONR^aR^b$, —$SR^a$, —$SOR^a$, —$SO_2R^a$, —$SO_2NR^aR^b$, nitro, —$NR^aR^b$, —$NR^aC(O)R^b$, —$NR^aC(O)NR^aR^b$, —$NR^aC(O)OR^a$, —$NR^aSO_2R^b$, —$NR^aSO_2NR^aR^b$, —$OR^a$, —$OC(O)R^a$, and —$OC(O)NR^aR^b$;

$R^a$ and $R^b$ are each independently hydrogen, ($C_1$-$C_8$)alkyl, ($C_2$-$C_8$)alkenyl, ($C_2$-$C_8$)alkynyl, ($C_3$-$C_8$)cycloalkyl, ($C_5$-$C_8$)cycloalkenyl, ($C_6$-$C_{10}$)bicycloalkyl, heterocycloalkyl, aryl, heteroaryl, wherein said ($C_1$-$C_8$)alkyl, ($C_2$-$C_8$)alkenyl, ($C_2$-$C_8$)alkynyl, cycloalkyl, cycloalkenyl, bicycloalkyl, heterocycloalkyl, aryl or heteroaryl group is optionally substituted by 1, 2 or 3 groups independently selected from halo, hydroxyl, ($C_1$-$C_4$)alkoxy, amino, ($C_1$-$C_4$)alkylamino, (($C_1$-$C_4$)alkyl)(($C_1$-$C_4$)alkyl)amino, —$CO_2H$, —$CO_2(C_1$-$C_4)$alkyl, —$CONH_2$, —$CONH(C_1$-$C_4)$alkyl, —$CON((C_1$-$C_4)$alkyl)(($C_1$-$C_4)$alkyl), —$SO_2(C_1$-$C_4)$alkyl, —$SO_2NH_2$, —$SO_2NH(C_1$-$C_4)$alkyl, or —$SO_2N((C_1$-$C_4)$alkyl)(($C_1$-$C_4)$alkyl);

or $R^a$ and $R^b$ taken together with the nitrogen to which they are attached represent a 5-8 membered saturated or unsaturated ring, optionally containing an additional heteroatom selected from oxygen, nitrogen, and sulfur, wherein said ring is optionally substituted by 1, 2 or 3 groups independently selected from ($C_1$-$C_4$)alkyl, ($C_1$-$C_4$)haloalkyl, amino, ($C_1$-$C_4$)alkylamino, (($C_1$-$C_4$)alkyl)(($C_1$-$C_4$)alkyl)amino, hydroxyl, oxo, ($C_1$-$C_4$)alkoxy, and ($C_1$-$C_4$)alkoxy($C_1$-$C_4$)alkyl, wherein said ring is optionally fused to a ($C_3$-$C_8$)cycloalkyl, heterocycloalkyl, aryl, or heteroaryl ring;

or $R^a$ and $R^b$ taken together with the nitrogen to which they are attached represent a 6- to 10-membered bridged bicyclic ring system optionally fused to a ($C_3$-$C_8$)cycloalkyl, heterocycloalkyl, aryl, or heteroaryl ring;

each $R^c$ is independently ($C_1$-$C_4$)alkylamino, —$NR^aSO_2R^b$, —$SOR^a$, —$SO_2R^a$, —$NR^aC(O)OR^a$, —$NR^aR^b$, or —$CO_2R^a$;

or a salt thereof.

Another aspect of the invention relates to the exemplified compounds.

In a further iteration of this invention it relates to a method of treating cancer.

Another aspect of the invention are pharmaceutical preparations comprising compounds of formula (I) and pharmaceutically acceptable excipients.

In a fourth aspect, there is provided the use of a compound of formula (I) or a pharmaceutically acceptable salt or solvate thereof, in the preparation of a medicament for use in the treatment of a disorder mediated by inhibiting EZH2, such as inducing apoptosis in cancer cells.

In a fifth aspect there is provided methods of co-administering the presently invented compounds of formula (I) with another active ingredient.

DETAILED DESCRIPTION OF THE INVENTION

For the avoidance of doubt, unless otherwise indicated, the term "substituted" means substituted by one or more defined groups. In the case where groups may be selected from a number of alternative groups the selected groups may be the same or different.

The term "independently" means that where more than one substituent is selected from a number of possible substituents, those substituents may be the same or different.

An "effective amount" means that amount of a drug or pharmaceutical agent that will elicit the biological or medical response of a tissue, system, animal or human that is being sought, for instance, by a researcher or clinician. Furthermore, the term "therapeutically effective amount" means any amount which, as compared to a corresponding subject who has not received such amount, results in improved treatment, healing, prevention, or amelioration of a disease, disorder, or side effect, or a decrease in the rate of advancement of a disease or disorder. The term also includes within its scope amounts effective to enhance normal physiological function.

As used herein the term "alkyl" refers to a straight- or branched-chain hydrocarbon radical having the specified number of carbon atoms, so for example, as used herein, the terms "$C_1$-$C_8$alkyl" refers to an alkyl group having at least 1 and up to 8 carbon atoms respectively. Examples of such branched or straight-chained alkyl groups useful in the present invention include, but are not limited to, methyl, ethyl, n-propyl, isopropyl, isobutyl, n-butyl, t-butyl, n-pentyl, isopentyl, n-hexyl, n-heptyl, and n-octyl and branched analogs of the latter 5 normal alkanes.

The term "alkoxy" as used herein means —O($C_1$-$C_8$alkyl) including —$OCH_3$, —$OCH_2CH_3$ and —$OC(CH_3)_3$ and the like per the definition of alkyl above.

The term "alkylthio" as used herein is meant —S($C_1$-$C_8$alkyl) including —$SCH_3$, —$SCH_2CH_3$ and the like per the definition of alkyl above.

The term "acyloxy" means —OC(O)$C_1$-$C_8$alkyl and the like per the definition of alkyl above.

"Acylamino" means -N(H)C(O)$C_1$-$C_8$alkyl and the like per the definition of alkyl above.

"Aryloxy" means —O(aryl), —O(substituted aryl), —O(heteroaryl) or —O(substituted heteroaryl).

"Arylamino" means —NH(aryl), —NH(substituted aryl), —NH(heteroaryl) or —NH(substituted heteroaryl), and the like.

When the term "alkenyl" (or "alkenylene") is used it refers to straight or branched hydrocarbon chains containing the specified number of carbon atoms and at least 1 and up to 5 carbon-carbon double bonds. Examples include ethenyl (or ethenylene) and propenyl (or propenylene).

When the term "alkynyl" (or "alkynylene") is used it refers to straight or branched hydrocarbon chains containing the specified number of carbon atoms and at least 1 and up to 5 carbon-carbon triple bonds. Examples include ethynyl (or ethynylene) and propynyl (or propynylene).

"Haloalkyl" refers to an alkyl group that is substituted with one or more halo substituents, suitably from 1 to 6 substituents. Haloalkyl includes trifluoromethyl.

When "cycloalkyl" is used it refers to a non-aromatic, saturated, cyclic hydrocarbon ring containing the specified number of carbon atoms. So, for example, the term "$C_3$-$C_8$cycloalkyl" refers to a non-aromatic cyclic hydrocarbon ring having from three to eight carbon atoms. Exemplary "$C_3$-$C_8$cycloalkyl" groups useful in the present invention include, but are not limited to, cyclopropyl, cyclobutyl, cyclopentyl, cyclohexyl, cycloheptyl and cyclooctyl.

The term "$C_5$-$C_8$cycloalkenyl" refers to a non-aromatic monocyclic carboxycyclic ring having the specified number of carbon atoms and up to 3 carbon-carbon double bonds. "Cycloalkenyl" includes by way of example cyclopentenyl and cyclohexenyl.

Where "$C_3$-$C_8$heterocycloalkyl" is used, it means a non-aromatic heterocyclic ring containing the specified number of ring atoms being, saturated or having one or more degrees of unsaturation and containing one or more heteroatom substitutions independently selected from O, S and N. Such a ring may be optionally fused to one or more other "heterocyclic" ring(s) or cycloalkyl ring(s). Examples are given herein below.

"Aryl" refers to optionally substituted monocyclic or polycarbocyclic unfused or fused groups having 6 to 14 carbon atoms and having at least one aromatic ring that complies with Hückel's Rule. Examples of aryl groups are phenyl, biphenyl, naphthyl, anthracenyl, phenanthrenyl, and the like, as further illustrated below.

"Heteroaryl" means an optionally substituted aromatic monocyclic ring or polycarbocyclic fused ring system wherein at least one ring complies with Hückel's Rule, has the specified number of ring atoms, and that ring contains at least one heteroatom independently selected from N, O and S. Examples of "heteroaryl" groups are given herein below.

The term "optionally" means that the subsequently described event(s) may or may not occur, and includes both event(s), which occur, and events that do not occur.

Herein, the term "pharmaceutically-acceptable salts" refers to salts that retain the desired biological activity of the subject compound and exhibit minimal undesired toxicological effects. These pharmaceutically-acceptable salts may be prepared in situ during the final isolation and purification of the compound, or by separately reacting the purified compound in its free acid or free base form with a suitable base or acid, respectively.

While the compounds encompassed by the general structure of formula (I) as defined herein are believed to be useful for inducing apoptosis in cancer cells, some of these compounds are more active that others. In that vein, the following subgroups delineate certain compounds believed to have greater potency or other properties which suggest they may be a better choice for use in therapy, versus other. Those subgroups are represented as follows:

Subgroup A

X and Z are selected from the group consisting of ($C_1$-$C_8$) alkyl, ($C_3$-$C_8$)cycloalkyl, heterocycloalkyl, aryl, heteroaryl, —$NR^aR^b$, and —$OR^a$;

Y is H or F;

$R^1$ is selected from the group consisting of ($C_1$-$C_8$)alkyl, ($C_3$-$C_8$)cycloalkyl, heterocycloalkyl, aryl, and heteroaryl;

$R^3$ is selected from the group consisting of hydrogen, ($C_1$-$C_8$)alkyl, cyano, trifluoromethyl, —$NR^aR^b$, and halo;

$R^6$ is selected from the group consisting of hydrogen, halo, cyano, trifluoromethyl, amino, ($C_1$-$C_8$)alkyl, ($C_3$-$C_8$)cycloalkyl, aryl, heteroaryl, acylamino; ($C_2$-$C_8$)alkynyl, arylalkynyl, heteroarylalkynyl, —$SO_2R^a$, —$SO_2NR^aR^b$, and —$NR^aSO_2R^b$;

wherein any ($C_1$-$C_8$)alkyl, ($C_3$-$C_8$)cycloalkyl, ($C_2$-$C_8$) alkynyl, arylalkynyl, heteroarylalkynyl group is optionally substituted by 1, 2 or 3 groups independently selected from —O($C_1$-$C_6$)alkyl($R^c$)$_{1-2}$, —S($C_1$-$C_6$) alkyl($R^c$)$_{1-2}$, —($C_1$-$C_6$)alkyl($R^c$)$_{1-2}$, ($C_1$-$C_8$)alkyl-heterocycloalkyl, ($C_3$-$C_8$)cycloalkyl-heterocycloalkyl, halo, ($C_1$-$C_6$)alkyl, ($C_3$-$C_8$)cycloalkyl, ($C_5$-$C_8$)cycloalkenyl, ($C_1$-$C_6$)haloalkyl, cyano, —$COR^a$, —$CO_2R^a$, —$CONR^aR^b$, —$SR^a$, —$SOR^a$, —$SO_2R^a$, —$SO_2NR^aR^b$, nitro, —$NR^aR^b$, —$NR^aC(O)R^b$, —$NR^aC(O)NR^aR^b$, —$NR^aC(O)OR^a$, —$NR^aSO_2R^b$, —$NR^aSO_2NR^aR^b$, —$OR^a$, —OC(O)$R^a$, —OC(O) $NR^aR^b$, heterocycloalkyl, aryl, heteroaryl, aryl($C_1$-$C_4$) alkyl, and heteroaryl($C_1$-$C_4$)alkyl;

each $R^c$ is independently ($C_1$-$C_4$)alkylamino, —$NR^aSO_2R^b$, —$SOR^a$, —$SO_2R^a$, —$NR^aC(O)OR^a$, —$NR^aR^b$, or —$CO_2R^a$;

$R^a$ and $R^b$ are each independently hydrogen, ($C_1$-$C_8$)alkyl, ($C_2$-$C_8$)alkenyl, ($C_2$-$C_8$)alkynyl, ($C_3$-$C_8$)cycloalkyl, ($C_5$-$C_8$) cycloalkenyl, ($C_6$-$C_{10}$)bicycloalkyl, heterocycloalkyl, aryl, heteroaryl, wherein said ($C_1$-$C_8$)alkyl, ($C_2$-$C_8$)alkenyl, ($C_2$-$C_8$)alkynyl, cycloalkyl, cycloalkenyl, bicycloalkyl, heterocycloalkyl, aryl or heteroaryl group is optionally substituted by 1, 2 or 3 groups independently selected from halo, hydroxyl, ($C_1$-$C_4$)alkoxy, amino, ($C_1$-$C_4$)alkylamino, (($C_1$-$C_4$)alkyl) (($C_1$-$C_4$)alkyl)amino, —$CO_2H$, —$CO_2$($C_1$-$C_4$)alkyl, —$CONH_2$, —CONH($C_1$-$C_4$)alkyl, —CON(($C_1$-$C_4$)alkyl) (($C_1$-$C_4$)alkyl), —$SO_2$($C_1$-$C_4$)alkyl, —$SO_2NH_2$, —$SO_2$NH ($C_1$-$C_4$)alkyl, and —$SO_2$N(($C_1$-$C_4$)alkyl)(($C_1$-$C_4$)alkyl);

or $R^a$ and $R^b$ taken together with the nitrogen to which they are attached represent a 5-8 membered saturated or unsaturated ring, optionally containing an additional heteroatom selected from oxygen, nitrogen, and sulfur, wherein said ring is optionally substituted by 1, 2 or 3 groups independently selected from ($C_1$-$C_4$)alkyl, ($C_1$-$C_4$)haloalkyl, amino, ($C_1$-$C_4$)alkylamino, (($C_1$-$C_4$)alkyl)(($C_1$-$C_4$)alkyl)amino, hydroxyl, oxo, ($C_1$-$C_4$)alkoxy, and ($C_1$-$C_4$)alkoxy($C_1$-$C_4$) alkyl, wherein said ring is optionally fused to a ($C_3$-$C_8$)cycloalkyl, heterocycloalkyl, aryl, or heteroaryl ring;

or $R^a$ and $R^b$ taken together with the nitrogen to which they are attached represent a 6- to 10-membered bridged bicyclic ring system optionally fused to a $(C_3-C_8)$cycloalkyl, heterocycloalkyl, aryl, or heteroaryl ring. An aryl or heteroaryl group in this particular subgroup A is selected independently from the group consisting of furan, thiophene, pyrrole, oxazole, thiazole, imidazole, pyrazole, oxadiazole, thiadiazole, triazole, tetrazole, benzofuran, benzothiophene, benzoxazole, benzothiazole, phenyl, pyridine, pyridazine, pyrimidine, pyrazine, triazine, tetrazine, quinoline, cinnoline, quinazoline, quinoxaline, and naphthyridine or another aryl or heteroaryl group as follows:

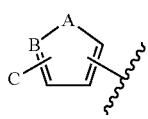

(1)

wherein in (1),
A is O, NH, or S; B is CH or N, and C is hydrogen or $C_1-C_8$ alkyl; or

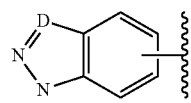

(2)

wherein in (2),
D is N or C optionally substituted by hydrogen or $C_1-C_8$ alkyl; or

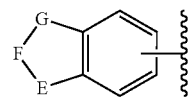

(3)

wherein in (3),
E is NH or $CH_2$; F is O or CO; and G is NH or $CH_2$; or

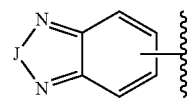

(4)

wherein in (4),
J is O, S or CO; or

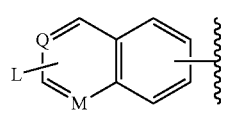

(5)

wherein in (5),
Q is CH or N;
M is CH or N; and
L/(5) is hydrogen, halo, amino, cyano, $(C_1-C_8)$alkyl, $(C_3-C_8)$cycloalkyl, —$COR^a$, —$CO_2R^a$, —$CONR^aR^b$, —CON-$R^aNR^aR^b$, —$SO_2R^a$, —$SO_2NR^aR^b$, —$NR^aR^b$, —$NR^aC(O)$ $R^b$, —$NR^aSO_2R^b$, —$NR^aSO_2NR^aR^b$, —$NR^aNR^aR^b$, —$NR^aNR^aC(O)R^b$, —$NR^aNR^aC(O)NR^aR^b$, —$OR^a$, wherein any $(C_1-C_8)$alkyl, $(C_3-C_8)$cycloalkyl, group is optionally substituted by 1, 2 or 3 groups independently selected from $(C_1-C_6)$alkyl, $(C_3-C_8)$cycloalkyl, $(C_5-C_8)$ cycloalkenyl, $(C_1-C_6)$haloalkyl, cyano, —$COR^a$, —$CO_2R^a$, —$CONR^aR^b$, —$SR^a$, —$SOR^a$, —$SO_2R^a$, —$SO_2NR^aR^b$, nitro, —$NR^aR^b$, —$NR^aC(O)R^b$, —$NR^aC(O)NR^aR^b$, —$NR^aC(O)OR^a$, —$NR^aSO_2R^b$, —$NR^aSO_2NR^aR^b$, —$OR^a$, —$OC(O)R^a$, —$OC(O)$ $NR^aR^b$; wherein $R^a$ and $R^b$ are defined as above; or

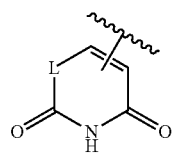

(6)

wherein in 6,
L/(6) is NH or $CH_2$; or

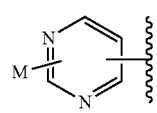

(7)

wherein in 7,
M/(7) is hydrogen, halo, amino, cyano, $(C_1-C_8)$alkyl, $(C_3-C_8)$cycloalkyl, heterocycloalkyl, —$COR^a$, $CO_2R^a$, —$CONR^aR^b$, —$CONR^aNR^aR^b$, —$SO_2R^a$, —$SO_2NR^aR^b$, —$NR^aR^b$, —$NR^aC(O)R^b$, —$NR^aSO_2R^b$, —$NR^aSO_2NR^aR^b$, —$NR^aNR^aR^b$, —$NR^aNR^aC(O)R^b$, —$NR^aNR^aC(O)NR^aR^b$, —$OR^a$ wherein any $(C_1-C_8)$alkyl, $(C_3-C_8)$cycloalkyl, heterocycloalkyl group is optionally substituted by 1, 2 or 3 groups independently selected from $(C_1-C_6)$alkyl, $(C_3-C_8)$cycloalkyl, $(C_5-C_8)$cycloalkenyl, $(C_1-C_6)$haloalkyl, cyano, —$COR^a$, $CO_2R^a$, —$CONR^aR^b$, —$SR^a$, —$SOR^a$, —$SO_2R^a$, —$SO_2NR^aR^b$, nitro, —$NR^aR^b$, —$NR^aC(O)R^b$, —$NR^aC(O)NR^aR^b$, —$NR^aC(O)OR^a$, —$NR^aSO_2R^b$, —$NR^aSO_2NR^aR^b$, —$OR^a$, —$OC(O)R^a$, —$OC(O)NR^aR^b$; wherein $R^a$ and $R^b$ are defined as above; or

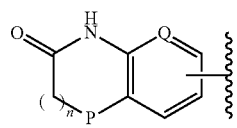

(8)

wherein in (8),
P is $CH_2$, NH, O, or S; Q/(8) is CH or N; and n is 0-2; or

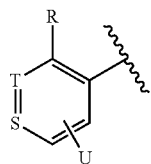

(9)

wherein in (9),

S/(9) and T(9) is C, or S/(9) is C and T(9) is N, or S/(9) is N and T/(9) is C;

R is hydrogen, amino, methyl, trifluoromethyl, halo;

U is hydrogen, halo, amino, cyano, nitro, trifluoromethyl, $(C_1-C_8)$alkyl, $(C_3-C_8)$cycloalkyl, —$COR^a$, —$CO_2R^a$, —$CONR^aR^b$, —$SO_2R^a$, —$SO_2NR^aR^b$, —$NR^aR^b$, —$NR^aC(O)R^b$, —$NR^aSO_2R^b$, —$NR^aSO_2NR^aR^b$, —$NR^aNR^aR^b$, —$NR^aNR^aC(O)R^b$, —$OR^a$, 4-(1H-pyrazol-4-yl), wherein any $(C_1-C_8)$alkyl, $(C_3-C_8)$cycloalkyl, group is optionally substituted by 1, 2 or 3 groups independently selected from $(C_1-C_6)$alkyl, $(C_3-C_8)$cycloalkyl, $(C_5-C_8)$cycloalkenyl, $(C_1-C_6)$haloalkyl, cyano, —$COR^a$, —$CO_2R^a$, —$CONR^aR^b$, —$SR^a$, —$SOR^a$, —$SO_2R^a$, —$SO_2NR^aR^b$, nitro, —$NR^aR^b$, —$NR^aC(O)R^b$, —$NR^aC(O)NR^aR^b$, —$NR^aC(O)OR^a$, —$NR^aSO_2R^b$, —$NR^aSO_2NR^aR^b$, —$OR^a$, —$OC(O)R^a$, —$OC(O)NR^aR^b$; wherein $R^a$ and $R^b$ are defined as above.

Subgroup B

X and Z are selected independently from the group consisting of $(C_1-C_8)$alkyl, $(C_3-C_8)$cycloalkyl, heterocycloalkyl, aryl, heteroaryl, —$NR^aR^b$, and —$OR^a$;

Y is H;

$R^1$ is $(C_1-C_8)$alkyl, $(C_3-C_8)$cycloalkyl, or heterocycloalkyl;

$R^3$ is hydrogen, $(C_1-C_8)$alkyl or halo;

$R^6$ is hydrogen, halo, cyano, trifluoromethyl, amino, $(C_1-C_8)$alkyl, $(C_3-C_8)$cycloalkyl; aryl, heteroaryl, acylamino; $(C_2-C_8)$alkynyl, arylalkynyl, heteroarylalkynyl; —$SO_2R^a$; —$SO_2NR^aR^b$, or —$NR^aSO_2R^b$;

wherein any $(C_1-C_8)$alkyl, $(C_3-C_8)$cycloalkyl, $(C_2-C_8)$alkynyl, arylalkynyl, heteroarylalkynyl group is optionally substituted by 1, 2 or 3 groups independently selected from halo, $(C_1-C_6)$alkyl, $(C_3-C_8)$cycloalkyl, $(C_5-C_8)$cycloalkenyl, $(C_1-C_6)$haloalkyl, cyano, —$COR^a$, —$CO_2R^a$, —$CONR^aR^b$, —$SR^a$, —$SOR^a$, —$SO_2R^a$, —$SO_2NR^aR^b$, nitro, —$NR^aR^b$, —$NR^aC(O)R^b$, —$NR^aC(O)NR^aR^b$, —$NR^aC(O)OR^a$, —$NR^aSO_2R^b$, —$NR^aSO_2NR^aR^b$, —$OR^a$, —$OC(O)R^a$, —$OC(O)NR^aR^b$, heterocycloalkyl, aryl, heteroaryl, aryl$(C_1-C_4)$alkyl, and heteroaryl$(C_1-C_4)$alkyl;

$R^a$ and $R^b$ are each independently hydrogen, $(C_1-C_8)$alkyl, $(C_2-C_8)$alkenyl, $(C_2-C_8)$alkynyl, $(C_3-C_8)$cycloalkyl, $(C_5-C_8)$cycloalkenyl, $(C_6-C_{10})$bicycloalkyl, heterocycloalkyl, aryl, heteroaryl, wherein said $(C_1-C_8)$alkyl, $(C_2-C_8)$alkenyl, $(C_2-C_8)$alkynyl, cycloalkyl, cycloalkenyl, bicycloalkyl, heterocycloalkyl, aryl or heteroaryl group is optionally substituted by 1, 2 or 3 groups independently selected from halo, hydroxyl, $(C_1-C_4)$alkoxy, amino, $(C_1-C_4)$alkylamino, $((C_1-C_4)$alkyl)$((C_1-C_4)$alkyl)amino, —$CO_2H$, —$CO_2(C_1-C_4)$alkyl, —$CONH_2$, —$CONH(C_1-C_4)$alkyl, —$CON((C_1-C_4)$alkyl)$((C_1-C_4)$alkyl), —$SO_2(C_1-C_4)$alkyl, —$SO_2NH_2$, —$SO_2NH(C_1-C_4)$alkyl, and —$SO_2N((C_1-C_4$alkyl)$((C_1-C_4$alkyl);

or $R^a$ and $R^b$ taken together with the nitrogen to which they are attached represent a 5-8 membered saturated or unsaturated ring, optionally containing an additional heteroatom selected from oxygen, nitrogen, and sulfur, wherein said ring is optionally substituted by 1, 2 or 3 groups independently selected from $(C_1-C_4)$alkyl, $(C_1-C_4)$haloalkyl, amino, $(C_1-C_4)$alkylamino, $((C_1-C_4)$alkyl)$((C_1-C_4)$alkyl)amino, hydroxyl, oxo, $(C_1-C_4)$alkoxy, and $(C_1-C_4)$alkoxy$(C_1-C_4)$alkyl, wherein said ring is optionally fused to a $(C_3-C_8)$cycloalkyl, heterocycloalkyl, aryl, or heteroaryl ring;

or $R^a$ and $R^b$ taken together with the nitrogen to which they are attached represent a 6- to 10-membered bridged bicyclic ring system optionally fused to a $(C_3-C_8)$cycloalkyl, heterocycloalkyl, aryl, or heteroaryl ring. Aryl and heteroaryl in this definition are selected from the group consisting of furan, thiophene, pyrrole, oxazole, thiazole, imidazole, pyrazole, oxadiazole, thiadiazole, triazole, tetrazole, benzofuran, benzothiophene, benzoxazole, benzothiazole, phenyl, pyridine, pyridazine, pyrimidine, pyrazine, triazine, tetrazine, quinoline, cinnoline, quinazoline, quinoxaline, and naphthyridine as or a compound of or another aryl or heteroaryl group as follows:

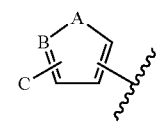

(1)

wherein in (1),

A is O, NH, or S; B is CH or N, and C is hydrogen or $C_1-C_8$ alkyl; or

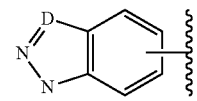

(2)

wherein in (2),

D is N or C optionally substituted by hydrogen or $C_1-C_8$ alkyl; or

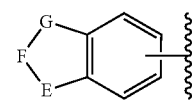

(3)

wherein in (3),

E is NH or $CH_2$; F is O or CO; and G is NH or $CH_2$; or

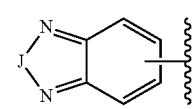

(4)

wherein in (4),

J is O, S or CO; or

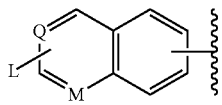 (5)

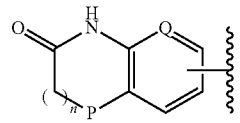 (8)

wherein in (5),

Q is CH or N;

M is CH or N; and

L/(5) is hydrogen, halo, amino, cyano, $(C_1-C_8)$alkyl, $(C_3-C_8)$cycloalkyl, —$COR^a$, $CO_2R^a$, —$CONR^aR^b$, —$CONR^aNR^aR^b$, —$SO_2R^a$, —$SO_2NR^aR^b$, —$NR^aR^b$, —$NR^aC(O)R^b$, —$NR^aSO_2R^b$, —$NR^aSO_2NR^aR^b$, —$NR^aNR^aR^b$, —$NR^aNR^aC(O)R^b$, —$NR^aNR^aC(O)NR^aR^b$, —$OR^a$, wherein any $(C_1-C_8)$alkyl, $(C_3-C_8)$cycloalkyl, group is optionally substituted by 1, 2 or 3 groups independently selected from $(C_1-C_6)$alkyl, $(C_3-C_8)$cycloalkyl, $(C_5-C_8)$cycloalkenyl, $(C_1-C_6)$haloalkyl, cyano, —$COR^a$, —$CO_2R^a$, —$CONR^aR^b$, —$SR^a$, —$SOR^a$, —$SO_2R^a$, —$SO_2NR^aR^b$, nitro, —$NR^aR^b$, —$NR^aC(O)R^b$, —$NR^aC(O)NR^aR^b$, —$NR^aC(O)OR^a$, —$NR^aSO_2R^b$, —$NR^aSO_2NR^aR^b$, —$OR^a$, —$OC(O)R^a$, —$OC(O)NR^aR^b$, wherein $R^a$ and $R^b$ are defined as above; or

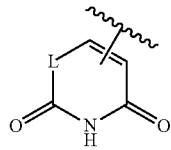 (6)

wherein in 6,

L/(6) is NH or $CH_2$; or

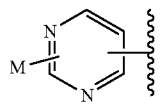 (7)

wherein in 7,

M/(7) is hydrogen, halo, amino, cyano, $(C_1-C_8)$alkyl, $(C_3-C_8)$cycloalkyl, heterocycloalkyl, —$COR^a$, —$CO_2R^a$, —$CONR^aR^b$, —$CONR^aNR^aR^b$, —$SO_2R$, —$SO_2NR^aR^b$, —$NR^aR^b$, —$NR^aC(O)R^b$, —$NR^aSO_2R^b$, —$NR^aSO_2NR^aR^b$, —$NR^aNR^aR^b$, —$NR^aNR^aC(O)R^b$, —$NR^aNR^aC(O)NR^aR^b$, —$OR^a$ wherein any $(C_1-C_8)$alkyl, $(C_3-C_8)$cycloalkyl, heterocycloalkyl group is optionally substituted by 1, 2 or 3 groups independently selected from $(C_1-C_6)$alkyl, $(C_3-C_8)$cycloalkyl, $(C_5-C_8)$cycloalkenyl, $(C_1-C_6)$haloalkyl, cyano, —$COR^a$, —$CO_2R^a$, —$CONR^aR^b$, —$SR^a$, —$SOR^a$, —$SO_2R^a$, —$SO_2NR^aR^b$, nitro, —$NR^aR^b$, —$NR^aC(O)R^b$, —$NR^aC(O)NR^aR^b$, —$NR^aC(O)OR^a$, —$NR^aSO_2R^b$, —$NR^aSO_2NR^aR^b$, —$OR^a$, —$OC(O)R^a$, —$OC(O)NR^aR^b$; wherein $R^a$ and $R^b$ are defined as above; or wherein in (8), P is $CH_2$, NH, O, or S; Q/(8) is CH or N; and n is 0-2; or

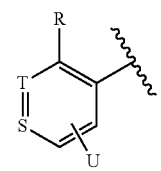 (9)

wherein in (9),

S/(9) and T(9) is C, or S/(9) is C and T(9) is N, or S/(9) is N and T/(9) is C;

R is hydrogen, amino, methyl, trifluoromethyl, halo;

U is hydrogen, halo, amino, cyano, nitro, trifluoromethyl, $(C_1-C_8)$alkyl, $(C_3-C_8)$cycloalkyl, —$COR^a$, —$CO_2R^a$, —$CONR^aR^b$, —$SO_2R^a$, —$SO_2NR^aR^b$, —$NR^aR^b$, —$NR^aC(O)R^b$, —$NR^aSO_2R^b$, —$NR^aSO_2NR^aR^b$, —$NR^aNR^aR^b$, —$NR^aNR^aC(O)R^b$, —$OR^a$, 4-(1H-pyrazol-4-yl), wherein any $(C_1-C_8)$alkyl, $(C_3-C_8)$cycloalkyl, group is optionally substituted by 1, 2 or 3 groups independently selected from $(C_1-C_6)$alkyl, $(C_3-C_8)$cycloalkyl, $(C_5-C_8)$cycloalkenyl, $(C_1-C_6)$haloalkyl, cyano, —$COR^a$, —$CO_2R^a$, —$CONR^aR^b$, —$SR^a$, —$SOR^a$, —$SO_2R^a$, —$SO_2NR^aR^b$, nitro, —$NR^aR^b$, —$NR^aC(O)R^b$, —$NR^aC(O)NR^aR^b$, —$NR^aC(O)OR^a$, $NR^aSO_2R^b$, —$NR^aSO_2NR^aR^b$, —$OR^a$, —$OC(O)R^a$, —$OC(O)NR^aR^b$, wherein $R^a$ and $R^b$ are defined as above.

Subgroup C

X is methyl, ethyl, n-propyl, isopropyl, cyclopropyl, cyclobutyl, cyclopentyl, cyclohexyl, phenyl, trifluoromethyl, tetrahydropyran, hydroxymethyl, methoxymethyl, or benzyl;

Y is H;

Z is methyl, ethyl, n-propyl, isopropyl, trifluoromethyl, or benzyl;

$R^1$ is isopropyl, tert-butyl, cyclobutyl, cyclopentyl, cyclohexyl, (1-methylethyl)cyclopropyl, 1,1-dioxo-tetrahydrothiophene-3-yl, 1-Me-piperidin-4-yl, tetrahydrofuran-3-yl, tetrahydropyran-4-yl, N,N-dimethyl-1-propanaminyl, benzyl, or 4-pyridyl;

$R^3$ is H, methyl, or Br; and $R^6$ is methyl, bis(1,1-dimethylethyl), bis(1-methylethyl), cyclopropyl, propyl, dimethylamino, ethylamino, (2-hydroxyethyl)amino, 2-propen-1-ylamino, 1-piperazinyl, 1-piperidinyl, 4-morpholinyl, 4-piperidinylamino, tetrahydro-2H-pyran-4-ylamino, phenylamino, (phenylmethyl)amino, (4-pyridinylmethyl)amino, [2-(2-pyridinylamino)ethyl]amino, 2-(dimethylamino)ethyl]amino, 4-pyridinylamino, 4-(aminocarbonyl)phenyl]amino, 3-hydroxy-3-methyl-1-butyn-1-yl, 4-pyridinylethynyl, phenylethynyl, 2-furanyl, 3-thienyl; 1H-pyrazol-4-yl, 1H-indazol-5-yl, 1H-indazol-6-yl, 3-methyl-1H-indazol-5-yl, 1H-1,2,3-benzotriazol-5-yl, 2-oxo-2,3-dihydro-1H-benzimidazol-5-yl, 2-oxo-2,3-dihydro-1H-indol-5-yl, 2-oxo-2,3-dihydro-1H-indol-6-yl, 2,1,3-benzoxadiazol-5-yl, 2-amino-6-quinazolinyl, 2,4-dioxo-1,2,3,4-tetrahydro-5-pyrimidinyl, 2-amino-5-pyrimidinyl, 7-oxo-1,5,6,7-tetrahydro-1,8-naphthyridin-3-yl, phenyl, 2-methylphenyl, 2-nitrophenyl, 2-phenylethyl, 3-aminophenyl, 4-aminophenyl, 4-chlorophenyl, 4-fluorophenyl, 4-(methyloxy)phenyl, 3-(acetylamino)phenyl, 4-(acetylamino)phenyl, 4-(aminocarbonyl)phenyl, 4-(1H-pyrazol-4-yl)phenyl, 4-(aminosulfonyl)phenyl, 4-(methylsulfonyl)phenyl, 4-[(dimethylamino)sulfonyl]phenyl, 4-[(methylamino)carbonyl]phenyl, 4-[(methylamino)sulfonyl]phenyl, 4-[(methylsulfonyl)amino]phenyl, 3-pyridinyl, 4-pyridinyl, 2-(4-morpholinyl)-4-pyridinyl, 2-amino-4-pyridinyl, 5-(methyloxy)-3-pyridinyl, 5-(methylsulfonyl)-3-pyridinyl, 5-[(cyclopropylsulfonyl)amino]-6-(methyloxy)-3-pyridinyl, 5-[(phenylsulfonyl)amino]-3-pyridinyl, 6-(4-methyl-1-piperazinyl)-3-pyridinyl, 6-(4-morpholinyl)-3-pyridinyl, 6-(acetylamino)-3-pyridinyl, 6-(dimethylamino)-3-pyridinyl, 6-(methyloxy)-3-pyridinyl, 6-[(methylamino)carbonyl]-3-pyridinyl, 6-[(methylamino)sulfonyl]-3-pyridinyl, 6-methyl-3-pyridinyl, 4-pyridinyloxy.

In one aspect, this invention also relates to the exemplified compounds.

Individual compounds can be found in the Examples set out below.

By the term "co-administering" and derivatives thereof as used herein is meant either simultaneous administration or any manner of separate sequential administration of one or more additional pharmaceutically active compounds, whether for treating cancer, the side effects of cancer or cancer therapy, or some other disease. Preferably, if the administration is not simultaneous, the compounds are administered in a close time proximity to each other. Furthermore, it does not matter if the compounds are administered in the same dosage form, e.g. one compound may be administered topically and another compound may be administered orally.

In certain embodiments, compounds according to Formula I may contain an acidic functional group, one acidic enough to form salts. Representative salts include pharmaceutically-acceptable metal salts such as sodium, potassium, lithium, calcium, magnesium, aluminum, and zinc salts; carbonates and bicarbonates of a pharmaceutically-acceptable metal cation such as sodium, potassium, lithium, calcium, magnesium, aluminum, and zinc; pharmaceutically-acceptable organic primary, secondary, and tertiary amines including aliphatic amines, aromatic amines, aliphatic diamines, and hydroxy alkylamines such as methylamine, ethylamine, 2-hydroxyethylamine, diethylamine, triethylamine, ethylenediamine, ethanolamine, diethanolamine, and cyclohexylamine.

In certain embodiments, compounds according to Formula (I) may contain a basic functional group and are therefore capable of forming pharmaceutically-acceptable acid addition salts by treatment with a suitable acid. Suitable acids include pharmaceutically-acceptable inorganic acids and pharmaceutically-acceptable organic acids. Representative pharmaceutically-acceptable acid addition salts include hydrochloride, hydrobromide, nitrate, methylnitrate, sulfate, bisulfate, sulfamate, phosphate, acetate, hydroxyacetate, phenylacetate, propionate, butyrate, isobutyrate, valerate, maleate, hydroxymaleate, acrylate, fumarate, malate, tartrate, citrate, salicylate, p-aminosalicyclate, glycollate, lactate, heptanoate, phthalate, oxalate, succinate, benzoate, o-acetoxybenzoate, chlorobenzoate, methylbenzoate, dinitrobenzoate, hydroxybenzoate, methoxybenzoate, mandelate, tannate, formate, stearate, ascorbate, palmitate, oleate, pyruvate, pamoate, malonate, laurate, glutarate, glutamate, estolate, methanesulfonate (mesylate), ethanesulfonate (esylate), 2-hydroxyethanesulfonate, benzenesulfonate (besylate), p-aminobenzenesulfonate, p-toluenesulfonate (tosylate) and napthalene-2-sulfonate.

All tautomeric forms of the compounds described herein, including mixtures thereof, are intended to be encompassed within the scope of the invention. Generally, the compounds exemplified herein have been assigned names based on the structure of the tautomer of formula (IA). It should be understood that any reference to named compounds of this invention is intended to encompass all tautomers of the named compounds and any mixtures of tautomers of the named compounds.

The compounds of formula (I) may be prepared in crystalline or non-crystalline form, and, if crystalline, may optionally be solvated, e.g. as the hydrate. This invention includes within its scope stoichiometric solvates (e.g. hydrates) as well as compounds containing variable amounts of solvent (e.g. water).

Certain of the compounds described herein may contain one or more chiral atoms, or may otherwise be capable of existing as two enantiomers. The compounds claimed below include mixtures of enantiomers as well as purified enantiomers or enantiomerically enriched mixtures. Also included within the scope of the invention are the individual isomers of the compounds represented by formula (I), or claimed below, as well as any wholly or partially equilibrated mixtures thereof. The present invention also covers the individual isomers of the claimed compounds as mixtures with isomers thereof in which one or more chiral centers are inverted.

Where there are different isomeric forms they may be separated or resolved one from the other by conventional methods, or any given isomer may be obtained by conventional synthetic methods or by stereospecific or asymmetric syntheses.

While it is possible that, for use in therapy, a compound of formula (I), as well as salts, solvates and the like, may be administered as a neat preparation, i.e. no additional carrier, the more usual practice is to present the active ingredient confected with a carrier or diluent. Accordingly, the invention further provides pharmaceutical compositions, which includes a compound of formula (I) and salts, solvates and the like, and one or more pharmaceutically acceptable carriers, diluents, or excipients. The compounds of formula (I) and salts, solvates, etc, are as described above. The carrier(s), diluent(s) or excipient(s) must be acceptable in the sense of being compatible with the other ingredients of the formulation and not deleterious to the recipient thereof. In accordance with another aspect of the invention there is also provided a process for the preparation of a pharmaceutical formulation including admixing a compound of the formula (I), or salts, solvates etc, with one or more pharmaceutically acceptable carriers, diluents or excipients.

It will be appreciated by those skilled in the art that certain protected derivatives of compounds of formula (I), which may be made prior to a final deprotection stage, may not possess pharmacological activity as such, but may, in certain instances, be administered orally or parenterally and thereafter metabolised in the body to form compounds of the invention which are pharmacologically active. Such derivatives may therefore be described as "prodrugs". Further, certain compounds of the invention may act as prodrugs of other compounds of the invention. All protected derivatives and prodrugs of compounds of the invention are included within the scope of the invention. It will further be appreciated by those skilled in the art, that certain moieties, known to those skilled in the art as "pro-moieties" may be placed on appropriate functionalities when such functionalities are present within compounds of the invention. Preferred prodrugs for compounds of the invention include: esters, carbonate esters, hemi-esters, phosphate esters, nitro esters, sulfate esters, sulfoxides, amides, carbamates, azo-compounds, phosphamides, glycosides, ethers, acetals and ketals.

Treatments

The compounds and compositions of the invention are used to treat cellular proliferation diseases. Disease states which can be treated by the methods and compositions provided herein include, but are not limited to, cancer (further discussed below), autoimmune disease, fungal disorders, arthritis, graft rejection, inflammatory bowel disease, proliferation induced after medical procedures, including, but not limited to, surgery, angioplasty, and the like. It is appreciated that in some cases the cells may not be in a hyper or hypo proliferation state (abnormal state) and still requires treatment. For example, during wound healing, the cells may be proliferating "normally", but proliferation enhancement may be desired. Thus, in one embodiment, the invention herein includes application to cells or individuals afflicted or impending affliction with any one of these disorders or states.

The compositions and methods provided herein are particularly deemed useful for the treatment of cancer including tumors such as prostate, breast, brain, skin, cervical carcinomas, testicular carcinomas, etc. They are particularly useful in treating metastatic or malignant tumors. More particularly, cancers that may be treated by the compositions and methods of the invention include, but are not limited to tumor types such as astrocytic, breast, cervical, colorectal, endometrial, esophageal, gastric, head and neck, hepatocellular, laryngeal, lung, oral, ovarian, prostate and thyroid carcinomas and sarcomas. More specifically, these compounds can be used to treat: Cardiac: sarcoma (angiosarcoma, fibrosarcoma, rhabdomyosarcoma, liposarcoma), myxoma, rhabdomyoma, fibroma, lipoma and teratoma; Lung: bronchogenic carcinoma (squamous cell, undifferentiated small cell, undifferentiated large cell, adenocarcinoma), alveolar (bronchiolar) carcinoma, bronchial adenoma, sarcoma, lymphoma, chondromatous hamartoma, mesothelioma; Gastrointestinal: esophagus (squamous cell carcinoma, adenocarcinoma, leiomyosarcoma, lymphoma), stomach (carcinoma, lymphoma, leiomyosarcoma), pancreas (ductal adenocarcinoma, insulinoma, glucagonoma, gastrinoma, carcinoid tumors, vipoma), small bowel (adenocarcinoma, lymphoma, carcinoid tumors, Karposi's sarcoma, leiomyoma, hemangioma, lipoma, neurofibroma, fibroma), large bowel (adenocarcinoma, tubular adenoma, villous adenoma, hamartoma, leiomyoma); Genitourinary tract: kidney (adenocarcinoma, Wilm's tumor (nephroblastoma), lymphoma, leukemia), bladder and urethra (squamous cell carcinoma, transitional cell carcinoma, adenocarcinoma), prostate (adenocarcinoma, sarcoma), testis (seminoma, teratoma, embryonal carcinoma, teratocarcinoma, choriocarcinoma, sarcoma, interstitial cell carcinoma, fibroma, fibroadenoma, adenomatoid tumors, lipoma); Liver: hepatoma (hepatocellular carcinoma), cholangiocarcinoma, hepatoblastoma, angiosarcoma, hepatocellular adenoma, hemangioma; Biliary tract: gall bladder carcinoma, ampullary carcinoma, cholangiocarcinoma; Bone: osteogenic sarcoma (osteosarcoma), fibrosarcoma, malignant fibrous histiocytoma, chondrosarcoma, Ewing's sarcoma, malignant lymphoma (reticulum cell sarcoma), multiple myeloma, malignant giant cell tumor chordoma, osteochronfroma (osteocartilaginous exostoses), benign chondroma, chondroblastoma, chondromyxofibroma, osteoid osteoma and giant cell tumors; Nervous system: skull (osteoma, hemangioma, granuloma, xanthoma, osteitis deformans), meninges (meningioma, meningiosarcoma, gliomatosis), brain (astrocytoma, medulloblastoma, glioma, ependymoma, germinoma (pinealoma), glioblastoma multiform, oligodendroglioma, schwannoma, retinoblastoma, congenital tumors), spinal cord neurofibroma, meningioma, glioma, sarcoma); Gynecological: uterus (endometrial carcinoma), cervix (cervical carcinoma, pre-tumor cervical dysplasia), ovaries (ovarian carcinoma (serous cystadenocarcinoma, mucinous cystadenocarcinoma, unclassified carcinoma), granulosa-thecal cell tumors, Sertoli-Leydig cell tumors, dysgerminoma, malignant teratoma), vulva (squamous cell carcinoma, intraepithelial carcinoma, adenocarcinoma, fibrosarcoma, melanoma), vagina (clear cell carcinoma, squamous cell carcinoma, botryoid sarcoma (embryonal rhabdomyosarcoma), fallopian tubes (carcinoma); Hematologic: blood (myeloid leukemia (acute and chronic), acute lymphoblastic leukemia, chronic lymphocytic leukemia, myeloproliferative diseases, multiple myeloma, myelodysplastic syndrome), Hodgkin's disease, non-Hodgkin's lymphoma (malignant lymphoma); Skin: malignant melanoma, basal cell carcinoma, squamous cell carcinoma, Karposi's sarcoma, moles dysplastic nevi, lipoma, angioma, dermatofibroma, keloids, psoriasis; and Adrenal glands: neuroblastoma. Thus, the term "cancerous cell" as provided herein, includes a cell afflicted by any one or related of the above identified conditions.

The instant compounds can be combined with or co-administered with other therapeutic agents, particularly agents that may enhance the activity or time of disposition of the compounds. Combination therapies according to the invention comprise the administration of at least one compound of the invention and the use of at least one other treatment method. In one embodiment, combination therapies according to the invention comprise the administration of at least one compound of the invention and surgical therapy. In one embodiment, combination therapies according to the invention comprise the administration of at least one compound of the invention and radiotherapy. In one embodiment, combination therapies according to the invention comprise the administration of at least one compound of the invention and at least one supportive care agent (e.g., at least one anti-emetic agent). In one embodiment, combination therapies according to the present invention comprise the administration of at least one compound of the invention and at least one other chemotherapeutic agent. In one particular embodiment, the invention comprises the administration of at least one compound of the invention and at least one anti-neoplastic agent. In yet another embodiment, the invention comprises a therapeutic regimen where the EZH2 inhibitors of this disclosure are not in and of themselves active or significantly active, but when combined with another therapy, which may or may not be active as a standalone therapy, the combination provides a useful therapeutic outcome.

By the term "co-administering" and derivatives thereof as used herein is meant either simultaneous administration or any manner of separate sequential administration of an EZH2 inhibiting compound, as described herein, and a further active ingredient or ingredients, known to be useful in the treatment of cancer, including chemotherapy and radiation treatment. The term further active ingredient or ingredients, as used herein, includes any compound or therapeutic agent known to or that demonstrates advantageous properties when administered to a patient in need of treatment for cancer. Preferably, if the administration is not simultaneous, the compounds are administered in a close time proximity to each other. Furthermore, it does not matter if the compounds are administered in the same dosage form, e.g. one compound may be administered topically and another compound may be administered orally.

Typically, any anti-neoplastic agent that has activity versus a susceptible tumor being treated may be co-administered in the treatment of specified cancers in the present invention. Examples of such agents can be found in Cancer Principles and Practice of Oncology by V. T. Devita and S. Hellman (editors), 6$^{th}$ edition (Feb. 15, 2001), Lippincott Williams & Wilkins Publishers. A person of ordinary skill in the art would be able to discern which combinations of agents would be useful based on the particular characteristics of the drugs and the cancer involved. Typical anti-neoplastic agents useful in the present invention include, but are not limited to, anti-microtubule agents such as diterpenoids and vinca alkaloids; platinum coordination complexes; alkylating agents such as nitrogen mustards, oxazaphosphorines, alkylsulfonates, nitrosoureas, and triazenes; antibiotic agents such as anthracyclins, actinomycins and bleomycins; topoisomerase II inhibitors such as epipodophyllotoxins; antimetabolites such as purine and pyrimidine analogues and anti-folate compounds; topoisomerase I inhibitors such as camptothecins; hormones and hormonal analogues; DNA methyltransferase inhibitors such as azacitidine and decitabine; signal transduction pathway inhibitors; non-receptor tyrosine kinase angiogenesis inhibitors; immunotherapeutic agents; proapoptotic agents; and cell cycle signaling inhibitors.

Typically, any chemotherapeutic agent that has activity against a susceptible neoplasm being treated may be utilized in combination with the compounds the invention, provided that the particular agent is clinically compatible with therapy employing a compound of the invention. Typical anti-neoplastic agents useful in the present invention include, but are not limited to: alkylating agents, antimetabolites, antitumor antibiotics, antimitotic agents, nucleoside analogues, topoisomerase I and II inhibitors, hormones and hormonal analogues; retinoids, histone deacetylase inhibitors; signal transduction pathway inhibitors including inhibitors of cell growth or growth factor function, angiogenesis inhibitors, and serine/threonine or other kinase inhibitors; cyclin dependent kinase inhibitors; antisense therapies and immunotherapeutic agents, including monoclonals, vaccines or other biological agents.

Nucleoside analogues are those compounds which are converted to deoxynucleotide triphosphates and incorporated into replicating DNA in place of cytosine. DNA methyltransferases become covalently bound to the modified bases resulting in an inactive enzyme and reduced DNA methylation. Examples of nucleoside analogues include azacitidine and decitabine which are used for the treatment of myelodysplastic disorder. Histone deacetylase (HDAC) inhibitors include vorinostat, for the treatment of cutaneous T-cell lymphoma. HDACs modify chromatin through the deactylation of histones. In addition, they have a variety of substrates including numerous transcription factors and signaling molecules. Other HDAC inhibitors are in development.

Signal transduction pathway inhibitors are those inhibitors which block or inhibit a chemical process which evokes an intracellular change. As used herein this change is cell proliferation or differentiation or survival. Signal transduction pathway inhibitors useful in the present invention include, but are not limited to, inhibitors of receptor tyrosine kinases, non-receptor tyrosine kinases, SH2/SH3 domain blockers, serine/threonine kinases, phosphatidyl inositol-3-OH kinases, myoinositol signaling, and Ras oncogenes. Signal transduction pathway inhibitors may be employed in combination with the compounds of the invention in the compositions and methods described above.

Receptor kinase angiogenesis inhibitors may also find use in the present invention. Inhibitors of angiogenesis related to VEGFR and TIE-2 are discussed above in regard to signal transduction inhibitors (both are receptor tyrosine kinases). Other inhibitors may be used in combination with the compounds of the invention. For example, anti-VEGF antibodies, which do not recognize VEGFR (the receptor tyrosine kinase), but bind to the ligand; small molecule inhibitors of integrin (alpha, beta$_3$) that inhibit angiogenesis; endostatin and angiostatin (non-RTK) may also prove useful in combination with the compounds of the invention. One example of a VEGFR antibody is bevacizumab (AVASTIN®).

Several inhibitors of growth factor receptors are under development and include ligand antagonists, antibodies, tyrosine kinase inhibitors, anti-sense oligonucleotides and aptamers. Any of these growth factor receptor inhibitors may be employed in combination with the compounds of the invention in any of the compositions and methods/uses described herein. Trastuzumab (Herceptin®) is an example of an anti-erbB2 antibody inhibitor of growth factor function. One example of an anti-erbB 1 antibody inhibitor of growth factor function is cetuximab (Erbitux™, C225). Bevacizumab (Avastin®) is an example of a monoclonal antibody directed against VEGFR. Examples of small molecule inhibitors of epidermal growth factor receptors include but are not limited to lapatinib (Tykerb™) and erlotinib (TARCEVA®). Imatinib mesylate (GLEEVEC®) is one example of a PDGFR inhibitor. Examples of VEGFR inhibitors include pazopanib, ZD6474, AZD2171, PTK787, sunitinib and sorafenib.

Anti-microtubule or anti-mitotic agents are phase specific agents active against the microtubules of tumor cells during M or the mitosis phase of the cell cycle. Examples of anti-microtubule agents include, but are not limited to, diterpenoids and vinca alkaloids.

Diterpenoids, which are derived from natural sources, are phase specific anti-cancer agents that operate at the G$_2$/M phases of the cell cycle. It is believed that the diterpenoids stabilize the β-tubulin subunit of the microtubules, by binding with this protein. Disassembly of the protein appears then to be inhibited with mitosis being arrested and cell death following. Examples of diterpenoids include, but are not limited to, paclitaxel and its analog docetaxel.

Paclitaxel, 5β,20-epoxy-1,2α,4,7β,10β,13α-hexa-hydroxytax-11-en-9-one 4,10-diacetate 2-benzoate 13-ester with (2R,3S)—N-benzoyl-3-phenylisoserine; is a natural diterpene product isolated from the Pacific yew tree *Taxus brevifolia* and is commercially available as an injectable solution TAXOL®. It is a member of the taxane family of terpenes. It was first isolated in 1971 by Wani et al. J. Am. Chem, Soc., 93:2325. 1971), who characterized its structure by chemical and X-ray crystallographic methods. One mechanism for its activity relates to paclitaxel's capacity to bind tubulin, thereby inhibiting cancer cell growth. Schiff et al., Proc. Natl, Acad, Sci. USA, 77:1561-1565 (1980); Schiff et al., Nature, 277:665-667 (1979); Kumar, J. Biol, Chem, 256: 10435-10441 (1981). For a review of synthesis and anticancer activity of some paclitaxel derivatives see: D. G. I. Kingston et al., Studies in Organic Chemistry vol. 26, entitled "New trends in Natural Products Chemistry 1986", Attaur-Rahman, P. W. Le Quesne, Eds. (Elsevier, Amsterdam, 1986) pp 219-235.

Paclitaxel has been approved for clinical use in the treatment of refractory ovarian cancer in the United States (Markman et al., Yale Journal of Biology and Medicine, 64:583, 1991; McGuire et al., Ann. Intem, Med., 111:273, 1989) and for the treatment of breast cancer (Holmes et al., J. Nat. Cancer Inst., 83:1797, 1991.) It is a potential candidate for treatment of neoplasms in the skin (Einzig et. al., Proc. Am.

Soc. Clin. Oncol., 20:46) and head and neck carcinomas (Forastire et. al., Sem. Oncol., 20:56, 1990). The compound also shows potential for the treatment of polycystic kidney disease (Woo et. al., Nature, 368:750. 1994), lung cancer and malaria. Treatment of patients with paclitaxel results in bone marrow suppression (multiple cell lineages, Ignoff, R. J. et. al, Cancer Chemotherapy Pocket Guide, 1998) related to the duration of dosing above a threshold concentration (50 nM) (Kearns, C. M. et. al., Seminars in Oncology, 3(6) p. 16-23, 1995).

Docetaxel, (2R,3S)— N-carboxy-3-phenylisoserine, N-tert-butyl ester, 13-ester with 5β-20-epoxy-1,2α,4,7β,10β, 13α-hexahydroxytax-11-en-9-one 4-acetate 2-benzoate, trihydrate; is commercially available as an injectable solution as TAXOTERE®. Docetaxel is indicated for the treatment of breast cancer. Docetaxel is a semisynthetic derivative of paclitaxel q.v., prepared using a natural precursor, 10-deacetyl-baccatin III, extracted from the needle of the European Yew tree. The dose limiting toxicity of docetaxel is neutropenia.

Vinca alkaloids are phase specific anti-neoplastic agents derived from the periwinkle plant. Vinca alkaloids act at the M phase (mitosis) of the cell cycle by binding specifically to tubulin. Consequently, the bound tubulin molecule is unable to polymerize into microtubules. Mitosis is believed to be arrested in metaphase with cell death following. Examples of vinca alkaloids include, but are not limited to, vinblastine, vincristine, and vinorelbine.

Vinblastine, vincaleukoblastine sulfate, is commercially available as VELBAN® as an injectable solution. Although, it has possible indication as a second line therapy of various solid tumors, it is primarily indicated in the treatment of testicular cancer and various lymphomas including Hodgkin's Disease; and lymphocytic and histiocytic lymphomas. Myelosuppression is the dose limiting side effect of vinblastine.

Vincristine, vincaleukoblastine, 22-oxo-, sulfate, is commercially available as ONCOVIN® as an injectable solution. Vincristine is indicated for the treatment of acute leukemias and has also found use in treatment regimens for Hodgkin's and non-Hodgkin's malignant lymphomas. Alopecia and neurologic effects are the most common side effect of vincristine and to a lesser extent myelosupression and gastrointestinal mucositis effects occur.

Vinorelbine, 3′,4′-didehydro-4′-deoxy-C′-norvincaleukoblastine [R—(R*,R*)-2,3-dihydroxybutanedioate (1:2) (salt)], commercially available as an injectable solution of vinorelbine tartrate (NAVELBINE®), is a semisynthetic vinca alkaloid. Vinorelbine is indicated as a single agent or in combination with other chemotherapeutic agents, such as cisplatin, in the treatment of various solid tumors, particularly non-small cell lung, advanced breast, and hormone refractory prostate cancers. Myelosuppression is the most common dose limiting side effect of vinorelbine.

Platinum coordination complexes are non-phase specific anti-cancer agents, which are interactive with DNA. The platinum complexes enter tumor cells, undergo, aquation and form intra- and interstrand crosslinks with DNA causing adverse biological effects to the tumor. Examples of platinum coordination complexes include, but are not limited to, cisplatin and carboplatin.

Cisplatin, cis-diaminedichloroplatinum, is commercially available as PLATINOL® as an injectable solution. Cisplatin is primarily indicated in the treatment of metastatic testicular and ovarian cancer and advanced bladder cancer. The primary dose limiting side effects of cisplatin are nephrotoxicity, which may be controlled by hydration and diuresis, and ototoxicity.

Carboplatin, platinum, diamine [1,1-cyclobutane-dicarboxylate(2-)—O,O′], is commercially available as PARAPLATIN® as an injectable solution. Carboplatin is primarily indicated in the first and second line treatment of advanced ovarian carcinoma. Bone marrow suppression is the dose limiting toxicity of carboplatin.

Alkylating agents are non-phase anti-cancer specific agents and strong electrophiles. Typically, alkylating agents form covalent linkages, by alkylation, to DNA through nucleophilic moieties of the DNA molecule such as phosphate, amino, sulfhydryl, hydroxyl, carboxyl, and imidazole groups. Such alkylation disrupts nucleic acid function leading to cell death. Examples of alkylating agents include, but are not limited to, nitrogen mustards such as cyclophosphamide, melphalan, and chlorambucil; alkyl sulfonates such as busulfan; nitrosoureas such as carmustine; and triazenes such as dacarbazine.

Cyclophosphamide, 2-[bis(2-chloroethyl)amino]tetrahydro-2H-1,3,2-oxazaphosphorine 2-oxide monohydrate, is commercially available as an injectable solution or tablets as CYTOXAN®. Cyclophosphamide is indicated as a single agent or in combination with other chemotherapeutic agents, in the treatment of malignant lymphomas, multiple myeloma, and leukemias. Alopecia, nausea, vomiting and leukopenia are the most common dose limiting side effects of cyclophosphamide.

Melphalan, 4-[bis(2-chloroethyl)amino]-L-phenylalanine, is commercially available as an injectable solution or tablets as ALKERAN®. Melphalan is indicated for the palliative treatment of multiple myeloma and non-resectable epithelial carcinoma of the ovary. Bone marrow suppression is the most common dose limiting side effect of melphalan.

Chlorambucil, 4-[bis(2-chloroethyl)amino]benzenebutanoic acid, is commercially available as LEUKERAN® tablets. Chlorambucil is indicated for the palliative treatment of chronic lymphatic leukemia, and malignant lymphomas such as lymphosarcoma, giant follicular lymphoma, and Hodgkin's disease. Bone marrow suppression is the most common dose limiting side effect of chlorambucil.

Busulfan, 1,4-butanediol dimethanesulfonate, is commercially available as MYLERAN® TABLETS. Busulfan is indicated for the palliative treatment of chronic myelogenous leukemia. Bone marrow suppression is the most common dose limiting side effects of busulfan.

Carmustine, 1,3-[bis(2-chloroethyl)-1-nitrosourea, is commercially available as single vials of lyophilized material as BiCNU®. Carmustine is indicated for the palliative treatment as a single agent or in combination with other agents for brain tumors, multiple myeloma, Hodgkin's disease, and non-Hodgkin's lymphomas. Delayed myelosuppression is the most common dose limiting side effects of carmustine.

Dacarbazine, 5-(3,3-dimethyl-1-triazeno)-imidazole-4-carboxamide, is commercially available as single vials of material as DTIC-Dome®. Dacarbazine is indicated for the treatment of metastatic malignant melanoma and in combination with other agents for the second line treatment of Hodgkin's Disease. Nausea, vomiting, and anorexia are the most common dose limiting side effects of dacarbazine.

Antibiotic anti-neoplastics are non-phase specific agents, which bind or intercalate with DNA. Typically, such action results in stable DNA complexes or strand breakage, which disrupts ordinary function of the nucleic acids leading to cell death. Examples of antibiotic anti-neoplastic agents include, but are not limited to, actinomycins such as dactinomycin, anthrocyclins such as daunorubicin and doxorubicin; and bleomycins.

Dactinomycin, also know as Actinomycin D, is commercially available in injectable form as COSMEGEN®. Dactinomycin is indicated for the treatment of Wilm's tumor and rhabdomyosarcoma. Nausea, vomiting, and anorexia are the most common dose limiting side effects of dactinomycin.

Daunorubicin, (8S-cis-)-8-acetyl-10-[(3-amino-2,3,6-trideoxy-α-L-lyxo-hexopyranosyl)oxy]-7,8,9,10-tetrahydro-6,8,11-trihydroxy-1-methoxy-5,12 naphthacenedione hydrochloride, is commercially available as a liposomal injectable form as DAUNOXOME® or as an injectable as CERUBIDINE®. Daunorubicin is indicated for remission induction in the treatment of acute nonlymphocytic leukemia and advanced HIV associated Kaposi's sarcoma. Myelosuppression is the most common dose limiting side effect of daunorubicin.

Doxorubicin, (8S,10S)-10-[(3-amino-2,3,6-trideoxy-α-L-lyxo-hexopyranosyl)oxy]-8-glycoloyl, 7,8,9,10-tetrahydro-6,8,11-trihydroxy-1-methoxy-5,12 naphthacenedione hydrochloride, is commercially available as an injectable form as RUBEX® or ADRIAMYCIN RDF®. Doxorubicin is primarily indicated for the treatment of acute lymphoblastic leukemia and acute myeloblastic leukemia, but is also a useful component in the treatment of some solid tumors and lymphomas. Myelosuppression is the most common dose limiting side effect of doxorubicin.

Bleomycin, a mixture of cytotoxic glycopeptide antibiotics isolated from a strain of *Streptomyces verticillus*, is commercially available as BLENOXANE®. Bleomycin is indicated as a palliative treatment, as a single agent or in combination with other agents, of squamous cell carcinoma, lymphomas, and testicular carcinomas. Pulmonary and cutaneous toxicities are the most common dose limiting side effects of bleomycin.

Topoisomerase II inhibitors include, but are not limited to, epipodophyllotoxins.

Epipodophyllotoxins are phase specific anti-neoplastic agents derived from the mandrake plant. Epipodophyllotoxins typically affect cells in the S and $G_2$ phases of the cell cycle by forming a ternary complex with topoisomerase II and DNA causing DNA strand breaks. The strand breaks accumulate and cell death follows. Examples of epipodophyllotoxins include, but are not limited to, etoposide and teniposide.

Etoposide, 4'-demethyl-epipodophyllotoxin 9[4,6-0-(R)-ethylidene-β-D-glucopyranoside], is commercially available as an injectable solution or capsules as VePESID® and is commonly known as VP-16. Etoposide is indicated as a single agent or in combination with other chemotherapy agents in the treatment of testicular and non-small cell lung cancers. Myelosuppression is the most common side effect of etoposide. The incidence of leucopenia tends to be more severe than thrombocytopenia.

Teniposide, 4'-demethyl-epipodophyllotoxin 9[4,6-0-(R)-thenylidene-β-D-glucopyranoside], is commercially available as an injectable solution as VUMON® and is commonly known as VM-26. Teniposide is indicated as a single agent or in combination with other chemotherapy agents in the treatment of acute leukemia in children. Myelosuppression is the most common dose limiting side effect of teniposide. Teniposide can induce both leucopenia and thrombocytopenia.

Antimetabolite neoplastic agents are phase specific anti-neoplastic agents that act at S phase (DNA synthesis) of the cell cycle by inhibiting DNA synthesis or by inhibiting purine or pyrimidine base synthesis and thereby limiting DNA synthesis. Consequently, S phase does not proceed and cell death follows. Examples of antimetabolite anti-neoplastic agents include, but are not limited to, fluorouracil, methotrexate, cytarabine, mercaptopurine, thioguanine, and gemcitabine.

5-fluorouracil, 5-fluoro-2,4-(1H,3H) pyrimidinedione, is commercially available as fluorouracil. Administration of 5-fluorouracil leads to inhibition of thymidylate synthesis and is also incorporated into both RNA and DNA. The result typically is cell death. 5-fluorouracil is indicated as a single agent or in combination with other chemotherapy agents in the treatment of carcinomas of the breast, colon, rectum, stomach and pancreas. Myelosuppression and mucositis are dose limiting side effects of 5-fluorouracil. Other fluoropyrimidine analogs include 5-fluoro deoxyuridine (floxuridine) and 5-fluorodeoxyuridine monophosphate.

Cytarabine, 4-amino-1-β-D-arabinofuranosyl-2 (1H)-pyrimidinone, is commercially available as CYTOSAR-U® and is commonly known as Ara-C. It is believed that cytarabine exhibits cell phase specificity at S-phase by inhibiting DNA chain elongation by terminal incorporation of cytarabine into the growing DNA chain. Cytarabine is indicated as a single agent or in combination with other chemotherapy agents in the treatment of acute leukemia. Other cytidine analogs include 5-azacytidine and 2',2'-difluorodeoxycytidine (gemcitabine). Cytarabine induces leucopenia, thrombocytopenia, and mucositis.

Mercaptopurine, 1,7-dihydro-6H-purine-6-thione monohydrate, is commercially available as PURINETHOL. Mercaptopurine exhibits cell phase specificity at S-phase by inhibiting DNA synthesis by an as of yet unspecified mechanism. Mercaptopurine is indicated as a single agent or in combination with other chemotherapy agents in the treatment of acute leukemia. Myelosuppression and gastrointestinal mucositis are expected side effects of mercaptopurine at high doses. A useful mercaptopurine analog is azathioprine.

Thioguanine, 2-amino-1,7-dihydro-6H-purine-6-thione, is commercially available as TABLOID®. Thioguanine exhibits cell phase specificity at S-phase by inhibiting DNA synthesis by an as of yet unspecified mechanism. Thioguanine is indicated as a single agent or in combination with other chemotherapy agents in the treatment of acute leukemia. Myelosuppression, including leucopenia, thrombocytopenia, and anemia, is the most common dose limiting side effect of thioguanine administration. However, gastrointestinal side effects occur and can be dose limiting. Other purine analogs include pentostatin, erythrohydroxynonyladenine, fludarabine phosphate, and cladribine.

Gemcitabine, 2'-deoxy-2',2'-difluorocytidine monohydrochloride (β-isomer), is commercially available as GEMZAR®. Gemcitabine exhibits cell phase specificity at S-phase and by blocking progression of cells through the G1/S boundary. Gemcitabine is indicated in combination with cisplatin in the treatment of locally advanced non-small cell lung cancer and alone in the treatment of locally advanced pancreatic cancer. Myelosuppression, including leucopenia, thrombocytopenia, and anemia, is the most common dose limiting side effect of gemcitabine administration.

Methotrexate, N-[4[[(2,4-diamino-6-pteridinyl)methyl]methylamino]benzoyl]-L-glutamic acid, is commercially available as methotrexate sodium. Methotrexate exhibits cell phase effects specifically at S-phase by inhibiting DNA synthesis, repair and/or replication through the inhibition of dyhydrofolic acid reductase which is required for synthesis of purine nucleotides and thymidylate. Methotrexate is indicated as a single agent or in combination with other chemotherapy agents in the treatment of choriocarcinoma, meningeal leukemia, non-Hodgkin's lymphoma, and carcinomas of the breast, head, neck, ovary and bladder. Myelosuppression (leucopenia, thrombocytopenia, and anemia) and mucositis are expected side effect of methotrexate administration.

Camptothecins, including, camptothecin and camptothecin derivatives are available or under development as Topoisomerase I inhibitors. Camptothecins cytotoxic activity is believed to be related to its Topoisomerase I inhibitory activity. Examples of camptothecins include, but are not limited to irinotecan, topotecan, and the various optical forms of 7-(4-methylpiperazino-methylene)-10,11-ethylenedioxy-20-camptothecin described below.

Irinotecan HCl, (4S)-4,11-diethyl-4-hydroxy-9-[(4-piperidinopiperidino) carbonyloxy]-1H-pyrano[3',4',6,7]indolizino[1,2-b]quinoline-3,14(4H,12H)-dione hydrochloride, is commercially available as the injectable solution CAMPTOSAR®.

Irinotecan is a derivative of camptothecin which binds, along with its active metabolite SN-38, to the topoisomerase I-DNA complex. It is believed that cytotoxicity occurs as a result of irreparable double strand breaks caused by interaction of the topoisomerase I:DNA:irintecan or SN-38 ternary complex with replication enzymes. Irinotecan is indicated for treatment of metastatic cancer of the colon or rectum. The dose limiting side effects of irinotecan HCl are myelosuppression, including neutropenia, and GI effects, including diarrhea.

Topotecan HCl, (S)-10-[(dimethylamino)methyl]-4-ethyl-4,9-dihydroxy-1H-pyrano[3',4',6,7]indolizino[1,2-b]quinoline-3,14-(4H,12H)-dione monohydrochloride, is commercially available as the injectable solution HYCAMTIN®. Topotecan is a derivative of camptothecin which binds to the topoisomerase I-DNA complex and prevents religation of singles strand breaks caused by Topoisomerase I in response to torsional strain of the DNA molecule. Topotecan is indicated for second line treatment of metastatic carcinoma of the ovary and small cell lung cancer. The dose limiting side effect of topotecan HCl is myelosuppression, primarily neutropenia.

Pharmaceutical compositions may be presented in unit dose forms containing a predetermined amount of active ingredient per unit dose. Such a unit may contain, for example, 0.5 mg to 1 g, preferably 1 mg to 700 mg, more preferably 5 mg to 100 mg of a compound of the formula (I), depending on the condition being treated, the route of administration and the age, weight and condition of the patient, or pharmaceutical compositions may be presented in unit dose forms containing a predetermined amount of active ingredient per unit dose. Preferred unit dosage compositions are those containing a daily dose or sub-dose, as herein above recited, or an appropriate fraction thereof, of an active ingredient. Furthermore, such pharmaceutical compositions may be prepared by any of the methods well known in the pharmacy art.

Pharmaceutical compositions may be adapted for administration by any appropriate route, for example by the oral (including buccal or sublingual), rectal, nasal, topical (including buccal, sublingual or transdermal), vaginal or parenteral (including subcutaneous, intramuscular, intravenous or intradermal) route. Such compositions may be prepared by any method known in the art of pharmacy, for example by bringing into association a compound of formal (I) with the carrier(s) or excipient(s).

Pharmaceutical compositions adapted for oral administration may be presented as discrete units such as capsules or tablets; powders or granules; solutions or suspensions in aqueous or non-aqueous liquids; edible foams or whips; or oil-in-water liquid emulsions or water-in-oil liquid emulsions.

Capsules are made by preparing a powder mixture, as described above, and filling formed gelatin sheaths. Glidants and lubricants such as colloidal silica, talc, magnesium stearate, calcium stearate or solid polyethylene glycol can be added to the powder mixture before the filling operation. A disintegrating or solubilizing agent such as agar-agar, calcium carbonate or sodium carbonate can also be added to improve the availability of the medicament when the capsule is ingested.

Moreover, when desired or necessary, suitable binders, lubricants, disintegrating agents and coloring agents can also be incorporated into the mixture. Suitable binders include starch, gelatin, natural sugars such as glucose or beta-lactose, corn sweeteners, natural and synthetic gums such as acacia, tragacanth or sodium alginate, carboxymethylcellulose, polyethylene glycol, waxes and the like. Lubricants used in these dosage forms include sodium oleate, sodium stearate, magnesium stearate, sodium benzoate, sodium acetate, sodium chloride and the like. Disintegrators include, without limitation, starch, methyl cellulose, agar, bentonite, xanthan gum and the like. Tablets are formulated, for example, by preparing a powder mixture, granulating or slugging, adding a lubricant and disintegrant and pressing into tablets. A powder mixture is prepared by mixing the compound, suitably comminuted, with a diluent or base as described above, and optionally, with a binder such as carboxymethylcellulose, an aliginate, gelatin, or polyvinyl pyrrolidone, a solution retardant such as paraffin, a resorption accelerator such as a quaternary salt and/or an absorption agent such as bentonite, kaolin or dicalcium phosphate. The powder mixture can be granulated by tablet forming dies by means of the addition of stearic acid, a stearate salt, talc or mineral oil. The lubricated mixture is then compressed into tablets. The compounds of the present invention can also be combined with a free flowing inert carrier and compressed into tablets directly without going through the granulating or slugging steps. A clear or opaque protective coating consisting of a sealing coat of shellac, a coating of sugar or polymeric material and a polish coating of wax can be provided. Dyestuffs can be added to these coatings to distinguish different unit dosages.

Oral fluids such as solution, syrups and elixirs can be prepared in dosage unit form so that a given quantity contains a predetermined amount of a compound of formula (I). Syrups can be prepared by dissolving the compound in a suitably flavored aqueous solution, while elixirs are prepared through the use of a non-toxic alcoholic vehicle. Suspensions can be formulated by dispersing the compound in a non-toxic vehicle. Solubilizers and emulsifiers such as ethoxylated isostearyl alcohols and polyoxy ethylene sorbitol ethers, preservatives, flavor additive such as peppermint oil or natural sweeteners or saccharin or other artificial sweeteners, and the like can also be added.

Where appropriate, dosage unit pharmaceutical compositions for oral administration can be microencapsulated. The formulation can also be prepared to prolong or sustain the release as for example by coating or embedding particulate material in polymers, wax or the like.

Pharmaceutical compositions adapted for rectal administration may be presented as suppositories or as enemas.

Pharmaceutical compositions adapted for vaginal administration may be presented as pessaries, tampons, creams, gels, pastes, foams or spray formulations.

Pharmaceutical formulations adapted for parenteral administration include aqueous and non-aqueous sterile injection solutions which may contain anti-oxidants, buffers, bacteriostats and solutes which render the composition isotonic with the blood of the intended recipient; and aqueous and non-aqueous sterile suspensions which may include suspending agents and thickening agents. The pharmaceutical compositions may be presented in unit-dose or multi-dose containers, for example sealed ampoules and vials, and may be stored in a freeze-dried (lyophilized) condition requiring only the addition of the sterile liquid carrier, for example water for injections, immediately prior to use. Extemporaneous injection solutions and suspensions may be prepared from sterile powders, granules and tablets.

It should be understood that in addition to the ingredients particularly mentioned above, the pharmaceutical compositions may include other agents conventional in the art having regard to the type of formulation in question, for example those suitable for oral administration may include flavouring agents.

A therapeutically effective amount of a compound of the present invention will depend upon a number of factors including, for example, the age and weight of the intended recipient, the precise condition requiring treatment and its severity, the nature of the formulation, and the route of administration, and will ultimately be at the discretion of the attendant prescribing the medication. However, an effective amount of a compound of formula (I) for the treatment of anemia will generally be in the range of 0.001 to 100 mg/kg body weight of recipient per day, suitably in the range of 0.01 to 10 mg/kg body weight per day. For a 70 kg adult mammal, the actual amount per day would suitably be from 7 to 700 mg and this amount may be given in a single dose per day or in a number (such as two, three, four, five or six) of sub-doses per day such that the total daily dose is the same. An effective amount of a salt or solvate, etc., may be determined as a proportion of the effective amount of the compound of formula (I) per se. It is envisaged that similar dosages would be appropriate for treatment of the other conditions referred to above.

Chemical Background

The compounds of this invention may be made by a variety of methods, including standard chemistry. Any previously defined variable will continue to have the previously defined meaning unless otherwise indicated. Illustrative general synthetic methods are set out below and then specific compounds of the invention as prepared are given in the examples.

Compounds of general formula (I) may be prepared by methods known in the art of organic synthesis as set forth in part by the following synthesis schemes. In all of the schemes described below, it is well understood that protecting groups for sensitive or reactive groups are employed where necessary in accordance with general principles of chemistry. Protecting groups are manipulated according to standard methods of organic synthesis (T. W. Green and P. G. M. Wuts (1991) *Protecting Groups in Organic Synthesis*, John Wiley & Sons). These groups are removed at a convenient stage of the compound synthesis using methods that are readily apparent to those skilled in the art. The selection of processes as well as the reaction conditions and order of their execution shall be consistent with the preparation of compounds of formula (I). Those skilled in the art will recognize if a stereocenter exists in compounds of formula (I). Accordingly, the present invention includes both possible stereoisomers and includes not only racemic compounds but the individual enantiomers as well. When a compound is desired as a single enantiomer, it may be obtained by stereospecific synthesis or by resolution of the final product or any convenient intermediate. Resolution of the final product, an intermediate, or a starting material may be effected by any suitable method known in the art. See, for example, *Stereochemistry of Organic Compounds* by E. L. Eliel, S. H. Wilen, and L. N. Mander (Wiley-Interscience, 1994).

EXAMPLES

The compounds of the present invention were prepared as depicted in schemes 1-5. The groups and substituents shown in the schemes 1-5, such as X, Y, Z and the various R groups have the same definition in what follows as they have herein above. The solvents and conditions referred to are illustrative and are not intended to be limiting.

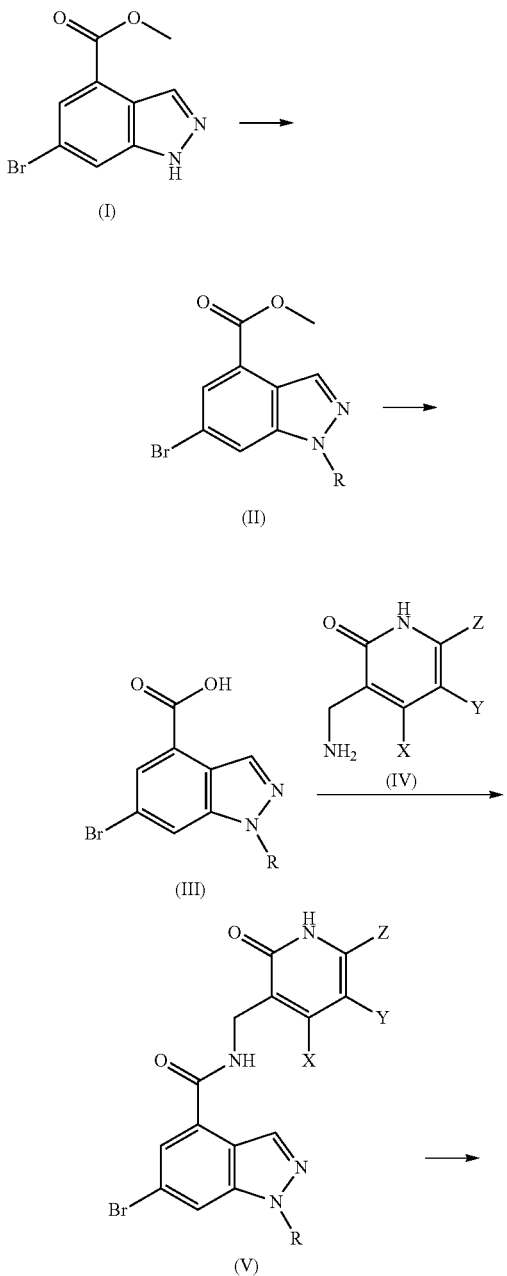

Scheme 1

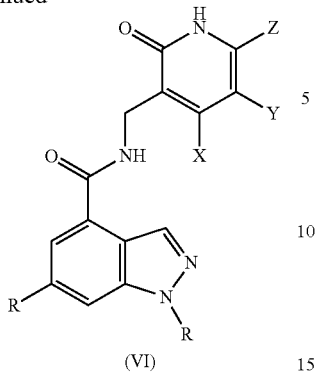

(VI)

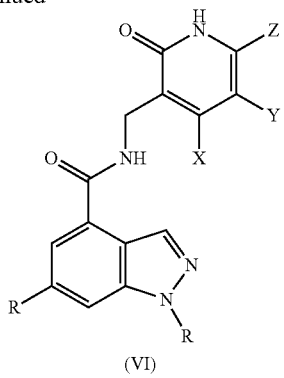

(VI)

Scheme 1 illustrates a route to prepare compounds of formula (VI). Compounds of formula (I) are commercially available and were alkylated using sodium hydride, DMF, and an appropriate alkyl halide to afford a mixture of N1/N2 alkylated regioisomers which were separated by chromatography and fully characterized. Compounds of formula (II) were converted to compounds of formula (III) by standard base-catalyzed hydrolysis. Treatment of compounds of formula (III) with substituted aminomethyl pyridones of formula (IV) using EDC, HOAT, N-methylmorpholine, and DMSO at room temperature for a period of 3-48 h stirring afforded compounds of formula (V). Compounds of formula (V) were substituted at the 6-position using standard methods known to those skilled in the art (i.e. palladium, copper, mediated cross couplings), to afford compounds of formula (VI).

Compounds of formula (VI) were also prepared as depicted in scheme 2. In this embodiment, compounds of formula (II) were substituted at the 6-pos. using standard methods known to those skilled in the art (i.e. palladium, copper, mediated cross couplings, nucleophilic substitution) to afford compounds of formula (VII), which were then converted to compounds of formula (VIII) by standard base-catalyzed hydrolysis. Treatment of compounds of formula (VIII) with substituted aminomethyl pyridones of formula (IV) using EDC, HOAT, N-methylmorpholine, and DMSO at room temperature for a period of 3-48 h stirring, afforded compounds of formula (VI). Compounds of formula (VI) wherein R6=sulfonamide were prepared from compounds of formula (II) in which the 6-nitro substituted conjeger was used as starting material. Conversion of the nitro group by standard reduction conditions afforded a compound of formula (VII) in which $R_6$=$NH_2$. Treatment of the putative amine intermediate with a sulfonyl chloride under standard conditions afforded compound of formula (VII), wherein R6=sulfonamide.

Scheme 2

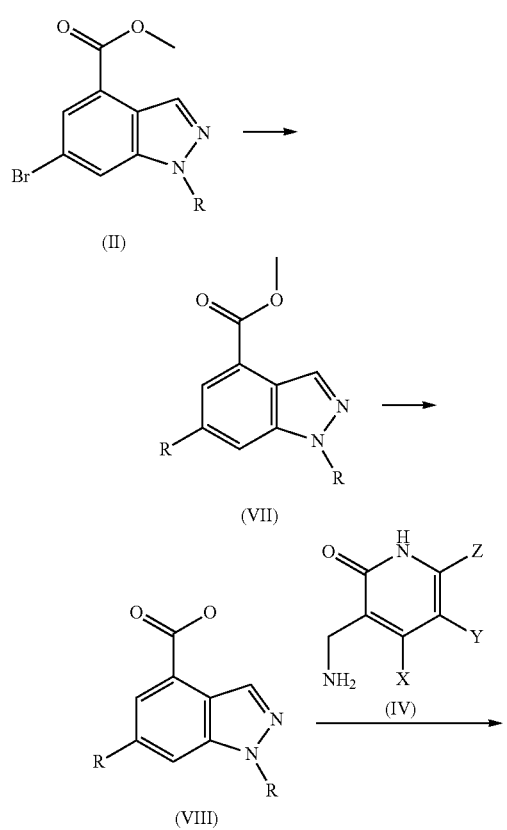

Scheme 3

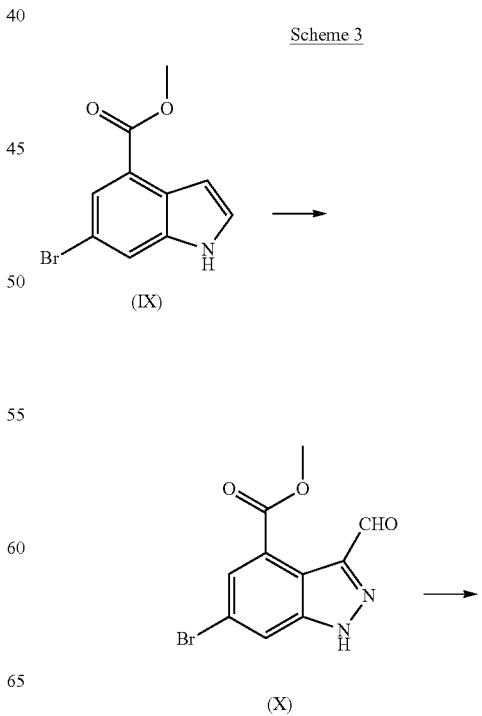

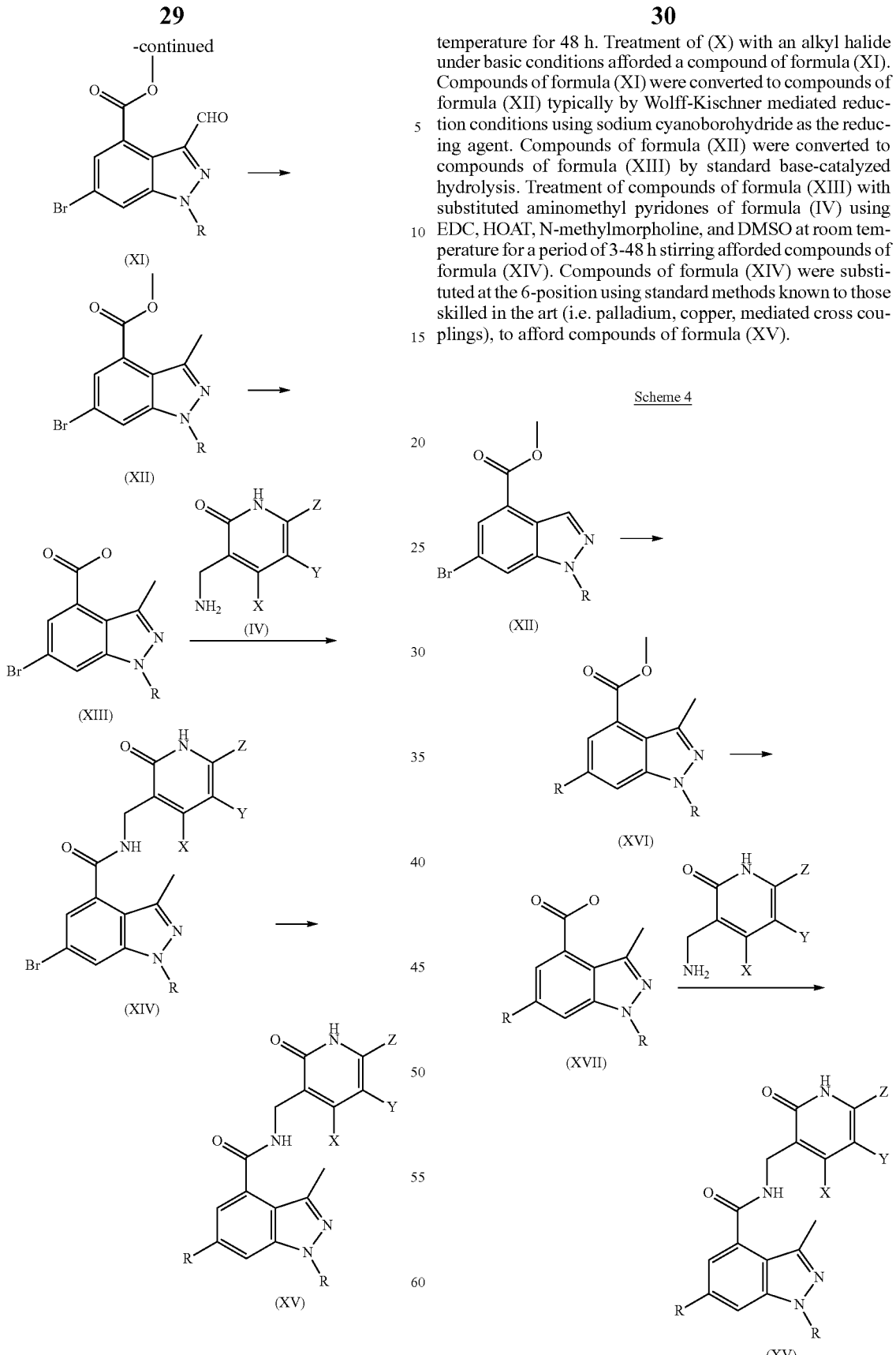

temperature for 48 h. Treatment of (X) with an alkyl halide under basic conditions afforded a compound of formula (XI). Compounds of formula (XI) were converted to compounds of formula (XII) typically by Wolff-Kischner mediated reduction conditions using sodium cyanoborohydride as the reducing agent. Compounds of formula (XII) were converted to compounds of formula (XIII) by standard base-catalyzed hydrolysis. Treatment of compounds of formula (XIII) with substituted aminomethyl pyridones of formula (IV) using EDC, HOAT, N-methylmorpholine, and DMSO at room temperature for a period of 3-48 h stirring afforded compounds of formula (XIV). Compounds of formula (XIV) were substituted at the 6-position using standard methods known to those skilled in the art (i.e. palladium, copper, mediated cross couplings), to afford compounds of formula (XV).

Scheme 3 illustrates a route to prepare compounds of formula (XV). A compound of formula (IX), which is commercially available, was converted to a compound of formula (X) using sodium nitrite, 6N HCl, water, and stirring at room Compounds of formula (XV) were also prepared as depicted in scheme 4. In this embodiment, compounds of formula (XII) were substituted at the 6-pos. using standard methods known to those skilled in the art (i.e. palladium, copper, mediated cross couplings, nucleophilic substitution) to afford compounds of formula (XVI), which were then converted to compounds of formula (XVII) by standard base-catalyzed hydrolysis. Treatment of compounds of formula (XVII) with substituted aminomethyl pyridones of formula (IV) using EDC, HOAT, N-methylmorpholine, and DMSO at room temperature for a period of 3-48 h stirring afforded compounds of formula (XV).

Scheme 5

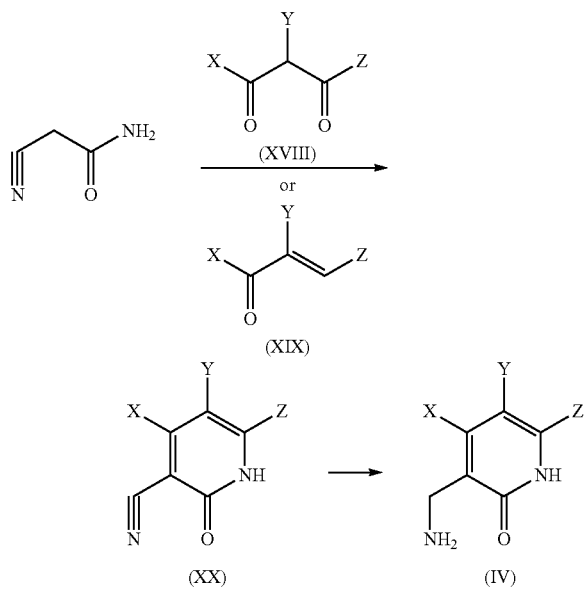

Scheme 5 illustrates the method to synthesize a compound of formula (IV). Heating of compounds of formula (XVIII) with cyanoacetamide in ethanol at reflux containing catalytic piperidine for typically 30 min, affords compounds of formula (XX). Alternatively, treatment of compounds of formula (XIX) with cyanoacetamide in DMSO at room temperature with an excess of potassium tert-butoxide under an atmosphere of oxygen for ca. 90 min. also affords compounds of formula (XX). Regioisomeric mixtures, are separable and the individual compounds regiochemical assignments can be confirmed by 2D H NMR techniques. Compounds of formula (XVIII) and (XIX) which were not commercially available were prepared using standard methods known to those skilled in the art, and are described herein. Compounds of formula (XX) were converted to compounds of formula (V) either by hydrogenation using sodium acetate, palladium on carbon, and platinum oxide, or reduction conditions using $NaBH_4$ with either iodine or $NiCl_2\text{-}6H_2O$.

General Experimental Methods

The following abbreviations are used throughout the experimental and have the following meaning:

| | |
|---|---|
| aq | aqueous |
| BINAP | 2,2'-bis(diphenylphosphino)-1,1'-binapthyl |
| ca. | circa |
| $CDCl_3$-d | chloroform-d |
| $CD_3OD$-$d_4$ | methanol-$d_4$ |
| $Cs_2CO_3$ | cesium carbonate |
| $CHCl_3$ | chloroform |

-continued

| | |
|---|---|
| ACN | acetonitrile |
| $CH_3CN$ | acetonitrile |
| Celite ® | registered trademark of Celite Corp. brand of diatomaceous earth |
| DBU | 1,8-diazabicyclo[5.4.0]undeca-7-ene |
| DCE | dichloroethane |
| DCM | methylene chloride |
| DME | 1,2 dimethoxyethane |
| DMF | N,N-dimethylformamide |
| DIEA | diisopropyl ethylamine |
| DMSO-$d_6$ | dimethylsulfoxide-$d_6$ |
| EtOAc | ethyl acetate |
| EDC | 1-(3-dimethylaminopropyl)-3-ethylcarbodimmide hydrochloride |
| h | hour(s) |
| $^1$H NMR | proton nuclear magnetic resonance |
| HCl | hydrochloric acid |
| HOAT | 1-hydroxy-7-azabenzotriazole |
| HPLC | high performance liquid chromatography |
| IPA | 2-propanol |
| $K_2CO_3$ | potassium carbonate |
| KOH | potassium hydroxide |
| LC/MS | liquid chromatography/mass spectroscopy |
| $MgSO_4$ | magnesium sulfate |
| MeOH | methanol |
| min | minute(s) |
| MTBE | methyl tert-butyl ether |
| MS | mass spectrometry |
| NaOH | sodium hydroxide |
| $Na_2SO_4$ | sodium sulfate |
| $NH_4OH$ | ammonium hydroxide |
| NMM | 4-methylmorpholine |
| NMP | N-Methyl-2-pyrrolidone |
| Pd/C | Palladium (10% by wt) on carbon |
| $PdCl_2(dppf)$-$CH_2Cl_2$ | 1,1'-Bis(diphenylphosphino)ferrocene-palladium(II)dichloride dichloromethane complex |
| $Pd(Ph_3P)_4$ | tetrakis(triphenylphosphine)palladium(0) |
| RT | room temperature |
| $SOCl_2$ | thionyl chloride |
| SPhos | 2-Dicyclohexylphosphino-2',6'-dimethoxybiphenyl |
| TFA | trifluoroacetic acd |
| THF | tetrahydrofuran |
| TLC | thin layer chromatography |

The following guidelines apply to all experimental procedures described herein. All reactions were conducted under a positive pressure of nitrogen using oven-dried glassware, unless otherwise indicated. Temperatures designated are external (i.e. bath temperatures), and are approximate. Air and moisture-sensitive liquids were transferred via syringe. Reagents were used as received. Solvents utilized were those listed as "anhydrous" by vendors. Molarities listed for reagents in solutions are approximate, and were used without prior titration against a corresponding standard. All reactions were agitated by stir bar, unless otherwise indicated. Heating was conducted using heating baths containing silicon oil, unless otherwise indicated. Reactions conducted by microwave irradiation (0-400 W at 2.45 GHz) were done so using a Biotage Initiator™ 2.0 instrument with Biotage microwave EXP vials (0.2-20 mL) and septa and caps. Irradiation levels utilized (i.e. high, normal, low) based on solvent and ionic charge were based on vendor specifications. Cooling to temperatures below −70° C. was conducted using dry ice/acetone or dry ice/2-propanol. Magnesium sulfate and sodium sulfate used as drying agents were of anhydrous grade, and were used interchangeably. Solvents described as being removed "in vacuo" or "under reduced pressure" were done so by rotary evaporation.

Preparative normal phase silica gel chromatography was carried out using either a Teledyne ISCO CombiFlash Companion instrument with RediSep or ISCO Gold silica gel cartridges (4 g-330 g), or an Analogix IF280 instrument with SF25 silica gel cartridges (4 g-3-00 g), or a Biotage SPI instrument with HP silica gel cartridges (10 g-100 g). Purification by reverse phase HPLC was conducted using a YMC-pack column (ODS-A 75×30 mm) as solid phase, unless otherwise noted. A mobile phase of 25 mL/min A (acetonitrile-0.1% TFA): B (water-0.1% TFA), 10-80% gradient A (10 min) was utilized with UV detection at 214 nM, unless otherwise noted.

A PE Sciex API 150 single quadrupole mass spectrometer (PE Sciex, Thornhill, Ontario, Canada) was operated using electrospray ionization in the positive ion detection mode. The nebulizing gas was generated from a zero air generator (Balston Inc., Haverhill, Mass., USA) and delivered at 65 psi and the curtain gas was high purity nitrogen delivered from a Dewar liquid nitrogen vessel at 50 psi. The voltage applied to the electrospray needle was 4.8 kV. The orifice was set at 25 V and mass spectrometer was scanned at a rate of 0.5 scan/sec using a step mass of 0.2 amu and collecting profile data.

Method A LCMS. Samples were introduced into the mass spectrometer using a CTC PAL autosampler (LEAP Technologies, Carrboro, N.C.) equipped with a hamilton 10 uL syringe which performed the injection into a Valco 10-port injection valve. The HPLC pump was a Shimadzu LC-10ADvp (Shimadzu Scientific Instruments, Columbia, Md.) operated at 0.3 mL/min and a linear gradient 4.5% A to 90% B in 3.2 min. with a 0.4 min. hold. The mobile phase was composed of 100% ($H_2O$ 0.02% TFA) in vessel A and 100% ($CH_3CN$ 0.018% TFA) in vessel B. The stationary phase is Aquasil (C18) and the column dimensions were 1 mm×40 mm. Detection was by UV at 214 nm, evaporative light-scattering (ELSD) and MS.

Method B, LCMS. Alternatively, an Agilent 1100 analytical HPLC system with an LC/MS was used and operated at 1 mL/min and a linear gradient 5% A to 100% B in 2.2 min with a 0.4 min hold. The mobile phase was composed of 100% ($H_2O$ 0.02% TFA) in vessel A and 100% ($CH_3CN$ 0.018% TFA) in vessel B. The stationary phase was Zobax (C8) with a 3.5 um particle size and the column dimensions were 2.1 mm×50 mm. Detection was by UV at 214 nm, evaporative light-scattering (ELSD) and MS.

Method C, LCMS. Alternatively, an MDSSCIEX API 2000 equipped with a capillary column of (50×4.6 mm, 5 μm) was used. HPLC was done on Agilent-1200 series UPLC system equipped with column Zorbax SB-C18 (50×4.6 mm, 1.8 μm) eluting with $CH_3CN$: ammonium acetate buffer. The reactions were performed in the microwave (CEM, Discover).

$^1$H-NMR spectra were taken using deuterated DMSO (unless otherwise noted) and were recorded at 400 MHz using a Bruker AVANCE 400 MHz instrument, with ACD Spect manager v. 10 used for reprocessing. Multiplicities indicated are: s=singlet, d=doublet, t=triplet, q=quartet, quint=quintet, sxt=sextet, m=multiplet, dd=doublet of doublets, dt=doublet of triplets etc. and br indicates a broad signal.

Analytical HPLC: Products were analyzed by Agilent 1100 Analytical Chromatography system, with 4.5×75 mm Zorbax XDB-C18 column (3.5 um) at 2 mL/min with a 4 min gradient from 5% $CH_3CN$ (0.1% formic acid) to 95% $CH_3CN$ (0.1% formic acid) in $H_2O$ (0.1% formic acid) and a 1 min hold.

1. EXPERIMENTALS

Example 1

6-chloro-1-(1-methylethyl)-N-[(6-methyl-2-oxo-4-propyl-1,2-dihydro-3-pyridinyl)methyl]-1H-indazole-4-carboxamide

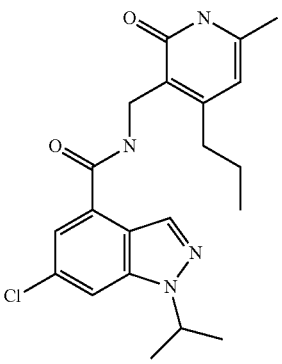 [SMILES: CCCc1cc(C)[nH]c(=O)c1CNC(=O)c1cc(Cl)cc2c1cnn2C(C)C]

a) Methyl 6-chloro-1-(1-methylethyl)-1H-indazole-4-carboxylate

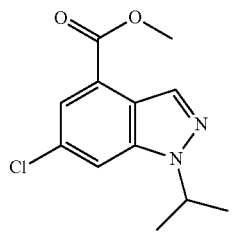 [SMILES: COC(=O)c1cc(Cl)cc2c1cnn2C(C)C]

Methyl 6-chloro-1H-indazole-4-carboxylate (0.410 g, 1.947 mmol) was dissolved in DMF (10 mL) and placed into an ice bath and stirred for 15 min. Sodium hydride (0.101 g, 2.53 mmol) was added, the contents stirred for 15 min., and then 2-iodopropane (0.389 mL, 3.89 mmol) was added. The contents were stirred with warming to RT. After stirring at RT for 2 h, a scoop of sodium carbonate and then 0.4 mL of methyl iodide were added. After stirring at RT for an additional 1 h, the reaction mixture was diluted with saturated $NH_4Cl$ and then extracted with EtOAc (2×). The combined organic layers were washed with brine, dried over $MgSO_4$, filtered, and concentrated in vacuo. The crude residue was dissolved in a minimal amount of DCM and purified by silica gel chromatography (eluent: 3-20% ethyl acetate in hexanes). The title compound was the less polar of the two products separated from chromatography, and was collected as 0.22 g (45% yield). $^1$H NMR (400 MHz, DMSO-d6) δ ppm 1.45 1.52 (m, 6H), 3.93-3.99 (m, 3H), 5.11 (quin, J=6.57 Hz, 1H), 7.73 (d, J=1.77 Hz, 1H), 8.30 (s, 1H), 8.42 (s, 1H).

b) 6-chloro-1-(1-methylethyl)-1H-indazole-4-carboxylic acid

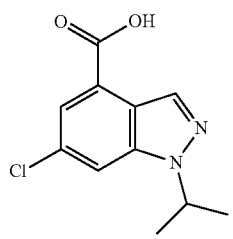 [SMILES: CC(C)n1ncc2c(C(=O)O)cc(Cl)cc21]

Methyl 6-chloro-1-(1-methylethyl)-1H-indazole-4-carboxylate (0.22 g, 0.871 mmol) was dissolved in methanol (6 mL) and THF (1 mL), followed by addition of NaOH (1.451 mL, 4.35 mmol) via syringe. The contents were stirred at RT for 3 h. The volatiles were removed in vacuo, the contents diluted with water, and then slowly acidified to pH 4-5 by addition of 1M HCl (solid precipitation occurred). The contents were then extracted with EtOAc (3×). The combined organic layers were washed with brine, dried over MgSO₄, filtered, and concentrated in vacuo. The collected solid was dried under hi-vac for 2 h, and collected as 0.19 g (90%). ¹H NMR (400 MHz, DMSO-d6) δ ppm 1.47 (d, J=6.57 Hz, 6H) 5.09 (quin, J=6.57 Hz, 1H) 7.70 (d, J=1.52 Hz, 1H) 8.25 (s, 1H) 8.40 (s, 1H), 13.54 (br. s., 1H).

c) 6-chloro-1-(1-methylethyl)-1H-indazole-4-carboxylic acid (0.10 g, 0.419 mmol), 3-(aminomethyl)-6-methyl-4-propyl-2(1H)-pyridinone (0.109 g, 0.503 mmol), 1-hydroxy-7-azabenzotriazole (0.080 g, 0.587 mmol), and then EDC (0.112 g, 0.587 mmol) were added to DMSO (4.0 mL). N-methylmorpholine (0.184 mL, 1.676 mmol) was quickly added via syringe. The contents were stirred at RT overnight Additional HOAT and EDC were added, and the contents were stirred for another 6 h. The contents were slowly poured onto 45 mL of ice-water wherein solid precipitation occurred. The contents were stirred for 10 min., and then allowed to stand for another 10 min. The contents were filtered, the collected solid washed with ca. 5 mL of water. The solid was air dried for 15 min. then dried in vacuum oven at 45° C. for 24 h. The title compound was collected as a white solid (0.160 g, 93% yield). ¹H NMR (400 MHz, DMSO-d6) δ ppm 0.89 (t, J=7.33 Hz, 3H) 1.42-1.58 (m, 8H) 2.14 (s, 3H) 2.52-2.58 (m, 1H) 4.36 (d, J=5.05 Hz, 2H) 5.04 (quin, J=6.57 Hz, 1H) 5.91 (s, 1H) 7.59 (d, J=1.52 Hz, 1H) 8.06 (s, 1H) 8.38 (s, 1H) 8.61 (t, J=4.80 Hz, 1H) 11.54 (s, 1H); MS (ES) [M+H]⁺ 400.9.

Example 2

N-[(4,6-dimethyl-2-oxo-1,2-dihydro-3-pyridinyl)methyl]-6-fluoro-1-(1-methylethyl)-1H-indazole-4-carboxamide

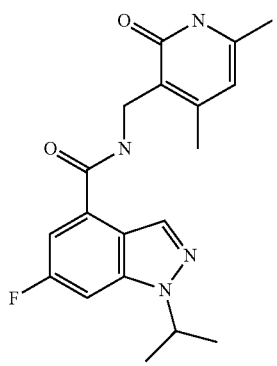 [SMILES: Cc1cc(C)c(CNC(=O)c2cc(F)cc3c2cnn3C(C)C)c(=O)[nH]1]

a) Methyl 6-fluoro-1-(1-methylethyl)-1H-indazole-4-carboxylate

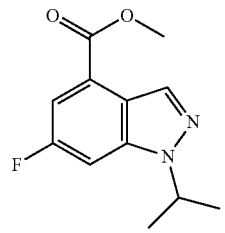 [SMILES: COC(=O)c1cc(F)cc2c1cnn2C(C)C]

The title compound was prepared in the same manner as described for example 1 (step a) from methyl 6-fluoro-1H-indazole-4-carboxylate (0.500 g, 2.58 mmol), sodium hydride (0.129 g, 3.22 mmol), and 2-iodopropane (0.386 mL, 3.86 mmol). The product was collected as a yellow solid (0.32 g, 52%); 1H NMR (400 MHz, DMSO-d6) δ ppm 1.48 (d, J=6.57 Hz, 6H) 3.96 (s, 3H) 5.04 (quin, J=6.57 Hz, 1H) 7.61 (dd, J=9.60, 2.27 Hz, 1H) 8.03 (dt, J=8.46, 1.20 Hz, 1H) 8.41 (s, 1H).

b) 6-fluoro-1-(1-methylethyl)-1H-indazole-4-carboxylic acid

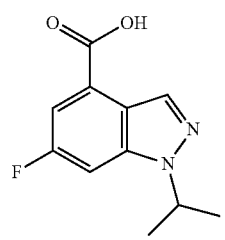 [SMILES: CC(C)n1ncc2c(C(=O)O)cc(F)cc21]

The title compound was prepared in the same manner as described for example 1 (step b) from methyl 6-fluoro-1-(1-methylethyl)-1H-indazole-4-carboxylate (0.31 g, 1.312 mmol) and NaOH (1.750 mL, 5.25 mmol) The product was collected as a yellow solid (0.27 g, 89%); ¹H NMR (400 MHz, DMSO-d6) δ ppm 1.48 (d, J=6.57 Hz, 6H), 5.03 (quin, J=6.63 Hz, 1H), 7.57 (dd, J=9.60, 2.27 Hz, 1H), 7.97 (dd, J=9.35, 1.26 Hz, 1H), 8.40 (s, 1H), 13.51 (br. s., 1H)

The title compound was prepared in the same manner as described for example 1 (step c) from 6-fluoro-1-(1-methylethyl)-1H-indazole-4-carboxylic acid (0.085 g, 0.383 mmol), 3-(aminomethyl)-4,6-dimethyl-2(1H)-pyridinone (0.108 g, 0.574 mmol), 1-hydroxy-7-azabenzotriazole (0.078 g, 0.574 mmol), EDC (0.110 g, 0.574 mmol), and N-methylmorpholine (0.210 mL, 1.913 mmol). The product was collected as a white solid (117 mg, 82%) ¹H NMR (400 MHz, DMSO-d6) δ ppm 1.42-1.50 (m, 6H) 2.09-2.17 (m, 3H) 2.21 (s, 3H) 4.34 (d, J=5.05 Hz, 2H) 4.98 (quin, J=6.57 Hz, 1H), 5.88 (s, 1H)

7.46 (dd, J=9.98, 2.15 Hz, 1H) 7.78 (dd, J=9.60, 1.26 Hz, 1H) 8.36 (s, 1H) 8.56 (t, J=4.93 Hz, 1H) 11.53 (br. s., 1H); MS (ES) [M+H]+ 357.2

Example 3

6-Bromo-N-[(4,6-dimethyl-2-oxo-1,2-dihydro-3-pyridinyl)methyl]-1-(1-methylethyl)-1H-indazole-4-carboxamide

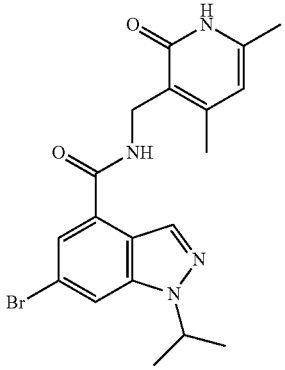 [SMILES: Cc1cc(C)c(CNC(=O)c2cc(Br)cc3c2cnn3C(C)C)c(=O)[nH]1]

a) Methyl 6-bromo-1-(1-methylethyl)-1H-indazole-4-carboxylate

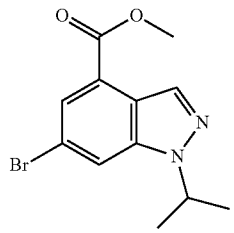

To a cooled (0° C.) solution of methyl 6-bromo-1H-indazole-4-carboxylate (1.25 g, 4.90 mmol) in N,N-dimethylformamide (25 mL) was added sodium hydride (0.216 g, 5.39 mmol). The reaction mixture was stirred for 15 min, then 2-bromopropane (0.920 mL, 9.80 mmol) was added and the reaction allowed to warm to RT. The reaction was maintained at RT overnight. The contents were concentrated to about ½ volume, then poured into saturated NH₄Cl (200 mL) with stirring. The contents were extracted with ether (2×) and the combined organics washed with brine, dried (MgSO₄), filtered, and concentrated to give an orange residue (1.55 g crude). Purification by silica gel chromatography (eluent: 5-25% ethyl acetate in hexanes) gave methyl 6-bromo-1-(1-methylethyl)-1H-indazole-4-carboxylate (0.60 g, 40% yield) and methyl 6-bromo-2-(1-methylethyl)-2H-indazole-4-carboxylate (0.65 g, 43% yield). Both products were isolated and methyl 6-bromo-1-(1-methylethyl)-1H-indazole-4-carboxylate was taken on to the next step. Data for 1-alkylated isomer: ¹H NMR (400 MHz, CHLOROFORM-d) δ ppm 8.48 (s, 1H) 8.02 (d, J=1.52 Hz, 1H) 7.85 (s, 1H) 4.83 (dt, J=13.33, 6.60 Hz, 1H) 4.04 (s, 3H) 1.63 (s, 3H) 1.61 (s, 3H); LC-MS (ES) [M+H]+ 297.5/299.5. Data for 2-alkylated isomer: ¹H NMR (400 MHz, DMSO-d₆) δ ppm 8.72 (s, 1H), 8.25 (s, 1H), 7.80 (d, J=1.5 Hz, 1H), 4.96 (m, 1H), 3.95 (s, 3H), 1.57 (d, J=6.6 Hz, 6H); LC-MS (ES) [M+H]+ 297.5/299.5.

b) 6-bromo-1-(1-methylethyl)-1H-indazole-4-carboxylic acid

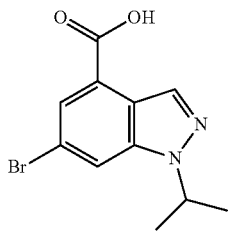

To a solution of 6-bromo-1-(1-methylethyl)-1H-indazole-4-carboxylate (0.58 g, 1.952 mmol in methanol (12 mL) and tetrahydrofuran (3 mL) was added 3 N NaOH (3.25 mL, 9.76 mmol) via syringe and stirred for 3 h at RT. The volatiles were removed in vacuo then diluted with water and slowly acidified with 1 N HCl to pH 4-5. The contents were extracted with 20% THF/EtOAc (3×). The combined organics were washed with brine, dried over MgSO₄, filtered, and concentrated to give 6-bromo-1-(1-methylethyl)-1H-indazole-4-carboxylic acid (0.52 g, 94% yield). ¹H NMR (400 MHz, DMSO-d₆) d ppm 13.54 (s, 1H) 8.36-8.43 (m, 2H) 7.82 (d, J=1.52 Hz, 1H) 5.11 (quin, J=6.57 Hz, 1H) 1.48 (s, 3H) 1.47 (s, 3H); LC-MS (ES) [M+H]+ 283.4/285.2 c) 6-Bromo-N-[(4,6-dimethyl-2-oxo-1,2-dihydro-3-pyridinyl)methyl]-1-(1-methylethyl)-1H-indazole-4-carboxamide

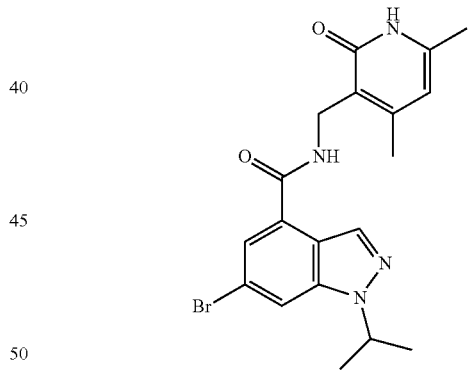

To a mixture of 6-bromo-1-(1-methylethyl)-1H-indazole-4-carboxylic acid (0.52 g, 1.837 mmol), 3-(aminomethyl)-4,6-dimethyl-2(1H)-pyridinone (0.485 g, 2.57 mmol), 1-hydroxy-7-azabenzotriazole (0.375 g, 2.76 mmol) and EDC (0.528 g, 2.76 mmol) in dimethyl sulfoxide (15 mL) was added N-methylmorpholine (0.606 mL, 5.51 mmol) via syringe. The reaction was stirred at RT for 48 h. The contents were slowly diluted into 200 mL of water, stirred for 10 min, then allowed to sit for 20 min. The suspension was filtered. The collected solid was washed with about 50 mL of water, filtered, air dried for 15 min then dried in vac oven to afford the title compound (0.67 g, 85%), which was used without further purification. ¹H NMR (400 MHz, DMSO-d6) δ ppm 1.45 (d, J=6.57 Hz, 6H) 2.12 (s, 3H) 2.20 (s, 3H) 4.33 (d, J=5.05 Hz, 2H) 5.05 (quin, J=6.57 Hz, 1H) 5.89 (s, 1H) 7.71

(d, J=1.26 Hz, 1H) 8.20 (s, 1H) 8.37 (s, 1H) 8.62 (t, J=4.67 Hz, 1H) 11.54 (s, 1H). MS (ES) [M+H]⁺ 417.1.

Example 4

6-bromo-N-((4-ethyl-6-methyl-2-oxo-1,2-dihydropyridin-3-yl)methyl)-1-isopropyl-1H-indazole-4-carboxamide

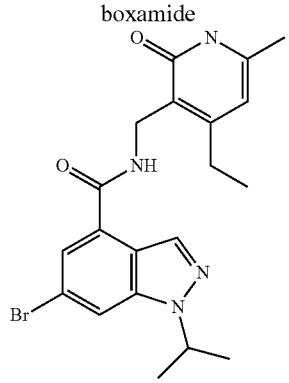

In a 25 mL sealable tube under nitrogen were combined 6-bromo-1-(1-methylethyl)-1H-indazole-4-carboxylic acid (400 mg, 1.41 mmol) and 3-(aminomethyl)-4-ethyl-6-methyl-2(1H)-pyridinone.HCl (401 mg, 1.98 mmol) in DMSO (15 mL). 1-hydroxy-7-azabenzotriazole (308 mg, 2.26 mmol) was added and the resulting mixture was degassed with nitrogen for 10 minutes. N-methylmorpholine (0.64 ml, 5.79 mmol) and EDC (433 mg, 2.26 mmol) were added, the vessel was sealed, and the mixture was stirred at room temperature for 2 days. The mixture was poured onto 10 mL of ice-water and solids crashed out. 10% K₂CO₃ was added to adjust the pH~8-9 and the contents were stirred for 10 min and then allowed to stand for another 10 min. Solids were filtered and air-dried. DMF along with some water were added and solids that precipitated were filtered. DCM was added and the contents purified by SiO₂ chromatography (eluent: gradient 0 to 80:20:2 DCM/MeOH/NH₄OH). The collected product was suspended in EtOAc along with some hexanes. Solids that precipitated were filtered and dried to afford the title compound as a white solid (504 mg, 82%). ¹H NMR (400 MHz, DMSO-d₆) δ ppm 11.54 (s, 1H) 8.63 (t, J=4.80 Hz, 1H) 8.37 (s, 1H) 8.20 (s, 1H) 7.70 (d, J=1.26 Hz, 1H) 5.93 (s, 1H) 5.06 (quin, J=6.57 Hz, 1H) 4.37 (s, 1H) 4.35 (s, 1H) 2.52-2.58 (m, 2H) 2.14 (s, 3H) 1.47 (s, 3H) 1.45 (s, 3H) 1.10 (t, J=7.58 Hz, 3H); LC-MS (ES) m/z=431.0/433.0

Example 5

6-bromo-1-(1-methylethyl)-N-{[6-methyl-2-oxo-4-(phenylmethyl)-1,2-dihydro-3-pyridinyl]methyl}-1H-indazole-4-carboxamide

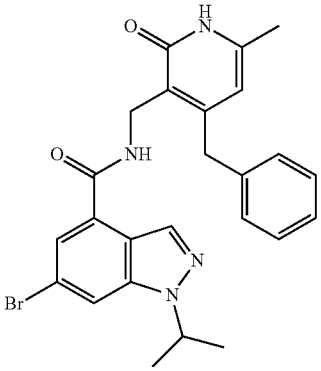 [SMILES: Cc1cc(Cc2ccccc2)c(CNC(=O)c2cc(Br)cc3c2cnn3C(C)C)c(=O)[nH]1]

The title compound was prepared in the same manner as described for the example 4 from 6-bromo-1-(1-methylethyl)-1H-indazole-4-carboxylic acid (100 mg, 0.353 mmol) and 3-(aminomethyl)-6-methyl-4-(phenylmethyl)-2(1H)-pyridinone (129 mg, 0.565 mmol), wherein the reaction stir time was 12 h. The product was collected as a white solid (130 mg, 71%). ¹H NMR (400 MHz, DMSO-d6) δ ppm 11.61 (s, 1H), 8.69 (s, 1H), 8.35 (s, 1H), 8.20 (s, 1H), 7.66 (s, 1H), 7.17-7.26 (m, 6H), 5.81 (s, 1H), 5.04 (m, 2H), 4.42 (s, 2H), 3.96 (s, 2H), 2.10 (s, 3H), 1.45 (d, 6H); MS (ES) [M+H]⁺ 495.0.

Example 6

6-bromo-1-(1-methylethyl)-N-[(6-methyl-2-oxo-1,2-dihydro-4,4'-bipyridin-3-yl)methyl]-1H-indazole-4-carboxamide

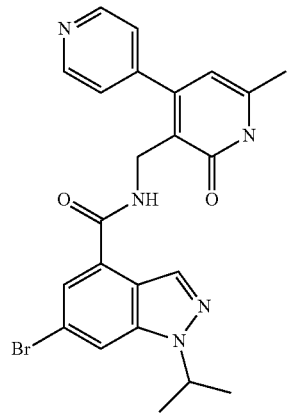 [SMILES: Cc1cc(-c2ccncc2)c(CNC(=O)c2cc(Br)cc3c2cnn3C(C)C)c(=O)[nH]1]

To a reaction vial were added 6-bromo-1-(1-methylethyl)-1H-indazole-4-carboxylic acid (90 mg, 0.318 mmol), 3-(aminomethyl)-6-methyl-4,4'-bipyridin-2(1H)-one (103 mg, 0.477 mmol), 1-hydroxy-7-azabenzotriazole (64.9 mg, 0.477 mmol), EDC (91 mg, 0.477 mmol) and DMSO (10 mL) followed by N-methylmorpholine (0.140 mL, 1.272 mmol) in one portion. The reaction contents were stirred at RT for 12 hr, after which time an additional 20 mg each of amine, EDC, and HOAt were added. After stirring for an additional 2 h, the reaction mixture was poured onto ice water (10 mL), stirred for 20 min, allowed to stand for 10 min, and filtered. The collected solid was rinsed with water (10 mL), and then purified by reverse phase HPLC (10-90% acetonitrile/water+ 0.1% TFA). The product fractions were treated with NaHCO₃ (sat aq), extracted with EtOAc, and evaporated from water to afford the final product as a white solid (69 mg, 43%). ¹H NMR (400 MHz, DMSO-d6) δ ppm 11.95 (s, 1H), 8.63-8.65 (d, 2H), 8.60 (s, 1H), 8.32 (s, 1H), 8.21 (s, 1H), 7.61 (s, 1H), 7.42 (s, 2H), 6.00 (s, 1H), 5.02 (m, 2H), 4.15 (s, 2H), 2.23 (s, 3H), 1.45 (d, 6H); MS (ES) [M+H]⁺ 481.8.

Example 7

1-(1-methylethyl)-N-{[6-methyl-2-oxo-4-(phenylmethyl)-1,2-dihydro-3-pyridinyl]methyl}-1H-indazole-4-carboxamide

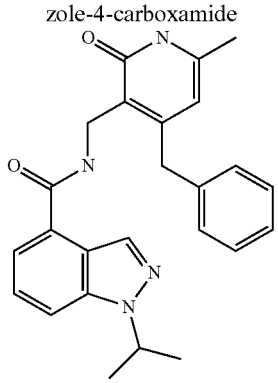

To a dried 50 mL round bottom flask was placed 10% Pd/C (0.020 g, 9.63 mol), followed by degassing with N₂. Added about 5 mL EtOH and then added 6-bromo-1-(1-methylethyl)-N-{[6-methyl-2-oxo-4-(phenylmethyl)-1,2-dihydro-3-pyridinyl]methyl}-1H-indazole-4-carboxamide (0.095 g, 0.193 mmol) and ethanol (5 mL) and THF (1 mL). Next added in triethylamine (0.081 mL, 0.578 mmol) via syringe. The mixture was stirred under atmosphere of hydrogen (balloon) for 6 h. The mixture was purged with nitrogen and then diluted with DCM (10 mL) and a small amount of celite, After stirring for 10 min, the contents were then filtered through analytical grade celite and washed with 10% MeOH/DCM, EtOH, and then DCM. The filtrate was concentrated in vacuo and dried under hi vacuum overnight. The crude product was purified by silica gel chromatography (eluent: 5-50% gradient of 10% methanol in dichloromethane and dichloromethane). The final product was concentrated from MTBE and dried in vacuum oven at 45° C. for 18 h. The title compound was collected as a white solid (0.75 g, 92% yield); ¹H NMR (400 MHz, DMSO-d6) δ ppm 1.48 (d, J=6.57 Hz, 6H) 2.10 (s, 3H) 3.98 (s, 2H) 4.43 (d, J=5.05 Hz, 2H) 5.03 (quin, J=6.63 Hz, 1H) 5.81 (s, 1H) 7.15-7.31 (m, 5H) 7.39 (t, J=7.71 Hz, 1H) 7.52 (d, J=6.82 Hz, 1H) 7.85 (d, J=8.34 Hz, 1H) 8.34 (s, 1H) 8.50 (t, J=5.05 Hz, 1H) 11.61 (s, 1H); MS (ES) [M+H]⁺ 415.0.

Example 8

N-((4,6-dimethyl-2-oxo-1,2-dihydropyridin-3-yl)methyl)-6-(4-(2-(dimethylamino)ethoxy)phenyl)-1-isopropyl-1H-indazole-4-carboxamide

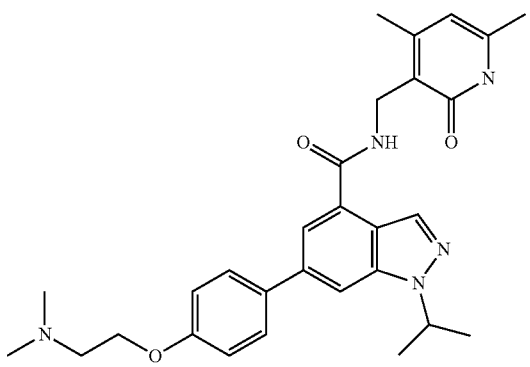

6-bromo-N-(4,6-dimethyl-2-oxo-1,2-dihydropyridin-3-yl)methyl)-1-isopropyl-1H-indazole-4-carboxamide (80 mg, 0.19 mmol), N,N-dimethyl-2-(4-(4,4,5,5-tetramethyl-1,3,2-dioxaborolan-2-yl)phenoxy)ethanamine (84 mg, 0.29 mmol) and PdCl₂(dppf)-CH₂Cl₂ adduct (7.8 mg, 0.009 mmol) in dioxane/water (3 ml:1 ml) were stirred for 10 min under nitrogen. Sodium bicarbonate (48.3 mg, 0.58 mmol) was added and the insoluble mixture was irradiated in a microwave at 100° C. for 20 min. The reaction mixture was evaporated, dissolved in DCM/MeOH (1:1), and preabsorbed on silica gel and purified using silica gel chromatography (eluent: DCM/MeOH/NH₄OH; gradient 0 to 80:20:2 in DCM). The isolated product was dissolved in hot DMSO/MeOH and purified using reversed-phase HPLC (25-80% gradient of MeCN in water with 0.1% TFA). Most of the solvent from the combined product fractions were evaporated and sat. sol. NaHCO3 was added, solids that crashed out were filtered, air-dried for 15 min, and dried in vacuum-oven overnight. The product was collected as a white solid (56 mg, 56%). ¹H NMR (400 MHz, DMSO-d₆) δ ppm 11.54 (br. s., 1H) 8.64 (t, J=4.80 Hz, 1H) 8.35 (s, 1H) 8.05 (s, 1H) 7.81-7.84 (m, 2H). LC-MS (ES) m/z=528.1 [M+H]⁺

Example 9

N-[(4,6-dimethyl-2-oxo-1,2-dihydro-3-pyridinyl)methyl]-1-(1-methylethyl)-6-[4-(1-piperazinyl)phenyl]-1H-indazole-4-carboxamide

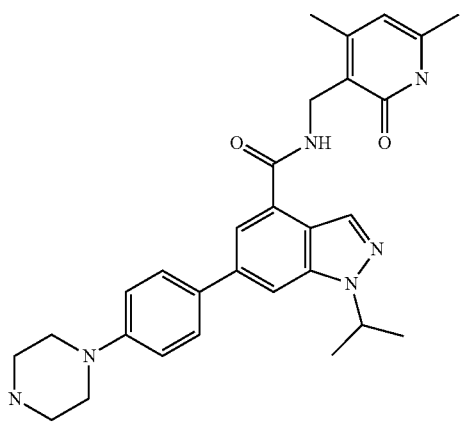 [SMILES: Cc1cc(C)c(CNC(=O)c2cc(-c3ccc(N4CCNCC4)cc3)cc3c2cnn3C(C)C)c(=O)[nH]1]

The title compound was prepared in a similar manner as described for example 8 from 6-bromo-1-(1-methylethyl)-N-[(6-methyl-2-oxo-4-propyl-1,2-dihydro-3-pyridinyl)methyl]-1H-indazole-4-carboxamide (80 mg, 0.192 mmol) and [4-(1-piperazinyl)phenyl]boronic acid (59 mg, 0.288 mmol). The product was collected as a white solid (34 mg, 35%). ¹H NMR (400 MHz, DMSO-d₆) δ ppm 11.53 (br. s., 1H) 8.66 (br. s., 1H) 8.33 (s, 1H) 8.00 (s, 1H) 7.82 (s, 1H) 7.73-7.76 (m, 1H) 7.72 (s, 1H) 7.01-7.09 (m, 2H) 5.89 (s, 1H) 5.14 (dt, J=13.33, 6.60 Hz, 1H) 4.39 (br. s., 1H) 4.38 (br. s., 1H) 3.38-3.52 (m, 4H) 3.09-3.14 (m, 1H) 3.00-3.09 (m, 3H) 2.81-2.90 (m, 1H) 2.21 (s, 3H) 2.13 (s, 3H) 1.50 (s, 3H) 1.48 (s, 3H). LC-MS (ES) m/z=499.4 [M+H]⁺

Example 10

N-[(4,6-dimethyl-2-oxo-1,2-dihydro-3-pyridinyl)methyl]-1-(1-methylethyl)-6-[6-(1-piperazinyl)-3-pyridinyl]-1H-indazole-4-carboxamide

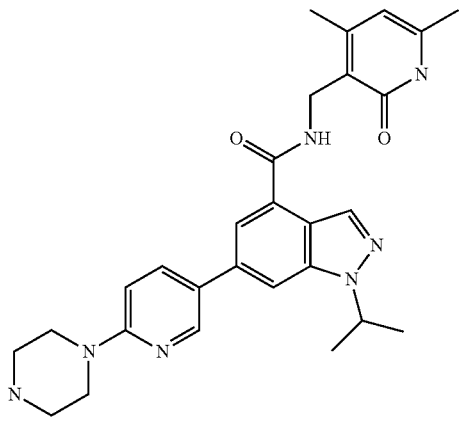

The title compound was prepared in a similar manner as described for example 8 from 6-bromo-1-(1-methylethyl)-N-[(6-methyl-2-oxo-4-methyl-1,2-dihydro-3-pyridinyl)methyl]-1H-indazole-4-carboxamide (90 mg, 0.216 mmol) and 1-[5-(4,4,5,5-tetramethyl-1,3,2-dioxaborolan-2-yl)-2-pyridinyl]piperazine (94 mg, 0.324 mmol). The product obtained from HPLC purification was treated with a saturated solution of NaHCO$_3$, and solids that crashed out were filtered. The product was evaporated from MeOH, triturated from ether and then CH$_3$CN. After drying in vacuum oven overnight, the final product was collected as a white solid (87 mg, 78%). $^1$H NMR (400 MHz, DMSO-d$_6$) δ ppm 11.53 (br. s., 1H) 8.59-8.67 (m, 1H) 8.54 (s, 1H) 8.35 (s, 1H) 8.02-8.09 (m, 2H) 7.84 (s, 1H) 6.94 (d, J=9.09 Hz, 1H) 5.89 (s, 1H) 5.14 (dt, J=13.07, 6.47 Hz, 1H) 4.39 (br. s., 1H) 4.38 (br. s., 1H) 3.41-3.47 (m, 4H) 3.17 (s, 1H) 2.22 (s, 3H) 2.13 (s, 3H) 1.50 (s, 3H) 1.49 (s, 3H). LC-MS (ES) m/z=500.4 [M+H]$^+$ Note: some piperinzyl proton atoms hidden under water peak.

Example 11

6-{4-[(dimethylamino)methyl]phenyl}-1-(1-methylethyl)-N-{[6-methyl-4-(1-methylethyl)-2-oxo-1,2-dihydro-3-pyridinyl]methyl}-1H-indazole-4-carboxamide

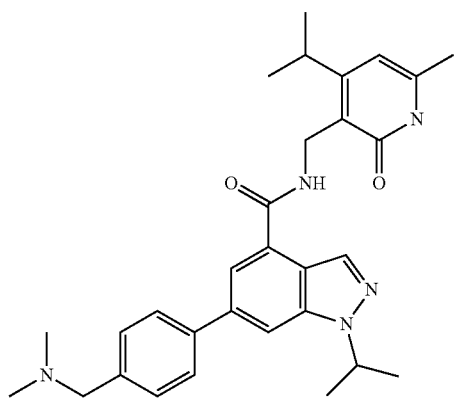

The title compound was prepared in a similar manner as described for example 8 from 6-bromo-1-(1-methylethyl)-N-{[6-methyl-4-(1-methylethyl)-2-oxo-1,2-dihydro-3-pyridinyl]methyl}-1H-indazole-4-carboxamide (90 mg, 0.202 mmol) and dimethyl{[4-(4,4,5,5-tetramethyl-1,3,2-dioxaborolan-2-yl)phenyl]methyl}amine (90 mg, 0.303 mmol). The product was collected as a white solid (54 mg, 49%). $^1$H NMR (400 MHz, DMSO-d$_6$) δ ppm 11.48 (br. s., 1H) 8.69 (br. s., 1H) 8.37 (s, 1H) 8.10 (s, 1H) 7.86 (s, 1H) 7.82 (s, 1H) 7.80 (s, 1H) 7.42 (s, 1H) 7.40 (s, 1H) 6.02 (s, 1H) 5.17 (dt, J=13.14, 6.57 Hz, 1H) 4.47 (d, J=4.80 Hz, 2H) 3.44 (s, 2H) 3.24 (dt, J=13.71, 6.92 Hz, 1H) 2.17 (s, 6H) 2.15 (s, 3H) 1.51 (s, 3H) 1.49 (s, 3H) 1.11 (s, 3H) 1.09 (s, 3H). LC-MS (ES) m/z=500.1 [M+H]$^+$

Example 12

1-isopropyl-N-((4-isopropyl-6-methyl-2-oxo-1,2-dihydropyridin-3-yl)methyl)-6-(6-(piperazin-1-yl)pyridin-3-yl)-1H-indazole-4-carboxamide

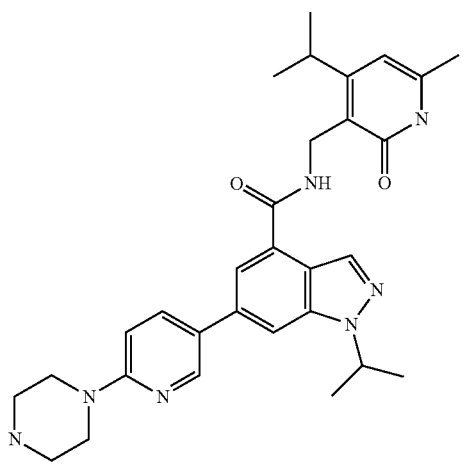 [SMILES: Cc1cc(C(C)C)c(CNC(=O)c2cc(-c3ccc(N4CCNCC4)nc3)cc3c2cnn3C(C)C)c(=O)[nH]1]

In a 25 mL sealable tube under nitrogen were combined 6-bromo-1-(1-methylethyl)-N-{[6-methyl-4-(1-methylethyl)-2-oxo-1,2-dihydro-3-pyridinyl]methyl}-1H-indazole-4-carboxamide (90 mg, 0.2 mmol), {1-[5-(4,4,5,5-tetramethyl-1,3,2-dioxaborolan-2-yl)-2-pyridinyl]piperazine (88 mg, 0.3 mmol) in dioxane/water (3 mL:1 mL). PdCl$_2$(dppf)-CH$_2$Cl$_2$ adduct (4.95 mg, 0.006 mmol) was added and the resulting mixture was degassed with nitrogen for 10 min. Sodium bicarbonate (50.9 mg, 0.61 mmol) was added, the vessel was sealed, and the insoluble mixture was heated in a microwave at 100° C. for 20 min. Upon cooling down, any solids that crashed out were filtered. DCM/MeOH (1:1) was added, the contents pre-absorbed on silica gel, and purified by SiO$_2$ chromatography (eluent: gradient 0 to 80:20:2 DCM/MeOH/NH$_4$OH). The collected product was then further purified by reverse-phase HPLC (15% to 80% CH$_3$CN in water with 0.1% TFA), which afforded the product as a TFA salt. CH$_3$CN was evaporated and a saturated solution of sodium bicarbonate was added to the water layer followed by DCM/isopropanol (70:30). The organic layer was separated, and the aqueous layer was further extracted with DCM/isopropanol (70:30). The combined organic layers were washed with brine, dried over MgSO$_4$, filtered, and concentrated. DMF was added along with some water, and after sitting overnight, the solids that precipitated were filtered. EtOAc was added along with some hexanes, the contents sonicated, and the solids that precipitated were filtered and dried to afford the title compound as an off-white solid (29.5 mg, 26%). $^1$H NMR (400 MHz, DMSO-d$_6$) δ ppm 11.54 (br. s., 1H) 8.59-8.68 (m, 2H) 8.35 (s, 1H) 8.00-8.12 (m, 2H) 7.83 (s, 1H) 6.92 (d, J=8.84 Hz, 1H) 6.03 (s, 1H) 5.13 (quin, J=6.63 Hz, 1H) 4.47 (br. s., 1H) 4.46 (br. s., 1H) 3.42-3.56 (m, 4H) 3.20-3.27 (m, 1H) 2.76-2.85 (m, 4H) 2.16 (s, 3H) 1.50 (s, 3H) 1.49 (s, 3H) 1.11 (s, 3H) 1.09 (s, 3H). LC-MS (ES) m/z=528.1 [M+H]$^+$

Example 13

N-((4,6-dimethyl-2-oxo-1,2-dihydropyridin-3-yl)methyl)-1-isopropyl-6-(1-methyl-1H-pyrazol-4-yl)-1H-indazole-4-carboxamide

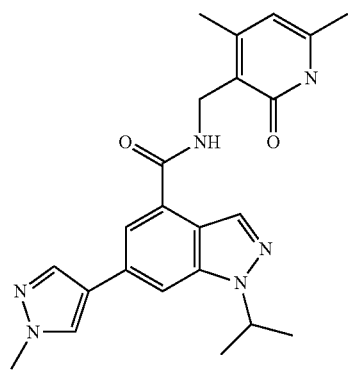

In a 25 mL sealable tube under nitrogen were combined 6-bromo-N-[(4,6-dimethyl-2-oxo-1,2-dihydro-3-pyridinyl)methyl]-1-(1-methylethyl)-1H-indazole-4-carboxamide (110 mg, 0.26 mmol), 1-methyl-4-(4,4,5,5-tetramethyl-1,3,2-dioxaborolan-2-yl)-1H-pyrazole (82 mg, 0.4 mmol) in dioxane/water (3 mL:1 mL). PdCl$_2$(dppf)-CH$_2$Cl$_2$ adduct (10.8 mg, 0.013 mmol) was added and the resulting mixture was degassed with nitrogen for 10 min. Sodium bicarbonate (66.4 mg, 0.79 mmol) was added, the vessel was sealed, and the insoluble mixture was heated in a microwave at 100° C. for 20 min. The mixture was evaporated, DCM/MeOH (1:1) was added, and the contents pre-absorbed on silica gel and purified by SiO$_2$ chromatography (eluent: gradient 0 to 80:20:2 DCM/MeOH/NH$_4$OH). The collected product was suspended in EtOAc along with some hexanes, it was sonicated, and the solids that precipitated were filtered. Acetonitrile was added, solids that precipitated were filtered, and further washed with acetonitrile/ether (2:8) and dried to afford the title compound as an off-white solid (84 mg, 76%). $^1$H NMR (400 MHz, DMSO-d$_6$) δ ppm 11.54 (s, 1H) 8.48 (t, J=4.93 Hz, 1H) 8.31 (s, 1H) 8.26 (s, 1H) 8.04 (s, 1H) 8.03 (s, 1H) 7.81 (d, J=1.01 Hz, 1H) 5.90 (s, 1H) 5.06 (quin, J=6.57 Hz, 1H) 4.39 (s, 1H) 4.38 (s, 1H) 3.90 (s, 3H) 2.23 (s, 3H) 2.13 (s, 3H) 1.50 (s, 3H) 1.48 (s, 3H); LC-MS (ES) m/z=419.0

Example 14

6-(4-((dimethylamino)methyl)phenyl)-N-((4-ethyl-6-methyl-2-oxo-1,2-dihydropyridin-3-yl)methyl)-1-isopropyl-1H-indazole-4-carboxamide

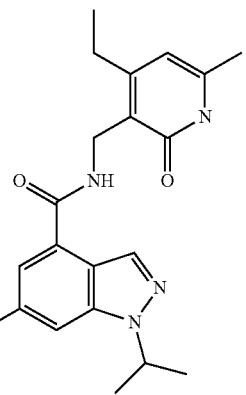

In a 25 mL sealable tube under nitrogen were combined 6-bromo-N-[(4-ethyl-6-methyl-2-oxo-1,2-dihydro-3-pyridinyl)methyl]-1-(1-methylethyl)-1H-indazole-4-carboxamide (90 mg, 0.21 mmol), dimethyl{[4-(4,4,5,5-tetramethyl-1,3,2-dioxaborolan-2-yl)phenyl]methyl}amine.HCl (93 mg, 0.31 mmol) in dioxane/water (3 mL:1 mL). PdCl$_2$(dppf)-CH$_2$Cl$_2$ adduct (8.52 mg, 0.01 mmol) was added and the resulting mixture was degassed with nitrogen for 10 min. Sodium bicarbonate (52.6 mg, 0.63 mmol) was added, the vessel was sealed, and the insoluble mixture was heated in a microwave at 110° C. for 20 min. The mixture was evaporated, DCM/MeOH (1:1) added, and the contents pre-absorbed on silica gel and purified by SiO$_2$ chromatography (eluent: gradient 0 to 80:20:2 DCM/MeOH/NH$_4$OH). The collected product was further purified by reversed-phase HPLC (15% to 80% CH$_3$CN in water with 0.1% TFA) which afforded the TFA salt. CH$_3$CN was evaporated, and a saturated solution of sodium bicarbonate was added to the water layer along with EtOAc. The organic layer was separated, and the aqueous layer was further extracted with EtOAc, DCM and DCM/isopropanol (8:2). The combined organic layers were washed with brine, dried over MgSO$_4$, filtered and concentrated. The solid was triturated in ether and dried to afford the title compound as an-off-white solid (40 mg, 38%). $^1$H NMR (400 MHz, DMSO-d$_6$) δ ppm 11.54 (s, 1H) 8.67 (t, J=4.93 Hz, 1H) 8.38 (s, 1H) 8.11 (s, 1H) 7.86 (s, 1H) 7.82 (s, 1H) 7.80 (s, 1H) 7.42 (s, 1H) 7.40 (s, 1H) 5.93 (s, 1H) 5.17 (quin, J=6.57 Hz, 1H) 4.43 (s, 1H) 4.41 (s, 1H) 3.44 (s, 2H) 2.57 (q, J=7.58 Hz, 2H) 2.17 (s, 6H) 2.14 (s, 3H) 1.51 (s, 3H) 1.49 (s, 3H) 1.10 (t, J=7.58 Hz, 3H); LC-MS (ES) m/z=486.3 [M+H]$^+$

Example 15

1-(1-methylethyl)-N-[(6-methyl-2-oxo-4-propyl-1,2-dihydro-3-pyridinyl)methyl]-6-[6-(1-piperazinyl)-3-pyridinyl]-1H-indazole-4-carboxamide

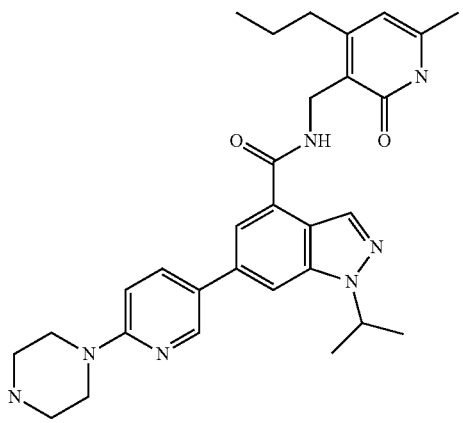 [SMILES: CCCc1cc(C)[nH]c(=O)c1CNC(=O)c1cc(-c2ccc(N3CCNCC3)nc2)cc2c1cnn2C(C)C]

The title compound was prepared in a similar manner as described for example 8 from 6-bromo-1-(1-methylethyl)-N-[(6-methyl-2-oxo-4-propyl-1,2-dihydro-3-pyridinyl)methyl]-1H-indazole-4-carboxamide (90 mg, 0.202 mmol) and 1-[5-(4,4,5,5-tetramethyl-1,3,2-dioxaborolan-2-yl)-2-pyridinyl]piperazine (88 mg, 0.303 mmol). The final product was collected as a white solid (91 mg, 83%). $^1$H NMR (400 MHz, DMSO-$d_6$) δ ppm 11.54 (br. s., 1H) 8.65 (d, J=2.53 Hz, 1H) 8.61 (t, J=4.80 Hz, 1H) 8.36 (s, 1H) 8.03-8.07 (m, 2H) 7.83 (s, 1H) 6.92 (d, J=9.09 Hz, 1H) 5.92 (s, 1H) 5.14 (quin, J=6.63 Hz, 1H) 4.42 (br. s., 1H) 4.41 (br. s., 1H) 3.45-3.51 (m, 4H) 2.75-2.84 (m, 4H) 2.54 (m, 2H) 2.14 (s, 3H) 1.51-1.58 (m, 2H) 1.50 (s, 3H) 1.49 (s, 3H) 0.88 (t, J=7.33 Hz, 3H). LC-MS (ES) m/z=528.0 [M+H]

Example 16

N-((4-ethyl-6-methyl-2-oxo-1,2-dihydropyridin-3-yl)methyl)-1-isopropyl-6-(6-(4-methylpiperazin-1-yl)pyridin-3-yl)-1H-indazole-4-carboxamide

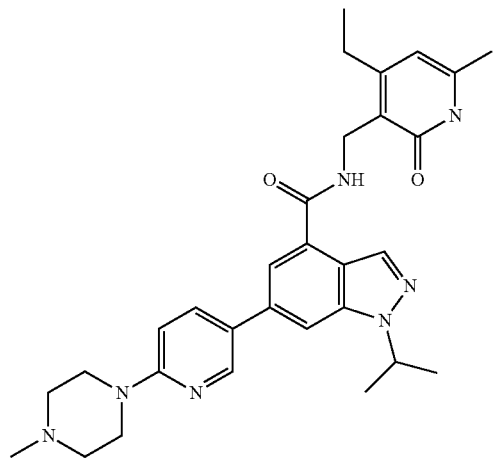

In a 25 mL sealable tube under nitrogen were combined 6-bromo-N-[(4-ethyl-6-methyl-2-oxo-1,2-dihydro-3-pyridinyl)methyl]-1-(1-methylethyl)-1H-indazole-4-carboxamide (90 mg, 0.21 mmol), 1-methyl-4-[5-(4,4,5,5-tetramethyl-1,3,2-dioxaborolan-2-yl)-2-pyridinyl]piperazine (95 mg, 0.31 mmol) in dioxane/water (3 mL:1 mL). PdCl$_2$(dppf)-CH$_2$Cl$_2$ adduct (8.52 mg, 0.01 mmol) was added and the resulting mixture was degassed with nitrogen for 10 min. Sodium bicarbonate (52.6 mg, 0.63 mmol) was added, the vessel was sealed, and the insoluble mixture was heated in a microwave at 110° C. for 20 min. The mixture was evaporated, DCM/MeOH (1:1) was added, and the contents pre-absorbed on silica gel and purified by SiO$_2$ chromatography (eluent: gradient 0 to 80:20:2 DCM/MeOH/NH$_4$OH). The collected product was further purified by reversed-phase HPLC (15% to 80% CH$_3$CN in water with 0.1% TFA) which afforded the TFA salt. CH$_3$CN was evaporated, and a saturated solution of sodium bicarbonate was added to the water layer along with EtOAc. The organic layer was separated, and the aqueous layer was further extracted with EtOAc, DCM and DCM/isopropanol (8:2). The combined organic layers were washed with brine, dried over MgSO$_4$, filtered and concentrated. EtOAc was added along with some hexanes, and the contents were sonicated and then allowed sit overnight at room temperature. Solids that precipitated were filtered and dried to afford the title compound (84 mg, 76%) as a white solid. $^1$H NMR (400 MHz, DMSO-$d_6$) δ ppm 11.54 (br. s., 1H) 8.65 (d, J=2.27 Hz, 1H) 8.62 (t, J=4.80 Hz, 1H) 8.36 (s, 1H) 8.04-8.08 (m, 2H) 7.82-7.85 (m, 1H) 6.97 (d, J=8.84 Hz, 1H) 5.94 (s, 1H) 5.14 (quin, J=6.57 Hz, 1H) 4.42 (s, 1H) 4.41 (s, 1H) 3.52-3.59 (m, 4H) 2.56 (q, J=7.58 Hz, 2H) 2.39-2.44 (m, 4H) 2.23 (s, 3H) 2.14 (s, 3H) 1.50 (s, 3H) 1.49 (s, 3H) 1.10 (t, J=7.58 Hz, 3H); LC-MS (ES) m/z=486.3

Example 17

1-isopropyl-N-((6-methyl-2-oxo-4-propyl-1,2-dihydropyridin-3-yl)methyl)-6-(2-methylpyrimidin-5-yl)-1H-indazole-4-carboxamide

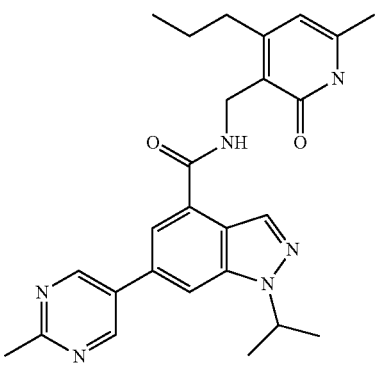

In a 25 mL sealable tube under nitrogen were combined 6-bromo-1-(1-methylethyl)-N-[(6-methyl-2-oxo-4-propyl-1,2-dihydro-3-pyridinyl)methyl]-1H-indazole-4-carboxamide (100 mg, 0.23 mmol), 2-methyl-5-(4,4,5,5-tetramethyl-1,3,2-dioxaborolan-2-yl)pyrimidine (64.2 mg, 0.29 mmol) in dioxane/water (3 mL:1 mL). PdCl$_2$(dppf)-CH$_2$Cl$_2$ adduct (9.2 mg, 0.011 mmol) was added and the resulting mixture was degassed with nitrogen for 10 min. Sodium bicarbonate (56.6 mg, 0.67 mmol) was added, the vessel was sealed, and the insoluble mixture was heated in a microwave at 110° C. for 20 min. The mixture was evaporated, DCM/MeOH (1:1) was added, and the contents pre-absorbed on silica gel and purified by SiO$_2$ chromatography (eluent: gradient 0 to 80:20:2 DCM/MeOH/NH$_4$OH). The collected product was suspended in acetonitrile along with a few drops of EtOH and some hexanes. The contents were sonicated, and solids that precipitated were filtered and dried to afford the title compound as an off-white solid (44 mg, 42%). $^1$H NMR (400 MHz, DMSO-$d_6$) δ ppm 11.55 (s, 1H) 9.21 (s, 2H) 8.63 (t, J=4.80 Hz, 1H) 8.43 (s, 1H) 8.32 (s, 1H) 7.94-7.96 (m, 1H) 5.92 (s, 1H) 5.17 (quin, J=6.63 Hz, 1H) 4.43 (br. s., 1H) 4.42 (br. s., 1H) 2.69 (s, 3H) 2.52-2.56 (m, 2H) 2.14 (s, 3H) 1.49-1.55 (m, 8H) 0.88 (t, J=7.33 Hz, 3H); LC-MS (ES) m/z=459.2

Example 18

6-[6-(dimethylamino)-3-pyridinyl]-1-(1-methylethyl)-N-[(6-methyl-2-oxo-4-propyl-1,2-dihydro-3-pyridinyl)methyl]-1H-indazole-4-carboxamide

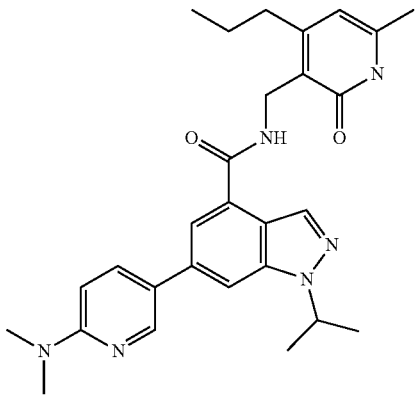

The title compound was prepared in a similar manner as described for example 13 from 6-bromo-1-(1-methylethyl)-N-[(6-methyl-2-oxo-4-propyl-1,2-dihydro-3-pyridinyl)methyl]-1H-indazole-4-carboxamide (100 mg, 0.225 mmol) and [6-(dimethylamino)-3-pyridinyl]boronic acid (49 mg, 0.292 mmol). The final product was collected as a white solid (49 mg, 44%). $^1$H NMR (400 MHz, DMSO-$d_6$) δ ppm 11.55 (s, 1H) 8.57-8.65 (m, 2H) 8.35 (s, 1H) 8.01-8.06 (m, 2H) 7.83 (s, 1H) 6.76 (d, J=8.84 Hz, 1H) 5.92 (s, 1H) 5.13 (dt, J=13.14, 6.57 Hz, 1H) 4.42 (br. s., 1H) 4.41 (br. s., 1H) 3.09 (s, 6H) 2.54 (m, 2H) 2.14 (s, 3H) 1.51-1.58 (m, 2H) 1.50 (s, 3H) 1.49 (s, 3H) 0.88 (t, J=7.33 Hz, 3H). LC-MS (ES) m/z=487.4 [M+H]$^+$ Example 19

1-(1-methylethyl)-N-[(6-methyl-2-oxo-4-propyl-1,2-dihydro-3-pyridinyl)methyl]-6-[6-(4-morpholinyl)-3-pyridinyl]-1H-indazole-4-carboxamide

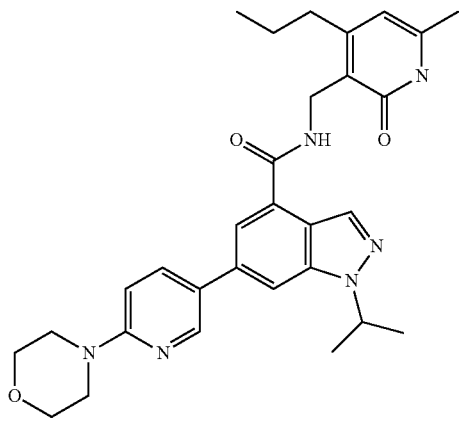 [SMILES: CCCc1cc(C)[nH]c(=O)c1CNC(=O)c1cc(-c2ccc(N3CCOCC3)nc2)cc2c1cnn2C(C)C]

The title compound was prepared in a similar manner as described for example 8 from 6-bromo-1-(1-methylethyl)-N-[(6-methyl-2-oxo-4-propyl-1,2-dihydro-3-pyridinyl)me-thyl]-1H-indazole-4-carboxamide (100 mg, 0.225 mmol) and [6-(4-morpholinyl)-3-pyridinyl]boronic acid (70 mg, 0.337 mmol). The final product was collected as a white solid (98 mg, 81%). $^1$H NMR (400 MHz, DMSO-$d_6$) δ ppm 11.46 (br. s., 1H) 8.68 (d, J=2.53 Hz, 2H) 8.37 (s, 1H) 8.07-8.12 (m, 2H) 7.84 (d, J=1.01 Hz, 1H) 6.98 (d, J=8.84 Hz, 1H) 5.91 (s, 1H) 5.14 (quin, J=6.57 Hz, 1H) 4.42 (d, J=4.80 Hz, 2H) 3.71-3.76 (m, 4H) 3.50-3.56 (m, 4H) 2.52-2.56 (m, 2H) 2.13 (s, 3H) 1.51-1.58 (m, 2H) 1.51 (s, 3H) 1.49 (s, 3H) 0.88 (t, J=7.33 Hz, 3H). LC-MS (ES) m/z=529.0 [M+H]$^+$ Example 20

6-(2-amino-5-pyrimidinyl)-1-(1-methylethyl)-N-[(6-methyl-2-oxo-4-propyl-1,2-dihydro-3-pyridinyl)methyl]-1H-indazole-4-carboxamide

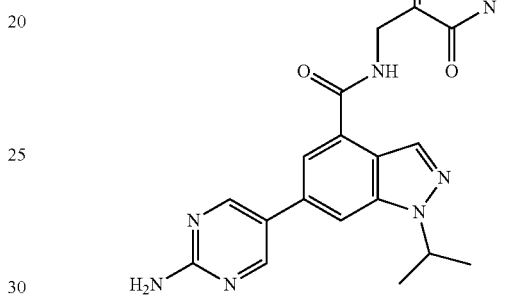

The title compound was prepared in the same manner as described for example 75 from 6-bromo-1-(1-methylethyl)-N-[(6-methyl-2-oxo-4-propyl-1,2-dihydro-3-pyridinyl)me-thyl]-1H-indazole-4-carboxamide (100 mg, 0.225 mmol) and 5-(4,4,5,5-tetramethyl-1,3,2-dioxaborolan-2-yl)-2-pyrimidinamine (75 mg, 0.337 mmol). The final product was collected as a white solid (87 mg, 82%). $^1$H NMR (400 MHz, DMSO-$d_6$) δ ppm 11.54 (s, 1H) 8.78 (s, 2H) 8.59 (t, J=4.80 Hz, 1H) 8.37 (s, 1H) 8.11 (s, 1H) 7.82 (s, 1H) 6.87 (s, 2H) 5.91 (s, 1H) 5.14 (quin, J=6.57 Hz, 1H) 4.42 (s, 1H) 4.41 (s, 1H) 2.52-2.57 (m, 2H) 2.13 (s, 3H) 1.51-1.58 (m, 2H) 1.50 (s, 3H) 1.49 (s, 3H) 0.88 (t, J=7.33 Hz, 3H). LC-MS (ES) m/z=460.7

Example 21

6-(6-amino-3-pyridinyl)-1-(1-methylethyl)-N-[(6-methyl-2-oxo-4-propyl-1,2-dihydro-3-pyridinyl)methyl]-1H-indazole-4-carboxamide

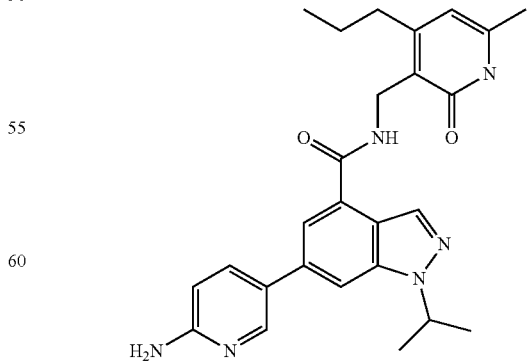

The title compound was prepared in the same manner as described for example 75 from 6-bromo-1-(1-methylethyl)-

N-[(6-methyl-2-oxo-4-propyl-1,2-dihydro-3-pyridinyl)methyl]-1H-indazole-4-carboxamide (100 mg, 0.225 mmol) and 5-(4,4,5,5-tetramethyl-1,3,2-dioxaborolan-2-yl)-2-pyridinamine (75 mg, 0.337 mmol). The final product was collected as a white solid (60 mg, 57%). $^1$H NMR (400 MHz, DMSO-$d_6$) δ ppm 11.55 (s, 1H) 8.61 (t, J=4.93 Hz, 1H) 8.45 (d, J=2.27 Hz, 1H) 8.34 (s, 1H) 8.00 (s, 1H) 7.90 (dd, J=8.59, 2.53 Hz, 1H) 7.78 (s, 1H) 6.55 (d, J=8.59 Hz, 1H) 6.10-6.17 (m, 2H) 5.91 (s, 1H) 5.13 (quin, J=6.57 Hz, 1H) 4.42 (br. s., 1H) 4.41 (br. s., 1H) 2.52-2.56 (m, 2H) 2.13 (s, 3H) 1.51-1.57 (m, 2H) 1.50 (s, 3H) 1.48 (s, 3H) 0.88 (t, J=7.33 Hz, 3H). LC-MS (ES) m/z=459.2

Example 22

1-(1-methylethyl)-N-[(6-methyl-2-oxo-4-propyl-1,2-dihydro-3-pyridinyl)methyl]-6-(5-pyrimidinyl)-1H-indazole-4-carboxamide

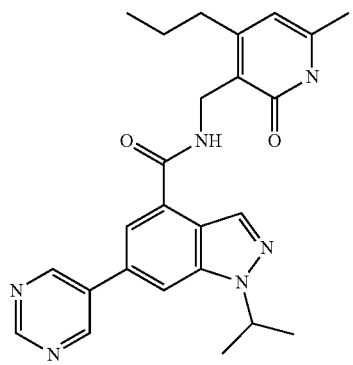 [SMILES: CCCc1cc(C)[nH]c(=O)c1CNC(=O)c1cc(-c2cncnc2)cc2c1cnn2C(C)C]

The title compound was prepared in the same manner as described for example 75 from 6-bromo-1-(1-methylethyl)-N-[(6-methyl-2-oxo-4-propyl-1,2-dihydro-3-pyridinyl)methyl]-1H-indazole-4-carboxamide (100 mg, 0.225 mmol) and 5-pyrimidinylboronic acid (42 mg, 0.337 mmol). The final product was collected as a white solid (77 mg, 75%). $^1$H NMR (400 MHz, DMSO-$d_6$) δ ppm 11.55 (s, 1H) 9.35 (s, 2H) 9.21-9.26 (m, 1H) 8.63 (t, J=4.93 Hz, 1H) 8.45 (s, 1H) 8.38 (s, 1H) 7.99 (d, J=1.26 Hz, 1H) 5.92 (s, 1H) 5.18 (quin, J=6.57 Hz, 1H) 4.44 (s, 1H) 4.42 (s, 1H) 2.52-2.56 (m, 2H) 2.13 (s, 3H) 1.52-1.56 (m, 4H) 1.48-1.52 (m, 4H) 0.88 (t, J=7.33 Hz, 3H). LC-MS (ES) m/z=445.2

Example 23

1-(1-methylethyl)-N-[(6-methyl-2-oxo-4-propyl-1,2-dihydro-3-pyridinyl)methyl]-6-[6-(methyloxy)-3-pyridinyl]-1H-indazole-4-carboxamide

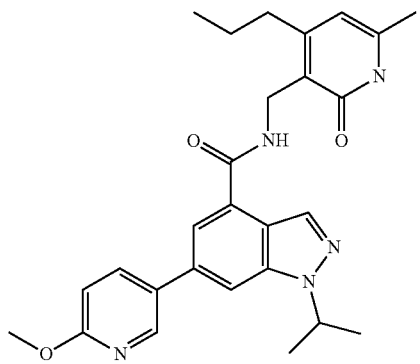

The title compound was prepared in the same manner as described for example 75 from 6-bromo-1-(1-methylethyl)-N-[(6-methyl-2-oxo-4-propyl-1,2-dihydro-3-pyridinyl)methyl]-1H-indazole-4-carboxamide (100 mg, 0.225 mmol) and [6-(methyloxy)-3-pyridinyl]boronic acid (52 mg, 0.337 mmol). The final product was collected as a white solid (72 mg, 67%). $^1$H NMR (400 MHz, DMSO-$d_6$) δ ppm 11.55 (br. s., 1H) 8.68 (br. s., 1H) 8.62 (br. s., 1H) 8.39 (s, 1H) 8.21 (br. s., 1H) 8.14 (s, 1H) 7.86 (s, 1H) 6.97 (d, J=8.59 Hz, 1H) 5.92 (s, 1H) 5.09-5.21 (m, 1H) 4.37-4.48 (m, 2H) 3.92 (s, 3H) 2.54 (br. s., 2H) 2.14 (s, 3H) 1.55 (m, 2H) 1.51 (br. s., 3H) 1.50 (br. s., 3H) 0.88 (t, J=7.20 Hz, 3H). LC-MS (ES) m/z=474.0

Example 24

1-(1-methylethyl)-N-[(6-methyl-2-oxo-4-propyl-1,2-dihydro-3-pyridinyl)methyl]-6-[6-(4-methyl-1-piperazinyl)-3-pyridinyl]-1H-indazole-4-carboxamide

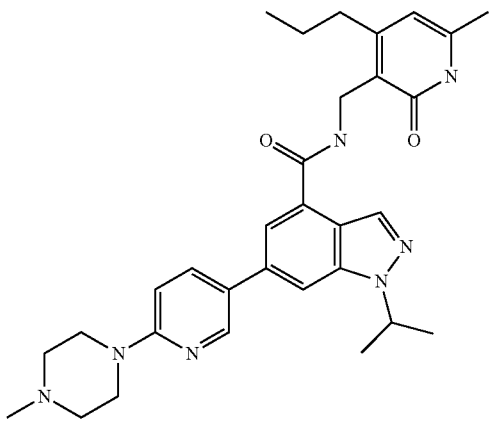

The title compound was prepared in a similar manner as described for example 8 from 6-bromo-1-(1-methylethyl)-N-[(6-methyl-2-oxo-4-propyl-1,2-dihydro-3-pyridinyl)methyl]-1H-indazole-4-carboxamide (90 mg, 0.202 mmol) and 1-methyl [5-(4,4,5,5-tetramethyl-1,3,2-dioxaborolan-2-yl)-2-pyridinyl]piperazine (92 mg, 0.303 mmol). The final product was collected as a light brown solid (54 mg, 49%). $^1$H NMR (400 MHz, DMSO-$d_6$) δ ppm 1H NMR (400 MHz, DMSO-d6) δ ppm 11.54 (br. s., 1H) 8.65 (d, J=2.27 Hz, 1H) 8.61 (t, J=4.80 Hz, 1H) 8.36 (s, 1H) 8.04-8.08 (m, 2H) 7.83 (s, 1H) 6.96 (d, J=9.09 Hz, 1H) 5.92 (s, 1H) 5.14 (quin, J=6.57 Hz, 1H) 4.42 (d, J=4.80 Hz, 2H) 3.53-3.59 (m, 4H) 2.53-2.61 (m, 2H) 2.40-2.45 (m, 4H) 2.23 (s, 3H) 2.14 (s, 3H) 1.51-1.58

(m, 2H) 1.50 (s, 3H) 1.49 (s, 3H) 0.88 (t, J=7.33 Hz, 3H). LC-MS (ES) m/z=542.2 [M+H]+

Example 25

1-(1-methylethyl)-N-[(6-methyl-2-oxo-4-propyl-1,2-dihydro-3-pyridinyl)methyl]-6-(2-methyl-3-pyridinyl)-1H-indazole-4-carboxamide

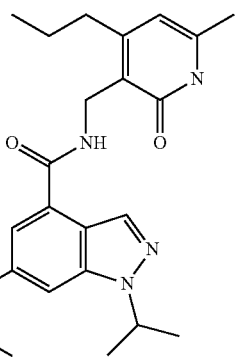

The title compound was prepared in a similar manner as described for example 8 from 6-bromo-1-(1-methylethyl)-N-[(6-methyl-2-oxo-4-propyl-1,2-dihydro-3-pyridinyl)methyl]-1H-indazole-4-carboxamide (100 mg, 0.225 mmol) and (2-methyl-3-pyridinyl)boronic acid (46 mg, 0.337 mmol). The product was collected as a white solid (68 mg, 66%). ¹H NMR (400 MHz, DMSO-d₆) δ ppm 11.44 (br. s., 1H) 8.57 (br. s., 1H) 8.50 (dd, J=4.93, 1.64 Hz, 1H) 8.43 (s, 1H) 7.90 (s, 1H) 7.73 (dd, J=7.71, 1.64 Hz, 1H) 7.59 (d, J=1.26 Hz, 1H) 7.34 (dd, J=7.33, 4.80 Hz, 1H) 5.90 (s, 1H) 5.10 (quin, J=6.57 Hz, 1H) 4.40 (s, 1H) 4.38 (s, 1H) 2.46 (s, 3H) 2.12 (s, 3H) 1.50-1.58 (m, 2H) 1.50 (s, 3H) 1.48 (s, 3H) 0.88 (t, J=7.33 Hz, 3H). LC-MS (ES) m/z=458.3 [M+H]+

Example 26

1-(1-methylethyl)-N-[(6-methyl-2-oxo-4-propyl-1,2-dihydro-3-pyridinyl)methyl]-6-(6-methyl-3-pyridinyl)-1H-indazole-4-carboxamide

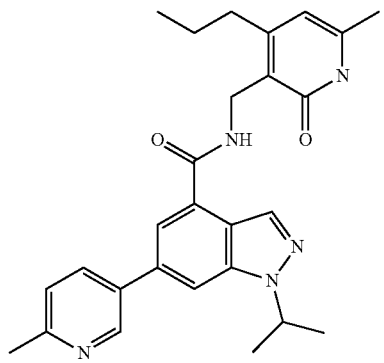

The title compound was prepared in a similar manner as described for example 8 from 6-bromo-1-(1-methylethyl)-N-[(6-methyl-2-oxo-4-propyl-1,2-dihydro-3-pyridinyl)methyl]-1H-indazole-4-carboxamide (100 mg, 0.225 mmol) and (6-methyl-3-pyridinyl)boronic acid (46 mg, 0.337 mmol). The product was collected as a white solid (99 mg, 94%). ¹H NMR (400 MHz, DMSO-d₆) δ ppm 11.47 (br. s., 1H) 8.96 (d, J=2.02 Hz, 1H) 8.67 (br. s., 1H) 8.40 (s, 1H) 8.20 (s, 1H) 8.17 (dd, J=8.08, 2.53 Hz, 1H) 7.89 (s, 1H) 7.39 (d, J=8.08 Hz, 1H) 5.91 (s, 1H) 5.18 (quin, J=6.57 Hz, 1H) 4.43 (br. s., 1H) 4.42 (br. s., 1H) 2.52-2.58 (m, 5H) 2.13 (s, 3H) 1.52-1.58 (m, 2H) 1.52 (s, 3H) 1.50 (s, 3H) 0.88 (t, J=7.33 Hz, 3H). LC-MS (ES) m/z=458.3 [M+H]+

Example 27

6-[6-(dimethylamino)-3-pyridinyl]-N-[(4,6-dimethyl-2-oxo-1,2-dihydro-3-pyridinyl)methyl]-1-(1-methylethyl)-1H-indazole-4-carboxamide

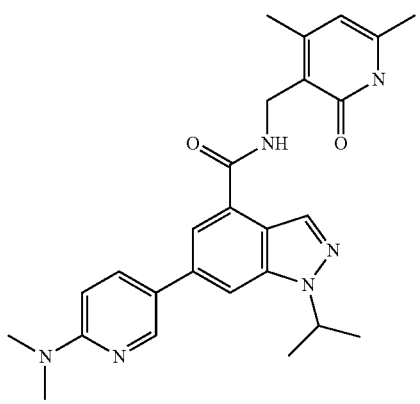

The title compound was prepared in a similar manner as described for example 8 from 6-bromo-N-[(4,6-dimethyl-2-oxo-1,2-dihydro-3-pyridinyl)methyl]-1-(1-methylethyl)-1H-indazole-4-carboxamide (110 mg, 0.264 mmol) and [6-(dimethylamino)-3-pyridinyl]boronic acid (66 mg, 0.395 mmol). The product was collected as a white solid (33 mg, 27%). ¹H NMR (400 MHz, DMSO-d₆) δ ppm 11.54 (s, 1H) 8.64 (d, J=2.27 Hz, 1H) 8.60 (t, J=4.80 Hz, 1H) 8.35 (s, 1H) 8.02-8.06 (m, 2H) 7.84 (s, 1H) 6.77 (d, J=8.84 Hz, 1H) 5.89 (s, 1H) 5.13 (dt, J=13.14, 6.57 Hz, 1H) 4.39 (br. s., 1H) 4.38 (br. s., 1H) 3.09 (s, 6H) 2.22 (s, 3H) 2.13 (s, 3H) 1.50 (s, 3H) 1.49 (s, 3H) LC-MS (ES) m/z=459.2 [M+H]+

Example 28

N-[(4,6-dimethyl-2-oxo-1,2-dihydro-3-pyridinyl)methyl]-1-(1-methylethyl)-6-[6-(trifluoromethyl)-3-pyridinyl]-1H-indazole-4-carboxamide

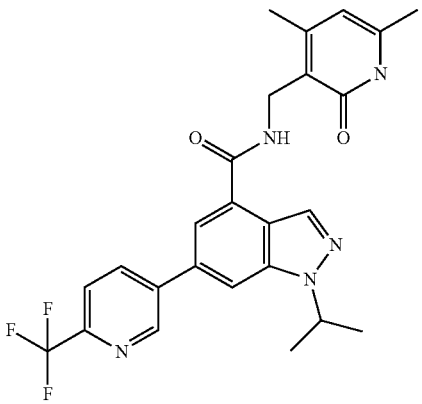 [SMILES: Cc1cc(C)c(CNC(=O)c2cc(-c3ccc(C(F)(F)F)nc3)cc3c2cnn3C(C)C)c(=O)[nH]1]

The title compound was prepared in a similar manner as described for example 8 from 6-bromo-N-[(4,6-dimethyl-2-oxo-1,2-dihydro-3-pyridinyl)methyl]-1-(1-methylethyl)-1H-indazole-4-carboxamide (110 mg, 0.264 mmol) and [6-(trifluoromethyl)-3-pyridinyl]boronic acid (75 mg, 0.395 mmol). The product was collected as a solid (75 mg, 57%). ¹H NMR (400 MHz, DMSO-d₆) δ ppm 11.54 (s, 1H) 9.30 (d, J=2.02 Hz, 1H) 8.66 (t, J=4.93 Hz, 1H) 8.58 (dd, J=8.08, 2.02 Hz, 1H) 8.45 (s, 1H) 8.38 (s, 1H) 8.07 (d, J=8.34 Hz, 1H) 7.98-8.01 (m, 1H) 5.90 (s, 1H) 5.20 (dt, J=13.14, 6.57 Hz, 1H) 4.41 (br. s., 1H) 4.40 (br. s., 1H) 2.22 (s, 3H) 2.13 (s, 3H) 1.53 (s, 3H) 1.51 (s, 3H). LC-MS (ES) m/z=484.1 [M+H]+

Example 29

6-{3-[(dimethylamino)methyl]phenyl}-N-[(4,6-dimethyl-2-oxo-1,2-dihydro-3-pyridinyl)methyl]-1-(1-methylethyl)-1H-indazole-4-carboxamide

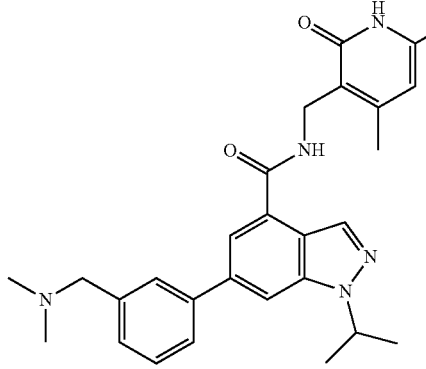

The title compound was prepared in a similar manner as described for example 12 from 6-bromo-1-(1-methylethyl)-N-[(6-methyl-2-oxo-4-methyl-1,2-dihydro-3-pyridinyl)methyl]-1H-indazole-4-carboxamide (100 mg, 0.240 mmol) and dimethyl{[3-(4,4,5,5-tetramethyl-1,3,2-dioxaborolan-2-yl)phenyl]methyl}amine (93 mg, 0.312 mmol). The product obtained from HPLC purification was treated with a saturated solution of NaHCO3, solids that crashed out were filtered, and air-dried for 15 min. The product was then triturated first from EtOAc (containing EtOH) and then hexanes. The solid was then concentrated from MeOH, and triturated with ether, and then dried in vacuum oven overnight. The product was collected as a white solid (56 mg, 56%). 1H NMR (400 MHz, DMSO-d6) δ ppm 11.53 (s, 1H) 8.66 (t, J=4.93 Hz, 1H) 8.37 (s, 1H) 8.09 (s, 1H) 7.83 (s, 1H) 7.71-7.76 (m, 2H) 7.46 (t, J=7.96 Hz, 1H) 7.33 (d, J=7.58 Hz, 1H) 5.89 (s, 1H) 5.19 (quin, J=6.63 Hz, 1H) 4.40 (s, 1H) 4.39 (s, 1H) 3.49 (s, 2H) 2.22 (s, 3H) 2.19 (s, 6H) 2.12 (s, 3H) 1.51 (s, 3H) 1.49 (s, 3H); LC-MS (ES) m/z=472.2 [M+H]+

Example 30

6-{4-[(dimethylamino)methyl]phenyl}-N-[(4,6-dimethyl-2-oxo-1,2-dihydro-3-pyridinyl)methyl]-1-(1-methylethyl)-1H-indazole-4-carboxamide

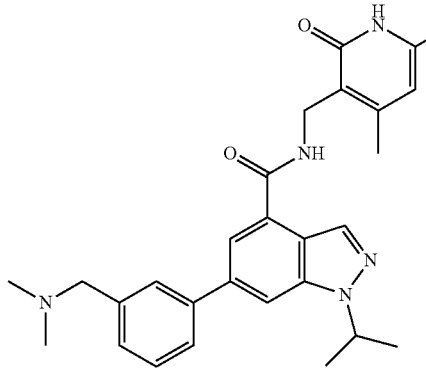

The title compound was prepared in a similar manner as described for example 12 from 6-bromo-1-(1-methylethyl)-N-[(6-methyl-2-oxo-4-methyl-1,2-dihydro-3-pyridinyl)methyl]-1H-indazole-4-carboxamide (100 mg, 0.240 mmol) and dimethyl{[3-(4,4,5,5-tetramethyl-1,3,2-dioxaborolan-3-yl)phenyl]methyl}amine (93 mg, 0.312 mmol). The product obtained from HPLC purification was treated with a saturated solution of NaHCO3, solids that crashed out were filtered, and air-dried for 15 min. The product was then triturated first from EtOAc and then hexanes. The solid was washed with acetonitrile, filtered, and then dried in vacuum oven overnight. The product was collected as a white solid (80 mg, 69%). 1H NMR (400 MHz, DMSO-d6) δ ppm 11.53 (br. s., 1H) 8.65 (t, J=4.93 Hz, 1H) 8.38 (s, 1H) 8.11 (s, 1H) 7.87 (d, J=1.01 Hz, 1H) 7.83 (s, 1H) 7.81 (s, 1H) 7.42 (s, 1H) 7.40 (s, 1H) 5.89 (s, 1H) 5.12-5.21 (m, 1H) 4.40 (s, 1H) 4.39 (s, 1H) 3.44 (s, 2H) 2.22 (s, 3H) 2.17 (s, 6H) 2.12 (s, 3H) 1.51 (s, 3H) 1.49 (s, 3H). LC-MS (ES) m/z=472.2 [M+H]+ 472.2

Example 31

N-((1,2-dihydro-6-methyl-2-oxo-4-propylpyridin-3-yl)methyl)-1-isopropyl-6-(thiophen-3-yl)-1H-indazole-4-carboxamide

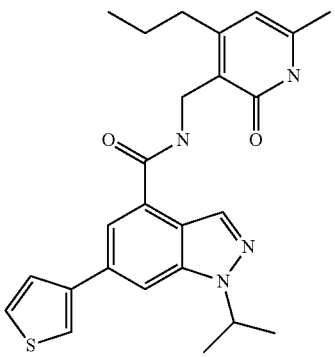 [SMILES: CCCc1cc(C)[nH]c(=O)c1CNC(=O)c1cc(-c2ccsc2)cc2c1cnn2C(C)C]

To a stirred solution of 6-bromo-N-((1,2-dihydro-6-methyl-2-oxo-4-propylpyridin-3-yl)methyl)-1-isopropyl-1H-indazole-4-carboxamide (0.2 g, 0.44 mmol) in DMF (10 mL) was added 4,4,5,5-tetramethyl-2-(thiophen-3-yl)-1,3,2-dioxaborolane (0.113 g, 0.53 mmol) followed by PdCl2(PPh3)2 (0.06 g, 0.08 mmol) and the reaction mixture was stirred for 5 min. Sodium carbonate (0.119 g, 0.940 mmol) dissolved in water (2 mL) was added and the contents were stirred at 120° C. for 3 h. The reaction mixture was diluted with NaHCO3 solution and extracted with ethyl acetate (3×20 mL). The combined organic layers were washed with brine solution (20 mL), dried over anhydrous Na2SO4, filtered, and concentrated in vacuo to afford the crude product. The crude product was purified by silica gel chromatography (eluent: 4% MeOH\EtOAc) to afford the title compound as an off white solid (75 mg, 38%). 1H NMR (DMSO-d6, 400 MHz): δ 0.883 (t, J=7.2 Hz, 3H), 1.491-1.550 (m, 8H), 2.13 (s, 3H), 2.501 (s, 2H), 4.419 (d, J=3.6 Hz, 2H), 5.130 (t, J=6.4 Hz, 1H), 5.912 (s, 1H), 7.691 (s, 1H), 7.766 (d, J=4.4 Hz, 1H), 7.930 (s, 1H), 8.041 (s, 1H), 8.171 (s, 1H), 8.353 (s, 1H), 8.563 (s, 1H), 11.530 (s, 1H). LCMS (ES+) m/z: 449.09.

Example 32

1-isopropyl-N-((6-methyl-2-oxo-4-propyl-1,2-dihydropyridin-3-yl)methyl)-6-(thiophen-3-yl)-1H-indazole-4-carboxamide

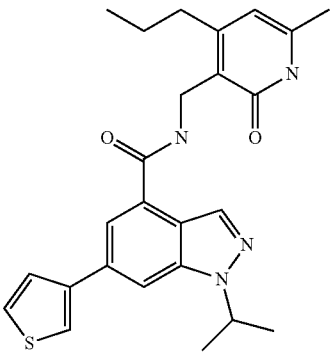 [SMILES: CCCc1cc(C)[nH]c(=O)c1CNC(=O)c1cc(-c2ccsc2)cc2c1cnn2C(C)C]

The title compound was prepared from 6-bromo-N-((1,2-dihydro-6-methyl-2-oxo-4-propylpyridin-3-yl)methyl)-1-isopropyl-1H-indazole-4-carboxamide (0.2 g, 0.44 mmol) and 2-(furan-3-yl)-4,4,5,5-tetramethyl-1,3,2-dioxaborolane (0.1 g, 0.51 mmol) in the same manner as described for example 31. The product was collected as an off-white solid (55 mg, 25.7%). $^1$H NMR (DMSO-$d_6$, 400 MHz): δ 0.896 (t, J=7.2 Hz, 3H), 1.483-1.576 (m, 8H), 2.138 (s, 3H), 2.533 (s, 2H), 4.408 (d, J=4.4 Hz, 2H), 5.076-5.140 (m, 1H), 5.915 (s, 1H), 6.656 (s, 1H), 7.105 (d, J=2.8 Hz, 1H), 7.814 (s, 1H), 7.909 (s, 1H), 8.092 (s, 1H), 8.340 (s, 1H), 8.573 (s, 1H), 11.540 (s, 1H). LCMS (ES+) m/z: 433.1

Example 33

6-{4-[(dimethylamino)methyl]phenyl}-1-(1-methylethyl)-N-[(6-methyl-2-oxo-4-propyl-1,2-dihydro-3-pyridinyl)methyl]-1H-indazole-4-carboxamide hydrochloride salt

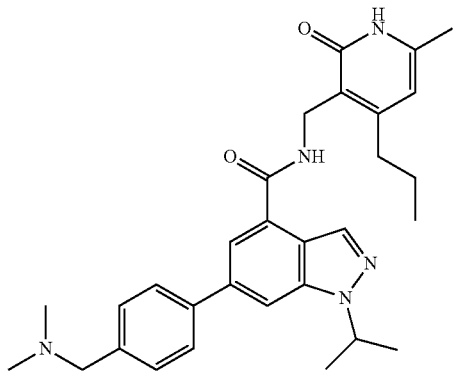

In a glass pressure tube was added 6-bromo-1-(1-methylethyl)-N-[(6-methyl-2-oxo-4-propyl-1,2-dihydro-3-pyridinyl)methyl]-1H-indazole-4-carboxamide (200 mg, 0.449 mmol), 4-(N,N-dimethylaminomethyl)phenylboronic acid pinacol ester hydrochloride (170 mg, 0.571 mmol), potassium phosphate (300 mg, 1.413 mmol), dioxane (12 mL) and water (3 mL). The suspension was stirred and purged with $N_2$ then PdCl$_2$(dppf)-CH$_2$Cl$_2$ adduct (50 mg, 0.061 mmol) was added. The reaction mixture was capped and stirred at 110° C. for 4 hr. The dark black reaction mixture was evaporated to dryness. The crude product was purified by silica gel chromatography (eluent: 0 to 70%, 20% (5% NH$_4$OH in MeOH)/CH$_2$Cl$_2$) in CH$_2$Cl$_2$). The pure fractions were combined and evaporated to dryness to give the product as a very dark brown-black solid. The solid was taken up in CH$_2$Cl$_2$ and treated with Silicycle Si-Thiol (2 g, 1.46 mMol/g). After stirring for 30 minutes on a rotary evaporator (no vacuum) the mixture was filtered through a pad of Celite, washed with CH$_2$Cl$_2$, and evaporated to dryness. The light yellow colored solid was taken up in a small volume of MeOH and treated with 6 N HCl (200 uL) and re-evaporated to dryness. The residue was dissolved in a small volume of MeOH, ppt. with Et$_2$O, triturated, filtered and dried under vacuum to give the product 6-{4-[(dimethylamino)methyl]phenyl}-1-(1-methylethyl)-N-[(6-methyl-2-oxo-4-propyl-1,2-dihydro-3-pyridinyl)methyl]-1H-indazole-4-carboxamide hydrochloride salt as a light tan solid (205 mg, 85% yield). $^1$H NMR (400 MHz, DMSO-$d_6$) δ=11.60 (br. s., 1H), 10.81 (br. s., 1H), 8.69 (t, J=4.9 Hz, 1H), 8.40 (s, 1H), 8.19 (s, 1H), 7.97 (d, J=8.3 Hz, 2H), 7.90 (d, J=1.0 Hz, 1H), 7.71 (d, J=8.3 Hz, 2H), 5.94 (s, 1H), 5.18 (dt, J=6.7, 13.2 Hz, 1H), 4.43 (d, J=4.8 Hz, 2H), 4.34 (d, J=5.3 Hz, 2H), 2.72 (d, J=5.1 Hz, 6H), 2.58-2.52 (m, 2H), 2.14 (s, 3H), 1.59-1.52 (m, 2H), 1.51 (d, J=6.6 Hz, 6H), 0.89 (t, J=7.3 Hz, 3H); LC-MS (ES)+m/e 500.2 [M+H]$^+$.

Example 34

6-{3-[(dimethylamino)methyl]phenyl}-1-(1-methylethyl)-N-[(6-methyl-2-oxo-4-propyl-1,2-dihydro-3-pyridinyl)methyl]-1H-indazole-4-carboxamide hydrochloride salt

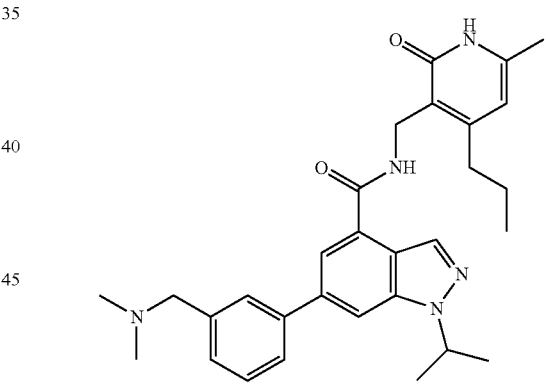

The title compound was prepared in the same manner as described for example 33 using from 6-bromo-1-(1-methylethyl)-N-[(6-methyl-2-oxo-4-propyl-1,2-dihydro-3-pyridinyl)methyl]-1H-indazole-4-carboxamide (200 mg, 0.449 mmol), 3-(N,N dimethylaminomethyl)phenylboronic acid pinacol ester hydrochloride (170 mg, 0.571 mmol), potassium phosphate (300 mg, 1.413 mmol), dioxane (12 mL), water (3 mL), and PdCl$_2$(dppf)-CH$_2$Cl$_2$ adduct (50 mg, 0.061 mmol). The product was obtained as a light tan solid (204 mg, 85% yield). $^1$H NMR (400 MHz, DMSO-$d_6$) δ=11.67 (br. s., 1H), 10.97 (br. s., 1H), 8.68 (t, J=5.1 Hz, 1H), 8.38 (s, 1H), 8.30 (s, 1H), 8.16 (s, 1H), 8.00-7.94 (m, 1H), 7.92 (d, J=1.0 Hz, 1H), 7.65-7.53 (m, 2H), 5.96 (s, 1H), 5.18 (dt, J=6.6, 13.3 Hz, 1H), 4.43 (d, J=5.1 Hz, 2H), 4.38 (d, J=5.6 Hz, 2H), 2.74 (d, J=4.8 Hz, 6H), 2.61-2.52 (m, 2H), 2.15 (s, 3H), 1.59-1.52 (m, 2H), 1.51 (d, J=6.6 Hz, 6H), 0.90 (t, J=7.3 Hz, 3H); LC-MS (ES)+ m/e 500.2 [M+H]$^+$.

Example 35

N-((1,2-dihydro-6-methyl-2-oxo-4-propylpyridin-3-yl)methyl)-1-isopropyl-6-(1H-pyrazol-4-yl)-1H-indazole-4-carboxamide

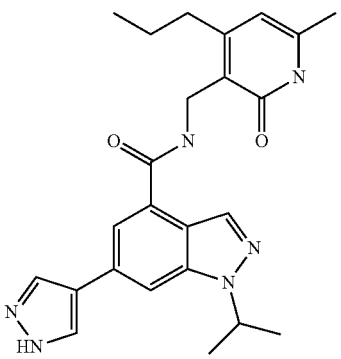

a) Methyl 1-isopropyl-6-(1H-pyrazol-4-yl)-1H-indazole-4-carboxylate

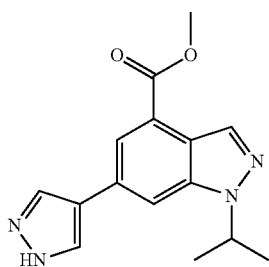 [SMILES: COC(=O)c1cc(-c2cn[nH]c2)cc2c1cnn2C(C)C]

To a stirred solution of methyl 6-bromo-1-isopropyl-1H-indazole-4-carboxylate, 1 (0.8 g, 2.7 mmol) in 1,4-dioxane (20 mL) were added 4-(4,4,5,5-tetramethyl-1,3,2-dioxaborolan-2-yl)-1H-pyrazole (0.576 g, 2.97 mmol) and NaHCO$_3$ (0.567 g, 6.75 mmol) dissolved in water (8 mL). The reaction mixture was degassed with argon gas for 30 min. To the resulting mixture was added PdCl$_2$(dppf)-CH$_2$Cl$_2$ adduct (0.110 g, 0.135 mmol) and the mixture heated at reflux for 3 h. The reaction mixture was diluted with water (30 mL) and extracted with ethyl acetate (100 mL). The organic layer was dried over anhydrous Na$_2$SO$_4$, filtered, and concentrated under reduced pressure to afford 800 mg of crude product. The crude compound was purified by silica gel chromatography (eluent: 5% MeOH/DCM) to the title compound as a pale liquid (375 mg, 47%). LCMS (ES−) m/z=283.11.

b) 1-isopropyl-6-(1H-pyrazol-4-yl)-1H-indazole-4-carboxylic acid

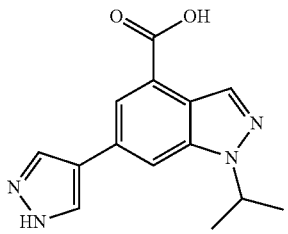 [SMILES: CC(C)n1ncc2c(C(=O)O)cc(-c3cn[nH]c3)cc21]

To a stirred solution of methyl 1-isopropyl-6-(1H-pyrazol-4-yl)-1H-indazole-4-carboxylate (750 mg, 2.64 mmol) in THF:H$_2$O (30 mL) was added LiOH.H$_2$O (330 mg, 7.85 mmol) and the resulting mixture was refluxed at 80° C. for 8 h. THF was distilled off under reduced pressure and the aqueous layer was acidified with 10% HCl (to pH ~5) at 0° C. The precipitated solid was collected by filtration and dried to afford the title compound 1-isopropyl-6-(1H-pyrazol-4-yl)-1H-indazole-4-carboxylic acid as an off-white solid (540 mg, 76%). LCMS (ES+) m/z=271.09.

c) N-((1,2-dihydro-6-methyl-2-oxo-4-propylpyridin-3-yl)methyl)-1-isopropyl-6-(1H-pyrazol-4-yl)-1H-indazole-4-carboxamide To a stirred solution of N-((1,2-dihydro-6-methyl-2-oxo-4-propylpyridin-3-yl)methyl)-1-isopropyl-6-(1H-pyrazol-4-yl)-1H-indazole-4-carboxamide (550 mg, 2.037 mmol) in DCM (20 mL) were added EDC.HCl (466 mg, 2.44 mmol), HOBT (374 mg, 2.44 mmol) and DIPEA (1.8 mL, 10.18 mmol) and the contents stirred at room temperature for 15 min. To the resulting mixture 3-(amino methyl)-4,6-dimethylpyridin-2(1H)-one (338 mg, 2.037 mmol) was added and stirred at RT for 3 h. The reaction mixture was diluted with DCM (50 mL) and washed with water (20 mL). The DCM layer was dried over anhydrous sodium sulphate, filtered, and concentrated to afford 200 mg of crude product. The crude product was diluted with DCM (5 mL), filtered, and dried to afford N-((1,2-dihydro-6-methyl-2-oxo-4-propylpyridin-3-yl)methyl)-1-isopropyl-6-(1H-pyrazol-4-yl)-1H-indazole-4-carboxamide as an off-white solid (80 mg, 10%). $^1$H NMR (DMSO-d$_6$, 400 MHz): δ 0.907-0.871 (t, 3H, J=14.4 Hz), 1.55-1.48 (m, 8H), 2.134 (s, 3H), 2.555 (s, 2H), 4.417-4.406 (d, 1H, J=4.4 Hz), 5.059 (m, 1H), 5.913 (s, 1H), 7.830 (s, 1H), 8.047 (s, 1H), 8.080 (s, 1H), 8.306 (s, 2H), 8.462 (s, 1H), 11.53 (s, 1H), 13 (bs, 1H). LCMS (ES+) m/z=433.17.

Example 36

N-((1,2-dihydro-6-methyl-2-oxo-4-propylpyridin-3-yl)methyl)-1-isopropyl-6-(1H-pyrrolo[2,3-b]pyridin-5-yl)-1H-indazole-4-carboxamide

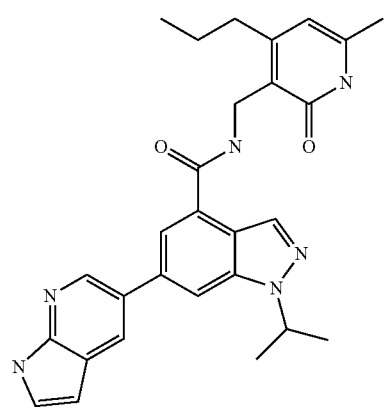

a) Methyl 1-isopropyl-6-(1H-pyrrolo[2,3-b]pyridin-5-yl)-1H-indazole-4-carboxylate

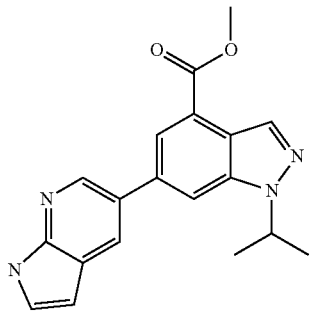 [SMILES: COC(=O)c1cc(-c2cnc3[nH]ccc3c2)cc2c1cnn2C(C)C]

The title compound was prepared in the same manner as described for example 35 (step a) from methyl 6-bromo-1-isopropyl-3-methyl-1H-indazole-4-carboxylate (1 g, 3.36 mmol) and 5-(4,4,5,5-tetramethyl-1,3,2-dioxaborolan-2-yl)-1H-pyrrolo[2,3-b]pyridine (0.98 g, 4.04 mmol) wherein the reaction mixture was stirred at 100° C. for 5 h. The product was collected as an off white solid (600 mg, 53%). LCMS (ES−) m/z: 333.08.

b) 1-isopropyl-6-(1H-pyrrolo[2,3-b]pyridin-5-yl)-1H-indazole-4-carboxylic acid

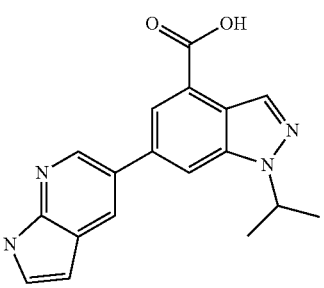 [SMILES: CC(C)n1ncc2c(C(=O)O)cc(-c3cnc4[nH]ccc4c3)cc21]

The title compound was prepared in the same manner as described for example 35 (step b) from methyl 1-isopropyl-6-(1H-pyrrolo[2,3-b]pyridin-5-yl)-1H-indazole-4-carboxylate 1 (0.6 g, 1.79 mmol) and LiOH.H$_2$O (0.22 g, 5.37 mmol) wherein the mixture was heated at 80° C. for 5 h. The product was collected as an off-white solid (0.5 g, 87.7%). $^1$H NMR (DMSO-d$_6$, 400 MHz): δ 1.530 (d, J=6.4 Hz, 6H), 5.199-5.265 (m, 1H), 6.552 (d, J=1.6 Hz, 1H), 7.550 (t, J=2.4 Hz, 1H), 8.11 (s, 1H), 8.328 (s, 1H), 8.383 (d, J=1.6 Hz, 1H), 8.401 (s, 1H), 8.671 (d, J=1.6 Hz, 1H), 11.77 (brs, 1H). LCMS (ES+) m/z: 321.24.

c) N-((1,2-dihydro-6-methyl-2-oxo-4-propylpyridin-3-yl)methyl)-1-isopropyl-6-(1H-pyrrolo[2,3-b]pyridin-5-yl)-1H-indazole-4-carboxamide The title compound was prepared in the same manner as described for example 35 (step c) from 1-isopropyl-3-methyl-6-(pyridin-3-yl)-1H-indazole-4-carboxylic acid and 3-(aminomethyl)-6-methyl-4-propylpyridin-2(1H)-one (0.28 g, 1.56 mmol). The crude product was purified by silica gel chromatography (eluent: 5% MeOH\EtOAc) to afford the product as an off-white solid (200 mg, 26%). $^1$H NMR (DMSO-d$_6$, 400 MHz): δ 0.886 (t, J=7.2 Hz, 3H), 1.513 (d, J=6.4 Hz, 8H), 2.131 (s, 3H), 2.552 (s, 2H), 4.431 (d, J=4.4 Hz, 1H), 5.153-5.216 (m, 1H), 5.911 (s, 1H), 6.535 (d, J=2 Hz, 2H), 7.535 (s, 1H), 7.930 (s, 1H), 8.174 (s, 1H), 8.40 (d, J=9.6 Hz, 2H), 8.656 (s, 1H), 8.730 (s, 1H), 11.526 (brs, 1H), 11.756 (brs, 1H); LC-MS (ES+) m/z: 483.19.

Example 37

6-(4-(dimethylamino)piperidin-1-yl)-1-isopropyl-N-((6-methyl-2-oxo-4-propyl-1,2-dihydropyridin-3-yl)methyl)-1H-indazole-4-carboxamide

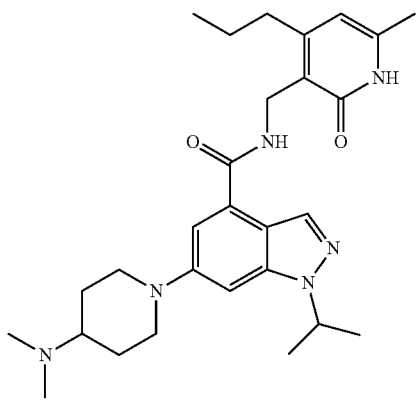

a) Methyl 6-(4-(dimethylamino)piperidin-1-yl)-1-isopropyl-1H-indazole-4-carboxylate

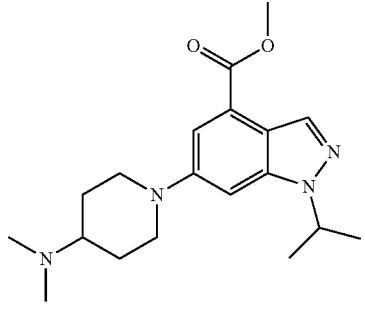 [SMILES: COC(=O)c1cc(N2CCC(N(C)C)CC2)cc2c1cnn2C(C)C]

To a 10-mL microwave tube were added methyl 6-bromo-1-(1-methylethyl)-1H-indazole-4-carboxylate (200 mg, 0.673 mmol), N,N-dimethyl-4-piperidinamine (95 mg, 0.740 mmol), toluene (3 mL), and cesium carbonate (329 mg, 1.010 mmol), and the mixture was degassed for 5 min by bubbling N$_2$. BINAP (62.9 mg, 0.101 mmol) and Pd$_2$(dba)$_3$ (30.8 mg, 0.034 mmol) were added. The tube was sealed and the mixture was heated at 115° C. with stirring for 15 h. The mixture was diluted with methanol (5 mL) and filtered. The filtrate was concentrated and the residue was purified using reverse-phase HPLC to give 58 mg of product as an off-white solid. $^1$H NMR (400 MHz, DMSO-d$_6$) δ ppm 1.45 (d, J=8.0 Hz, 6H), 1.54-1.61 (m, 2H), 1.87-1.96 (m, 2H), 2.31 (m, 6H), 2.80-2.83 (m, 2H), 3.83-3.86 (m, 2H), 3.93 (s, 3H), 4.98-5.04 (m, 1H), 7.29 (s, 1H), 7.57 (s, 1H), 8.17 (s, 1H). LCMS: (M+H)$^+$=345.2 b) 6-(4-(dimethylamino)piperidin-1-yl)-1-isopropyl-1H-indazole-4-carboxylic acid

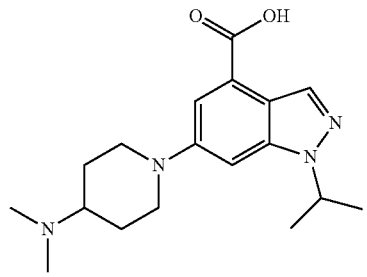 [SMILES: CC(C)n1ncc2c(C(=O)O)cc(N3CCC(N(C)C)CC3)cc21]

To a solution of methyl 6-bromo-3-methyl-1-(1-methylethyl)-1H-indole-4-carboxylate (520 mg, 1.676 mmol) in methanol (8 mL) and tetrahydrofuran (3.00 mL) was added sodium hydroxide (2.79 mL, 8.38 mmol), and the mixture was stirred overnight. The mixture was concentrated to remove organic solvents and diluted with water (5 mL). The aqueous solution was acidified to ~pH 3 using 1N HCl and the precipitate was collected by filtration and dried under high vacuum to give 480 mg of product as a white solid. $^1$H NMR (400 MHz, DMSO-$d_6$) δ ppm 1.45-1.46 (d, J=8.0 Hz, 6H), 1.75-1.78 (m, 2H), 2.10-2.12 (m, 2H), 2.80-2.89 (m, 8H), 3.35-3.40 (m, 1H), 3.97-4.00 (m, 2H), 4.97-5.04 (m, 1H), 7.34 (s, 1H), 7.58 (s, 1H), 8.18 (s, 1H); LCMS: (M+H)$^+$=296.3 c) 6-(4-(dimethylamino)piperidin-1-yl)-1-isopropyl-N-((6-methyl-2-oxo-4-propyl-1,2-dihydropyridin-3-yl)methyl)-1H-indazole-4-carboxamide To a solution of 6-[4-(dimethylamino)-1-piperidinyl]-1-(1-methylethyl)-1H-indazole-4-carboxylic acid (34 mg, 0.103 mmol) in DMSO (1 mL) were added 3-(aminomethyl)-6-methyl-4-propyl-2(1H)-pyridinone (29.0 mg, 0.134 mmol), N-methylmorpholine (0.045 mL, 0.412 mmol), 1-hydroxy-7-azabenzotriazole (28.0 mg, 0.206 mmol) and EDC (39.5 mg, 0.206 mmol), and the mixture was stirred for 48 h. The mixture was purified using reverse-phase HPLC to afford the title compound as a pale yellow solid (34 mg). $^1$H NMR (400 MHz, DMSO-$d_6$) δ ppm 0.77-0.96 (m, 3H), 1.43 (d, J=6.57 Hz, 6H), 1.46-1.66 (m, 4H), 1.89 (m, 2H), 2.13 (s, 3H), 2.31 (s, 6H), 2.33 (m, 2H), 2.55 (s, 3H), 2.65-2.84 (m, 2H), 3.86 (m. 2H), 4.38 (m, 2H), 4.85-5.04 (m, 1H), 5.91 (s, 1H), 7.07 (s, 1H), 7.32 (m, 1H), 8.15 (m, 1H), 8.25 (br. s., 1H), 8.44 (t, J=4.93 Hz, 1H); LCMS: (M+H)=493.2

Example 38

6-(4-((dimethylamino)methyl)piperidin-1-yl)-1-isopropyl-N-((6-methyl-2-oxo-4-propyl-1,2-dihydropyridin-3-yl)methyl)-1H-indazole-4-carboxamide

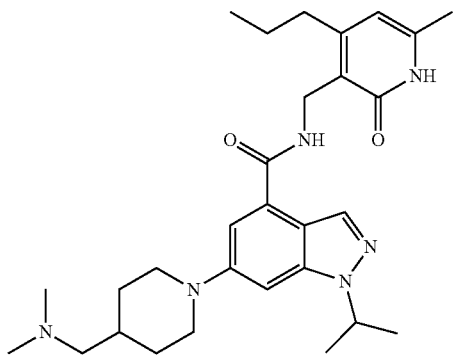

a) Methyl 6-(4-((dimethylamino)methyl)piperidin-1-yl)-1-isopropyl-1H-indazole-4-carboxylate

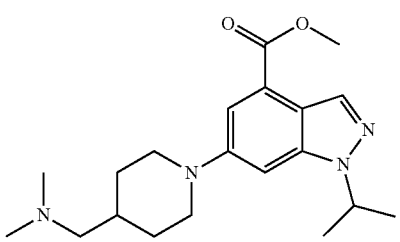 [SMILES: COC(=O)c1cc(N2CCC(CN(C)C)CC2)cc2c1cnn2C(C)C]

To a 10-mL microwave tube were added methyl 6-bromo-1-(1-methylethyl)-1H-indazole-4-carboxylate (250 mg, 0.841 mmol), N,N-dimethyl-1-(4-piperidinyl)methanamine (132 mg, 0.925 mmol), Toluene (3 mL), and cesium carbonate (411 mg, 1.262 mmol), and the mixture was degassed for 5 min by bubbling N2 through. BINAP (79 mg, 0.126 mmol) and Pd$_2$(dba)$_3$ (38.5 mg, 0.042 mmol) were added. The tube was sealed and the mixture was heated at 115° C. with stirring for 15 h. The mixture was diluted with methanol (5 mL) and filtered. The filtrate was concentrated and the residue was purified using reverse-phase HPLC to give 35 mg of product as a off-white solid. LCMS MH+=359.3 b) 6-(4-((dimethylamino)methyl)piperidin-1-yl)-1-isopropyl-1H-indazole-4-carboxylic acid

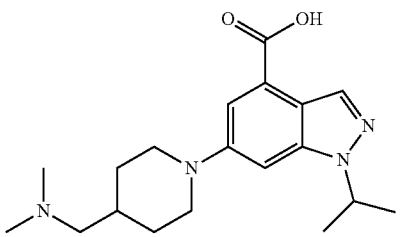 [SMILES: CC(C)n1ncc2c(C(=O)O)cc(N3CCC(CN(C)C)CC3)cc21]

The title compound was prepared using the procedure described for example 37 (step b) $^1$H NMR (400 MHz, DMSO-$d_6$) δ ppm 1.26-1.29 (m, 2H), 1.43-1.45 (m, 6H), 2.27-2.30 (m, 8H), 2.76-2.78 (m, 2H), 3.77-3.81 (m, 2H), 3.97-4.00 (m, 2H), 4.97-5.03 (m, 1H), 7.20 (s, 1H), 7.53 (s, 1H), 8.16 (s, 1H); LCMS: (M+H)$^+$=345.2 c) 6-(4-((dimethylamino)methyl)piperidin-1-yl)-1-isopropyl-N-((6-methyl-2-oxo-4-propyl-1,2-dihydropyridin-3-yl)methyl)-1H-indazole-4-carboxamide The title compound was prepared using the procedure described for example 37 (step c) from 6-(4-((dimethylamino)methyl)piperidin-1-yl)-1-isopropyl-1H-indazole-4-carboxylic acid and 3-(aminomethyl)-6-methyl-4-propyl-2(1H)-pyridinone. $^1$H NMR (400 MHz, DMSO-$d_6$) δ ppm 0.89 (t, J=7.33 Hz, 3H), 1.14-1.32 (m, 2H), 1.42 (m, 6H), 1.45-1.55 (m, 2H), 1.57-1.68 (m, 1H), 1.72-1.89 (m, 3H), 2.03-2.21 (m, 12H), 2.63-2.79 (m, 2H), 3.54-3.66 (m, 1H), 3.81 (m, 2H), 4.37 (d, J=4.80 Hz, 2H), 4.94 (quin, J=6.63 Hz, 1H), 5.91 (s, 1H), 7.05 (s, 1H), 7.32 (d, J=1.77 Hz, 1H), 8.14 (s, 1H), 8.44 (t, J=5.05 Hz, 2H), 11.24-11.80 (m, 1H); LCMS: (M+H)+=507.1

Example 39

N-((4-ethyl-6-methyl-2-oxo-1,2-dihydropyridin-3-yl)methyl)-1-isopropyl-6-morpholino-1H-indazole-4-carboxamide

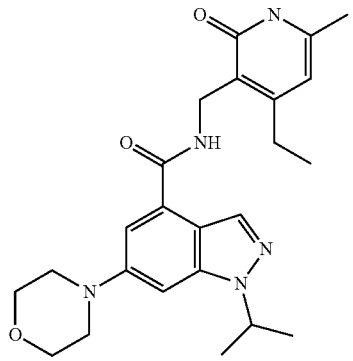 [SMILES: CCc1cc(C)[nH]c(=O)c1CNC(=O)c1cc(N2CCOCC2)cc2c1cnn2C(C)C]

a) 1-isopropyl-6-morpholino-1H-indazole-4-carboxylic acid

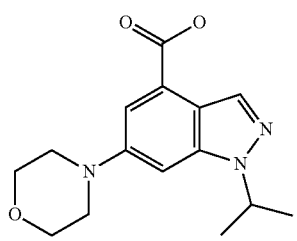 [SMILES: CC(C)n1ncc2c(C(=O)O)cc(N3CCOCC3)cc21]

In a 25 mL sealable tube under nitrogen were combined methyl 6-bromo-1-(1-methylethyl)-1H-indazole-4-carboxylate (250 mg, 0.84 mmol), sodium tert-butoxide (178 mg, 1.85 mmol), Pd-XPhos precatalyst (chloro(2-dicyclohexylphosphino-2',4',6'-tri-i-propyl-1,1'-biphenyl)[2-(2-aminoethyl)phenyl]Pd(II); Me-t-butylether adduct) (34.8 mg, 0.042 mmol) and morpholine (81 mg, 0.93 mmol) in Dioxane (4 mL). The resulting mixture was degassed with nitrogen for 10 minutes. The vessel was sealed and the mixture was heated at 98° C. for 20 hours. The contents were diluted with water and 1N HCl was added to adjust the pH~3-4. The contents were extracted with EtOAc and DCM/isopropanol (8:2), and the combined organic layers were washed with brine, dried over MgSO$_4$, filtered and concentrated. The residue was dissolved in DCM and purified by SiO$_2$ chromatography (eluent: Hexanes/EtOAc gradient 0 to 100% EtOAc). Fractions were evaporated and solids were dried to afford the title compound as a light yellow solid (115 mg, 46%). LC-MS (ES) m/z=290.2. $^1$H NMR (400 MHz, DMSO-d$_6$) δ ppm 13.13 (br. s., 1H) 8.18 (s, 1H) 7.56 (d, J=2.02 Hz, 1H) 7.26-7.29 (m, 1H) 5.00 (quin, J=6.57 Hz, 1H) 3.77-3.81 (m, 4H) 3.22-3.26 (m, 4H) 1.46 (s, 3H) 1.44 (s, 3H)

b) In a 25 mL sealable tube under nitrogen were combined 1-(1-methylethyl)-6-(4-morpholinyl)-1H-indazole-4-carboxylic acid (55 mg, 0.19 mmol) and 3-(aminomethyl)-4-ethyl-6-methyl-2(1H)-pyridinone.HCl (57.8 mg, 0.29 mmol) in DMSO (2 mL). 1-hydroxy-7-azabenzotriazole (44 mg, 0.32 mmol) was added and the resulting mixture was degassed with nitrogen for 10 minutes. N-methylmorpholine (0.088 ml, 0.8 mmol) and EDC (62 mg, 0.32 mmol) were added, the vessel was sealed, and the mixture was stirred at room temperature overnight. The crude product was purified by reversed-phase HPLC (15% to 80% CH$_3$CN in water with 0.1% TFA) which afforded the TFA salt. CH$_3$CN was evaporated, a saturated solution of sodium bicarbonate was added, and solids that precipitated were filtered. EtOAc was added along with some hexanes and the contents were sonicated. Solids that precipitated were filtered and dried to afford the title compound as an off-white solid (47.5 mg, 56%). $^1$H NMR (400 MHz, DMSO-d$_6$) δ ppm 11.46 (br. s., 1H) 8.48 (br. s., 1H) 8.18 (s, 1H) 7.32-7.37 (m, 1H) 7.10 (s, 1H) 5.93 (s, 1H) 4.95 (dt, J=13.14, 6.57 Hz, 1H) 4.38 (br. s., 1H) 4.37 (br. s., 1H) 3.74-3.81 (m, 4H) 3.20-3.25 (m, 4H) 2.53-2.60 (m, 2H) 2.14 (s, 3H) 1.45 (s, 3H) 1.43 (s, 3H) 1.09 (t, J=7.45 Hz, 3H); LC-MS (ES) m/z=437.9

Example 40

N-((4,6-dimethyl-2-oxo-1,2-dihydropyridin-3-yl)methyl)-1-isopropyl-6-morpholino-1H-indazole-4-carboxamide

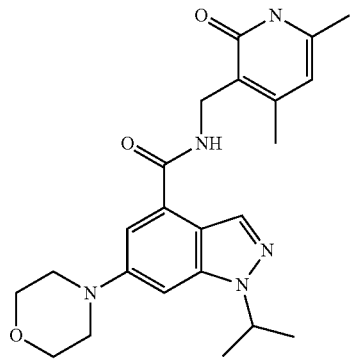 [SMILES: Cc1cc(C)c(CNC(=O)c2cc(N3CCOCC3)cc3c2cnn3C(C)C)c(=O)[nH]1]

The title compound was prepared in the same manner as described for example 39 from 1-(1-methylethyl)-6-(4-morpholinyl)-1H-indazole-4-carboxylic acid (55 mg, 0.19 mmol) and 3-(aminomethyl)-4,6-dimethyl-2(1H)-pyridinone.HCl (53.8 mg, 0.29 mmol) The product was collected as an off-white solid (48 mg, 57%). $^1$H NMR (400 MHz, DMSO-d$_6$) δ ppm 11.44 (br. s., 1H) 8.49 (br. s., 1H) 8.18 (s, 1H) 7.35 (d, J=1.77 Hz, 1H) 7.10 (s, 1H) 5.88 (s, 1H) 4.95 (quin, J=6.57 Hz, 1H) 4.36 (br. s., 1H) 4.34 (br. s., 1H) 3.75-3.80 (m, 4H) 3.21-3.25 (m, 4H) 2.20 (s, 3H) 2.12 (s, 3H) 1.44 (s, 3H) 1.43 (s, 3H); LC-MS (ES) m/z=423.9

Example 41

N-((4-cyclohexyl-6-methyl-2-oxo-1,2-dihydropyridin-3-yl)methyl)-6-cyclopropyl-1-isopropyl-1H-indazole-4-carboxamide

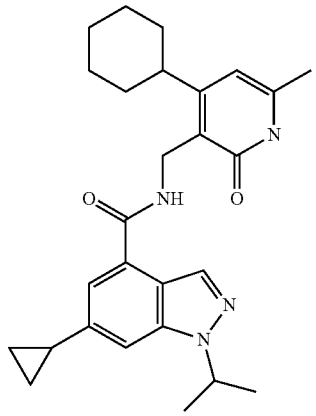 [SMILES: Cc1cc(C2CCCCC2)c(CNC(=O)c2cc(C3CC3)cc3c2cnn3C(C)C)c(=O)[nH]1]

a) 6-bromo-N-((4-cyclohexyl-6-methyl-2-oxo-1,2-dihydropyridin-3-yl)methyl)-1-isopropyl-1H-indazole-4-carboxamide

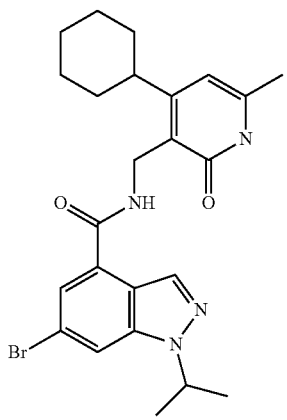 [SMILES: Cc1cc(C2CCCCC2)c(CNC(=O)c2cc(Br)cc3c2cnn3C(C)C)c(=O)[nH]1]

6-bromo-1-(1-methylethyl)-1H-indazole-4-carboxylic acid (237 mg, 0.84 mmol), 3-(aminomethyl)-4-cyclohexyl-6-methyl-2(1H)-pyridinone TFA (378 mg, 1.13 mmol) and 1-hydroxy-7-azabenzotriazole (171 mg, 1.26 mmol) were stirred in 10 mL of DMSO for 10 min under nitrogen. N-methylmorpholine (0.37 ml, 3.35 mmol) was added along with EDC (241 mg, 1.26 mmol) and the mixture was stirred at rt overnight. An additional 0.2 eq of pyridinone, HOAt, NMM and EDC were added and the contents were stirred at rt overnight. The reaction mixture was then poured onto ice-water. A solution of 10% $K_2CO_3$ in water was added to afford a pH ~8-9 solution. The reaction mixture was stirred at rt for 30 min and then allowed to stand at rt for 30 min. Precipitated solids were filtered and air-dried. The collected solid was treated with EtOAc (not soluble) and hexanes, and then concentrated in vacuo. To the isolated solid was then added DMF followed by heating and sonication. Water was added and beige solids crashed out. The precipitated solids were filtered, washed with water, air-dried, and dried in vacuum oven for 2 hours. The title compound was collected as a solid (308 mg, 74%). $^1$H NMR (400 MHz, DMSO-$d_6$) δ ppm 11.53 (s, 1H) 8.63 (t, J=4.80 Hz, 1H) 8.37 (s, 1H) 8.20 (s, 1H) 7.68 (d, J=1.26 Hz, 1H) 6.01 (s, 1H) 5.05 (dt, J=13.14, 6.57 Hz, 1H) 4.43 (d, J=4.80 Hz, 2H) 2.84 (t, J=11.24 Hz, 1H) 2.15 (s, 3H) 1.70 (d, J=13.39 Hz, 2H) 1.60 (d, J=12.13 Hz, 3H) 1.47 (s, 3H) 1.45 (s, 3H) 1.42 (br. s., 1H) 1.17-1.39 (m, 4H); LCMS: 485.2/487.2 (Br pattern).

b) N-((4-cyclohexyl-6-methyl-2-oxo-1,2-dihydropyridin-3-yl)methyl)-6-cyclopropyl-1-isopropyl-1H-indazole-4-carboxamide In a 25 mL sealable tube under nitrogen were combined 6-bromo-N-[(4-cyclohexyl-6-methyl-2-oxo-1,2-dihydro-3-pyridinyl)methyl]-1-(1-methylethyl)-1H-indazole-4-carboxamide (98 mg, 0.2 mmol), 2-cyclopropyl-4,4,5,5-tetramethyl-1,3,2-dioxaborolane (50.9 mg, 0.3 mmol) in dioxane/water (3 mL:1 mL). $PdCl_2$(dppf)-$CH_2Cl_2$ adduct (8.24 mg, 0.011 mmol) was added and the resulting mixture was degassed with nitrogen for 10 min. Sodium bicarbonate (50.9 mg, 0.61 mmol) was added, the vessel was sealed, and the insoluble mixture was heated in a microwave at 110° C. for 20 min, then at 120° C. for 15 min and then at 130° C. for 15 min. Upon cooling down, water was added, and solids that crashed out were filtered. DCM/MeOH (1:1) was added, the contents pre-absorbed on silica gel, and purified by $SiO_2$ chromatography (eluent: gradient 0 to 80:20:2 DCM/MeOH/$NH_4OH$). The collected product was further purified by reverse-phase HPLC (15% to 80% $CH_3CN$ in water with 0.1% TFA) which afforded the TFA salt. $CH_3CN$ was evaporated, a saturated solution of sodium bicarbonate was added to the water layer and it was further concentrated. Upon sitting for 2 weeks, solids that precipitated were filtered and dried to afford the title compound as a light orange solid (17 mg, 18%). $^1$H NMR (400 MHz, DMSO-$d_6$) δ ppm 11.48 (br. s., 1H) 8.46 (br. s., 1H) 8.25 (s, 1H) 7.57 (s, 1H) 7.16 (s, 1H) 6.01 (s, 1H) 4.93-5.04 (m, 1H) 4.45 (br. s., 1H) 4.43 (br. s., 1H) 2.84 (t, J=11.49 Hz, 1H) 2.15 (s, 3H) 2.03-2.10 (m, 1H) 1.60 (br. s., 5H) 1.47 (s, 3H) 1.45 (s, 3H) 1.16-1.42 (m, 5H) 0.96-1.02 (m, 2H) 0.80-0.85 (m, 2H). LC-MS (ES) m/z=447

Example 42

6-bromo-1-ethyl-1H-indazole-4-carboxylic acid (6-methyl-2-oxo-4-propyl-1,2-dihydro-pyridin-3-ylmethyl)-amide

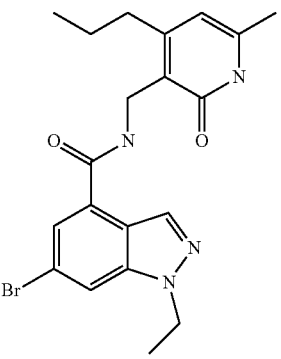 [SMILES: CCCc1cc(C)[nH]c(=O)c1CNC(=O)c1cc(Br)cc2c1cnn2CC]

a) 6-bromo-1-ethyl-1H-indazole-4-carboxylic acid methyl ester and methyl 6-bromo-2-ethyl-2H-indazole-4-carboxylate

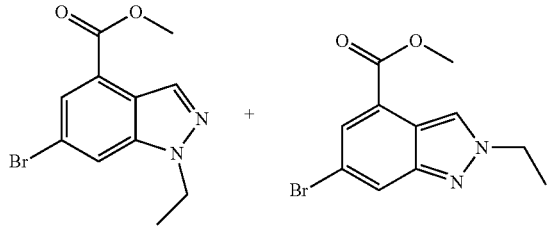 [SMILES: CCn1ncc2c(C(=O)OC)cc(Br)cc21 ; CCn1cc2c(C(=O)OC)cc(Br)cc2n1]

To a stirred suspension of 6-bromo-1H-indazole-4-carboxylic acid methyl ester (2.5 g, 9.8 mmol) and $K_2CO_3$ (2 g, 14.7 mmol) in DMF (50 mL) was added 1-bromoethane (1.28 g, 11.76 mmol) at RT. The contents were stirred for 2 h at 50° C. The reaction mixture was then diluted with water (100 mL) and extracted with ethyl acetate (3×50 mL). The combined organic layers were washed with water (3×30 mL), brine solution (2×30 mL), dried over anhydrous sodium sulphate, and filtered. The crude product was purified by silica gel chromatography (eluent: 0 to 30% EtOAc in petroleum ether) to afford the title compound 6-bromo-1-ethyl-1H-indazole-4-carboxylic acid methyl ester (700 mg, 25%) and the undesired isomer 6-bromo-2-ethyl-2H-indazole-4-carboxylic acid methyl ester (500 mg, 18%) as white solids. $^1$H NMR (400 MHz, DMSO-$d_6$) (1-ethyl isomer): δ 1.41-1.37 (t, 3H), 3.95 (s, 3H), 4.51-4.49 (m, 2H), 7.85-7.84 (d, J=1.2 Hz, 1H), 8.41-8.39 (d, J=10 Hz, 1H). LCMS (ES+): m/z=283 [M+1], 285.02 [M+2].

b) 6-bromo-1-ethyl-1H-indazole-4-carboxylic acid (6-methyl-2-oxo-4-propyl-1,2-dihydro-pyridin-3-ylmethyl)-amide Step 1: To a stirred solution of 6-bromo-1-ethyl-1H-indazole-4-carboxylic acid methyl ester (700 mg, 2.47 mmol) in THF (35 mL) was added a solution of LiOH.H$_2$O (312 mg, 7.42 mmol) in water (15 mL) and the mixture was stirred at RT for 4 h. The reaction mixture was concentrated under reduced pressure, diluted with water (30 mL) and washed with EtOAc (2×25 mL). The aqueous layer was acidified (pH ~5) with 1N HCl. The precipitated solid was collected by filtration and dried to furnish 6-bromo-1-ethyl-1H-indazole-4-carboxylic acid as a white solid (450 mg, 68%).

Step 2: To a stirred suspension of 6-bromo-1-ethyl-H-indazole-4-carboxylic acid, 4 (450 mg, 1.67 mmol) in DCM (50 mL) were added EDC.HCl (384 mg, 2.00 mmol), HOBt.H$_2$O (306 mg, 2.00 mmol) and then stirred for 15 min at RT. To the resulting mixture, DIPEA (1.2 mL, 5.59 mmol) followed by 3-aminomethyl-6-methyl-4-propyl-1H-pyridin-2-one (301 mg, 1.67 mmol) were added and the contents stirred for 18 h at RT. The reaction mixture was diluted with DCM (50 mL) and washed with water (2×50 mL), 10% aq citric acid solution (2×50 mL), saturated aq NaHCO$_3$ solution (2×30 mL) and brine (2×50 mL). The organic layer was dried over Na$_2$SO$_4$, filtered, and concentrated under reduced pressure. The obtained solid was washed with diethyl ether (2×50 mL) to afford the title compound as a white solid (230 mg, 32%). $^1$H NMR (400 MHz, DMSO-d$_6$): δ 0.83-0.79 δ (t, 3H), 1.38 (t, 3H), 1.55 (m, 2H), 2.15 (s, 3H), 2.49 (s, 2H), 4.38 (d, 2H), 4.43 (m, 2H), 5.90 (s, 1H), 7.64 (d, 1H), 8.19 (s, 1H), 8.38 (s, 1H), 8.61 (m, 1H), 11.51 (bs, 1H). LCMS (ES+): m/z=431.15.

Example 43

6-bromo-N-((6-methyl-2-oxo-4-propyl-1,2-dihydropyridin-3-yl)methyl)-1-propyl-1H-indazole-4-carboxamide

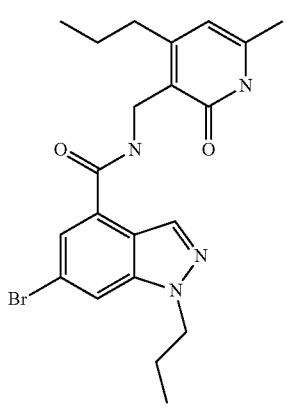 [SMILES: CCCc1cc(C)[nH]c(=O)c1CNC(=O)c1cc(Br)cc2c1cnn2CCC]

a) 6-Bromo-1-propyl-1H-indazole-4-carboxylic acid methyl ester

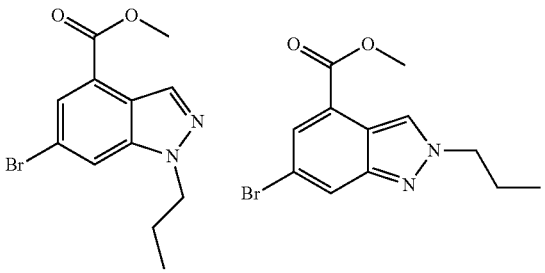 [SMILES: CCCn1ncc2c(C(=O)OC)cc(Br)cc21 ; CCCn1cc2c(C(=O)OC)cc(Br)cc2n1]

The title compounds were prepared in the same manner as described for example 42 (step a) from 6-bromo-1H-indazole-4-carboxylic acid methyl ester (3.0 g, 11.66 mmol) and 1-propyl bromide (1.59 g, 12.94 mmol) wherein the contents were heated at 40° C. for 30 min. The obtained crude products were purified by silica gel chromatography (eluent: 10% ethyl acetate in petroleum ether) to afford the title compounds 6-bromo-1-propyl-1H-indazole-4-carboxylic acid methyl ester (700 mg, 20%) and undesired isomer 6-bromo-2-propyl-2H-indazole-4-carboxylic acid methyl ester (700 mg, 20%) as white solids. $^1$H NMR (400 MHz, DMSO-d$_6$): (N1-propyl isomer): δ 0.83-0.80 δ (t, J=7.6, 3H), 1.84-1.81 (t, J=14.4 Hz, 2H), 3.95-3.94 (d, J=5.2 Hz 3H), 4.45-4.43 (t, 2H), 7.84 (d, J=1.2 Hz, 1H), 8.43 (d, J=14 Hz, 2H). LCMS (ES+): m/z=297.06.

b) 6-bromo-1-propyl-1H-indazole-4-carboxylic acid

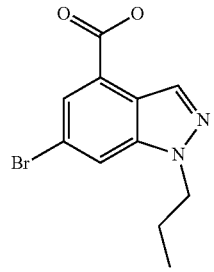 [SMILES: CCCn1ncc2c(C(=O)O)cc(Br)cc21]

The title compound was prepared in the same manner as described for example 42 (step b, part 1) from 6-bromo-1-propyl-1H-indazole-4-carboxylic acid, 7 (700 mg, 2.35 mmol) and LiOH.H$_2$O (290 mg, 7.07 mmol). The product was collected as an off-white solid (600 mg, 90%). $^1$H NMR (400 MHz, DMSO-d$_6$): δ 0.83-0.80 δ (t, 3H), 1.86-1.81 (m, 2H), 4.44-4.40 (t, 2H), 7.81 (d, J=1.2 Hz, 1H), 8.38 (d, J=4.4 Hz, 2H). LCMS (ES−): m/z=281.14 [M−2H].

c) 6-bromo-N-((6-methyl-2-oxo-4-propyl-1,2-dihydropyridin-3-yl)methyl)-1-propyl-1H-indazole-4-carboxamide The title compound was prepared in the same manner as described for example 42 (step b, part 2) from 6-bromo-1-propyl-1H-indazole-4-carboxylic acid (300 mg, 1.06 mmol) and 3-aminomethyl-6-methyl-4-propyl-1H-pyridin-2-one (190 mg, 1.06 mmol). The crude product was triturated with diethyl ether (10 mL) and n-pentane (10 mL) to afford the title compound as a white solid (200 mg, 42.5%). $^1$H NMR (400 MHz, DMSO-d$_6$): δ 0.88 (t, 3H), 0.90 (t, 3H), 1.48-1.46 (t, 2H), 1.86-1.80 (m, 2H), 2.13 (s, 3H), 2.50-2.32 (t, 2H), 4.40-

4.35 (m, 4H), 5.90 (s, 1H), 7.69 (s, 1H), 8.20 (s, 1H), 8.35 (s, 1H), 8.62 (s, 1H), 11.52 (s, 1H). LCMS (ES+): m/z=445.17.

Example 44

6-bromo-1-cyclopentyl-N-((4,6-dimethyl-2-oxo-1,2-dihydropyridin-3-yl)methyl)-1H-indazole-4-carboxamide

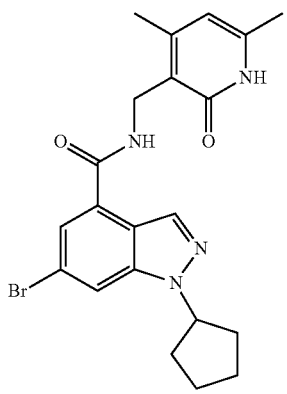 [SMILES: Cc1cc(C)c(CNC(=O)c2cc(Br)cc3c2cnn3C2CCCC2)c(=O)[nH]1]

a) methyl 6-bromo-1-cyclopentyl-1H-indazole-4-carboxylate

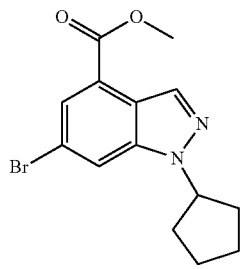 [SMILES: COC(=O)c1cc(Br)cc2c1cnn2C1CCCC1]

Ice-cooled methyl 6-bromo-1H-indazole-4-carboxylate (2 g, 7.84 mmol) in 30 mL of DMF was treated with NaH (60%, 345 mg, 8.63 mmol) and the mixture was stirred for 1 hr at 0° C. Iodocyclopentane (2.31 g, 11.8 mmol) was then added and the mixture was stirred at 100° C. overnight. After cooling to RT, the reaction mixture was partitioned between water and ethyl acetate. The organic phase was washed with water and brine, dried over $MgSO_4$, filtered and evaporated. Hexanes was added to the brown oil and it was purified using silica gel chromatography (eluent: Hex/EtOAc, gradient 0 to 25%). The less polar product was evaporated to give an orange oil, and was dried on hivac overnight. The product was confirmed to be the alkylated 1-isomer as suggested by 2D H NMR, and was collected as 807 mg (32%). $^1$H NMR (400 MHz, DMSO-$d_6$): δ 8.40 (s, 1H) 8.37 (s, 1H) 7.81 (d, J=1.52 Hz, 1H) 5.26 (quin, J=7.07 Hz, 1H) 3.95 (s, 3H) 2.08-2.17 (m, 2H) 1.93-2.01 (m, 2H) 1.82-1.92 (m, 2H) 1.64-1.73 (m, 2H); LCMS (ES+): m/z=323.3/325.3 b) 6-bromo-1-cyclopentyl-N-((4,6-dimethyl-2-oxo-1,2-dihydropyridin-3-yl)methyl)-1H-indazole-4-carboxamide Step 1: Methyl 6-bromo-1-cyclopentyl-1H-indazole-4-carboxylate (1.5 g, 4.64 mmol) was suspended in Methanol (8 mL) and Tetrahydrofuran (THF) (16 mL) followed by addition of 3N Sodium Hydroxide (3.09 mL, 9.28 mmol). The solution was heated to 55° C. with stirring overnight (16 h). The organic solvents were removed in vacuo and the residue was diluted with water (20 mL) and stirred in an ice bath. To the chilled aqueous solution was added 1N HCl, dropwise, until precipitation stopped. The suspension was stirred in the ice bath for 20 min and then filtered. The solid cake was washed with water, dried, and used directly in step 2.

Step 2: 6-bromo-1-cyclopentyl-1H-indazole-4-carboxylic acid (1.44 g, 4.61 mmol), 3-(aminomethyl)-4,6-dimethyl-2 (1H)-pyridinone hydrochloride (1.138 g, 6.03 mmol), N-[3-(dimethylamino)propyl]-N'-ethylcarbodiimide hydrochloride (1.335 g, 6.96 mmol), and 3H-[1,2,3]triazolo[4,5-b]pyridin-3-ol hydrate (1.073 g, 6.96 mmol) were suspended in DMSO (8.00 mL), followed by N-methylmorpholine (2.82 g, 27.8 mmol). The reaction mixture was stirred at room temperature overnight to afford a slurry. The slurry was diluted with DMSO (10 mL) and added dropwise to a ice-chilled aqueous solution of 1N $Na_2CO_3$ (50 ml) and water (200 mL), and stirred rapidly for 30 min. The precipitate was collected by vacuum filtration and washed with water. The cake was dried in the vacuum oven at 60° C. overnight (16 h). The title compound was obtained as a pale yellow-white solid (2.05 g, 98% yield). $^1$H NMR (400 MHz, DMSO-$d_6$) δ 11.50 (br. s., 1H), 8.64 (br. s., 1H), 8.37 (s, 1H), 8.20 (s, 1H), 7.70 (d, J=1.52 Hz, 1H), 5.89 (s, 1H), 5.22 (quin, J=7.01 Hz, 1H), 4.34 (d, J=4.55 Hz, 2H), 2.20 (s, 3H), 2.13 (s, 3H), 2.06-2.11 (m, 2H), 1.91-2.03 (m, 2H), 1.80-1.91 (m, 2H), 1.61-1.75 (m, 2H). LC-MS (ES) [M+H]$^+$ 443.0.

Example 45

6-bromo-1-cyclopentyl-N-((4-ethyl-6-methyl-2-oxo-1,2-dihydropyridin-3-yl)methyl)-1H-indazole-4-carboxamide

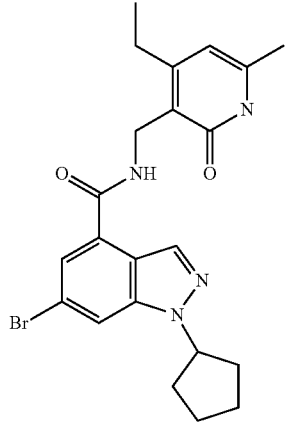 [SMILES: CCc1cc(C)[nH]c(=O)c1CNC(=O)c1cc(Br)cc2c1cnn2C1CCCC1]

In a 25 mL sealable tube under nitrogen were combined 6-bromo-1-cyclopentyl-1H-indazole-4-carboxylic acid (370 mg, 1.2 mmol) and 3-(aminomethyl)-4-ethyl-6-methyl-2 (1H)-pyridinone.HCl (340 mg, 1.68 mmol) in DMSO (3 mL). 1-hydroxy-7-azabenzotriazole (277 mg, 2.04 mmol) was added and the resulting mixture was degassed with nitrogen for 10 minutes. N-methylmorpholine (0.55 ml, 5 mmol) and EDC (390 mg, 2 mmol) were added, the vessel was sealed, and the mixture was stirred at room temperature overnight. The mixture was poured onto 10 mL of ice-water and solids crashed out. 10% $K_2CO_3$ was added to adjust the pH~8-9. The mixture was stirred for 4 hours and then allowed to stand for another 2 hours. Solids were filtered and air-dried. DMF along with some water was then added. Solids that precipitated were filtered and dried to afford the title compound as a light orange solid (515 mg, 91%). $^1$H NMR (400 MHz, DMSO-d$_6$) δ ppm 11.54 (s, 1H) 8.63 (t, J=4.80 Hz, 1H) 8.36 (s, 1H) 8.20 (s, 1H) 7.70 (d, J=1.52 Hz, 1H) 5.93 (s, 1H) 5.23 (t, J=7.07 Hz, 1H) 4.36 (s, 1H) 4.35 (s, 1H) 2.53-2.59 (m, 2H) 2.14 (s, 3H) 2.07-2.13 (m, 2H) 1.93-2.01 (m, 2H) 1.83-1.91 (m, 2H) 1.65-1.73 (m, 2H) 1.10 (t, J=7.58 Hz, 3H); LC-MS (ES) m/z=456.9/459.1

Example 46

1-cyclopentyl-N-((4,6-dimethyl-2-oxo-1,2-dihydro-pyridin-3-yl)methyl)-6-(2-(4-methylpiperazin-1-yl)pyrimidin-5-yl)-1H-indazole-4-carboxamide

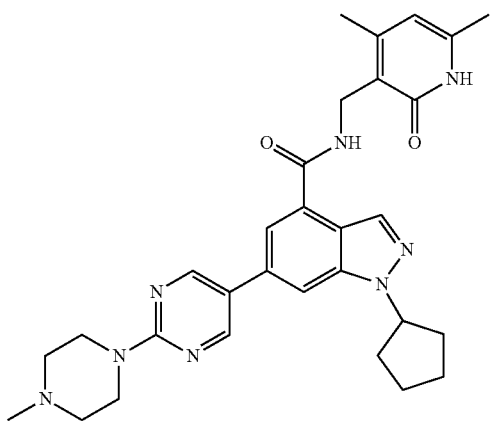

To a 2 mL microwave vial were added 6-bromo-1-cyclopentyl-N-[(4,6-dimethyl-2-oxo-1,2-dihydro-3-pyridinyl)methyl]-1H-indazole-4-carboxamide (150 mg, 0.338 mmol), 2-(4-methyl-1-piperazinyl)-5-(4,4,5,5-tetramethyl-1,3,2-dioxaborolan-2-yl)pyrimidine (134 mg, 0.440 mmol), Na$_2$CO$_3$ (108 mg, 1.015 mmol), PdCl$_2$(dppf)-CH$_2$Cl$_2$ adduct (27.6 mg, 0.034 mmol), 1,2-Dimethoxyethane (1269 μl) and water (423 μl). The contents were irradiated in a microwave reactor at 150° C. for 30 min. The reaction solution was filtered through a Whatman 0.45 μl Teflon syringless filter device and diluted with DMSO (6 mL). The DMSO solution was purified by HPLC reverse phase chromatography (phenomenex Gemini-NX, 30×100 5μ column, 5-30% acetonitrile/water 0.01% formic acid, 8 min gradient). The fractions containing the desired product were concentrated to dryness using a Genovac HT-4 instrument at 40° C. The title compound was obtained as a pale cream colored foam (28 mg, 14.83% yield). $^1$H NMR (400 MHz, CHLOROFORM-6) δ 8.62 (s, 2H), 8.39 (s, 1H), 7.99 (t, J=5.56 Hz, 1H), 7.71 (s, 1H), 7.57 (s, 1H), 5.98 (s, 1H), 5.03 (quin, J=7.14 Hz, 1H), 4.66 (d, J=5.81 Hz, 2H), 3.97 (br. s., 4H), 2.64 (br. s., 4H), 2.44 (s, 6H), 2.12-2.25 (m, 7H), 1.89-2.07 (m, 2H), 1.67-1.85 (m, 2H). LCMS (ES) [M+H]$^+$ 541.5.

Examples 47-52 were prepared in a similar manner as described above using 6-bromo-1-cyclopentyl-N-[(4,6-dimethyl-2-oxo-1,2-dihydro-3-pyridinyl)methyl]-1H-indazole-4-carboxamide and the appropriate boronic acid reagent.

Example 47

1-cyclopentyl-N-((4,6-dimethyl-2-oxo-1,2-dihydro-pyridin-3-yl)methyl)-6-(3-(pyrrolidin-1-yl)phenyl)-1H-indazole-4-carboxamide

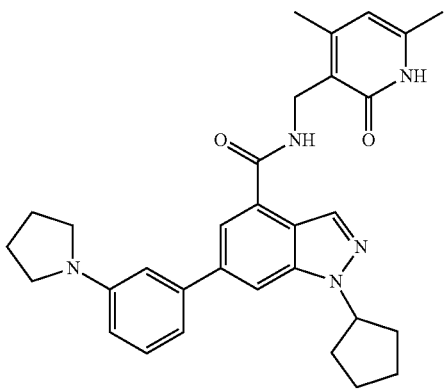 [SMILES: Cc1cc(C)c(CNC(=O)c2cc(-c3cccc(N4CCCC4)c3)cc3c2cnn3C2CCCC2)c(=O)[nH]1]

$^1$H NMR (400 MHz, MeOD) δ 8.35 (s, 1H), 7.93 (s, 1H), 7.81 (d, J=1.26 Hz, 1H), 7.29 (t, J=7.96 Hz, 1H), 6.99 (d, J=8.08 Hz, 1H), 6.91 (t, J=2.02 Hz, 1H), 6.63 (dd, J=1.77, 8.08 Hz, 1H), 6.14 (s, 1H), 5.27 (quin, J=7.26 Hz, 1H), 4.60 (s, 2H), 3.36-3.44 (m, 4H), 2.45 (s, 3H), 2.27 (s, 8H), 2.07 (dt, J=3.38, 6.63 Hz, 3H), 1.90-2.05 (m, 2H), 1.74-1.88 (m, 2H). LCMS (ES) [M+H]$^+$ 510.1.

Example 48

1-cyclopentyl-N-((4,6-dimethyl-2-oxo-1,2-dihydro-pyridin-3-yl)methyl)-6-(4-methylthiophen-2-yl)-1H-indazole-4-carboxamide

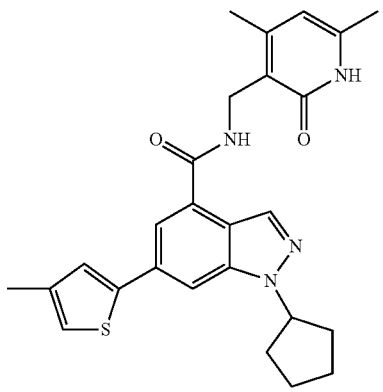

$^1$H NMR (400 MHz, DMSO-δ6) δ 11.55 (s, 1H), 8.64 (t, J=4.93 Hz, 1H), 8.32 (s, 1H), 8.05 (s, 1H), 7.80 (d, J=1.26 Hz, 1H), 7.55 (d, J=1.26 Hz, 1H), 7.19 (t, J=1.26 Hz, 1H), 5.90 (s, 1H), 5.30 (s, 1H), 4.38 (d, J=4.80 Hz, 2H), 2.28 (s, 3H), 2.23 (s, 3H), 2.13 (s, 5H), 1.95-2.06 (m, J=6.32 Hz, 2H), 1.82-1.94 (m, 2H), 1.64-1.77 (m, J=4.55 Hz, 2H). LCMS (ES) [M+H]$^+$ 461.1.

Example 49

1-cyclopentyl-N-((4,6-dimethyl-2-oxo-1,2-dihydropyridin-3-yl)methyl)-6-(2-(piperazin-1-yl)pyrimidin-5-yl)-1H-indazole-4-carboxamide

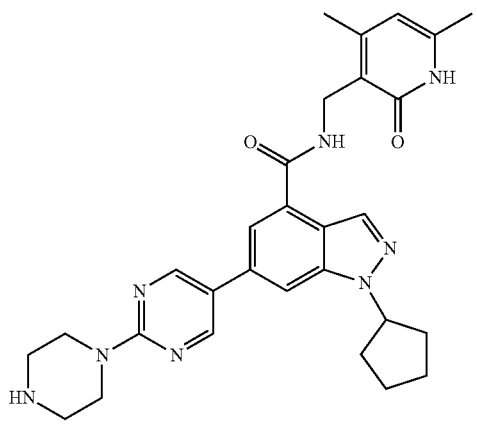 [SMILES: Cc1cc(C)c(CNC(=O)c2cc(-c3cnc(N4CCNCC4)nc3)cc3c2cnn3C2CCCC2)c(=O)[nH]1]

$^1$H NMR (400 MHz, MeOD) δ 8.97 (s, 2H), 8.43 (s, 1H), 8.15 (s, 1H), 8.02 (s, 1H), 6.99 (br. s., 1H), 5.31 (qd, J=6.69, 6.86 Hz, 1H), 4.72 (br. s., 2H), 4.21 (br. s., 4H), 3.38 (br. s., 4H), 2.69 (s, 3H), 2.53 (s, 3H), 2.20-2.32 (m, 2H), 2.07-2.20 (m, 2H), 2.03 (d, J=18.19 Hz, 2H), 1.73-1.90 (m, 2H). LCMS (ES) [M+H]$^+$ 527.2.

Example 50

1-cyclopentyl-N-((4,6-dimethyl-2-oxo-1,2-dihydropyridin-3-yl)methyl)-6-(3-(3-hydroxypropyl)phenyl)-1H-indazole-4-carboxamide

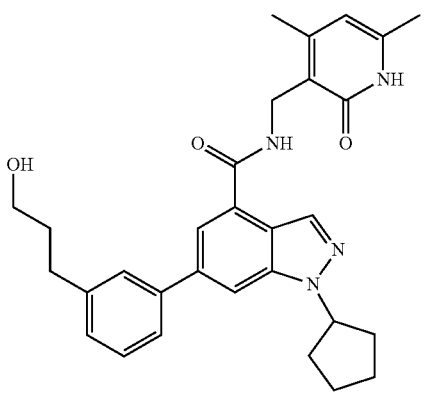 [SMILES: Cc1cc(C)c(CNC(=O)c2cc(-c3cccc(CCCO)c3)cc3c2cnn3C2CCCC2)c(=O)[nH]1]

$^1$H NMR (400 MHz, MeOD) δ 8.37 (s, 1H), 7.97 (s, 1H), 7.83 (d, J=1.26 Hz, 1H), 7.64 (s, 1H), 7.60 (d, J=7.83 Hz, 1H), 7.41 (t, J=7.58 Hz, 1H), 7.27 (d, J=7.58 Hz, 1H), 6.15 (s, 1H), 5.28 (quin, J=7.26 Hz, 1H), 4.57-4.62 (m, 2H), 3.63 (t, J=6.44 Hz, 2H), 2.77-2.85 (m, 2H), 2.45 (s, 3H), 2.27 (s, 3H), 2.19-2.26 (m, 2H), 2.09-2.20 (m, 2H), 1.87-2.07 (m, 4H), 1.74-1.87 (m, 2H). LCMS (ES) [M+H]$^+$ 499.5.

Example 51

1-cyclopentyl-N-((4,6-dimethyl-2-oxo-1,2-dihydropyridin-3-yl)methyl)-6-(3-(trifluoromethoxy)phenyl)-1H-indazole-4-carboxamide

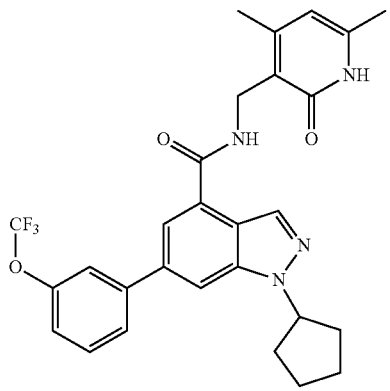 [SMILES: Cc1cc(C)c(CNC(=O)c2cc(-c3cccc(OC(F)(F)F)c3)cc3c2cnn3C2CCCC2)c(=O)[nH]1]

$^1$H NMR (400 MHz, MeOD) δ 8.39 (s, 1H), 8.04 (s, 1H), 7.79-7.85 (m, 2H), 7.73 (s, 1H), 7.61 (t, J=7.96 Hz, 1H), 7.34 (dt, J=1.17, 8.27 Hz, 1H), 6.15 (s, 1H), 5.26-5.35 (m, 1H), 4.60 (s, 2H), 2.45 (s, 3H), 2.27 (s, 3H), 2.24 (br. s., 2H), 2.09-2.20 (m, 2H), 1.94-2.07 (m, 2H), 1.81 (d, J=4.55 Hz, 2H). LCMS (ES) [M+H]$^+$ 525.2.

Example 52

1-cyclopentyl-N-((4,6-dimethyl-2-oxo-1,2-dihydropyridin-3-yl)methyl)-6-(6-methoxypyridin-3-yl)-1H-indazole-4-carboxamide

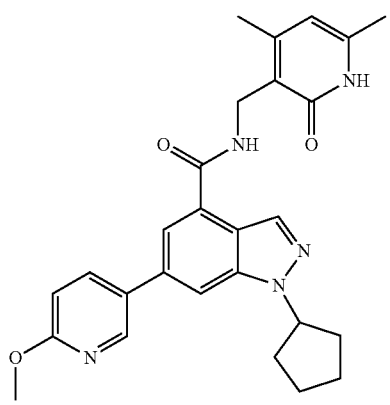 [SMILES: COc1ccc(-c2cc(C(=O)NCc3c(C)cc(C)[nH]c3=O)c3cnn(C4CCCC4)c3c2)cn1]

$^1$H NMR (400 MHz, DMSO-d$_6$) δ 11.54 (s, 1H), 8.69 (d, J=1.77 Hz, 1H), 8.61 (t, J=4.93 Hz, 1H), 8.38 (s, 1H), 8.22 (dd, J=2.65, 8.72 Hz, 1H), 8.16 (s, 1H), 7.87 (d, J=1.26 Hz, 1H), 6.97 (d, J=8.59 Hz, 1H), 5.89 (s, 1H), 5.32 (quin, J=7.14 Hz, 1H), 4.39 (d, J=4.80 Hz, 2H), 3.92 (s, 3H), 2.22 (s, 3H), 2.13 (s, 5H), 1.99 (s, 2H), 1.84-1.95 (m, 2H), 1.65-1.78 (m, 2H). LCMS (ES) [M+H]$^+$ 472.4.

Example 53

1-cyclopentyl-N-((4,6-dimethyl-2-oxo-1,2-dihydro-pyridin-3-yl)methyl)-6-(4-fluorophenyl)-1H-indazole-4-carboxamide

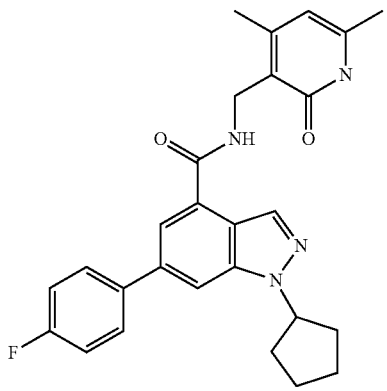 [SMILES: Cc1cc(C)c(CNC(=O)c2cc(-c3ccc(F)cc3)cc3c2cnn3C2CCCC2)c(=O)[nH]1]

In a 25 mL sealable tube under nitrogen were combined 6-bromo-1-cyclopentyl-N-[(4,6-dimethyl-2-oxo-1,2-dihydro-3-pyridinyl)methyl]-1H-indazole-4-carboxamide (100 mg, 0.23 mmol) and (4-fluorophenyl)boronic acid (47.3 mg, 0.34 mmol) in dioxane/water (3 mL:1 mL). PdCl$_2$(dppf)-CH$_2$Cl$_2$ adduct (9.2 mg, 0.011 mmol) was added and the resulting mixture was degassed with nitrogen for 10 min. Sodium bicarbonate (56.8 mg, 0.68 mmol) was added, the vessel was sealed, and the insoluble mixture was heated in a microwave at 100° C. for 20 min. Upon cooling down, water was added, and solids that crashed out were filtered. DCM/MeOH (1:1) was added, the contents pre-absorbed on silica gel and purified by SiO$_2$ chromatography (eluent: gradient 0 to 80:20:2 DCM/MeOH/NH$_4$OH). The collected product was suspended in EtOAc along with some hexanes. The mixture was sonicated, and the solids that precipitated were filtered and dried to afford the title compound as a light grey solid (78 mg, 75%). $^1$H NMR (400 MHz, DMSO-d$_6$) δ ppm 11.54 (s, 1H) 8.64 (t, J=4.80 Hz, 1H) 8.37 (s, 1H) 8.13 (s, 1H) 7.89-7.94 (m, 2H) 7.85 (s, 1H) 7.35 (t, J=8.97 Hz, 2H) 5.89 (s, 1H) 5.34 (quin, J=7.14 Hz, 1H) 4.40 (br. s., 1H) 4.38 (br. s., 1H) 2.22 (s, 3H) 2.11-2.18 (m, 5H) 1.98-2.06 (m, 2H) 1.86-1.94 (m, 2H) 1.66-1.75 (m, 2H). LC-MS (ES) m/z=459.1

Example 54

1-cyclopentyl-N-[(4,6-dimethyl-2-oxo-1,2-dihydro-3-pyridinyl)methyl]-6-(1-methyl-1H-pyrazol-4-yl)-1H-indazole-4-carboxamide

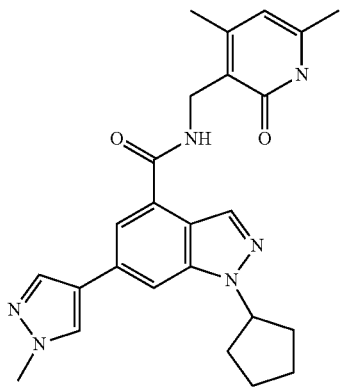 [SMILES: Cc1cc(C)c(CNC(=O)c2cc(-c3cnn(C)c3)cc3c2cnn3C2CCCC2)c(=O)[nH]1]

The title compound was prepared in a similar manner as described for example 8 from 6-bromo-1-cyclopentyl-N-[(4,6-dimethyl-2-oxo-1,2-dihydro-3-pyridinyl)methyl]-1H-indazole-4-carboxamide (100 mg, 0.226 mmol) and 1-methyl-4-(4,4,5,5-tetramethyl-1,3,2-dioxaborolan-2-yl)-1H-pyrazole (70 mg, 0.338 mmol). The product was collected as a white solid (82 mg, 81%). $^1$H NMR (400 MHz, DMSO-d$_6$) δ ppm 11.53 (br. s., 1H) 8.48 (t, J=4.93 Hz, 1H) 8.30 (s, 1H) 8.26 (s, 1H) 8.04 (s, 2H) 7.81 (s, 1H) 5.90 (s, 1H) 5.22 (quin, J=7.14 Hz, 1H) 4.39 (s, 1H) 4.38 (s, 1H) 3.87-3.92 (m, 3H) 2.23 (s, 3H) 2.14-2.19 (m, 1H) 2.13 (s, 4H) 1.96-2.05 (m, 2H) 1.84-1.94 (m, 2H) 1.66-1.76 (m, 2H). LC-MS (ES) m/z=445.2 [M+H]$^+$

Example 55

1-cyclopentyl-N-((6-methyl-2-oxo-4-propyl-1,2-dihydropyridin-3-yl)methyl)-6-(6-(4-methylpiperazin-1-yl)pyridin-3-yl)-1H-indazole-4-carboxamide

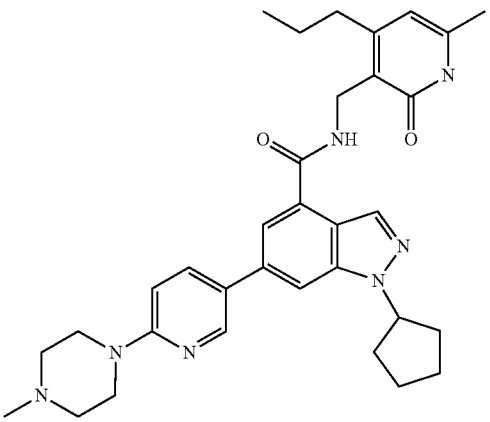

In a 25 mL sealable tube under nitrogen were combined 6-bromo-1-cyclopentyl-N-[(6-methyl-2-oxo-4-propyl-1,2-dihydro-3-pyridinyl)methyl]-1H-indazole-4-carboxamide (100 mg, 0.21 mmol), 1-methyl-4-[5-(4,4,5,5-tetramethyl-1,3,2-dioxaborolan-2-yl)-2-pyridinyl]piperazine (96 mg, 0.32 mmol) in DME/water (3 mL:1 mL). PdCl$_2$(dppf)-CH$_2$Cl$_2$ adduct (8.7 mg, 0.01 mmol) was added and the resulting mixture was degassed with nitrogen for 10 min. Sodium bicarbonate (53.5 mg, 0.64 mmol) was added, the vessel was sealed, and the insoluble mixture was heated in a microwave at 110° C. for 20 min. The mixture was evaporated, DCM/MeOH (1:1) was added, and the contents pre-absorbed on silica gel and purified by SiO$_2$ chromatography (eluent: gradient 0 to 80:20:2 DCM/MeOH/NH$_4$OH). The collected product was further purified by reversed-phase HPLC (15% to 80% CH$_3$CN in water with 0.1% TFA) which afforded the TFA salt. CH$_3$CN was evaporated and a saturated solution of sodium bicarbonate was added. Solids that precipitated were filtered and dried to afford the title compound as a white solid (87 mg, 71%). $^1$H NMR (400 MHz, DMSO-d$_6$) δ ppm 11.45 (br. s., 1H) 8.68 (br. s., 1H) 8.39 (s, 1H) 8.24 (s, 1H) 8.21 (d, J=5.30 Hz, 1H) 7.84-7.88 (m, 1H) 7.20 (s, 1H) 7.13 (dd, J=5.31, 1.26 Hz, 1H) 5.91 (s, 1H) 5.38 (quin, J=7.07 Hz, 1H) 4.43 (br. s., 1H) 4.42 (br. s., 1H) 3.55-3.63 (m, 4H) 2.53-2.56 (m, 2H) 2.41-2.46 (m, 4H) 2.24 (s, 3H) 2.12-2.20 (m, 5H) 1.97-2.06 (m, 2H) 1.86-1.95 (m, 2H) 1.67-1.76 (m, 2H) 1.48-1.57 (m, 2H) 0.89 (t, J=7.33 Hz, 3H); LC-MS (ES) m/z=568.3

Example 56

1-cyclopentyl-N-[(4,6-dimethyl-2-oxo-1,2-dihydro-3-pyridinyl)methyl]-6-[6-(1-piperazinyl)-3-pyridinyl]-1H-indazole-4-carboxamide

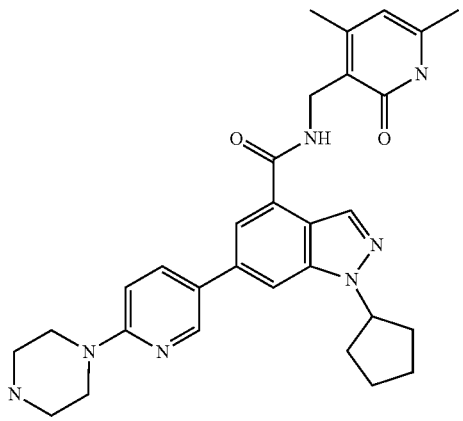 [SMILES: Cc1cc(C)c(CNC(=O)c2cc(-c3ccc(N4CCNCC4)nc3)cc3c2cnn3C2CCCC2)c(=O)[nH]1]

The title compound was prepared in a similar manner as described for example 8 from 6-bromo-1-cyclopentyl-N-[(4,6-dimethyl-2-oxo-1,2-dihydro-3-pyridinyl)methyl]-1H-indazole-4-carboxamide (200 mg, 0.451 mmol) and 1-[5-(4,4,5,5-tetramethyl-1,3,2-dioxaborolan-2-yl)-2-pyridinyl]piperazine (196 mg, 0.677 mmol). The product was collected as a white solid (92 mg, 37%). $^1$H NMR (400 MHz, DMSO-$d_6$) δ ppm 11.54 (br. s., 1H) 8.64-8.67 (m, 1H) 8.60 (t, J=4.80 Hz, 1H) 8.35 (s, 1H) 8.03-8.09 (m, 2H) 7.84 (d, J=1.26 Hz, 1H) 6.89-6.99 (m, 1H) 5.89 (s, 1H) 5.27-5.35 (m, 1H) 4.39 (br. s., 1H) 4.38 (br. s., 1H) 3.41-3.56 (m, 4H) 2.69-2.91 (m, 4H) 2.22 (s, 3H) 2.07-2.20 (m, 6H) 1.97-2.06 (m, 2H) 1.85-1.93 (m, 2H) 1.65-1.74 (m, 2H). LC-MS (ES) m/z=526.3 [M+H]$^+$

Example 57

1-cyclopentyl-N-((4,6-dimethyl-2-oxo-1,2-dihydro-pyridin-3-yl)methyl)-6-(4-((dimethylamino)methyl)phenyl)-1H-indazole-4-carboxamide

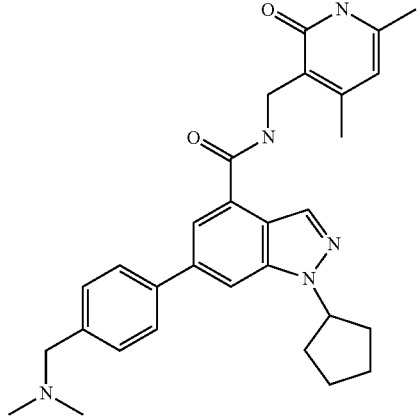

To a sealed tube were added 6-bromo-1-cyclopentyl-N-[(4,6-dimethyl-2-oxo-1,2-dihydro-3-pyridinyl)methyl]-1H-indazole-4-carboxamide (0.10 g, 0.226 mmol), N,N-dimethyl-1-[4-(4,4,5,5-tetramethyl-1,3,2-dioxaborolan-2-yl)phenyl]methanamine (0.081 g, 0.271 mmol), and potassium phosphate (tribasic) (0.192 g, 0.902 mmol) followed by 1,4-dioxane (2.0 mL) and water (0.5 mL). The suspension was stirred with degassing under $N_2$ for 10 min, followed by addition of PdCl$_2$(dppf)-CH$_2$Cl$_2$ adduct (0.018 g, 0.023 mmol). The reaction vessel was sealed and stirred with heating at 100° C. (heat block) for 2 h. The contents were allowed to stir with cooling to RT overnight. The mixture was diluted with EtOAc followed by addition of silica gel. The mixture was concentrated in vacuo and the obtained solid purified by silica gel chromatography (dry loaded, eluent: 8-95% gradient of chloroform (containing 10% 2M Ammonia in Methanol) and DCM. The collected product was concentrated from DCM/MTBE and then dried in vacuum oven for 16 h. The title compound was collected as an off-white solid (45 mg, 39%). $^1$H NMR (400 MHz, DMSO-d6) δ ppm 1.65-1.76 (m, 2H), 1.83-1.94 (m, 2H), 1.97-2.07 (m, 2H), 2.09-2.19 (m, 11H), 2.21 (s, 3H), 3.44 (s, 2H), 4.39 (d, J=4.80 Hz, 2H), 5.34 (quin, J=7.14 Hz, 1H), 5.88 (s, 1H), 7.41 (m, J=8.34 Hz, 2H), 7.81 (m, J=8.08 Hz, 2H), 7.87 (d, J=1.01 Hz, 1H), 8.12 (s, 1H), 8.36 (s, 1H), 8.65 (t, J=4.93 Hz, 1H), 11.53 (s, 1H); LC-MS (ES) m/z=498.3 [M+H]$^+$

Example 58

6-chloro-1-cyclopentyl-N-[(4,6-dimethyl-2-oxo-1,2-dihydro-3-pyridinyl)methyl]-1H-indazole-4-carboxamide

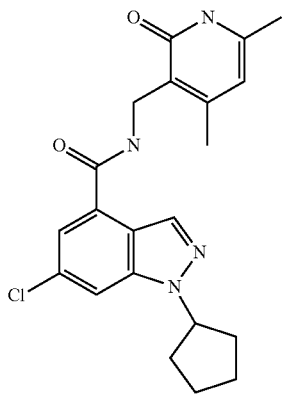 [SMILES: Cc1cc(C)c(CNC(=O)c2cc(Cl)cc3c2cnn3C2CCCC2)c(=O)[nH]1]

a) Methyl 6-chloro-1-cyclopentyl-1H-indazole-4-carboxylate

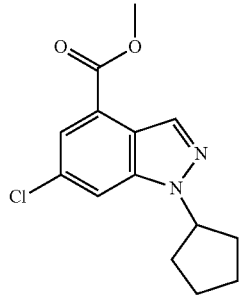 [SMILES: COC(=O)c1cc(Cl)cc2c1cnn2C1CCCC1]

Methyl 6-chloro-1-cyclopentyl-1H-indazole-4-carboxylate (2.1 g, 9.97 mmol) was suspended in DMF (40 mL), placed into an ice bath, and stirred for 15 min. Next added sodium hydride (0.997 g, 24.93 mmol) slowly over 5 min (gas evolution) and stirred for 15 min. Bromocyclopentane (3.21 mL, 29.9 mmol) was added at once via syringe, and the mixture allowed to stir with warming to RT. After 15 min stirring at RT, the contents were stirred with heating at 45° C. for 16 h. The contents were cooled to RT, and then 0.5 g sodium carbonate and 1 mL of iodomethane were added. The contents were stirred at RT for 3 h, after which time the mixture was poured onto 400 mL of ice/water with stirring. After 5 min stirring, the contents were extracted with ether (2×100 mL). The combined organic layers were concentrated in vacuo. The crude product was purified by silica gel chromatography (eluent: gradient 3-25% EtOAc in hexanes) The first product off the column was determined to be the desired N1-substituted isomer, and was collected after drying (vacuum pump, 1 h) as an orange solid (1.11 g, 39%). $^1$H NMR (400 MHz, DMSO-d6) δ ppm 1.64-1.74 (m, 2H), 1.82-1.93 (m, 2H), 1.94-2.04 (m, 2H), 2.09-2.19 (m, 2H), 3.96 (s, 3H), 5.27 (t, J=7.07 Hz, 1H), 7.72 (d, J=1.77 Hz, 1H), 8.28 (s, 1H), 8.40 (s, 1H); LC-MS (ES) m/z=278.7 [M+H]$^+$ b) 6-chloro-1-cyclopentyl-1H-indazole-4-carboxylic acid

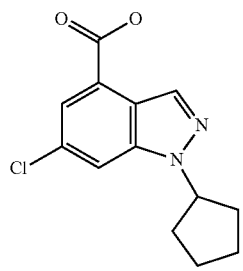 [SMILES: O=C(O)c1cc(Cl)cc2c1cnn2C1CCCC1]

The title compound was prepared in the same manner as described for example 1 (step 2) from methyl 6-chloro-1-cyclopentyl-1H-indazole-4-carboxylate (1.11 g, 3.98 mmol), wherein the reaction stir time was 12 h. The product was collected as 0.99 g (85%). $^1$H NMR (400 MHz, DMSO-d6) δ ppm 1.63-1.75 (m, 2H) 1.82-1.93 (m, 2H) 1.93-2.05 (m, 2H) 2.08-2.19 (m, 2H) 5.25 (quin, J=7.07 Hz, 1H) 7.69 (d, J=1.77 Hz, 1H) 8.20 (s, 1H) 8.40 (s, 1H) 11.88-15.25 (m, 1H); LC-MS (ES) m/z=264.9 [M+H]$^+$ c) 6-chloro-1-cyclopentyl-N-[(4,6-dimethyl-2-oxo-1,2-dihydro-3-pyridinyl)methyl]-1H-indazole-4-carboxamide The title compound was prepared in the same manner as described for example 3 (step c) from 6-chloro-1-cyclopentyl-1H-indazole-4-carboxylic acid (0.12 g, 0.453 mmol) and 3-(aminomethyl)-4,6-dimethyl-2(1H)-pyridinone (0.128 g, 0.680 mmol), wherein the stir time was 12 h. The crude product was purified by silica gel chromatography (eluent: 5-85% gradient chloroform (containing 10% 2M Ammonia in methanol) and dichloromethane). The isolated product was concentrated from MTBE to afford an off-white solid that was dried in hi-vac oven for 6 h. The final product was collected as 0.165 g (89%); $^1$H NMR (400 MHz, DMSO-d6) δ ppm 1.62-1.74 (m, 2H) 1.81-1.91 (m, 2H) 1.91-2.02 (m, 2H) 2.06-2.17 (m, 5H) 2.20 (s, 3H) 4.34 (d, J=4.80 Hz, 2H) 5.16-5.28 (m, 1H) 5.88 (s, 1H) 7.60 (d, J=1.52 Hz, 1H) 8.05 (s, 1H) 8.37 (s, 1H) 8.61 (t, J=4.93 Hz, 1H) 11.54 (s, 1H); LC-MS (ES) m/z=398.8 [M+H]+

Example 59

6-chloro-1-cyclopentyl-N-[(6-methyl-2-oxo-4-propyl-1,2-dihydro-3-pyridinyl)methyl]-1H-indazole-4-carboxamide

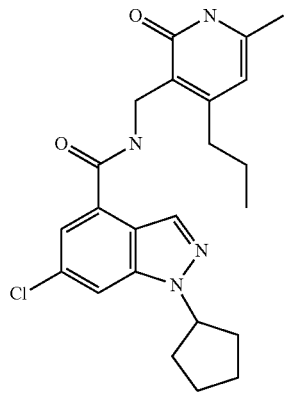 [SMILES: CCCc1cc(C)[nH]c(=O)c1CNC(=O)c1cc(Cl)cc2c1cnn2C1CCCC1]

The title compound was prepared in the same manner as described for example 3 (step c) from 6-chloro-1-cyclopentyl-1H-indazole-4-carboxylic acid (0.12 g, 0.453 mmol) and 3-(aminomethyl)-6-methyl-4-propyl-2(1H)-pyridinone (0.128 g, 0.680 mmol). The final product was collected as 0.170 g (86%); $^1$H NMR (400 MHz, DMSO-d6) δ ppm 0.89 (t, J=7.33 Hz, 3H), 1.45-1.57 (m, 2H), 1.61-1.74 (m, 2H), 1.80-1.92 (m, 2H), 1.92-2.03 (m, 2H), 2.05-2.19 (m, 5H), 4.36 (d, J=5.05 Hz, 2H), 5.21 (t, J=7.07 Hz, 1H), 5.91 (s, 1H), 7.59 (d, J=1.52 Hz, 1H), 8.06 (s, 1H), 8.37 (s, 1H), 8.62 (t, J=4.80 Hz, 1H), 11.55 (s, 1H); LC-MS (ES) m/z=426.7 [M+H]$^+$ Example 60

6-cyano-1-cyclopentyl-N-[(4,6-dimethyl-2-oxo-1,2-dihydro-3-pyridinyl)methyl]-1H-indazole-4-carboxamide

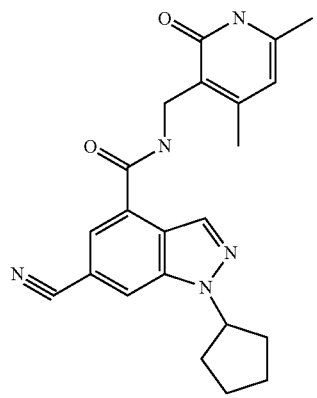 [SMILES: Cc1cc(C)c(CNC(=O)c2cc(C#N)cc3c2cnn3C2CCCC2)c(=O)[nH]1]

To 20 mL microwave vial containing a mixture of 6-bromo-1-cyclopentyl-N-[(4,6-dimethyl-2-oxo-1,2-dihydro-3-pyridinyl)methyl]-1H-indazole-4-carboxamide (0.25 g, 0.564 mmol), zinc cyanide (0.066 g, 0.564 mmol), zinc (7.37 mg, 0.113 mmol), and dppf (0.063 g, 0.113 mmol) was added N,N-Dimethylacetamide (DMA) (5.0 mL). The suspension was stirred with degassing under nitrogen for 5 min. Next added PdCl$_2$(dppf)-CH$_2$Cl$_2$ adduct (0.046 g, 0.056 mmol). The reaction contents were sealed and stirred with heating at 135° C. (heat block) for 16 h. The reaction mixture was allowed to cool to RT, diluted with 80 mL of water, and adjusted to pH~8 with sat NaHCO$_3$. The contents were stirred for 30 min, filtered, and the filter cake was washed with water. The collected solid was dried under hi vacuum for 4 h. The crude product was dissolved in DCM/MeOH followed by addition of silica gel, and concentrated in vacuo to dryness. The contents were purified by silica gel chromatography (dry loaded; eluent: 2-65% gradient of 10% methanol in dichloromethane and dichloromethane). The product was concentrated from MTBE and dried in hi-vac oven for 6 h at 45° C. to afford the title compound as 0.190 g (85%). $^1$H NMR (400 MHz, DMSO-d6) δ ppm 1.64-1.75 (m, 2H) 1.83-1.93 (m, 2H) 1.94-2.06 (m, 2H) 2.10-2.19 (m, 5H) 2.21 (s, 3H) 4.35 (d, J=4.80 Hz, 2H) 5.31 (t, J=7.07 Hz, 1H) 5.89 (s, 1H) 7.91 (d, J=1.26 Hz, 1H) 8.51 (s, 1H) 8.60 (s, 1H) 8.66 (t, J=4.93 Hz, 1H) 11.54 (s, 1H); LC-MS (ES) m/z=390.2 [M+H]$^+$ Example 61

6-(aminomethyl)-1-cyclopentyl-N-[(4,6-dimethyl-2-oxo-1,2-dihydro-3-pyridinyl)methyl]-1H-indazole-4-carboxamide

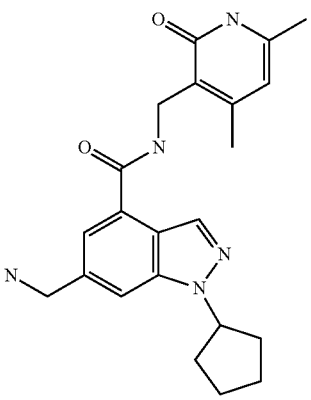 [SMILES: Cc1cc(C)c(CNC(=O)c2cc(CN)cc3c2cnn3C2CCCC2)c(=O)[nH]1]

6-cyano-1-cyclopentyl-N-[(4,6-dimethyl-2-oxo-1,2-dihydro-3-pyridinyl)methyl]-1H-indazole-4-carboxamide (0.10 g, 0.257 mmol) was suspended in acetic acid (8 mL). The contents were placed heated at 40° C. under an atmosphere of hydrogen (50 psi; H-cube reactor) at a flow rate of 1 mL/min with recirculation 2 h. Then contents were diluted with MeOH, concentrated in vacuo, and dried under hi vacuum for 18 h. The crude product was dissolved in DCM and purified by silica gel chromatography (eluent: 10-100% gradient of chloroform (containing 10% 2M ammonia in methanol) and dichloromethane. The product was concentrated from MTBE and dried in a vacuum oven at 45° C. for 4 h. The title compound was collected as 68 mg (66%); $^1$H NMR (400 MHz, DMSO-d6) δ ppm 1.64-1.75 (m, 2H), 1.82-1.93 (m, 2H), 1.94-2.04 (m, 2H), 2.06-2.17 (m, 6H), 2.21 (s, 3H), 3.85 (s, 2H), 4.35 (d, J=5.05 Hz, 2H), 5.14 (t, J=7.07 Hz, 1H), 5.89 (s, 1H), 7.54 (s, 1H), 7.76 (s, 1H), 8.27 (s, 1H), 8.32 (t, J=5.05 Hz, 1H); LC-MS (ES) m/z=394.0 [M+H]$^+$ Example 62

6-amino-1-cyclopentyl-N-[(4,6-dimethyl-2-oxo-1,2-dihydro-3-pyridinyl)methyl]-1H-indazole-4-carboxamide

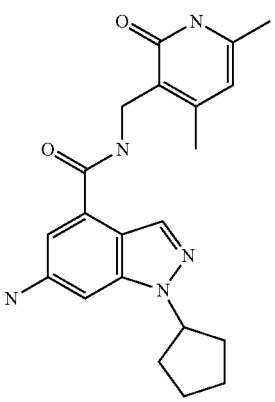 [SMILES: Cc1cc(C)c(CNC(=O)c2cc(N)cc3c2cnn3C2CCCC2)c(=O)[nH]1]

To a 20 mL microwave vial containing a mixture of 6-bromo-1-cyclopentyl-N-[(4,6-dimethyl-2-oxo-1,2-dihydro-3-pyridinyl)methyl]-1H-indazole-4-carboxamide (0.25 g, 0.564 mmol), benzophenone imine (0.142 mL, 0.846 mmol) and Cs$_2$CO$_3$ (0.735 g, 2.256 mmol) was added 1,4-dioxane (5 mL) and the suspension stirred with degassing under N$_2$ for 5 min. Next added Xantphos (0.098 g, 0.169 mmol), degassed for 5 min, and then added Pd$_2$(dba)$_3$ (0.077 g, 0.085 mmol) and degassed for 1 min. The reaction vial was sealed and the mixture heated at 100° C. (heat block) with stirring for 2 h. The contents were cooled to RT, diluted with water (80 mL), and extracted with EtOAc (2×). The combined organic layers were dried over MgSO$_4$, filtered through Celite, and concentrated in vacuo. The crude solid was dissolved in THF (5 mL) and treated with HCl (0.564 mL, 1.692 mmol). The volatiles were removed in vacuo. The residue was dried under hi-vacuum, and then dissolved in MeOH/DCM followed by addition of silica gel. The contents were concentrated to dryness and dried under hi-vacuum for 1 h. The contents were purified by silica gel chromatography (dry loaded, eluent: 3-95% gradient chloroform (containing 10% 2M ammonia in methanol) and DCM). The collected solid was triturated from hot acetonitrile, and then placed in freezer for 15 min. The contents were filtered cold and washed with additional acetonitrile. The title compound was collected as 90 mg (41%); $^1$H NMR (400 MHz, DMSO-d6) δ ppm 1.60-1.72 (m, 2H), 1.78-1.89 (m, 2H), 1.91-2.00 (m, 2H), 2.01-2.10 (m, 2H), 2.12 (s, 3H), 2.22 (s, 3H), 4.32 (d, J=5.05 Hz, 2H), 4.84 (t, J=7.07 Hz, 1H), 5.41 (s, 2H), 5.88 (s, 1H), 6.65 (s, 1H), 6.88 (d, J=1.52 Hz, 1H), 7.95 (s, 1H), 8.14 (t, J=5.18 Hz, 1H), 11.53 (s, 1H); LC-MS (ES) m/z=379.2 [M+H]

Example 63

1-cyclopentyl-N-[(4,6-dimethyl-2-oxo-1,2-dihydro-3-pyridinyl)methyl]-6-[(phenylsulfonyl)amino]-1H-indazole-4-carboxamide

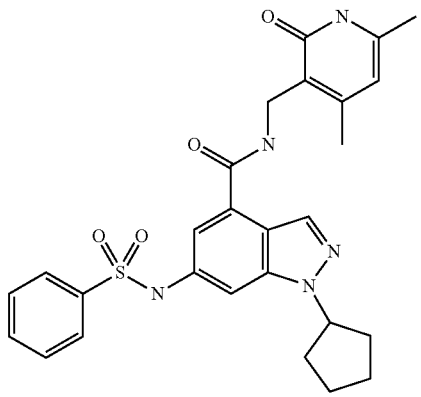 [SMILES: Cc1cc(C)c(CNC(=O)c2cc(NS(=O)(=O)c3ccccc3)cc3c2cnn3C2CCCC2)c(=O)[nH]1]

6-amino-1-cyclopentyl-N-[(4,6-dimethyl-2-oxo-1,2-dihydro-3-pyridinyl)methyl]-1H-indazole-4-carboxamide (30 mg, 0.079 mmol) was suspended in DCM (3 mL) followed by pyridine (0.032 mL, 0.395 mmol). The contents were vigorously stirred and then benzenesulfonyl chloride (0.011 mL, 0.087 mmol) was added and the contents stirred at RT for 1 h. The volatiles were removed in vacuo and dried on hi-vac for 1 h. The crude product was purified by reverse phase HPLC (Gradient B: 15-70%. A: Water+0.1% TFA. B: CH3CN+0.1% TFA). The product was neutralized with water and sat. NaHCO3, and extracted with 10% THF/EtOAC (hot) in duplicate. The combined organic layers were dried over MgSO₄, filtered, and concentrated in vacuo. The solid was concentrated from DCM and dried in vacuum oven for 4 h at 45° C. The title compound was collected as 30 mg (72%); $^1$H NMR (400 MHz, DMSO-d6) δ ppm 1.68 (td, J=5.49, 3.41 Hz, 2H), 1.75-1.94 (m, 4H), 1.99-2.10 (m, 2H), 2.12 (s, 3H), 2.20 (s, 3H), 4.30 (d, J=5.05 Hz, 2H), 4.89-5.04 (m, 1H), 5.89 (s, 1H), 7.22 (d, J=1.52 Hz, 1H), 7.36 (s, 1H), 7.48-7.63 (m, 3H), 7.77-7.84 (m, 2H), 8.11 (s, 1H), 8.36 (t, J=5.05 Hz, 1H), 10.56 (s, 1H), 11.55 (s, 1H); LC-MS (ES) m/z=519.2 [M+H]

Example 64

1-cyclopentyl-N-[(4,6-dimethyl-2-oxo-1,2-dihydro-3-pyridinyl)methyl]-6-(3-hydroxy-3-methyl-1-butyn-1-yl)-1H-indazole-4-carboxamide

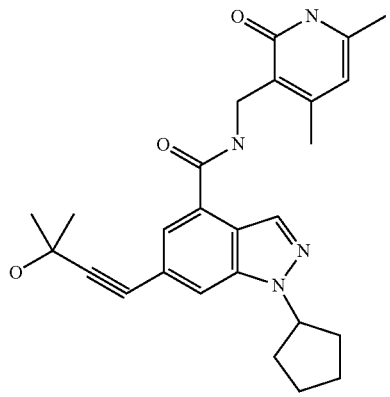 [SMILES: Cc1cc(C)c(CNC(=O)c2cc(C#CC(C)(C)O)cc3c2cnn3C2CCCC2)c(=O)[nH]1]

To a 10 mL microwave vial containing a mixture of 6-bromo-1-cyclopentyl-N-[(4,6-dimethyl-2-oxo-1,2-dihydro-3-pyridinyl)methyl]-1H-indazole-4-carboxamide (0.12 g, 0.271 mmol), sodium iodide (8.11 mg, 0.054 mmol) and zinc (3.54 mg, 0.054 mmol) were added DMSO (2.5 mL), TEA (0.075 mL, 0.541 mmol), and DBU (0.082 mL, 0.541 mmol). The suspension was stirred and degassed with N₂ for 5 min. Next added in 2-methyl-3-butyn-2-ol (0.131 mL, 1.353 mmol) and Pd(Ph₃P)₄ (0.031 g, 0.027 mmol). The reaction vial was sealed and stirred with heating at 85° C. (heat block) for 3 h. The mixture was then diluted into water and 20% THF/EtOAc. The contents were stirred and the layers were separated. The organic layer was washed with brine, dried over MgSO₄, filtered through Celite, and concentrated in vacuo. The residue was dried on hi-vacuum pump overnight. The crude product was purified by silica gel chromatography (eluent: 5-80% gradient chloroform (containing 10% 2M ammonia in methanol) in DCM). The collected product was purified by reverse phase HPLC (Gradient B: 15-75%; A: Water+0.1% TFA. B: CH3CN+0.1% TFA). The product was suspended in 10% MeOH/CHCl₃. Next added 0.5 g Silicycle carbonate resin and stirred for 15 min. After standing for 10 min, the contents were filtered through celite and concentrated in vacuo. The product was further concentrated from DCM and MTBE and then dried in hi-vac oven at 45° C. overnight. The title compound was collected as a white solid (38 mg, 30%); $^1$H NMR (400 MHz, DMSO-d6) δ ppm 1.47-1.52 (m, 6H), 1.64-1.73 (m, 2H), 1.80-1.91 (m, 2H), 1.92-2.02 (m, 2H), 2.06-2.15 (m, 5H), 2.18-2.23 (m, 3H), 4.28-4.38 (m, 2H), 5.25 (quin, J=7.07 Hz, 1H), 5.52 (s, 1H), 5.84-5.91 (m, 1H), 7.54 (d, J=1.01 Hz, 1H), 7.93 (s, 1H), 8.35 (s, 1H), 8.60 (t, J=4.93 Hz, 1H), 11.51 (br. s., 1H); LC-MS (ES) m/z=446.9 [M+H]

Example 65

6-bromo-1-cyclopropyl-N-[(4,6-dimethyl-2-oxo-1,2-dihydro-3-pyridinyl)methyl]-1H-indazole-4-carboxamide

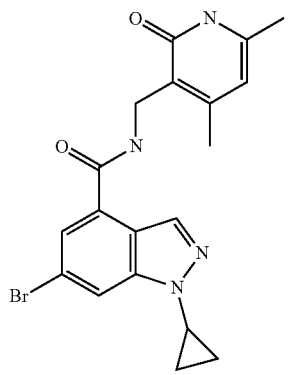 [SMILES: Cc1cc(C)c(CNC(=O)c2cc(Br)cc3c2cnn3C2CC2)c(=O)[nH]1]

a) Methyl 6-bromo-1-cyclopropyl-1H-indazole-4-carboxylate

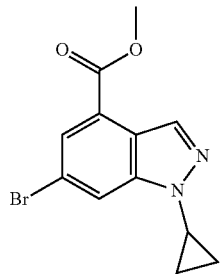 [SMILES: COC(=O)c1cc(Br)cc2c1cnn2C1CC1]

Methyl 6-bromo-1H-indazole-4-carboxylate (1.0 g, 3.92 mmol) was dissolved in 1,2-Dichloroethane (DCE) (14 mL) and stirred for 15 min. Next added cyclopropylboronic acid (0.674 g, 7.84 mmol) and sodium carbonate (0.831 g, 7.84 mmol). The reaction was stirred at RT (suspension). Copper (II) acetate (0.712 g, 3.92 mmol) and 2,2'-bipyridine (0.612 g, 3.92 mmol) were suspended in DCE (24 mL) with heating and the hot suspension was added to the reaction mixture. The contents were stirred with heating at 70° C. overnight. After cooling to RT, the reaction mixture was poured onto sat. NH$_4$Cl and ice. Next added DCM and stirred for 10 min. The contents were filtered through Celite, washing with water and DCM. The layers were separated and the aq. layer was extracted with DCM (1×). The combined organic layers were washed with brine, dried over MgSO$_4$, filtered, and concentrated in vacuo. The crude product was purified by silica gel chromatography (3-25% gradient ethyl acetate in hexanes) wherein the less polar product was observed to be the title compound, and was collected as a yellow solid (0.54 g, 46%); $^1$H NMR (400 MHz, DMSO-d6) δ ppm 1.10-1.20 (m, 4H), 3.81-3.90 (m, 1H), 3.95 (s, 3H), 7.86 (d, J=1.52 Hz, 1H), 8.30 (d, J=1.77 Hz, 1H), 8.32 (d, J=1.01 Hz, 1H); LC-MS (ES) m/z=295.1 [M+H]

b) 6-bromo-1-cyclopropyl-1H-indazole-4-carboxylate6-bromo-1-cyclopropyl-1H-indazole-4-carboxylic acid

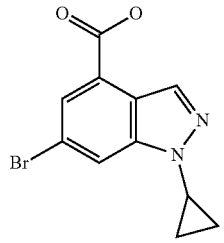

Methyl 6-bromo-1-cyclopropyl-1H-indazole-4-carboxylate (0.54 g, 1.830 mmol) was dissolved in methanol (16 mL) and THF (4 mL) with stirring at RT. A solution of 3N NaOH (1.830 mL, 5.49 mmol) was added the contents were stirred at RT for 2 days. The volatiles were removed in vacuo. The residue was diluted with water and slowly acidified to pH 3-4 with 1M HCl wherein solids were observed to precipitate. The contents were extracted with EtOAc (2×). The combined organic layers were washed with brine, dried over MgSO$_4$, filtered, and concentrated in vacuo to a solid to which was dried under vacuum for 1 h. The title compound was collected as a white solid (0.48 g, 91%); $^1$H NMR (400 MHz, DMSO-d6) δ ppm 1.10-1.17 (m, 4H), 3.80-3.89 (m, 1H), 7.84 (d, J=1.77 Hz, 1H), 8.26 (s, 1H), 8.31 (s, 1H), 13.60 (br. s., 1H); LC-MS (ES) m/z=281.1 [M+H].

c) 6-bromo-1-cyclopropyl-N-[(4,6-dimethyl-2-oxo-1,2-dihydro-3-pyridinyl)methyl]-1H-indazole-4-carboxamide The title compound was prepared in the same manner as described for example 3 (step c) from 6-bromo-1-cyclopropyl-1H-indazole-4-carboxylic acid (0.22 g, 0.783 mmol) and 3-(aminomethyl)-4,6-dimethyl-2(1H)-pyridinone (0.221 g, 1.174 mmol), wherein the reaction stir time was 12 h. The title compound was collected as a white solid (0.27 g, 81%); $^1$H NMR (400 MHz, DMSO-d6) δ ppm 1.06-1.17 (m, 4H), 2.12 (s, 3H), 2.20 (s, 3H), 3.76-3.85 (m, 1H), 4.33 (d, J=5.05 Hz, 2H), 5.88 (s, 1H), 7.76 (d, J=1.52 Hz, 1H), 8.10 (s, 1H), 8.30 (d, J=1.01 Hz, 1H), 8.64 (t, J=4.93 Hz, 1H), 11.54 (s, 1H); LC-MS (ES) m/z=414.8 [M+H].

Example 66

6-bromo-1-cyclopropyl-N-[(6-methyl-2-oxo-4-propyl-1,2-dihydro-3-pyridinyl)methyl]-1H-indazole-4-carboxamide

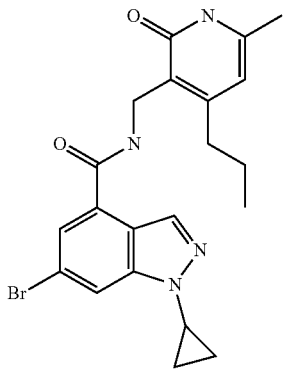 [SMILES: CCCc1cc(C)[nH]c(=O)c1CNC(=O)c1cc(Br)cc2c1cnn2C1CC1]

The title compound was prepared in the same manner as described for example 3 (step c) from 6-bromo-1-cyclopropyl-1H-indazole-4-carboxylic acid (0.22 g, 0.783 mmol) and 3-(aminomethyl)-6-methyl-4-propyl-2(1H)-pyridinone (0.236 g, 1.089 mmol), wherein the reaction stir time was 12 h. The title compound was collected as a white solid (0.36 g, 91%); $^1$H NMR (400 MHz, DMSO-d6) δ ppm 0.88 (t, J=7.33 Hz, 3H), 1.06-1.16 (m, 4H), 1.50 (sxt, J=7.53 Hz, 2H), 2.13 (s, 3H), 3.76-3.86 (m, 1H), 4.36 (d, J=5.05 Hz, 2H), 5.90 (s, 1H), 7.74 (d, J=1.52 Hz, 1H), 8.09 (s, 1H), 8.31 (s, 1H), 8.64 (t, J=4.80 Hz, 1H), 11.54 (br. s., 1H); LC-MS (ES) m/z=443.0 [M+H].

Example 67

1-cyclopropyl-6-{4-[(dimethylamino)methyl]phenyl}-N-[(4,6-dimethyl-2-oxo-1,2-dihydro-3-pyridinyl)methyl]-1H-indazole-4-carboxamide

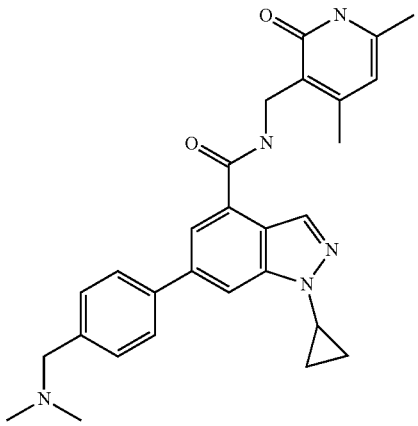

To a 20 mL microwave vial containing a mixture of 6-bromo-1-cyclopropyl-N-[(4,6-dimethyl-2-oxo-1,2-dihydro-3-pyridinyl)methyl]-1H-indazole-4-carboxamide (0.070 g, 0.169 mmol), N,N-dimethyl-1-[4-(4,4,5,5-tetramethyl-1,3,2-dioxaborolan-2-yl)phenyl]methanamine (0.060 g, 0.202 mmol), and potassium phosphate (tribasic) (0.107 g, 0.506 mmol) were added 1,4-dioxane (2.0 mL) and water (0.5 mL). The suspension was stirred with degassing under $N_2$ for 10 min. (emulsion), and then $PdCl_2$(dppf)-$CH_2Cl_2$ adduct (0.021 g, 0.025 mmol) was added. The contents were sealed and heated at 100° C. (heat block) for 2 h. After cooling to RT, the reaction mixture was diluted with EtOAc. Silica gel was added the mixture was concentrated in vacuo to dryness. The contents were purified by silica gel chromatography (dry loaded, eluent: 8-95% gradient chloroform (containing 10% 2M Ammonia in Methanol) and DCM). The collected product was concentrated from MTBE and dried in a vacuum oven for 2 h. The title compound was collected as a white solid (67 mg, 81%); $^1$H NMR (400 MHz, DMSO-d6) δ ppm 1.12-1.20 (m, 4H), 2.12 (s, 3H), 2.15-2.24 (m, 9H), 3.44 (s, 2H), 3.87 (t, J=5.31 Hz, 1H), 4.38 (d, J=4.80 Hz, 2H), 5.88 (s, 1H), 7.42 (m, J=8.34 Hz, 2H), 7.80 (m, J=8.08 Hz, 2H), 7.90 (s, 1H), 8.04 (s, 1H), 8.31 (s, 1H), 8.67 (t, J=4.93 Hz, 1H), 11.53 (s, 1H); LC-MS (ES) m/z=470.3 [M+H].

Example 68

1-cyclopropyl-6-{4-[(dimethylamino)methyl]phenyl}-N-[(6-methyl-2-oxo-4-propyl-1,2-dihydro-3-pyridinyl)methyl]-1H-indazole-4-carboxamide

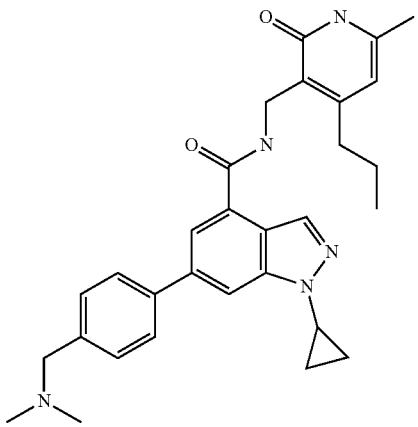

The title compound was prepared in the same manner as described for example 67 from 6-bromo-1-cyclopropyl-N-[(6-methyl-2-oxo-4-propyl-1,2-dihydro-3-pyridinyl)methyl]-1H-indazole-4-carboxamide (0.075 g, 0.169 mmol) and N,N-dimethyl-1-[4-(4,4,5,5-tetramethyl-1,3,2-dioxaborolan-2-yl)phenyl]methanamine (0.060 g, 0.203 mmol). The title compound was collected as a white solid (59 mg, 69%); $^1$H NMR (400 MHz, DMSO-d6) δ ppm 0.88 (t, J=7.33 Hz, 3H), 1.12-1.21 (m, 4H), 1.45-1.58 (m, 2H), 2.13 (s, 3H), 2.18 (s, 6H), 3.45 (s, 2H), 3.88 (quin, J=5.37 Hz, 1H), 4.41 (d, J=5.05 Hz, 2H), 5.91 (s, 1H), 7.43 (m, J=8.34 Hz, 2H), 7.80 (m, J=8.08 Hz, 2H), 7.89 (d, J=1.26 Hz, 1H), 8.04 (s, 1H), 8.32 (s, 1H), 8.68 (t, J=4.93 Hz, 1H), 11.54 (s, 1H); LC-MS (ES) m/z=498.4 [M+H].

Example 69

6-bromo-N-((1,2-dihydro-4,6-dimethyl-2-oxopyridin-3-yl)methyl)-1-isopropyl-3-methyl-1H-indazole-4-carboxamide

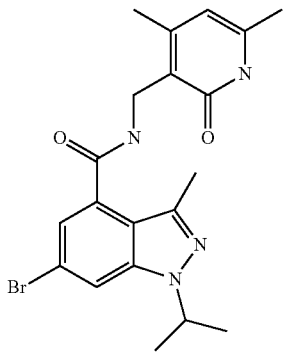 [SMILES: Cc1cc(C)c(CNC(=O)c2cc(Br)cc3c2c(C)nn3C(C)C)c(=O)[nH]1]

a) 5-Bromo-2-methyl-3-nitro-benzoic acid

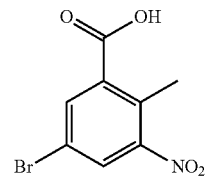

To a stirred solution of 2-methyl-3-nitro benzoic acid (300 g, 1647 mmol) in conc. $H_2SO_4$ (1.5 L) was added 1,3-dibromo-5,5 dimethyl-2,4-imadazolidinedione (258 g, 906 mmol) and the mixture was stirred at room temperature for 5 h. The reaction mixture was slowly added to ice water (4 L), and solid was precipitated out. The solid was filtered off and washed with water (1.2 L), pet ether (1 l) and dried to afford the title compound as a white solid (411 g, 96%), which was used without further purification. $^1$H NMR (DMSO, 400 MHz): δ 2.446 (s, 3H), 8.136 (s, 1H), 8.294 (s, 1H). LCMS (ES-) m/z=257.93 (M-H)- b) Methyl 6-bromo-1H-indole-4-carboxylate

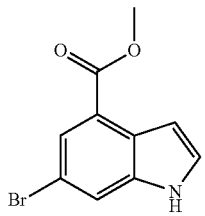

To a stirred solution of 5-Bromo-2-methyl-3-nitro-benzoic acid (140 g, 538.4 mmol) in DMF (550 ml) was added DMF-DMA (599 mL, 4846 mmol) at room temperature. The reaction mixture was stirred at 115° C. for 18 h. The reaction mixture was then concentrated in vacuo. The residual contents (176 g, 536.5 mmol) were dissolved in acetic acid (696 mL) and added to a suspension of Iron (329.2 g, 5902 mmol) in acetic acid (1.4 L) at 50° C. After completion of addition, the reaction mixture was stirred at 80-90° C. for 4 h. The reaction mixture was then filtered through a celite pad. The filtrate was poured onto ice water (1 L) and extracted with diethyl ether (3×700 ml). The combined organic layers were washed with sat NaHCO$_3$, brine, and dried over anhydrous Na$_2$SO$_4$, filtered, and evaporated under vacuum. The crude product was purified by silica gel chromatography (eluent: 10% ethyl acetate in pet ether) and afforded the title compound as a solid (80 g, 59%). $^1$H NMR (DMSO-d$_6$, 400 MHz) δ: 3.980 (s, 3H), 7.168 (d, J=3.2 Hz, 1H), 7.334 (d, J=3.2 Hz, 1H), 7.734 (s, 1H), 8.017 (s, 1H), 8.384 (brs, 1H); LCMS (ES−) m/z=251.9 (M−H).

c) Methyl 6-bromo-3-formyl-1H-indazole-4-carboxylate

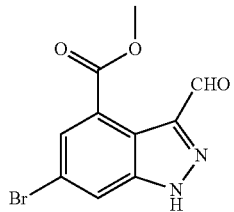

To a stirred solution of sodium nitrite (68.4 g, 991.3 mmol) in water (1425 mL) was added methyl 6-bromo-1H-indole-4-carboxylate (20.64 g, 81.25 mmol) at RT and the mixture stirred for 15 min at RT. To the mixture was added 6N HCl (159.6 mL) slowly dropwise over a period of 1 h and the reaction mixture was then stirred at room temperature for 48 h. The reaction mixture was extracted with 10% THF in ethyl acetate (5×500 mL). The combined organic layers were washed with water, brine, dried over anhydrous Na$_2$SO$_4$, and filtered. The filtrate was concentrated to ⅓ volume and cooled in freezer for 4 h. Precipitated solids were filtered and washed with cold ethyl acetate and dried under high vacuum to afford the title compound as an off white solid (13.7 g, 59.6%). $^1$H NMR (DMSO-d$_6$, 400 MHz): δ 3.905 (s, 3H), 7.754 (s, 1H), 8.183 (s, 1H), 10.274 (s, 1H), 14.563 (brs, 1H). LCMS (ES+): 281.06 [M−H] ion present.

d) Methyl 6-bromo-3-formyl-1-isopropyl-1H-indazole-4-carboxylate

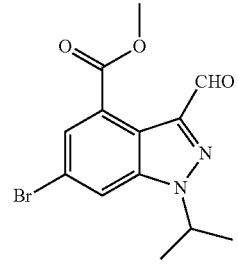

To a stirred solution of methyl 6-bromo-3-formyl-1H-indazole-4-carboxylate 1 (11.5 g, 40.63 mmol) in DMF (230 mL)) was added K$_2$CO$_3$ (14.08 g, 102.02 mmol) at RT under argon, and stirred for 10 min. Then 2-iodopropane (7.24 g, 42.58 mmol) was added at RT and the mixture stirred at 40° C. for 2 h. The reaction mixture was diluted with cold water and extracted with ethyl acetate (4×300 mL). The combined organic layers were washed with water, brine, dried over anhydrous Na$_2$SO$_4$, filtered, and concentrated. The crude residue (12.4 g) was purified by silica gel chromatography (eluent: 0-10% ethyl acetate: pet ether) to afford the title compound as an off white solid (5.55 g, 42%). $^1$H NMR (CDCl$_3$, 400 MHz): δ 1.659 (d, J=6.4 Hz, 6H), 4.017 (s, 3H), 4.862-4.960 (m, 1H), 7.807 (s, 1H), 7.854 (s, 1H), 10.375 (s, 1H). HPLC: 98.66%.

e) Methyl 6-bromo-1-isopropyl-3-methyl-1H-indazole-4-carboxylate

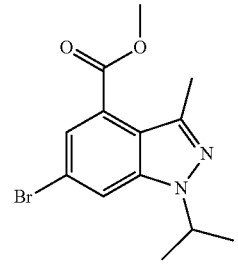 [SMILES: COC(=O)c1cc(Br)cc2c1c(C)nn2C(C)C]

To a stirred solution of methyl 6-bromo-3-formyl-1-isopropyl-1H-indazole-4-carboxylate (4.5 g, 13.84 mmol) in DMF (31.5 mL) was added p-toluenesulfonic acid monohydrate (0.342 g, 1.8 mmol), p-toluenesulfonyl hydrazide (3.35 g, 18.0 mmol) followed by sulfolane (31.5 mL), and the reaction mixture was stirred at 100° C. for 1 h. The reaction mixture was cooled to room temperature and sodium cyanoborohydride (3.489 g, 55.0 mmol) was added portion wise over a period of 25 min. The resulting reaction mixture was stirred at 100° C. for 2 h and then at RT for 6 h. The reaction mixture was diluted with water and extracted with ethyl acetate (4×300 mL). The combined organic layers were washed with water, brine, dried over anhydrous Na$_2$SO$_4$, filtered, and concentrated. The crude residue (4.4 g) was purified by silica gel chromatography (eluent: 0-5% ethyl acetate: pet ether) to afford the title compound as an off white solid (2.95 g, 68%). $^1$H NMR (CDCl$_3$, 400 MHz): δ 1.559 (d, J=6.8 Hz, 6H), 2.674 (s, 3H), 3.976 (s, 3H), 4.667-4.767 (m, 1H), 7.715 (d, J=1.6 Hz, 1H), 7.761 (d, J=1.6 Hz, 1H). LCMS (ES+): 98.63%, 313.06 [M+H] ion present.

93 f) 6-bromo-1-isopropyl-3-methyl-1H-indazole-4-carboxylic acid

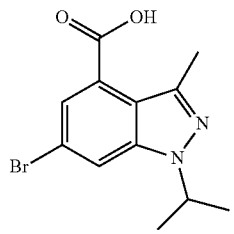 [SMILES: Cc1nn(C(C)C)c2cc(Br)cc(C(=O)O)c12]

To a stirred solution of methyl 6-bromo-1-isopropyl-3-methyl-1H-indazole-4-carboxylate (7.5 g, 24.11 mmol) in ethanol (400 mL) was added sodium hydroxide (1.45 g, 36.17 mmol) in water (60 mL) and the reaction mixture was stirred at reflux for 6 h. The reaction mixture was concentrated under reduced pressure and the residue was diluted with water (150 mL), and acidified with 2N HCl to pH~2. The precipitated acid was collected by filtration, washed with ether (200 mL, and dried to afford 6-bromo-1-isopropyl-3-methyl-1H-indazole-4-carboxylic acid as an off white solid (6.85 g, 95.6%). LCMS (ES−): 294.9 [M−H].

g) 6-bromo-N-((1,2-dihydro-4,6-dimethyl-2-oxopyridin-3-yl)methyl)-1-isopropyl-3-methyl-1H-indazole-4-carboxamide To a stirred solution of 6-bromo-1-isopropyl-3-methyl-1H-indazole-4-carboxylic acid, 1 (6.5 g, 21.88 mmol) in DCM (250 mL) was added EDC.HCl (5.01 g, 26.23 mmol), HOBt (3.545 g, 26.20 mmol) followed by diisopropyl ethyl amine (14.11 g, 109.37 mmol) and stirred at room temperature for 15 min. To the resulting mixture, 3-(amino methyl)-4,6-dimethylpyridin-2(1H)-one (3.32 g, 21.84 mmol) followed by DMAP (catalytic amount) was added and the reaction mixture was stirred at room temperature for 5 h. The reaction mixture was diluted with DCM (300 mL) and washed with 1N HCl solution (250 mL), saturated NaHCO$_3$ solution (250 mL) and brine solution. The organic layer was dried over anhydrous Na$_2$SO$_4$, filtered, and concentrated under reduced pressure. The residue was triturated with diethyl ether (100 mL), filtered, and dried to afford 6-bromo-N-((1,2-dihydro-4,6-dimethyl-2-oxopyridin-3-yl)methyl)-1-isopropyl-3-methyl-1H-indazole-4-carboxamide as an off white solid (5.5 g, 58%). H NMR (DMSO-d$_6$, 400 MHz): δ 1.412 (d, J=6.4 Hz, 6H), 2.112 (s, 3H), 2.215 (s, 3H), 2.383 (s, 3H), 4.319 (d, J=5.2 Hz, 2H), 4.907-4.972 (m, 1H), 5.864 (s, 1H), 7.129 (d, J=1.2 Hz, 1H), 8.011 (d, J=1.2 Hz, 1H), 8.473 (t, J=5 Hz, 1H), 11.479 (brs, 1H). LCMS (ES+): 431.02 [M+H].

94

Example 70

6-bromo-1-isopropyl-3-methyl-N-((6-methyl-2-oxo-4-propyl-1,2-dihydropyridin-3-yl)methyl)-1H-indazole-4-carboxamide

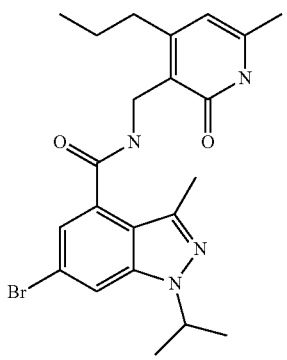 [SMILES: CCCc1cc(C)[nH]c(=O)c1CNC(=O)c1cc(Br)cc2c1c(C)nn2C(C)C]

The title compound was prepared in the same manner as described for example 3 (step c) from 6-bromo-3-methyl-1-(1-methylethyl)-1H-indazole-4-carboxylic acid (0.24 g, 0.808 mmol) and 3-(aminomethyl)-6-methyl-4-propyl-2(1H)-pyridinone (0.219 g, 1.010 mmol). The title compound was collected as a white solid (0.35 g, 92%); $^1$H NMR (400 MHz, DMSO-d6) δ ppm 0.92 (t, J=7.33 Hz, 3H) 1.41 (d, J=6.57 Hz, 6H) 1.49-1.60 (m, 2H) 2.12 (s, 3H) 2.39 (s, 3H) 2.53 (s, 1H) 4.33 (d, J=5.05 Hz, 2H) 4.88-5.00 (m, 1H) 5.89 (s, 1H) 7.12 (d, J=1.52 Hz, 1H) 8.02 (d, J=1.77 Hz, 1H) 8.48 (t, J=4.93 Hz, 1H) 11.50 (s, 1H); LCMS (ES+): 459.1 [M+H].

Example 71

1-isopropyl-3-methyl-N-((6-methyl-2-oxo-4-propyl-1,2-dihydropyridin-3-yl)methyl)-6-(2-(4-methylpiperazin-1-yl)pyridin-4-yl)-1H-indazole-4-carboxamide

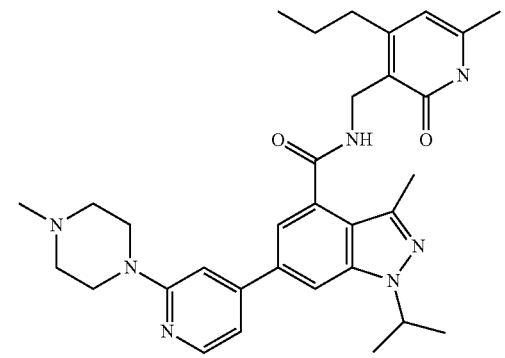

In a 25 mL sealable tube under nitrogen were combined 6-bromo-3-methyl-1-(1-methylethyl)-N-[(6-methyl-2-oxo-4-propyl-1,2-dihydro-3-pyridinyl)methyl]-1H-indazole-4-carboxamide (85 mg, 0.19 mmol), 1-methyl-4-[4-(4,4,5,5-tetramethyl-1,3,2-dioxaborolan-2-yl)-2-pyridinyl] piperazine (72.9 mg, 0.24 mmol) in dioxane/water (3 mL:1 mL). PdCl$_2$(dppf)-CH$_2$Cl$_2$ adduct (7.6 mg, 0.0093 mmol) was added and the resulting mixture was degassed with nitrogen for 10 min. Sodium bicarbonate (46.6 mg, 0.55 mmol)

was added, the vessel was sealed, and the insoluble mixture was heated in a microwave at 110° C. for 20 min. The mixture was evaporated, DCM was added and the contents purified by SiO$_2$ chromatography (eluent: gradient 0 to 80:20:2 DCM/MeOH/NH$_4$OH). The collected product was suspended in EtOAc along with some hexanes. The contents were sonicated and solids that precipitated were filtered. Acetonitrile was added, the solids were triturated, and again filtered. The collected solid was then suspended in DMF along with some water and then allowed to sit at room temperature overnight. Solids that precipitated were filtered, washed with DCM, and dried to afford the title compound as a light grey solid (34 mg, 32%). $^1$H NMR (400 MHz, DMSO-d$_6$) δ ppm 11.50 (s, 1H) 8.45 (t, J=4.93 Hz, 1H) 8.19 (d, J=5.31 Hz, 1H) 8.06-8.09 (m, 1H) 7.40 (s, 1H) 7.17 (s, 1H) 7.08 (d, J=5.05 Hz, 1H) 5.91 (s, 1H) 5.11 (quin, J=6.57 Hz, 1H) 4.39 (br. s., 1H) 4.38 (br. s., 1H) 3.55-3.62 (m, 4H) 2.53-2.57 (m, 2H) 2.41-2.46 (m, 7H) 2.24 (s, 3H) 2.13 (s, 3H) 1.53-1.61 (m, 2H) 1.47 (s, 3H) 1.46 (s, 3H) 0.93 (t, J=7.33 Hz, 3H); LC-MS (ES) m/z=459.2

Example 72

3-methyl-1-(1-methylethyl)-N-[(6-methyl-2-oxo-4-propyl-1,2-dihydro-3-pyridinyl)methyl]-6-[6-(1-piperazinyl)-3-pyridinyl]-1H-indazole-4-carboxamide

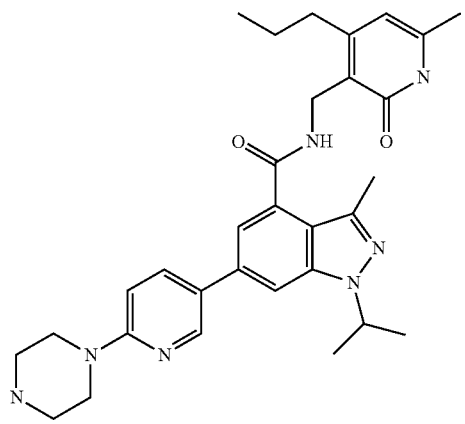 [SMILES: CCCc1cc(C)[nH]c(=O)c1CNC(=O)c1cc(-c2ccc(N3CCNCC3)nc2)cc2c1c(C)nn2C(C)C]

The title compound was prepared in a similar manner as described for example 8 from 6-bromo-3-methyl-1-(1-methylethyl)-N-[(6-methyl-2-oxo-4-propyl-1,2-dihydro-3-pyridinyl)methyl]-1H-indazole-4-carboxamide (65 mg, 0.141 mmol) and 1-[5-(4,4,5,5-tetramethyl-1,3,2-dioxaborolan-2-yl)-2-pyridinyl]piperazine (61 mg, 0.212 mmol). The product was collected as a white solid (54 mg, 49%). $^1$H NMR (400 MHz, DMSO-d$_6$) δ ppm 11.54 (br. s., 1H) 8.49-8.63 (m, 2H) 8.43 (br. s., 1H) 7.97 (dd, J=8.84, 2.53 Hz, 1H) 7.89 (s, 1H) 7.32 (s, 1H) 6.87-6.96 (m, 1H) 5.91 (s, 1H) 5.03 (dt, J=13.07, 6.47 Hz, 1H) 4.38 (d, J=4.55 Hz, 2H) 3.40-3.61 (m, 5H) 2.77-2.82 (m, 3H) 2.53-2.57 (m, 2H) 2.43 (s, 3H) 2.13 (s, 3H) 1.53-1.60 (m, 2H) 1.46 (s, 3H) 1.44 (s, 3H) 0.93 (t, J=7.33 Hz, 3H); LC-MS (ES) m/z=542.2 [M+H]$^+$ Example 73

6-(6-(dimethylamino)pyridin-3-yl)-N-((1,2-dihydro-4,6-dimethyl-2-oxopyridin-3-yl)methyl)-1-isopropyl-3-methyl-1H-indazole-4-carboxamide

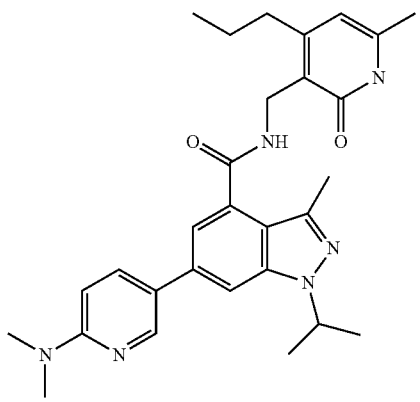

To a stirred solution of 6-bromo-N-((1,2-dihydro-4,6-dimethyl-2-oxopyridin-3-yl)methyl)-1-isopropyl-3-methyl-1H-indazole-4-carboxamide (300 mg, 0.696 mmol) in DMF (30 mL) was added 6-(dimethylamino)pyridin-3-yl-3-boronic acid, 1 (127 mg, 0.765 mmol) followed by sodium carbonate (184.4 mg, 1.74 mmol) dissolved in water (3 mL) and degassed with argon for 1 h. Then PdCl$_2$(PPh$_3$)$_2$ (48.8 mg, 0.069 mmol) was added and again degassed with argon for 15 min and stirred at 110° C. for 4 h. The reaction mixture was filtered through Celite pad and washed with ethyl acetate (50 mL). The filtrate was diluted with water and extracted with ethyl acetate (4×90 mL). The combined organic layers were separated and washed with cold water (2×50 mL), brine solution (50 mL), dried over anhydrous Na$_2$SO$_4$, filtered, and concentrated to afford the crude product (450 mg). The crude compound was purified by silica gel chromatography (eluent: 5% MeOH: DCM) to afford 100 mg of desired product which was triturated with hexane and the solid was filtered and dried to afford the title compound as an off white solid (100 mg, 30%). $^1$H NMR (DMSO-d$_6$, 400 MHz): δ 1.559 (d, J=6.8 Hz, 6H), 2.102 (s, 3H), 2.403 (s, 3H), 2.539 (s, 3H), 3.125 (s, 6H), 4.616 (s, 2H), 4.754-4.820 (m, 1H), 5.893 (s, 1H), 6.557 (d, J=8.8 Hz, 1H), 7.313 (s, 1H), 7.401 (d, J=5.2 Hz, 1H), 7.448 (s, 1H), 7.707 (d, J=8.8 Hz, 1H), 8.438 (s, 1H), 11.502 (brs, 1H). $^1$H NMR (D$_2$O Ex in DMSO, 400 MHz): δ 1.559 (d, J=6.8 Hz, 6H), 2.115 (s, 3H), 2.408 (s, 3H), 2.538 (s, 3H), 3.124 (s, 6H), 4.616 (s, 2H), 4.754-4.820 (m, 1H), 5.899 (s, 1H), 6.557 (d, J=8.8 Hz, 1H), 7.318 (s, 1H), 7.450 (s, 1H), 7.718 (d, J=8.8 Hz, 1H), 8.438 (s, 1H). LCMS (ES+): 473.19.

Example 74

6-(3-((dimethylamino)methyl)phenyl)-N-((1,2-dihydro-4,6-dimethyl-2-oxopyridin-3-yl)methyl)-1-isopropyl-1H-indazole-4-carboxamide

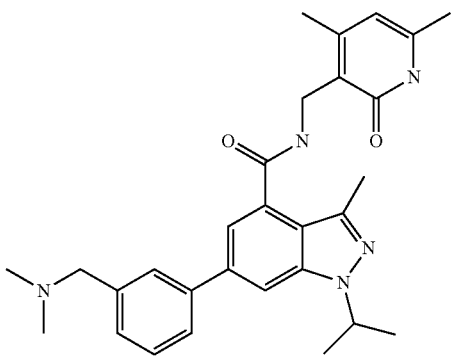

The title compound was prepared from 6-bromo-N-((1,2-dihydro-4,6-dimethyl-2-oxopyridin-3-yl)methyl)-1-isopropyl-1H-indazole-4-carboxamide (500 mg, 1.14 mmol) and N,N-dimethyl(3-(4,4,5,5-tetramethyl-1,3,2-dioxaborolan-2-yl)phenyl)methanamine (300 mg, 1.14 mmol) in the same manner as described for example 73 wherein the contents were heated at 120° C. for 2 h. The product was collected as a pale red solid (120 mg, 21%). $^1$H NMR (CDCl$_3$, 400 MHz): δ 1.568 (d, J=6.8 Hz, 6H), 2.12 (s, 3H), 2.41 (s, 8H), 2.55 (s, 3H), 3.67 (s, 2H), 4.614 (d, J=5.2 Hz, 2H), 4.899-4.834 (m, 1H), 5.90 (s, 1H), 7.326-7.308 (m, 1H), 7.408-7.368 (m, 3H), 7.558 (d, J=7.6 Hz, 1H,), 7.639 (s, 1H), 7.699 (s, 1H), 11.193 (brs, 1H). LCMS (ES+) m/z: 486.31.

Example 75

N-((4,6-dimethyl-2-oxo-1,2-dihydropyridin-3-yl)methyl)-6-(4-fluorophenyl)-1-isopropyl-3-methyl-1H-indazole-4-carboxamide

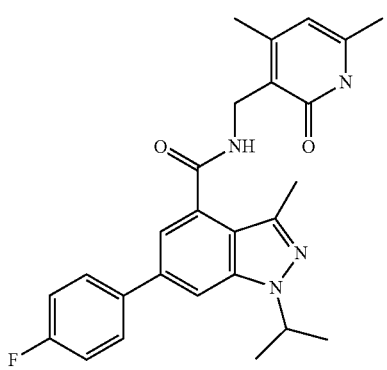 [SMILES: Cc1cc(C)c(CNC(=O)c2cc(-c3ccc(F)cc3)cc3c2c(C)nn3C(C)C)c(=O)[nH]1]

In a 25 mL sealable tube under nitrogen were combined 6-bromo-N-[(4,6-dimethyl-2-oxo-1,2-dihydro-3-pyridinyl)methyl]-3-methyl-1-(1-methylethyl)-1H-indazole-4-carboxamide (90 mg, 0.21 mmol), (4-fluorophenyl)boronic acid (43.8 mg, 0.31 mmol) in dioxane/water (3 mL:1 mL). PdCl$_2$(dppf)-CH$_2$Cl$_2$ adduct (5.11 mg, 0.006 mmol) was added and the resulting mixture was degassed with nitrogen for 10 min. Sodium bicarbonate (52.6 mg, 0.63 mmol) was added, the vessel was sealed, and the insoluble mixture was heated in a microwave at 100° C. for 20 min. The mixture was evaporated, DCM/MeOH (1:1) was added, the contents pre-absorbed on silica gel and purified by SiO$_2$ chromatography (eluent: gradient 0 to 80:20:2 DCM/MeOH/NH$_4$OH). The collected product was suspended in EtOAc along with some hexanes. The mixture was sonicated, and the solids that precipitated were filtered and dried to afford the title compound as a white solid (73 mg, 77%). $^1$H NMR (400 MHz, DMSO-d$_6$) δ ppm 11.50 (s, 1H) 8.46 (t, J=5.05 Hz, 1H) 7.94 (d, J=1.26 Hz, 1H) 7.83-7.88 (m, 2H) 7.31-7.36 (m, 3H) 5.88 (s, 1H) 5.06 (quin, J=6.63 Hz, 1H) 4.38 (s, 1H) 4.36 (s, 1H) 2.43 (s, 3H) 2.24 (s, 3H) 2.12 (s, 3H) 1.47 (s, 3H) 1.45 (s, 3H). LC-MS (ES) m/z=446.9

Example 76

N-((1,2-dihydro-4,6-dimethyl-2-oxopyridin-3-yl)methyl)-1-isopropyl-3-methyl-6-(6-(4-methylpiperazin-1-yl)pyridin-3-yl)-1H-indazole-4-carboxamide

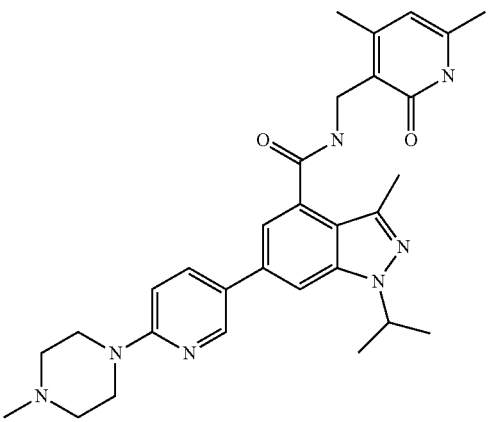

To a stirred solution of 6-bromo-N-((1,2-dihydro-4,6-dimethyl-2-oxopyridin-3-yl)methyl)-1-isopropyl-3-methyl-1H-indazole-4-carboxamide (0.3 g, 0.69 mmol) in DMF (15 mL) was added 1-methyl-4-(5-(4,4,5,5-tetramethyl-1,3,2-dioxaborolan-2-yl)pyridin-2-yl)piperazine (0.25 g, 0.82 mmol) followed by PdCl$_2$(PPh$_3$)$_2$ (0.097 g, 0.13 mmol) and the mixture stirred 5 min. Sodium carbonate (0.184 g, 1.73 mmol) dissolved in water (2 mL) was added and the resulting reaction mixture was stirred at 110° C. for 4 h. The contents were then diluted with sodium bicarbonate solution and extracted with ethyl acetate (3×20 mL). The combined organic layers were washed with brine solution (20 mL), dried over anhydrous Na$_2$SO$_4$, filtered, and concentrated to afford the crude product. The crude compound was purified by silica gel chromatography (eluent: 5% MeOH\DCM). The desired product was isolated as an off white solid with trace impurities. The impure compound was washed several times with cold water and triturated with hexane to afford the title compound as an off-white solid (80 mg, 22%). $^1$H NMR (DMSO-d$_6$, 400 MHz): δ 1.447 (d, J=6.4 Hz, 6H), 2.112 (s, 3H), 2.235 (s, 6H), 2.411 (s, 7H), 3.551 (s, 4H), 4.363 (d, J=4.4 Hz, 2H), 4.991-5.054 (m, 1H), 5.870 (s, 1H), 6.942 (d, J=9.2 Hz, 1H), 7.321

(s, 1H), 7.880 (s, 1H), 7.99 (d, J=8.8 Hz, 1H), 8.403 (s, 1H), 8.569 (s, 1H), 11.483 (brs, 1H). LCMS (ES+) m/z: 528.29.

Example 77

6-(4-((dimethylamino)methyl)phenyl)-N-((1,2-dihydro-4,6-dimethyl-2-oxopyridin-3-yl)methyl)-1-isopropyl-3-methyl-1H-indazole-4-carboxamide

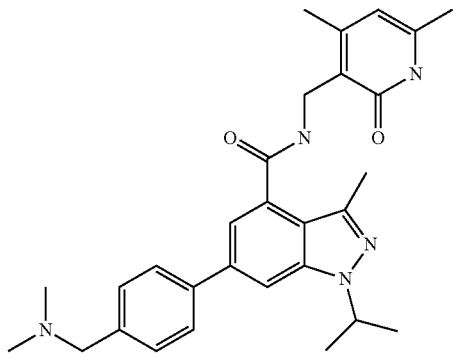

The title compound was prepared from 6-bromo-N-((1,2-dihydro-4,6-dimethyl-2-oxopyridin-3-yl)methyl)-1-isopropyl-1H-indazole-4-carboxamide (300 mg, 0.696 mmol) and dimethyl-[4-(4,4,5,5-tetramethyl-[1,3,2]dioxaborolan-2-yl)-benzyl]-amine (199 mg, 0.765 mmol) in the same manner as described for example 73. The final product was collected as a grey colored solid (80 mg, 26%). $^1$H NMR (DMSO-d$_6$, 400 MHz): δ 1.458 (d, J=6.4 Hz, 6H), 2.108 (s, 3H), 2.176 (s, 8H), 2.55 (s, 3H), 3.67 (s, 2H), 4.614 (d, J=5.2 Hz, 2H), 4.899-4.834 (m, 1H), 5.90 (s, 1H), 7.326-7.308 (m, 1H), 7.408-7.368 (m, 3H), 7.558 (d, J=7.6 Hz, 1H), 7.639 (s, 1H), 7.699 (s, 1H), 11.193 (brs, 1H). LCMS (ES+) m/z: 486.20 (M+H).

Example 78

N-((1,2-dihydro-4,6-dimethyl-2-oxopyridin-3-yl)methyl)-1-isopropyl-3-methyl-6-(6-(piperazin-1-yl)pyridin-3-yl)-1H-indazole-4-carboxamide hydrochloride

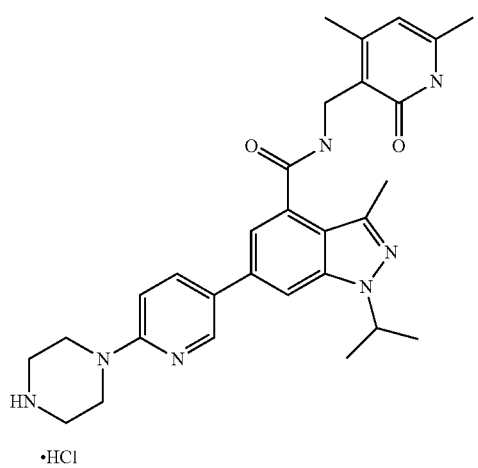 [SMILES: Cc1cc(C)c(CNC(=O)c2cc(-c3ccc(N4CCNCC4)nc3)cc3c2c(C)nn3C(C)C)c(=O)[nH]1 ; Cl]

Example 79 a) tert-butyl 4-(5-(4-((1,2-dihydro-4,6-dimethyl-2-oxopyridin-3-yl)methylcarbamoyl)-1-isopropyl-3-methyl-1H-indazol-6-yl)pyridin-2-yl)piperazine-1-carboxylate

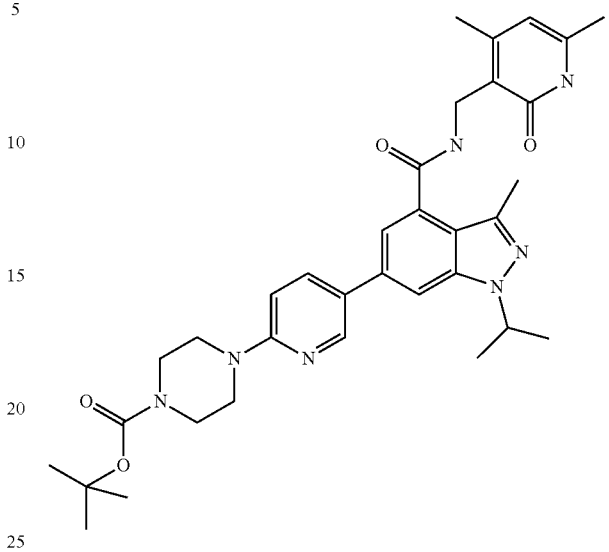

To a stirred solution of 6-bromo-N-((1,2-dihydro-4,6-dimethyl-2-oxopyridin-3-yl)methyl)-1-isopropyl-3-methyl-1H-indazole-4-carboxamide (400 mg, 0.928 mmol) in DMF (20 mL) was added tert-butyl 4-(5-(4,4,5,5-tetramethyl-1,3,2-dioxaborolan-2-yl)pyridin-2-yl)piperazine-1-carboxylate (397 mg, 1.02 mmol) followed by sodium carbonate (246 mg, 2.32 mmol) dissolved in water (4 mL) and degassed with argon for 30 min. PdCl$_2$(PPh$_3$)$_2$ (65 mg, 0.092 mmol) was added and the mixture again degassed with argon for 10 min. The reaction mixture was stirred at 100° C. for 3 h. The reaction mixture was diluted with water (100 mL) and extracted with ethyl acetate (3×150 mL). The combined organic layers were dried over anhydrous Na$_2$SO$_4$, filtered, and concentrated to afford the crude product (650 mg). The crude compound was purified by silica gel chromatography (eluent: 0-10% MeOH:DCM). The product was triturated with diethyl ether (150 mL) to afford the title compound as an off white solid (270 mg, 47%). $^1$H NMR (DMSO-d$_6$, 400 MHz): δ 1.498 (s, 9H), 1.560 (d, J=6.4 Hz, 6H), 2.128 (s, 3H), 2.413 (s, 3H), 2.526 (s, 3H), 3.579 (s, 8H), 4.610 (d, J=5.6 Hz, 2H), 4.760-4.824 (m, 1H), 5.907 (s, 1H), 6.70 (d, J=8.8 Hz, 1H), 7.311-7.346 (m, 2H), 7.454 (s, 1H), 7.735 (d, J=8.8 Hz, 1H), 8.463 (s, 1H), 10.991 (brs, 1H). LCMS (ES+): 614.25.

b) N-((1,2-dihydro-4,6-dimethyl-2-oxopyridin-3-yl)methyl)-1-isopropyl-3-methyl-6-(6-(piperazin-1-yl)pyridin-3-yl)-1H-indazole-4-carboxamide hydrochloride To a stirred solution of tert-butyl 4-(5-(4-((1,2-dihydro-4,6-dimethyl-2-oxopyridin-3-yl)methylcarbamoyl)-1-isopropyl-3-methyl-1H-indazol-6-yl)pyridin-2-yl)piperazine-1-carboxylate (250 mg, 0.407 mmol) in DCM (50 mL) was added 4M HCl in 1,4-dioxane (6 mL) at 0° C. and stirred at room temperature for 2 h. The reaction mixture was concentrated and then co-distilled with toluene (50 mL). The residue was dried under reduced pressure to get the crude HCl salt (195 mg). The residue was triturated with diethyl ether (100 mL), DCM (100 mL) and n-hexane (100 mL) to afford the title compound as a pale brown solid (135 mg, 60%). $^1$H NMR (DMSO-d$_6$, 400 MHz): δ 1.454 (d, J=6.4 Hz, 6H), 2.119 (s, 3H), 2.244 (s, 3H), 2.412 (s, 3H), 3.222 (s, 4H), 3.839 (s, 4H), 4.369 (d, J=4.4 Hz, 2H), 5.005-5.071 (m, 1H), 5.888 (s, 1H), 7.125 (d, J=8.8 Hz, 1H), 7.348 (s, 1H), 7.942 (s, 1H), 8.158 (d, J=8 Hz, 1H), 8.429 (t, J=4.6 Hz, 1H), 8.613 (d, J=2.0 Hz, 1H), 9.145 (s, 2H), 11.519 (brs, 1H). LCMS (ES+): 514.24 [M+H].

Example 79

N-((4,6-dimethyl-2-oxo-1,2-dihydropyridin-3-yl)methyl)-1-isopropyl-3-methyl-6-(6-(4-methylpiperazin-1-yl)pyridin-2-yl)-1H-indazole-4-carboxamide

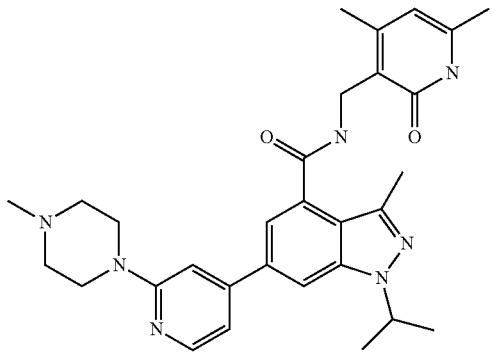

A stirred solution of 6-bromo-N-((4,6-dimethyl-2-oxo-1,2-dihydropyridin-3-yl)methyl)-1-isopropyl-3-methyl-1H-indazole-4-carboxamide, 3 (200 mg, 0.464 mmol), 1-methyl-4-(4-(4,4,5,5-tetramethyl-1,3,2-dioxaborolan-2-yl)pyridin-2-yl)piperazine (154 mg, 0.510 mmol) and Na$_2$CO$_3$ (123 mg, 1.160 mmol) in a mixture of water (3 mL) and DMF (15 mL) was degassed with argon gas for 30 min. Then PdCl$_2$(PPh$_3$)$_2$ (16.28 mg, 0.023 mmol) was added and heated to 120° C. for 3 h. Then the reaction mixture was filtered through Celite bed and the Celite bed was washed with ice cold water (2×100 mL). The filtrate was extracted with EtOAc (20 mL), dried over anhydrous sodium sulphate, filtered, and concentrated to afford 150 mg of crude product. The crude product was purified by silica gel chromatography over (eluent: 5% MeOH/DCM) to afford the title compound as an off-white solid (85 mg, 32%). $^1$H NMR (DMSO-d$_6$, 400 MHz): δ 0.889 (t, J=14.4 Hz, 3H), 1.554-1.483 (m, 8H), 2.134 (s, 3H), 2.55 (s, 3H), 4.411 (d, J=1.6 Hz, 2H), 5.059 (m, 1H), 5.913 (s, 1H), 7.830 (s, 1H), 8.047 (s, 1H), 8.08 (s, 1H), 8.306 (s, 1H), 8.462 (s, 1H), 11.53 (s, 1H), 13 (brs, 1H). LCMS (ES+) m/z=528.2.

Example 80

N-((1,2-dihydro-4,6-dimethyl-2-oxopyridin-3-yl)methyl)-1-isopropyl-3-methyl-6-(pyridin-3-yl)-1H-indazole-4-carb oxamide

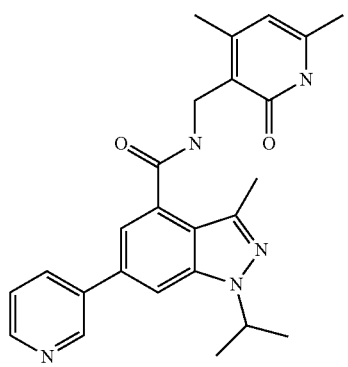 [SMILES: Cc1cc(C)c(CNC(=O)c2cc(-c3cccnc3)cc3c2c(C)nn3C(C)C)c(=O)[nH]1]

a) methyl 3-methyl-1-(1-methylethyl)-6-(3-pyridinyl)-1H-indazole-4-carboxylate

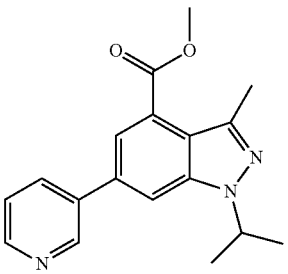 [SMILES: COC(=O)c1cc(-c2cccnc2)cc2c1c(C)nn2C(C)C]

To a stirred solution of methyl 6-bromo-1-isopropyl-3-methyl-1H-indazole-4-carboxylate (0.5 g, 1.60 mmol) in 1,4-dioxane (25 mL) was added 3-(4,4,5,5-tetramethyl-1,3,2-dioxaborolan-2-yl)pyridine (0.39 g, 1.92 mmol) followed by PdCl$_2$(dppf)-CH$_2$Cl$_2$ adduct (0.26 g, 0.32 mmol). The reaction mixture was stirred for 5 min, then sodium bicarbonate (0.4 g, 4.80 mmol) dissolved in water (8 mL) was added and the reaction mixture was stirred at 100° C. for 6 h. The reaction mixture was diluted with water and extracted with ethyl acetate (3×40 mL). The combined organic layers were washed with cold water (2×25 mL), brine solution (25 mL), dried over anhydrous Na$_2$SO$_4$, filtered, and concentrated to afford the crude product. The crude compound was purified by silica gel chromatography (eluent: 100% ethyl acetate) to afford the title compound as an off-white solid (470 mg, 94%). $^1$H NMR (DMSO-d$_6$, 400 MHz): δ 1.485 (d, J=6.4 Hz, 6H), 2.601 (s, 3H), 3.945 (s, 3H), 5.121-5.186 (m, 1H), 7.523-7.554 (m, 1H), 7.902 (s, 1H), 8.232 (d, J=7.6 Hz, 1H), 8.316 (s, 1H), 8.625 (d, J=4 Hz, 1H), 9.045 (s, 1H).

b) 1-isopropyl-3-methyl-6-(pyridin-3-yl)-1H-indazole-4-carboxylic acid

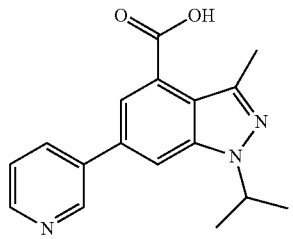 [SMILES: Cc1nn(C(C)C)c2cc(-c3cccnc3)cc(C(=O)O)c12]

To a stirred solution of methyl 1-isopropyl-3-methyl-6-(pyridin-3-yl)-1H-indazole-4-carboxylate, 1 (0.5 g, 1.618 mmol) in a mixture of THF and H$_2$O (30 mL) was added LiOH.H$_2$O (0.2 g, 4.85 mmol) and the mixture was refluxed at 80° C. for 8 h. THF was distilled off and the aqueous layer was adjusted to pH~5 with 10% HCl at 0° C. and the precipitated solid was collected by filtration and dried to afford 1-isopropyl-3-methyl-6-(pyridin-3-yl)-1H-indazole-4-carboxylic acid as an off-white solid (0.51 g). LCMS (ES+) m/z: 296.7.

c) N-((1,2-dihydro-4,6-dimethyl-2-oxopyridin-3-yl)methyl)-1-isopropyl-3-methyl-6-(pyridin-3-yl)-1H-indazole-4-carboxamide To a stirred solution of 1-isopropyl-3-methyl-6-(pyridin-3-yl)-1H-indazole-4-carboxylic acid (0.5 g, 1.69 mmol) in DCM (30 mL) was added EDC.HCl (0.39 g, 2.03 mmol), HOBT (2.74 g, 2.03 mmol) followed by DIPEA (1.47 mL, 8.45 mmol) and stirred at room temperature for 15 min. To the resulting reaction mixture, 3-(amino methyl)-4,6-dimethylpyridin-2(1H)-one (0.257 g, 1.69 mmol) was added and stirred at room temperature for overnight. The reaction mixture was filtered and the precipitate was washed with water followed by ether and dried. The solid compound was further purified by silica gel chromatography (eluent: 10% MeOH in ethyl acetate) to afford the title compound as an off-white solid (225 mg, 31%). $^1$H NMR (DMSO-$d_6$, 400 MHz): δ 1.461 (d, J=6.4 Hz, 6H), 2.109 (s, 3H), 2.240 (s, 3H), 2.438 (s, 3H), 4.372 (d, J=4.8 Hz, 2H), 5.042-5.107 (m, 1H), 5.870 (s, 1H), 7.410 (s, 1H), 7.501-7.533 (m, 1H), 8.061 (s, 1H), 8.215 (d, J=8 Hz, 1H), 8.461 (t, J=4.8 Hz, 1H), 8.593 (d, J=4.8 Hz, 1H), 9.036 (s, 1H), 11.489 (brs, 1H). LCMS (ES+) m/z: 430.12

Example 81

N-((1,2-dihydro-6-methyl-2-oxo-4-propylpyridin-3-yl)methyl)-1-isopropyl-3-methyl-6-(1H-pyrrolo[2,3-b]pyridin-5-yl)-1H-indazole-4-carboxamide

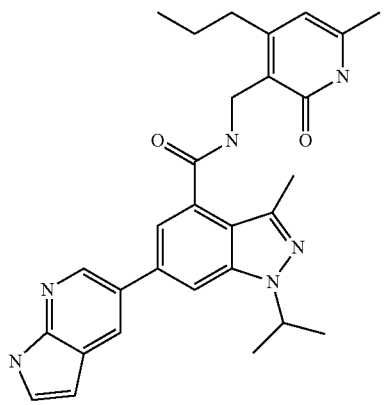 [SMILES: CCCc1cc(C)[nH]c(=O)c1CNC(=O)c1cc(-c2cnc3[nH]ccc3c2)cc2c1c(C)nn2C(C)C]

a) Methyl 1-isopropyl-3-methyl-6-(1H-pyrrolo[2,3-b]pyridin-5-yl)-1H-indazole-4-carboxylate

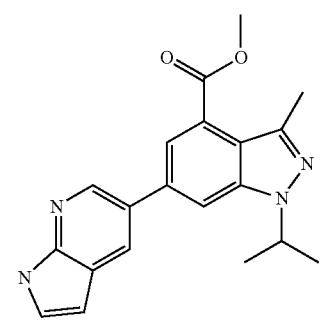 [SMILES: COC(=O)c1cc(-c2cnc3[nH]ccc3c2)cc2c1c(C)nn2C(C)C]

The title compound was prepared from methyl 6-bromo-1-isopropyl-3-methyl-1H-indazole-4-carboxylate, (0.7 g, 2.25 mmol) and 5-(4,4,5,5-tetramethyl-1,3,2-dioxaborolan-2-yl)-1H-pyrrolo[2,3-b]pyridine (0.65 g, 2.70 mmol) in the same manner as described for example 80 (step a). The product was collected as an off-white solid (600 mg, 82.5%). $^1$H NMR (DMSO-$d_6$, 400 MHz): δ 1.489 (d, J=6.4 Hz, 6H), 2.603 (s, 3H), 3.949 (s, 3H), 5.140-5.172 (m, 1H), 6.547 (s, 1H), 7.545 (s, 1H), 7.935 (s, 1H), 8.253 (s, 1H), 8.377 (s, 1H), 8.667 (s, 1H), 11.774 (s, 1H). LCMS (ES+) m/z: 349.

b) 1-isopropyl-3-methyl-6-(1H-pyrrolo[2,3-b]pyridin-5-yl)-1H-indazole-4-carboxylic acid

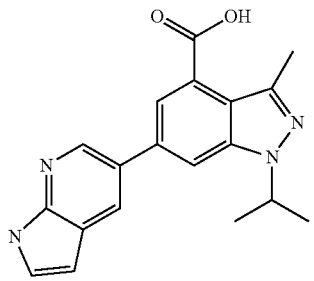 [SMILES: Cc1nn(C(C)C)c2cc(-c3cnc4[nH]ccc4c3)cc(C(=O)O)c12]

The title compound was prepared from methyl 1-isopropyl-3-methyl-6-(1H-pyrrolo[2,3-b]pyridin-5-yl)-1H-indazole-4-carboxylate, 1 (50 mg, 0.14 mmol) and LiOH.H$_2$O (20 mg, 0.43 mmol) in the same manner as described for example 80 (step b). The product was collected as an off-white solid (60 mg) and used in the next step without any further purification. LCMS (ES+) m/z: 335.15.

c) N-((1,2-dihydro-6-methyl-2-oxo-4-propylpyridin-3-yl)methyl)-1-isopropyl-3-methyl-6-(1H-pyrrolo[2,3-b]pyridin-5-yl)-1H-indazole-4-carboxamide The title compound was prepared in the same manner as described for example 80 (step c) from 1-isopropyl-3-methyl-6-(1H-pyrrolo[2,3-b]pyridin-5-yl)-1H-indazole-4-carboxylic acid (50 mg, 0.149 mmol) and 3-(aminomethyl)-6-methyl-4-propylpyridin-2(1H)-one (26 mg, 0.149 mmol) wherein the contents were stirred at RT for 5 h. The crude product was washed with DCM, filtered, and dried to afford the title compound as an off-white solid. (48 mg, 64%). $^1$H NMR (DMSO-$d_6$, 400 MHz): δ 0.930 (t, J=7.6 Hz, 3H), 1.468 (d, J=6.4 Hz, 6H), 1.544-1.601 (m, 2H), 2.123 (s, 3H), 2.452 (s, 3H), 2.501 (s, 2H), 4.394 (d, J=4 Hz, 2H), 5.060-5.093 (m, 1H), 5.902 (s, 1H), 6.526 (s, 1H), 7.420 (s, 1H), 7.528 (s, 1H), 7.996 (s, 1H), 8.348 (s, 1H), 8.445 (s, 1H), 8.656 (s, 1H), 11.490 (brs, 1H), 11.735 (brs, 1H). LCMS (ES+) m/z: 497.49

Example 82

N-((1,2-dihydro-4,6-dimethyl-2-oxopyridin-3-yl)methyl)-1-isopropyl-3-methyl-6-(1H-pyrazol-4-yl)-1H-indazole-4-carboxamide

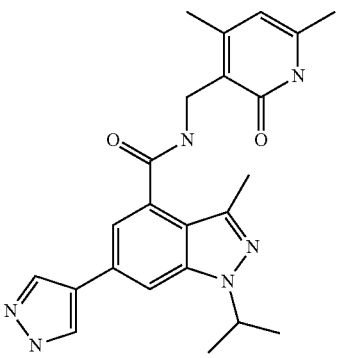 [SMILES: Cc1cc(C)c(CNC(=O)c2cc(-c3cn[nH]c3)cc3c2c(C)nn3C(C)C)c(=O)[nH]1]

a) Methyl 1-isopropyl-3-methyl-6-(1H-pyrazol-4-yl)-1H-indazole-4-carboxylate

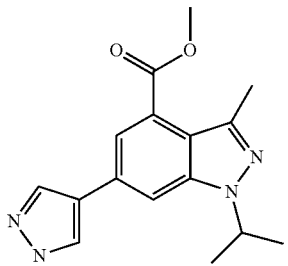 [SMILES: COC(=O)c1cc(-c2cn[nH]c2)cc2c1c(C)nn2C(C)C]

The title compound was prepared in the same manner as described for example 80 (step a) from methyl 6-bromo-1-isopropyl-3-methyl-1H-indazole-4-carboxylate (0.5 g, 1.60 mmol) and 4-(4,4,5,5-tetramethyl-1,3,2-dioxaborolan-2-yl)-1H-pyrazole (0.37 g, 1.92 mmol) wherein the reaction mixture was heated at 115° C. for 3 h. The crude compound was purified silica gel chromatography (eluent: 50% ethyl acetate\pet ether) to afford the title compound as an off-white solid. $^1$H NMR (DMSO-d$_6$, 400 MHz): δ 1.470 (d, J=6.4 Hz, 6H), 2.543 (s, 3H), 3.928 (s, 3H), 5.000-5.063 (m, 1H), 7.822 (s, 1H), 8.102 (d, J=9.6 Hz, 2H), 8.374 (s, 1H), 13.030 (brs, 1H). LCMS (ES+) m/z: 299.25.

b) 1-isopropyl-3-methyl-6-(1H-pyrazol-4-yl)-1H-indazole-4-carboxylic acid

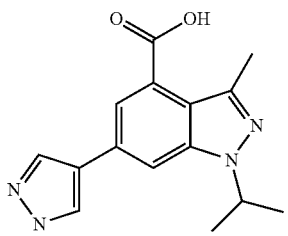 [SMILES: Cc1nn(C(C)C)c2cc(-c3cn[nH]c3)cc(C(=O)O)c12]

The title compound was prepared from methyl 1-isopropyl-3-methyl-6-(1H-pyrazol-4-yl)-1H-indazole-4-carboxylate (0.2 g, 0.67 mmol) and LiOH.H$_2$O (0.084 g, 2.01 mmol) in the same manner as described for example 80 (step b). The product was collected as a white solid (0.2 g). $^1$H NMR (DMSO-d$_6$, 400 MHz): δ 1.467 (d, J=6.4 Hz, 6H), 2.568 (s, 3H), 4.984-5.048 (m, 1H), 7.790 (s, 1H), 8.058 (s, 1H), 8.219 (brs, 2H), 13.05 (brs, 2H). LCMS (ES+) m/z: 285.10 [M+H].

c) N-((1,2-dihydro-4,6-dimethyl-2-oxopyridin-3-yl)methyl)-1-isopropyl-3-methyl-6-(1H-pyrazol-4-yl)-1H-indazole-4-carboxamide The title compound was prepared from 1-isopropyl-3-methyl-6-(1H-pyrazol-4-yl)-1H-indazole-4-carboxylic acid and 3-(aminomethyl)-4,6-dimethylpyridin-2(1H)-one (0.059 g, 0.387 mmol) in the same manner as described for example 80 (step c) wherein the contents were stirred at RT for 5 h. The product was collected as a pale yellow solid (30 mg, 20%). $^1$H NMR (DMSO-d$_6$, 400 MHz): δ 1.563 (d, J=6.8 Hz, 6H), 2.207 (s, 3H), 2.455 (s, 3H), 2.556 (s, 3H), 4.616 (d, J=6 Hz, 2H), 4.781-4.798 (m, 1H), 5.899 (s, 1H), 7.236 (s, 1H), 7.488 (s, 1H) 7.522 (s, 1H), 7.797 (d, J=9.6 Hz, 2H). LCMS (ES+) m/z: 419.45.

Example 83

N-((1,2-dihydro-4,6-dimethyl-2-oxopyridin-3-yl)methyl)-1-isopropyl-3-methyl-6-(pyridin-3-yl)-1H-indazole-4-carb oxamide

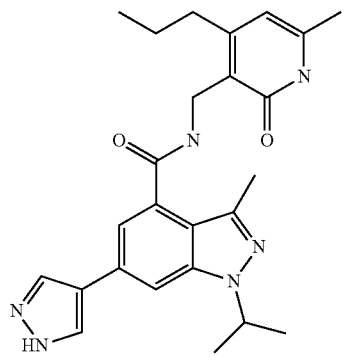 [SMILES: CCCc1cc(C)[nH]c(=O)c1CNC(=O)c1cc(-c2cn[nH]c2)cc2c1c(C)nn2C(C)C]

The title compound was prepared in the same manner as described for example 80 (step c) from 1-isopropyl-3-methyl-6-(1H-pyrazol-4-yl)-1H-indazole-4-carboxylic acid (0.15 g, 0.52 mmol) and 3-(aminomethyl)-6-methyl-4-propylpyridin-2(1H)-one (0.09 g, 0.52 mmol) wherein the contents were stirred at RT for 5 h. The crude compound was purified by silica gel chromatography (eluent: 2% MeOH\DCM) to afford the title compound as an off-white solid (60 mg, 25%). $^1$H NMR (DMSO-d$_6$, 400 MHz): δ 0.938 (t, J=7.2 Hz, 3H), 1.447 (d, J=6.8 Hz, 6H), 1.540-1.597 (m, 2H), 2.122 (s, 3H), 2.380 (s, 3H), 2.548 (t, J=3.6 Hz, 2H), 4.369 (d, J=5.2 Hz, 2H), 4.920-4.987 (m, 1H), 5.899 (s, 1H), 7.330 (s, 1H), 7.869 (s, 1H), 8.021 (s, 1H), 8.293 (t, J=4.8 Hz, 2H), 11.483 (brs, 1H), 12.963 (brs, 1H). LCMS (ES+) m/z: 447.48.

Example 84

N-[(4,6-dimethyl-2-oxo-1,2-dihydro-3-pyridinyl)methyl]-3-methyl-1-(1-methylethyl)-6-(6-methyl-3-pyridinyl)-1H-indazole-4-carboxamide

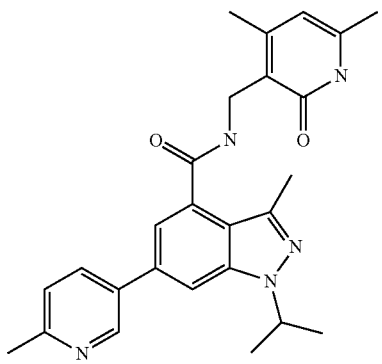

The title compound was prepared in the same manner as described for example 76 from 6-bromo-N-((1,2-dihydro-4,6-dimethyl-2-oxopyridin-3-yl)methyl)-1-isopropyl-3-methyl-1H-indazole-4-carboxamide (300 mg, 0.696 mmol) and 2-methyl-5-(4,4,5,5-tetramethyl-1,3,2-dioxaborolan-2-yl)pyridine (183 mg, 0.835 mmol). The title compound was collected as 75 mg (24%); H NMR (DMSO-d$_6$, 400 MHz): δ

1.45 (d, J=6.4 Hz, 3H), 2.11 (s, 3H), 2.24 (s, 3H), 2.49 (s, 3H), 2.51 (s, 3H), 4.36-4.38 (m, 2H), 5.03-5.09 (m, 1H), 5.87 (s, 1H), 7.36 (s, 1H), 7.38 (s, 1H), 8.01 (s, 1H), 8.11 (d, J=2.4 Hz, 1H), 8.45 (s, 1H), 8.89 (s, 1H), 11.48 (s, 1H); LCMS (ES+) m/z: 444.21.

Example 85

6-[6-(dimethylamino)-3-pyridinyl]-3-methyl-1-(1-methylethyl)-N-[(6-methyl-2-oxo-4-propyl-1,2-dihydro-3-pyridinyl)methyl]-1H-indazole-4-carboxamide

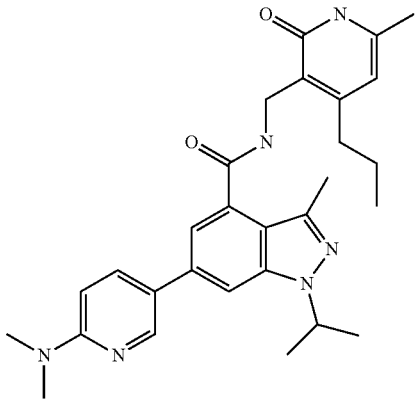

The title compound was prepared in the same manner as described for example 67 from 6-bromo-3-methyl-1-(1-methylethyl)-N-[(6-methyl-2-oxo-4-propyl-1,2-dihydro-3-pyridinyl)methyl]-1H-indazole-4-carboxamide (0.079 g, 0.172 mmol) and [6-(dimethylamino)-3-pyridinyl]boronic acid (0.034 g, 0.206 mmol). The product was triturated from EtOAc spiked with DCM, and dried in a hi-vacuum oven for 4 h. The title compound was collected as a white solid (49 mg, 56%); $^1$H NMR (400 MHz, DMSO-d6) δ ppm 0.93 (t, J=7.33 Hz, 3H), 1.45 (d, J=6.57 Hz, 6H), 1.51-1.64 (m, 2H), 2.12 (s, 3H), 2.42 (s, 3H), 2.52-2.59 (m, 2H), 3.08 (s, 6H), 4.38 (d, J=5.05 Hz, 2H), 4.96-5.09 (m, 1H), 5.90 (s, 1H), 6.75 (d, J=9.09 Hz, 1H), 7.31 (d, J=1.26 Hz, 1H), 7.86 (d, J=1.26 Hz, 1H), 7.96 (dd, J=8.97, 2.65 Hz, 1H), 8.40 (t, J=4.93 Hz, 1H), 8.55 (d, J=2.27 Hz, 1H), 11.50 (s, 1H); LCMS (ES+) m/z: 501.1.

Example 86

6-{3-[(dimethylamino)methyl]phenyl}-3-methyl-1-(1-methylethyl)-N-[(6-methyl-2-oxo-4-propyl-1,2-dihydro-3-pyridinyl)methyl]-1H-indazole-4-carboxamide

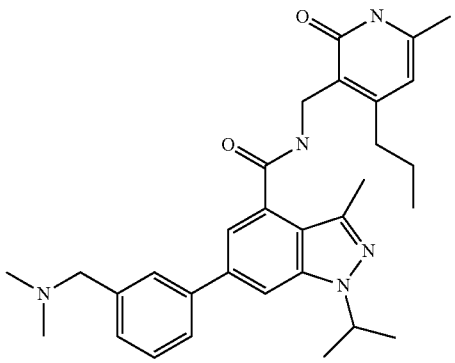

The title compound was prepared in the same manner as described for example 67 from 6-bromo-3-methyl-1-(1-methylethyl)-N-[(6-methyl-2-oxo-4-propyl-1,2-dihydro-3-pyridinyl)methyl]-1H-indazole-4-carboxamide (0.090 g, 0.196 mmol). The crude product was purified by reverse phase HPLC (Gradient B: 10-60%. 8 min A: Water+0.1% TFA. B: CH3CN+0.1% TFA). The isolated product was then treated with 1.0 g of Silicycle Carbonate resin, and filtered through celite washing with 10% MeOH/DCM. The product was collected as a white solid (58 mg, 57%); $^1$H NMR (400 MHz, DMSO-d6) δ ppm 0.93 (t, J=7.33 Hz, 3H) 1.46 (d, J=6.57 Hz, 6H) 1.52-1.63 (m, 2H) 2.10-2.21 (m, 9H) 2.44 (s, 3H) 2.52-2.59 (m, 2H) 3.47 (s, 2H) 4.38 (d, J=5.05 Hz, 2H) 5.02-5.14 (m, 1H) 5.90 (s, 1H) 7.28-7.36 (m, 2H) 7.44 (t, J=7.58 Hz, 1H) 7.63-7.73 (m, 2H) 7.92 (d, J=1.26 Hz, 1H) 8.47 (t, J=4.93 Hz, 1H) 11.50 (s, 1H); LCMS (ES+) m/z: 514.3.

Example 87

6-{4-[(dimethylamino)methyl]phenyl}-3-methyl-1-(1-methylethyl)-N-[(6-methyl-2-oxo-4-propyl-1,2-dihydro-3-pyridinyl)methyl]-1H-indazole-4-carboxamide

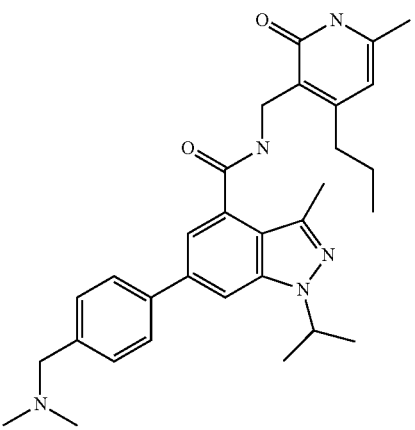

The title compound was prepared in the same manner as described for example 67 from 6-bromo-3-methyl-1-(1-methylethyl)-N-[(6-methyl-2-oxo-4-propyl-1,2-dihydro-3-pyridinyl)methyl]-1H-indazole-4-carboxamide (0.090 g, 0.196 mmol) and N,N-dimethyl-1-[4-(4,4,5,5-tetramethyl-1,3,2-dioxaborolan-2-yl)phenyl]methanamine (0.070 g, 0.235 mmol). The product was collected as a white solid (72 mg, 70%); $^1$H NMR (400 MHz, DMSO-d6) δ ppm 0.93 (t, J=7.33 Hz, 3H), 1.45 (d, J=6.57 Hz, 6H), 1.56 (sxt, J=7.53 Hz, 2H), 2.07-2.23 (m, 9H), 2.44 (s, 3H), 2.52-2.59 (m, 2H), 3.43 (s, 2H), 4.38 (d, J=5.05 Hz, 2H), 5.06 (quin, J=6.63 Hz, 1H), 5.90 (s, 1H), 7.33-7.45 (m, 3H), 7.75 (d, J=8.08 Hz, 2H), 7.93 (d, J=1.26 Hz, 1H), 8.45 (t, J=4.93 Hz, 1H), 11.50 (s, 1H); LCMS (ES+) m/z: 514.5.

Example 88

3-methyl-1-(1-methylethyl)-N-[(6-methyl-2-oxo-4-propyl-1,2-dihydro-3-pyridinyl)methyl]-6-(3-pyridinyl)-1H-indazole-4-carboxamide

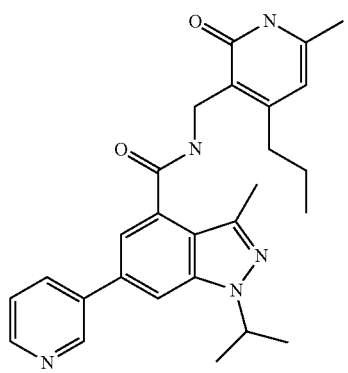 [SMILES: CCCc1cc(C)[nH]c(=O)c1CNC(=O)c1cc(-c2cccnc2)cc2c1c(C)nn2C(C)C]

The title compound was prepared in the same manner as described for example 67 from 6-bromo-3-methyl-1-(1-methylethyl)-N-[(6-methyl-2-oxo-4-propyl-1,2-dihydro-3-pyridinyl)methyl]-1H-indazole-4-carboxamide (0.10 g, 0.218 mmol). The product was collected as a white solid (0.097 g, 95%); $^1$H NMR (400 MHz, DMSO-d6) δ ppm 0.92 (t, J=7.33 Hz, 3H), 1.46 (d, J=6.57 Hz, 6H), 1.51-1.64 (m, 2H), 2.12 (s, 3H), 2.45 (s, 3H), 2.54 (dd, J=8.72, 6.95 Hz, 2H), 4.38 (d, J=5.05 Hz, 2H), 5.08 (quin, J=6.57 Hz, 1H), 5.90 (s, 1H), 7.40 (d, J=1.52 Hz, 1H), 7.52 (dd, J=8.46, 5.18 Hz, 1H), 8.07 (d, J=1.52 Hz, 1H), 8.21 (dt, J=8.27, 1.80 Hz, 1H), 8.46 (t, J=4.93 Hz, 1H), 8.59 (dd, J=4.67, 1.64 Hz, 1H), 9.03 (d, J=1.52 Hz, 1H), 11.51 (s, 1H); LCMS (ES+) m/z: 457.2.

Example 89

3-methyl-1-(1-methylethyl)-N-[(6-methyl-2-oxo-4-propyl-1,2-dihydro-3-pyridinyl)methyl]-6-[6-(4-methyl-1-piperazinyl)-3-pyridinyl]-1H-indazole-4-carboxamide

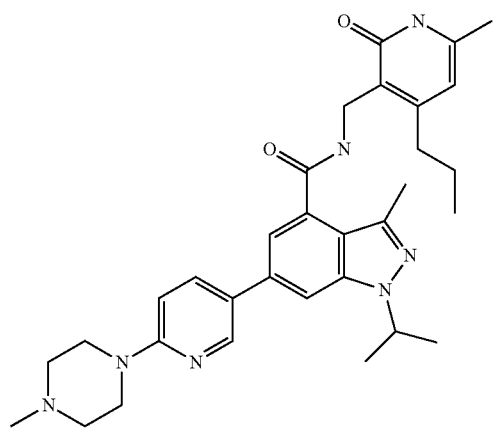

The title compound was prepared in the same manner as described for example 67 from 6-bromo-3-methyl-1-(1-methylethyl)-N-[(6-methyl-2-oxo-4-propyl-1,2-dihydro-3-pyridinyl)methyl]-1H-indazole-4-carboxamide (0.10 g, 0.218 mmol) and 1-methyl-4-[5-(4,4,5,5-tetramethyl-1,3,2-dioxaborolan-2-yl)-2-pyridinyl]piperazine (0.086 g, 0.283 mmol). The title compound was collected as a white solid (0.105 g, 84%); $^1$H NMR (400 MHz, DMSO-d6) δ ppm 0.92 (t, J=7.33 Hz, 3H), 1.45 (d, J=6.57 Hz, 6H), 1.50-1.63 (m, 2H), 2.12 (s, 3H), 2.22 (s, 3H), 2.38-2.45 (m, 7H), 2.52-2.59 (m, 2H), 3.51-3.60 (m, 4H), 4.37 (d, J=5.05 Hz, 2H), 4.96-5.10 (m, 1H), 5.90 (s, 1H), 6.94 (d, J=8.84 Hz, 1H), 7.32 (d, J=1.26 Hz, 1H), 7.89 (d, J=1.26 Hz, 1H), 7.98 (dd, J=8.84, 2.53 Hz, 1H), 8.40 (t, J=5.05 Hz, 1H), 8.56 (d, J=2.27 Hz, 1H), 11.50 (s, 1H); LCMS (ES+) m/z: 556.1.

Example 90

6-cyano-N-((4,6-dimethyl-2-oxo-1,2-dihydropyridin-3-yl)methyl)-1-isopropyl-3-methyl-1H-indazole-4-carboxamide

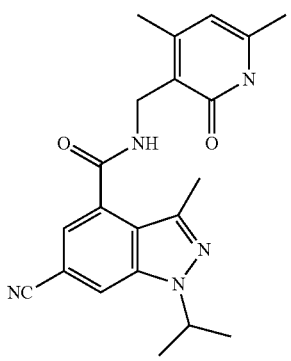 [SMILES: Cc1cc(C)c(CNC(=O)c2cc(C#N)cc3c2c(C)nn3C(C)C)c(=O)[nH]1]

In a 25 mL sealable tube under nitrogen were combined 6-bromo-N-[(4,6-dimethyl-2-oxo-1,2-dihydro-3-pyridinyl)methyl]-3-methyl-1-(1-methylethyl)-1H-indazole-4-carboxamide (130 mg, 0.3 mmol), dicyanozinc (40.7 mg, 0.35 mmol), Pd$_2$(dba)$_3$ (317 mg, 0.35 mmol), dppf (21.7 mg, 0.04 mmol) and zinc (4.9 mg, 0.08 mmol) in DMF (4 mL) and the resulting mixture was degassed with nitrogen for 10 min. The vessel was sealed, and the insoluble mixture was heated to 120° C. for 6 hours. Upon cooling down, the mixture was quenched with water, and dark grey solids that crashed out and were filtered. DCM/MeOH (1:1) was added, the contents pre-absorbed on silica gel and purified by SiO$_2$ chromatography (eluent: gradient 0 to 80:20:2 DCM/MeOH/NH$_4$OH). The collected product was further purified by reverse-phase HPLC (20% to 80% CH$_3$CN in water with 0.1% TFA) which afforded the TFA salt. CH$_3$CN was evaporated, and a saturated solution of sodium bicarbonate was added to the water layer. The solids that precipitated were filtered and dried to afford the title compound as a white solid (70.3 mg, 60%). $^1$H NMR (400 MHz, DMSO-d$_6$) δ ppm 11.39 (br. s., 1H) 8.56 (t, J=4.80 Hz, 1H) 8.43 (d, J=1.01 Hz, 1H) 7.35 (d, J=1.01 Hz, 1H) 5.88 (s, 1H) 5.04 (quin, J=6.57 Hz, 1H) 4.35 (s, 1H) 4.34 (s, 1H) 2.43 (s, 3H) 2.23 (s, 3H) 2.12 (s, 3H) 1.46 (s, 3H) 1.44 (s, 3H); LC-MS (ES) m/z=378.3[M+H]$^+$

Example 91

1-cyclopentyl-6-(cyclopropylsulfonyl)-N-((4,6-dimethyl-2-oxo-1,2-dihydropyridin-3-yl)methyl)-1H-indazole-4-carboxamide

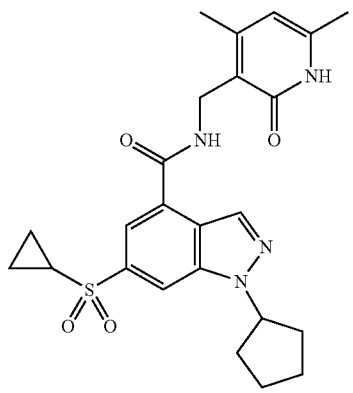 [SMILES: Cc1cc(C)c(CNC(=O)c2cc(S(=O)(=O)C3CC3)cc3c2cnn3C2CCCC2)c(=O)[nH]1]

To a 10-mL microwave tube were added 6-bromo-1-cyclopentyl-N-[(4,6-dimethyl-2-oxo-1,2-dihydro-3-pyridinyl)methyl]-1H-indazole-4-carboxamide (70 mg, 0.158 mmol), cyclopropanesulfinic acid (40.8 mg, 0.316 mmol), dimethyl sulfoxide (3 mL), N,N'-dimethyl-1,2-ethanediamine methyl [2-(methylamino)ethyl]amine (55.7 mg, 0.632 mmol), and copper(II) trifluoromethanesulfonate (57.1 mg, 0.158 mmol), and the mixture was degassed for 5 min by bubbling nitrogen. The tube was sealed and the mixture irradiated at 120° C. (microwave) for 3 h. The mixture was filtered and the DMSO solution was purified using reverse-phase HPLC to give 45 mg of product. The product was collected as an off-white solid. $^1$H NMR (400 MHz, DMSO-d$_6$) δ ppm 1.00-1.12 (m, 2H), 1.15-1.31 (m, 2H), 1.67-1.79 (m, 2H), 1.84-1.94 (m, 2H), 1.96-2.08 (m, 2H), 2.12-2.28 (m, 8H), 2.93-3.05 (m, 1H), 4.38 (d, J=5.05 Hz, 2H), 5.43 (quin, J=7.01 Hz, 1H), 5.90 (s, 1H), 8.01 (d, J=1.26 Hz, 1H), 8.44 (s, 1H), 8.52 (s, 1H), 8.83 (t, J=4.93 Hz, 1H), 11.57 (s, 1H); LCMS: (M+H)$^+$=469.0

Example 92

6-(cyclopropylsulfonyl)-N-((4-ethyl-6-methyl-2-oxo-1,2-dihydropyridin-3-yl)methyl)-1-isopropyl-1H-indazole-4-carboxamide

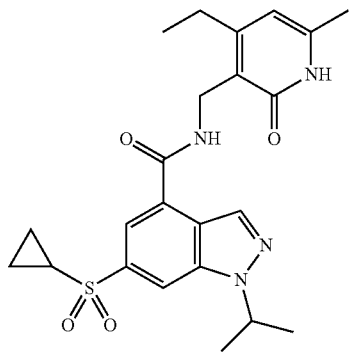 [SMILES: CCc1cc(C)[nH]c(=O)c1CNC(=O)c1cc(S(=O)(=O)C2CC2)cc2c1cnn2C(C)C]

The title compound was prepared from 6-bromo-N-[(4-ethyl-6-methyl-2-oxo-1,2-dihydro-3-pyridinyl)methyl]-1-(1-methylethyl)-1H-indazole-4-carboxamide (70 mg, 0.162 mmol) and the sodium salt of cyclopropanesulfinic acid (41.9 mg, 0.325 mmol) in the same manner as described for example 91. The product was collected an off-white solid (52 mg). $^1$H NMR (400 MHz, DMSO-d$_6$) δ ppm 1.02-1.16 (m, 5H), 1.19-1.27 (m, 2H), 1.50 (d, J=6.57 Hz, 6H), 2.15 (s, 3H), 2.58 (m, 2H), 2.97 (m, 1H), 4.41 (d, J=4.80 Hz, 2H), 5.26 (m, 1H), 5.94 (s, 1H), 8.01 (d, J=1.26 Hz, 1H), 8.43 (s, 1H), 8.53 (s, 1H), 8.83 (m, 1H), 11.58 (s, 1H); LCMS: (M+H)$^+$=457.0

Example 93

N-((4-ethyl-6-methyl-2-oxo-1,2-dihydropyridin-3-yl)methyl)-1-isopropyl-6-(methylsulfonyl)-1H-indazole-4-carboxamide

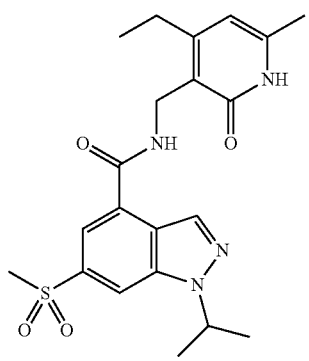

The title compound was prepared from 6-bromo-N-[(4-ethyl-6-methyl-2-oxo-1,2-dihydro-3-pyridinyl)methyl]-1-(1-methylethyl)-1H-indazole-4-carboxamide (70 mg, 0.162 mmol) and the sodium salt of methanesulfinic acid (33.5 mg, 0.325 mmol), in the same manner as described for example 91. The product was collected as a white solid (21 mg) $^1$H NMR (400 MHz, DMSO-d$_6$) δ ppm 1.06-1.17 (m, 3H), 1.47-1.56 (m, 6H), 2.15 (s, 3H), 2.58 (q, J=7.58 Hz, 2H), 3.03 (s, 3H), 4.33-4.47 (m, 2H), 5.17-5.30 (m, 1H), 5.94 (s, 1H), 8.01 (d, J=1.26 Hz, 1H), 8.45 (m, 1H), 8.53 (s, 1H), 8.78 (t, J=4.93 Hz, 1H); LCMS: (M+H)$^+$=431.1

Example 94

N-[(4,6-dimethyl-2-oxo-1,2-dihydro-3-pyridinyl)methyl]-1-(1-methylethyl)-6-(methylsulfonyl)-1H-indazole-4-carboxamide

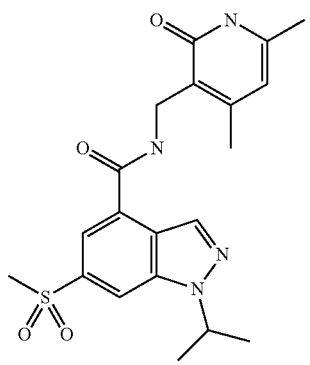

To a 10 mL microwave vial containing a stirring mixture of L-valine (8.42 mg, 0.072 mmol), NaOH (0.024 mL, 0.072 mmol), and DMSO (1.6 mL) were added sodium methanesulfinate (0.065 g, 0.539 mmol), copper(I) iodide (6.85 mg, 0.036 mmol) and 1-Ethyl-3-methylimidazoliym bromide (0.014 g, 0.072 mmol). After stirring for 15 min, 6-bromo-N-[(4,6-dimethyl-2-oxo-1,2-dihydro-3-pyridinyl)methyl]-1-(1-methylethyl)-1H-indazole-4-carboxamide (0.15 g, 0.359 mmol) was added. The reaction vial was sealed and the mixture was stirred with heating at 90° C. (heat block) for 18 h. The contents were then irradiated (microwave) at 130° C. for 2 hr. After cooling to RT, the reaction mixture was poured onto 50 mL of water and stirred. The contents were extracted with hot 30% THF/EtOAc (2×) (need to heat to break up emulsion). The combined organic layers were washed with brine, dried over $MgSO_4$, filtered, and concentrated in vacuo. The crude product was purified by silica gel chromatography (eluent: 5-75% chloroform (containing 10% 2M ammonia in methanol) and dichloromethane. The isolated product was concentrated from DCM and MTBE, and dried under hi vacuum. The title compound was collected as 75 mg (49%); $^1$H NMR (400 MHz, DMSO-d6) δ ppm 1.50 (d, J=6.57 Hz, 6H) 2.13 (s, 3H) 2.22 (s, 3H) 3.30 (s, 3H) 4.38 (d, J=4.80 Hz, 2H) 5.23 (quin, J=6.57 Hz, 1H) 5.90 (s, 1H) 8.02 (d, J=1.01 Hz, 1H) 8.45 (s, 1H) 8.52 (s, 1H) 8.77 (t, J=4.80 Hz, 1H) 11.56 (s, 1H); LCMS: (M+H)$^+$=417.1.

Methyl 1-(1-methylethyl)-6-nitro-1H-indazole-4-carboxylate

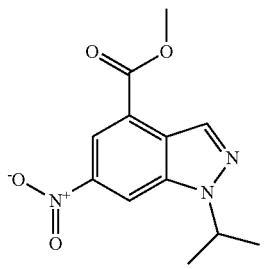

Sodium hydride (1.142 g, 45.2 mmol) was added to N,N-Dimethylformamide (DMF) (100 mL) which was cooled in a ice water bath. A DMSO solution (20 mL) of methyl 6-nitro-1H-indazole-4-carboxylate (5 g, 22.61 mmol) was then added dropwise. After 15 minutes was added 2-bromopropane (4.25 mL, 45.2 mmol) dropwise and the contents were stirred at room temperature for 16 hours. Next added iodomethane (2.83 mL, 45.2 mmol) and let stir at room temperature for 3 hours followed by heating at 50° C. for 3 hours. The solvent was removed in vacuo. The residue was purified via silica gel chromatography (eluent: 0% to 25% EtOAc:Hex) to afford the product as 1.39 g (23%). $^1$H NMR (400 MHz, CHLOROFORM-d) δ ppm 4.07 (s, 3H), 8.61-8.63 (m, 1H), 8.64 (s, 1H), 8.73 (d, J=2.02 Hz, 1H); LCMS (ES) [M+H]$^+$ 264.0

Methyl 6-amino-1-(1-methylethyl)-1H-indazole-4-carboxylate

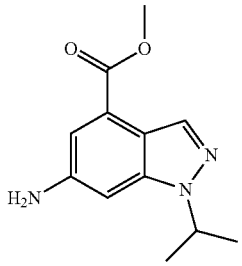 [SMILES: COC(=O)c1cc(N)cc2c1cnn2C(C)C]

Methyl 1-(1-methylethyl)-6-nitro-1H-indazole-4-carboxylate (1.39 g, 5.28 mmol) was dissolved in ethanol (70 mL) and hydrogenated using an H-Cube instrument (full $H_2$ mode and 10% Pd/C). The solvent was removed in vacuo and the residue was purified via silica gel chromatography (eluent: 0% to 40% gradient; EtOAc:Hex). The product was obtained as 1.05 g (85%). $^1$H NMR (400 MHz, CHLOROFORM-d) δ ppm 1.58 (d, J=6.57 Hz, 6H), 4.00 (s, 5H), 4.70 (dt, J=13.39, 6.69 Hz, 1H), 6.80 (s, 1H), 7.37 (d, J=2.02 Hz, 1H), 8.30 (s, 1H). LCMS (ES) [M+H]$^+$ 234.0

Methyl 6-(chlorosulfonyl)-1-(1-methylethyl)-1H-indazole-4-carboxylate

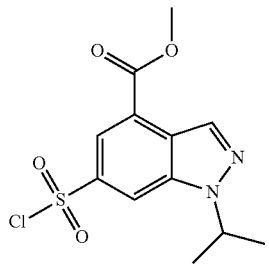 [SMILES: COC(=O)c1cc(S(=O)(=O)Cl)cc2c1cnn2C(C)C]

Methyl 6-amino-1-(1-methylethyl)-1H-indazole-4-carboxylate (500 mg, 2.143 mmol) was dissolved in conc. hydrochloric acid (5 mL) and cooled in an ice water bath. A solution of sodium nitrite (155 mg, 2.251 mmol) in 2 mL of water was then added dropwise, and the contents were stirred for 90 min. The contents were added portion-wise to a solution of ca. 5 mL of $SO_2$, copper(II) chloride (303 mg, 2.251 mmol) and acetic acid (20 mL). The contents were stirred at room temperature for 15 h, and then concentrated in vacuo. The residue was suspended in 100 mL DCM, washed with water (2×50 mL), dried ($MgSO_4$), filtered and concentrated in vacuo. The residue was purified via silica gel chromatography (eluent: 0% to 10 gradient EtOAc:Hex). The product was collected as 510 mg (75%). $^1$H NMR (400 MHz, CHLOROFORM-d) δ ppm 1.68 (d, 6H), 4.09 (s, 3H), 5.01 (dt, J=13.33, 6.60 Hz, 1H), 8.40 (s, 1H), 8.51 (d, J=1.52 Hz, 1H), 8.70 (s, 1H). LCMS (ES) [M+H]$^+$ 317.0

Methyl 1-(1-methylethyl)-6-(4-morpholinylsulfonyl)-1H-indazole-4-carboxylate

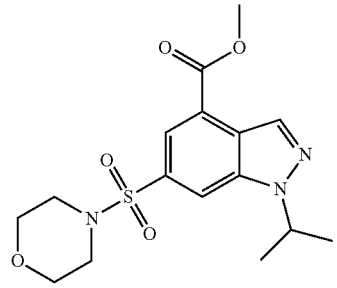 [SMILES: COC(=O)c1cc(S(=O)(=O)N2CCOCC2)cc2c1cnn2C(C)C]

A solution of morpholine (0.030 mL, 0.347 mmol), triethylamine (0.055 mL, 0.395 mmol) and dichloromethane (DCM) (20 mL) were cooled in an ice-water bath. A DCM solution (5 mL) of methyl 6-(chlorosulfonyl)-1-(1-methylethyl)-1H-indazole-4-carboxylate (100 mg, 0.316 mmol) was added dropwise. The contents were stirred at room temperature for 10 min. The contents were then washed with water, brine, dried over $MgSO_4$, filtered, and concentrated in vacuo. The product was collected as 90 mg (77%). $^1$H NMR (400 MHz, CHLOROFORM-d) δ ppm 1.67 (d, 6H), 2.99-3.19 (m, 4H), 3.75-3.86 (m, 4H), 4.08 (s, 3H), 4.98 (ddd, J=13.26, 6.82, 6.69 Hz, 1H), 8.14 (s, 1H), 8.22 (d, J=1.26 Hz, 1H), 8.65 (s, 1H); LCMS (ES) [M+H]+ 368.0

The following intermediates were prepared using the general procedures outlined for the above compound from methyl 6-(chlorosulfonyl)-1-(1-methylethyl)-1H-indazole-4-carboxylate and the appropriate amine.

Methyl 6-[(cyclopropylamino)sulfonyl]-1-(1-methylethyl)-1H-indazole-4-carboxylate

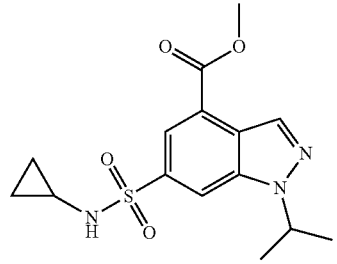 [SMILES: COC(=O)c1cc(S(=O)(=O)NC2CC2)cc2c1cnn2C(C)C]

$^1$H NMR (400 MHz, CHLOROFORM-d) δ ppm 0.57-0.76 (m, 4H), 1.66 (d, J=6.82 Hz, 6H), 2.22-2.39 (m, 1H), 4.07 (s, 3H), 4.89-5.17 (m, 2H), 8.33 (s, 1H), 8.36 (d, J=1.26 Hz, 1H), 8.63 (s, 1H); LCMS (ES) [M+H]+ 324.4

Methyl 1-(1-methylethyl)-6-(1-pyrrolidinylsulfonyl)-1H-indazole-4-carboxylate

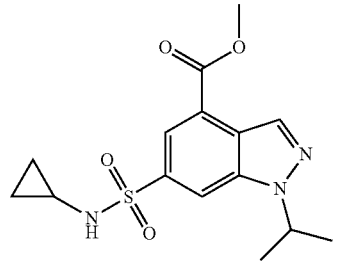 [SMILES: COC(=O)c1cc(S(=O)(=O)NC2CC2)cc2c1cnn2C(C)C]

$^1$H NMR (400 MHz, CHLOROFORM-d) δ ppm 1.62-1.74 (m, 6H), 1.85 (ddd, J=6.57, 3.66, 3.41 Hz, 4H), 3.37 (t, J=6.69 Hz, 4H), 5.01 (spt, J=6.65 Hz, 1H), 8.30 (s, 1H), 8.42 (d, J=1.26 Hz, 1H), 8.69 (s, 1H); LCMS (ES) [M+H]+ 338.3

Methyl 6-({[3-(dimethylamino)propyl]amino}sulfonyl)-1-(1-methylethyl)-1H-indazole-4-carboxylate

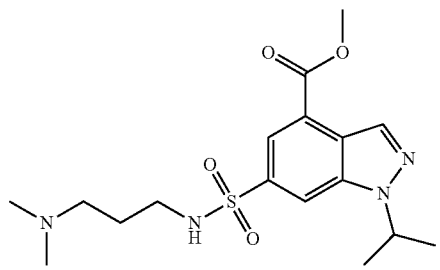 [SMILES: COC(=O)c1cc(S(=O)(=O)NCCCN(C)C)cc2c1cnn2C(C)C]

$^1$H NMR (400 MHz, CHLOROFORM-d) δ ppm 1.60-1.67 (m, 6H), 1.74 (quin, J=5.81 Hz, 2H), 2.37 (s, 6H), 2.55 (t, J=5.81 Hz, 2H), 3.07-3.16 (m, 2H), 4.04 (s, 3H), 4.98 (dt, J=13.33, 6.60 Hz, 1H), 8.30 (d, J=1.77 Hz, 2H), 8.59 (s, 1H). LCMS (ES) [M+H]+ 383.1

Methyl 1-(1-methylethyl)-6-[(phenylamino)sulfonyl]-1H-indazole-4-carboxylate

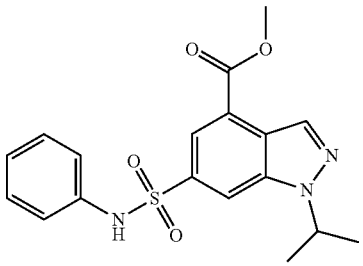 [SMILES: COC(=O)c1cc(S(=O)(=O)Nc2ccccc2)cc2c1cnn2C(C)C]

$^1$H NMR (400 MHz, CHLOROFORM-d) δ ppm 1.53 (d, 6H), 4.01 (s, 3H), 4.81 (dt, J=13.33, 6.60 Hz, 1H), 6.94 (s, 1H), 7.02-7.16 (m, 3H), 7.20-7.26 (m, 2H), 8.04 (s, 1H), 8.32 (d, J=1.26 Hz, 1H), 8.55 (s, 1H). LCMS (ES) [M+H]+ 373.9

1-(1-methylethyl)-6-(4-morpholinylsulfonyl)-1H-indazole-4-carboxylic acid

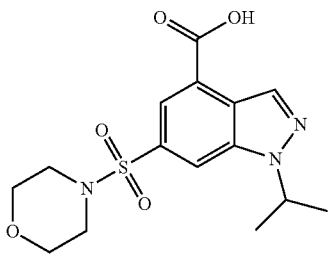 [SMILES: CC(C)n1ncc2c(C(=O)O)cc(S(=O)(=O)N3CCOCC3)cc21]

Sodium hydroxide (0.980 mL, 0.980 mmol) was added to a solution of methyl 1-(1-methylethyl)-6-(4-morpholinylsulfonyl)-1H-indazole-4-carboxylate (90 mg, 0.245 mmol) in ethanol (30 mL) and heated at reflux for 1 hour. The solvent was removed in vacuo and the residue suspended in water (20 mL). The contents were acidified by addition of acetic acid, and extracted with DCM (4×30 mL). The combined organic layers were washed with water, brine, dried over MgSO$_4$, filtered, and concentrated in vacuo. The product was collected as 90 mg. $^1$H NMR (400 MHz, CHLOROFORM-d) δ ppm 1.63-1.78 (m, 6H), 3.02-3.24 (m, 4H), 3.67-3.88 (m, 4H), 5.00 (dt, J=13.20, 6.66 Hz, 1H), 8.21 (s, 1H), 8.31 (s, 1H), 8.71 (s, 1H), LCMS (ES) [M+H]+ 354.2

The following intermediates were prepared using the general procedure outlined for the above compound.

6-[(cyclopropylamino)sulfonyl]-1-(1-methylethyl)-1H-indazole-4-carboxylic acid

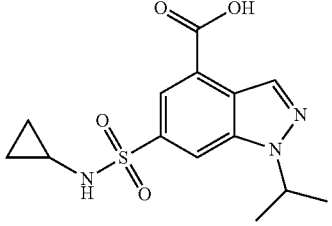 [SMILES: CC(C)n1ncc2c(C(=O)O)cc(S(=O)(=O)NC3CC3)cc21]

$^1$H NMR (400 MHz, CHLOROFORM-d) δ ppm 0.62-0.72 (m, 4H), 1.67 (d, J=6.57 Hz, 6H), 2.27-2.44 (m, 1H), 5.02

(spt, J=6.61 Hz, 1H), 5.37 (s, 1H), 8.41 (s, 1H), 8.44 (d, J=1.52 Hz, 1H), 8.65 (s, 1H); LCMS (ES) [M+H]+ 324.4

1-(1-methylethyl)-6-(1-pyrrolidinylsulfonyl)-1H-indazole-4-carboxylic acid

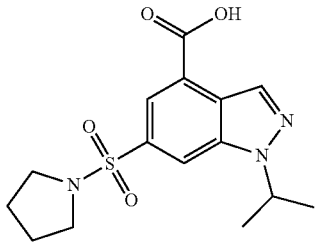 [SMILES: CC(C)n1ncc2c(C(=O)O)cc(S(=O)(=O)N3CCCC3)cc21]

¹H NMR (400 MHz, CHLOROFORM-d) δ ppm 1.62-1.74 (m, 6H), 1.85 (ddd, J=6.57, 3.66, 3.41 Hz, 4H), 3.37 (t, J=6.69 Hz, 4H), 5.01 (spt, J=6.65 Hz, 1H), 8.30 (s, 1H), 8.42 (d, J=1.26 Hz, 1H), 8.69 (s, 1H); LCMS (ES) [M+H]+ 338.3

6-({[3-(dimethylamino)propyl]amino}sulfonyl)-1-(1-methylethyl)-1H-indazole-4-carboxylic acid

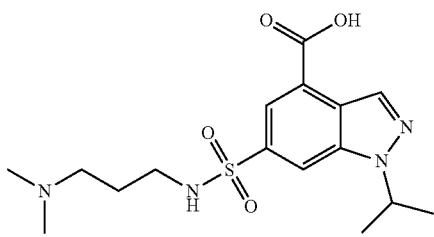 [SMILES: CC(C)n1ncc2c(C(=O)O)cc(S(=O)(=O)NCCCN(C)C)cc21]

¹H NMR (400 MHz, DMSO-d₆) δ ppm 1.50 (d, 6H), 1.62 (qd, J=7.07, 6.82 Hz, 2H), 2.30 (s, 6H), 2.82 (t, J=6.82 Hz, 2H), 5.19 (dt, J=13.14, 6.57 Hz, 1H), 7.98 (d, J=8.59 Hz, 1H), 8.13 (d, J=1.26 Hz, 1H), 8.32 (s, 1H), 8.55 (s, 1H); LCMS (ES) [M+H]+ 368.9

1-(1-methylethyl)-6-[(phenylamino)sulfonyl]-1H-indazole-4-carboxylic acid

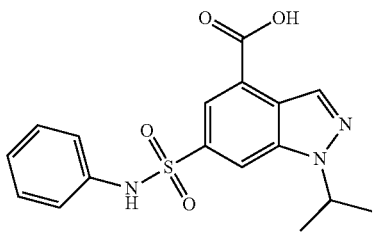 [SMILES: CC(C)n1ncc2c(C(=O)O)cc(S(=O)(=O)Nc3ccccc3)cc21]

¹H NMR (400 MHz, MeOD) δ ppm 1.52 (d, J=6.82 Hz, 6H), 4.98 (ddd, J=13.26, 6.82, 6.69 Hz, 1H), 7.00-7.16 (m, 3H), 7.18-7.28 (m, 2H), 8.15 (s, 1H), 8.25 (d, J=1.52 Hz, 1H), 8.52 (s, 1H); LCMS (ES) [M+H]+ 360.1

Example 95

N-[(4,6-dimethyl-2-oxo-1,2-dihydro-3-pyridinyl)methyl]-1-(1-methylethyl)-6-(4-morpholinylsulfonyl)-1H-indazole-4-carboxamide

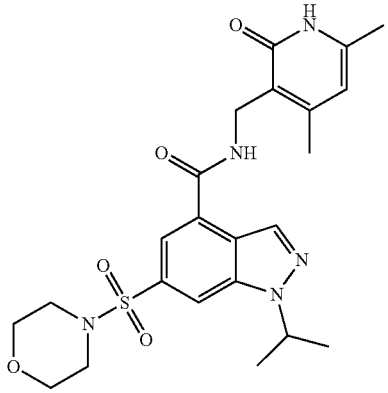 [SMILES: Cc1cc(C)c(CNC(=O)c2cc(S(=O)(=O)N3CCOCC3)cc3c2cnn3C(C)C)c(=O)[nH]1]

1-(1-methylethyl)-6-(4-morpholinylsulfonyl)-1H-indazole-4-carboxylic acid (90 mg, 0.255 mmol), 3-(aminomethyl)-4,6-dimethyl-2(1H)-pyridinone (62.5 mg, 0.331 mmol), 1-hydroxy-7-azabenzotriazole (69.3 mg, 0.509 mmol), EDC (98 mg, 0.509 mmol) and N-methylmorpholine (0.112 mL, 1.019 mmol) were added to Dimethyl Sulfoxide (DMSO) (10 mL) and stirred at room temperature for 16 hours. Next added 40 mL of water and stirred for 10 minutes. The contents were extracted with DCM (5×30 mL), washed with water, dried (MgSO₄), filtered, and concentrated in vacuo. The residue was purified via chromatography (eluent: 0% to 100% gradient Hex:EtOAc then 0 to 10% MeOH:EtOAc). The product was collected as 110 mg (88%). ¹H NMR (400 MHz, DMSO-d₆) δ ppm 1.50 (d, 6H), 2.13 (s, 3H), 2.23 (s, 3H), 2.89-3.05 (m, 4H), 3.54-3.71 (m, 4H), 4.38 (d, J=4.80 Hz, 2H), 5.27 (dt, J=13.07, 6.47 Hz, 1H), 5.90 (s, 1H), 7.80 (d, J=1.01 Hz, 1H), 8.29 (s, 1H), 8.52 (s, 1H), 8.88 (t, J=5.05 Hz, 1H), 11.56 (br. s., 1H); LCMS (ES) [M+H]+ 488.3

Examples 96-99 were prepared using the general procedures outlined for the above compound.

Example 96

6-[(cyclopropylamino)sulfonyl]-N-[(4,6-dimethyl-2-oxo-1,2-dihydro-3-pyridinyl)methyl]-1-(1-methylethyl)-1H-indazole-4-carboxamide

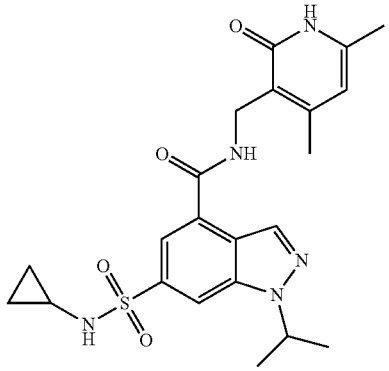 [SMILES: Cc1cc(C)c(CNC(=O)c2cc(S(=O)(=O)NC3CC3)cc3c2cnn3C(C)C)c(=O)[nH]1]

¹H NMR (400 MHz, CHLOROFORM-d) δ ppm 0.42-0.65 (m, 4H), 1.61 (d, J=6.57 Hz, 6H), 2.19 (dt, J=6.63, 3.38 Hz, 1H), 2.25 (s, 3H), 2.45 (s, 3H), 4.63 (d, J=5.56 Hz, 2H), 4.95 (quin, J=6.63 Hz, 1H), 6.02 (s, 1H), 6.32 (br. s., 1H), 8.17 (s, 1H), 8.20 (s, 1H), 8.25 (t, J=5.18 Hz, 1H), 8.60 (s, 1H), 11.46 (br. s., 1H); LCMS (ES) [M+H]⁺ 458.1

Example 97

N-[(4,6-dimethyl-2-oxo-1,2-dihydro-3-pyridinyl)methyl]-1-(1-methylethyl)-6-(1-pyrrolidinylsulfonyl)-1H-indazole-4-carboxamide

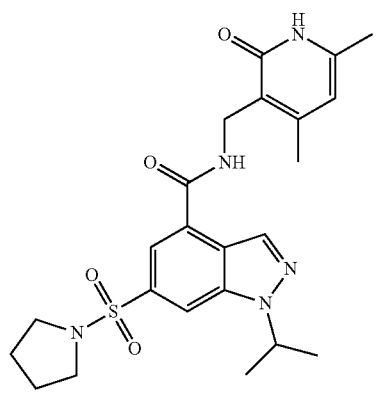 [SMILES: Cc1cc(C)c(CNC(=O)c2cc(S(=O)(=O)N3CCCC3)cc3c2cnn3C(C)C)c(=O)[nH]1]

¹H NMR (400 MHz, DMSO-d₆) δ ppm 1.49 (d, 6H), 1.58-1.71 (m, 4H), 2.13 (s, 3H), 2.23 (s, 3H), 3.18-3.29 (m, 4H), 4.38 (d, J=5.05 Hz, 2H), 5.28 (quin, J=6.57 Hz, 1H), 5.90 (s, 1H), 7.89 (d, J=1.01 Hz, 1H), 8.33 (s, 1H), 8.51 (s, 1H), 8.90 (t, J=4.93 Hz, 1H), 11.56 (s, 1H); LCMS (ES) [M+H]⁺ 472.4

Example 98

6-({[3-(dimethylamino)propyl]amino}sulfonyl)-N-[(4,6-dimethyl-2-oxo-1,2-dihydro-3-pyridinyl)methyl]-1-(1-methylethyl)-1H-indazole-4-carboxamide

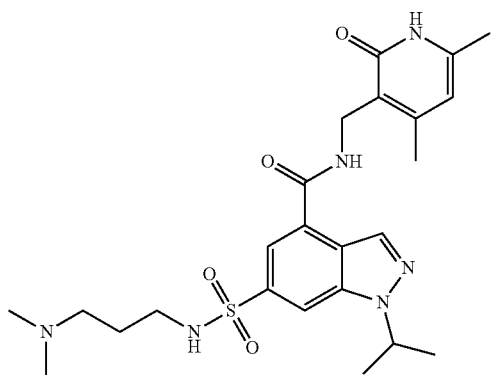

¹H NMR (400 MHz, DMSO-d₆) δ ppm 1.37-1.54 (m, 8H), 1.97 (s, 6H), 2.05-2.17 (m, 5H), 2.22 (s, 3H), 2.78 (t, J=6.95 Hz, 2H), 4.36 (d, J=4.55 Hz, 2H), 5.16 (quin, J=6.57 Hz, 1H), 5.89 (s, 1H), 7.87 (s, 1H), 8.25 (s, 1H), 8.43 (s, 1H), 8.53 (s, 0H), 8.73 (br. s., 1H); LCMS (ES) [M+H]⁺ 502.9

Example 99

N-((4,6-dimethyl-2-oxo-1,2-dihydropyridin-3-yl)methyl)-1-isopropyl-6-((4-methylpiperazin-1-yl)sulfonyl)-1H-indazole-4-carboxamide

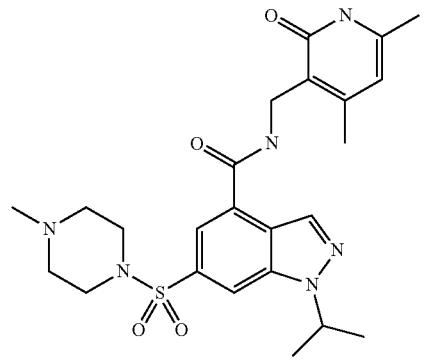

¹H NMR (400 MHz, CHLOROFORM-d) δ ppm 1.62 (d, J=6.82 Hz, 6H), 2.27 (d, J=6.32 Hz, 6H), 2.43 (s, 3H), 2.52 (br. s., 4H), 3.14 (br. s., 4H), 4.65 (d, J=5.81 Hz, 2H), 4.93 (dq, J=6.82, 6.65 Hz, 1H), 5.99 (s, 1H), 7.86 (s, 1H), 8.01 (s, 1H), 8.06-8.16 (m, 1H), 8.56 (s, 1H), 12.02 (br. s., 1H); LCMS (ES) [M+H]⁺ 501.0.

Example 100

6-bromo-N-((4-(sec-butyl)-6-methyl-2-oxo-1,2-dihydropyridin-3-yl)methyl)-1-isopropyl 1H-indazole-4-carboxamide

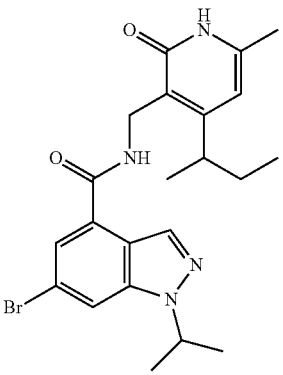 [SMILES: CCC(C)c1cc(C)[nH]c(=O)c1CNC(=O)c1cc(Br)cc2c1cnn2C(C)C]

The title compound was prepared in the same manner as described for example 3 (step c) from 6-bromo-1-(1-methylethyl)-1H-indazole-4-carboxylic acid (0.50 g, 1.77 mmol) and 3-(aminomethyl)-4-(sec-butyl)-6-methylpyridin-2(1H)-one (0.446 g, 2.296 mmol). The product was collected as 0.81 g (98%). ¹H NMR (400 MHz, DMSO-d₆) δ ppm 11.53 (s, 1H), 8.62 (t, J=4.7 Hz, 1H), 8.37 (s, 1H), 8.20 (s, 1H), 7.70 (d, J=1.5 Hz, 1H), 5.96 (s, 1H), 5.05 (quin, J=6.6 Hz, 1H), 4.41

(d, J=4.3 Hz, 2H), 2.95 (q, J=7.1 Hz, 1H), 2.15 (s, 3H), 1.48 (m, 8H), 1.07 (d, J=6.6 Hz, 3H), 0.74 (t, J=7.3 Hz, 3H). LC-MS (ES) [M+H]⁺ 459.2.

Example 101

6-Bromo-1-(1-methylethyl)-N-[(6-methyl-2-oxo-4-propyl-1,2-dihydro-3-pyridinyl)methyl]-1H-indazole-4-carboxamide

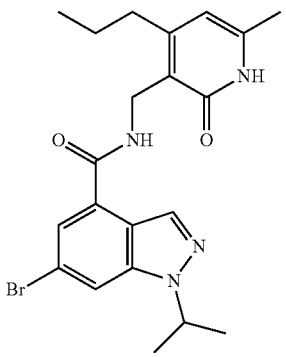 [SMILES: CCCc1cc(C)[nH]c(=O)c1CNC(=O)c1cc(Br)cc2c1cnn2C(C)C]

6-Bromo-1-(1-methylethyl)-1H-indazole-4-carboxylic acid (80 mg, 0.28 mmol), 3-(aminomethyl)-6-methyl-4-propyl-2(1H)-pyridinone (112 mg, 0.38 mmol) and 1-hydroxy-7-azabenzotriazole (57.7 mg, 0.42 mmol) were stirred in 3 mL of DMSO for 10 min under nitrogen. N-Methylmorpholine (0.12 ml, 1.13 mmol) was added along with EDC (81 mg, 0.42 mmol) and the mixture was stirred at room temperature overnight under nitrogen. Ice-water was added and solids crashed out. Then 10% $K_2CO_3$ was added to adjust the pH to about 8-9. Then the reaction was stirred at room temperature for 10 min and let stand for 10 min. Solids were filtered off, dissolved in DMF and water was added. Solids that precipitated out were filtered off, air-dried for 15 min and dried in vacuum oven for 2 h to give the title compound (94 mg, 73%). ¹H NMR (400 MHz, DMSO-d₆) δ ppm 11.54 (s, 1H) 8.62 (t, J=4.93 Hz, 1H) 8.37 (s, 1H) 8.20 (s, 1H) 7.69 (d, J=1.26 Hz, 1H) 5.91 (s, 1H) 5.06 (dt, J=13.14, 6.57 Hz, 1H) 4.36 (d, J=4.80 Hz, 2H) 2.14 (s, 3H) 1.48-1.56 (m, 2H) 1.47 (s, 3H) 1.45 (s, 3H) 0.89 (t, J=7.33 Hz, 3H); MS (ES) [M+H]⁺ 445.1, 446.9.

Example 102

6-Bromo-1-(1-methylethyl)-N-{[6-methyl-4-(1-methylethyl)-2-oxo-1,2-dihydro-3-pyridinyl]methyl}-1H-indazole-4-carboxamide

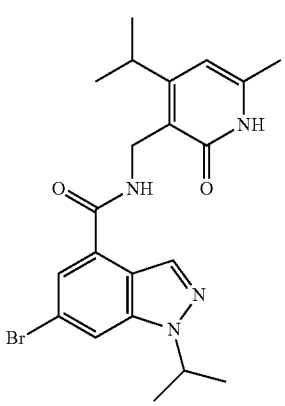 [SMILES: Cc1cc(C(C)C)c(CNC(=O)c2cc(Br)cc3c2cnn3C(C)C)c(=O)[nH]1]

The title compound was prepared in the same manner as example 101 from 6-Bromo-1-(1-methylethyl)-1H-indazole-4-carboxylic acid and 3-(aminomethyl)-6-methyl-4-(1-methylethyl)2(1H)-pyridinone. ¹H NMR (400 MHz, DMSO-d₆) δ ppm 11.53 (s, 1H) 8.63 (t, J=4.80 Hz, 1H) 8.37 (s, 1H) 8.20 (s, 1H) 7.69 (d, J=1.26 Hz, 1H) 6.02 (s, 1H) 5.05 (quin, J=6.57 Hz, 1H) 4.41 (d, J=4.80 Hz, 2H) 3.21 (quin, J=6.76 Hz, 1H) 2.16 (s, 3H) 1.47 (s, 3H) 1.45 (s, 3H) 1.11 (s, 3H) 1.09 (s, 3H); MS (ES) [M+H]⁺ 445.1, 446.9.

Example 103

N-[(4,6-Dimethyl-2-oxo-1,2-dihydro-3-pyridinyl)methyl]-1-(1-methylethyl)-6-phenyl-1H-indazole-4-carboxamide

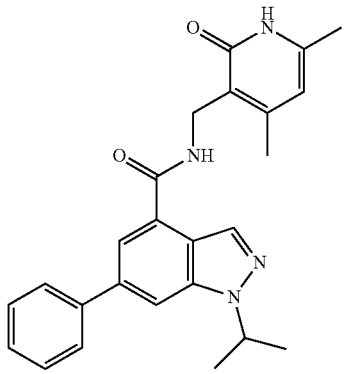 [SMILES: Cc1cc(C)c(CNC(=O)c2cc(-c3ccccc3)cc3c2cnn3C(C)C)c(=O)[nH]1]

To a mixture of 6-bromo-N-[(4,6-dimethyl-2-oxo-1,2-dihydro-3-pyridinyl)methyl]-1-(1-methylethyl)-1H-indazole-4-carboxamide (0.15 g, 0.359 mmol), phenylboronic acid (0.088 g, 0.719 mmol) and potassium phosphate (tribasic) (0.229 g, 1.078 mmol) was added 1,4-dioxane (3 mL) and water (0.75 mL). The suspension was degassed with $N_2$ for 10 min, at which time $PdCl_2(dppf)\text{-}CH_2Cl_2$ (0.044 g, 0.054 mmol) was added and the sealed reaction heated at 100° C. overnight. Diluted reaction with EtOAc and filtered through Celite, washing with EtOAc and concentrating in vacuo to a residue that was dissolve in a minimum amount of DCM. Purification by silica gel chromatography (12 gram Isco GOLD silica column; Gradient B: 5-80%; A: dichloromethane, B: 10% (2 M ammonia in methanol) in chloroform) gave N-[(4,6-dimethyl-2-oxo-1,2-dihydro-3-pyridinyl)methyl]-1-(1-methylethyl)-6-phenyl-1H-indazole-4-carboxamide (0.105 g, 0.248 mmol, 69.1% yield). ¹H NMR (400 MHz, DMSO-d6) δ ppm 1.50 (d, J=6.57 Hz, 6H) 2.12 (s, 3H) 2.22 (s, 3H) 4.39 (d, J=4.80 Hz, 2H) 5.10-5.24 (m, 1H) 5.89 (s, 1H) 7.37-7.46 (m, 1H) 7.48-7.55 (m, 2H) 7.82-7.93 (m, 3H) 8.12 (s, 1H) 8.38 (s, 1H) 8.66 (t, J=4.93 Hz, 1H) 11.54 (s, 1H). MS (ES) [M+H]⁺ 415.1.

Example 104

N-[(4,6-Dimethyl-2-oxo-1,2-dihydro-3-pyridinyl)methyl]-1-(1-methylethyl)-6-(4-pyridinyl)-1H-indazole-4-carboxamide

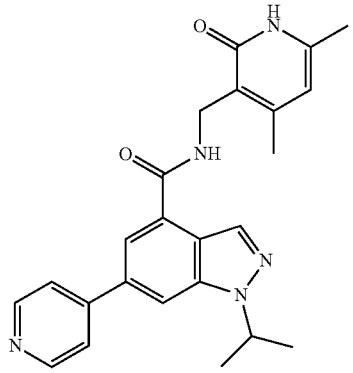 [SMILES: Cc1cc(C)c(CNC(=O)c2cc(-c3ccncc3)cc3c2cnn3C(C)C)c(=O)[nH]1]

To a mixture of 6-bromo-N-[(4,6-dimethyl-2-oxo-1,2-dihydro-3-pyridinyl)methyl]-1-(1-methylethyl)-1H-indazole-4-carboxamide (0.15 g, 0.359 mmol), 4-pyridinylboronic acid (0.088 g, 0.647 mmol) and potassium phosphate (tribasic) (0.229 g, 1.078 mmol) was added 1,4-dioxane (3 mL) and water (0.75 mL). The suspension was degassed with $N_2$ for 10 min, at which time $PdCl_2(dppf)$-$CH_2Cl_2$ (0.044 g, 0.054 mmol) was added and the sealed reaction heated at 100° C. overnight (reaction got very dark). Diluted reaction with EtOAc and filtered through Celite, washing with EtOAc and concentrated in vacuo to a residue that was dissolved in a minimum amount of DCM. Purification by silica gel chromatography (12 gram Isco GOLD silica column; Gradient B: 5-90%; A: dichloromethane, B: 10% (2 M ammonia in methanol) in chloroform) gave N-[(4,6-dimethyl-2-oxo-1,2-dihydro-3-pyridinyl)methyl]-1-(1-methylethyl)-6-(4-pyridinyl)-1H-indazole-4-carboxamide (112 mg, 0.264 mmol, 73.5% yield). $^1$H NMR (400 MHz, DMSO-d6) δ ppm 1.51 (d, J=6.57 Hz, 6H) 2.12 (s, 3H) 2.22 (s, 3H) 4.40 (d, J=4.80 Hz, 2H) 5.15-5.27 (m, 1H) 5.89 (s, 1H) 7.90-8.00 (m, 3H) 8.34 (s, 1H) 8.43 (s, 1H) 8.65-8.75 (m, 3H) 11.55 (s, 1H). MS (ES) [M+H]+ 416.1.

Example 105

N-[(4,6-Dimethyl-2-oxo-1,2-dihydro-3-pyridinyl)methyl]-6-{4-[(methylamino)sulfonyl]phenyl}-1-(1-methylethyl)-1H-indazole-4-carboxamide

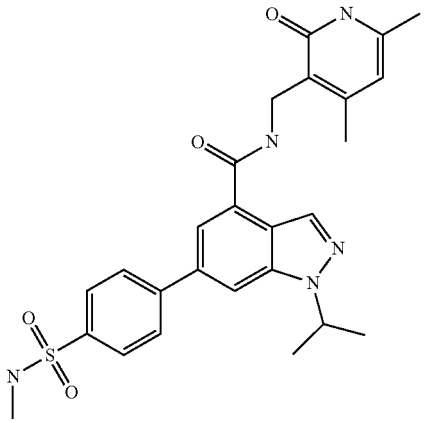 [SMILES: CNS(=O)(=O)c1ccc(-c2cc(C(=O)NCc3c(C)cc(C)[nH]c3=O)c3cnn(C(C)C)c3c2)cc1]

In a 25 mL sealable tube under nitrogen were combined 6-bromo-N-[(4,6-dimethyl-2-oxo-1,2-dihydro-3-pyridinyl)methyl]-1-(1-methylethyl)-1H-indazole-4-carboxamide (100 mg, 0.24 mmol), {4-[(methylamino)sulfonyl]phenyl}boronic acid (77 mg, 0.36 mmol) in DME/water (3 mL:1 mL). $PdCl_2(dppf)$-$CH_2Cl_2$ (9.8 mg, 0.012 mmol) was added and the resulting mixture was degassed with nitrogen for 10 min. Sodium bicarbonate (60.4 mg, 0.72 mmol) was added, the vessel was sealed, and the insoluble mixture was heated in a microwave at 140° C. for 30 min. EtOAc was added and the solution was filtered thru Celite and evaporated. DCM/MeOH (1:1) was added, it was pre-absorbed on silica gel and purified by $SiO_2$ chromatography (eluent: gradient 100% DCM to 90:10:1 DCM/MeOH/$NH_4OH$). Fractions were evaporated. EtOAc was added along with some hexanes, it was sonicated and the solids that precipitated were filtered, washed with DCM and dried to afford the title compound (67 mg, 54%) as a beige solid. $^1$H NMR (400 MHz, DMSO-d6) δ ppm 11.54 (s, 1H) 9.87 (br. s., 1H) 8.62 (t, J=4.80 Hz, 1H) 8.37 (s, 1H) 8.07 (s, 1H) 7.82-7.86 (m, 3H) 7.35 (s, 1H) 7.32 (s, 1H) 5.89 (s, 1H) 5.15 (quin, J=6.63 Hz, 1H) 4.39 (d, J=4.80 Hz, 2H) 3.04 (s, 3H) 2.22 (s, 3H) 2.12 (s, 3H) 1.51 (s, 3H) 1.49 (s, 3H). MS (ES) [M+H]+ 507.9.

Example 106

N-[(4,6-Dimethyl-2-oxo-1,2-dihydro-3-pyridinyl)methyl]-1-(1-methylethyl)-6-[6-(4-methyl-1-piperazinyl)-3-pyridinyl]-1H-indazole-4-carboxamide

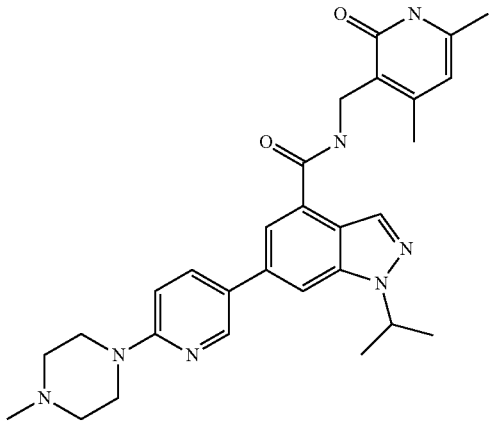

In a 25 mL sealable tube under nitrogen were combined 6-bromo-N-[(4,6-dimethyl-2-oxo-1,2-dihydro-3-pyridinyl)methyl]-1-(1-methylethyl)-1H-indazole-4-carboxamide (100 mg, 0.24 mmol), 1-methyl-4-[5-(4,4,5,5-tetramethyl-1,3,2-dioxaborolan-2-yl)-2-pyridinyl]piperazine (109 mg, 0.36 mmol) in DME/water (3 mL:1 mL). $PdCl_2(dppf)$-$CH_2Cl_2$ (9.8 mg, 0.012 mmol) was added and the resulting mixture was degassed with nitrogen for 10 min. Sodium bicarbonate (60.4 mg, 0.72 mmol) was added, the vessel was sealed, and the insoluble mixture was heated in a microwave at 130° C. for 30 min. Solvent was evaporated, DCM was added and it was purified by $SiO_2$ chromatography (eluent: gradient 100% DCM to 80:20:2 DCM/MeOH/$NH_4OH$). Further purification by reversed-phase HPLC (C18, 15% to 80% $CH_3CN$ in water with 0.1% TFA, 12 minute gradient) afforded the TFA salt. The $CH_3CN$ was evaporated and the mixture was diluted with saturated sodium bicarbonate and EtOAc. The organic layer was separated and the aqueous layer was further extracted with DCM and DCM/isopropanol (80:20). The combined organic layers were washed with water, dried ($MgSO_4$), filtered and concentrated. EtOAc was added along with some hexanes, it was sonicated and the solids that precipitated were filtered and dried to afford the title compound (71 mg, 56%) as a white solid. $^1$H NMR (400 MHz, DMSO-d$_6$) δ ppm 11.55 (br. s., 1H) 8.66 (d, J=2.27 Hz, 1H) 8.61 (t, J=4.93 Hz, 1H) 8.36 (s, 1H) 8.04-8.09 (m, 2H) 7.84 (d, J=1.26 Hz, 1H) 6.96 (d, J=8.84 Hz, 1H) 5.89 (s, 1H) 5.14 (quin, J=6.57 Hz, 1H) 4.39 (d, J=5.05 Hz, 2H) 3.52-3.60 (m, 4H) 2.38-2.46 (m, 4H) 2.22 (d, J=4.55 Hz, 6H) 2.13 (s, 3H) 1.50 (s, 3H) 1.49 (s, 3H). MS (ES) [M+H]$^+$ 514.5.

Example 107

N-[(4,6-Dimethyl-2-oxo-1,2-dihydro-3-pyridinyl)methyl]-1-(1-methylethyl)-6-(2-oxo-2,3-dihydro-1H-benzimidazol-5-yl)-1H-indazole-4-carboxamide

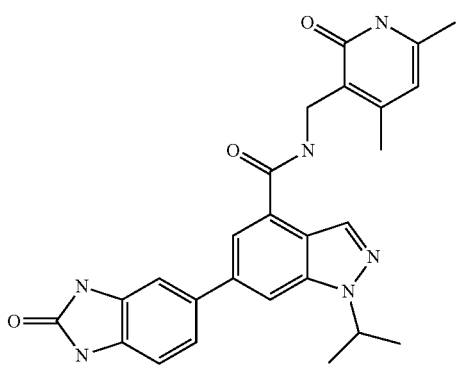 [SMILES: Cc1cc(C)c(CNC(=O)c2cc(-c3ccc4[nH]c(=O)[nH]c4c3)cc3c2cnn3C(C)C)c(=O)[nH]1]

In a 25 mL sealable tube under nitrogen were combined 6-bromo-N-[(4,6-dimethyl-2-oxo-1,2-dihydro-3-pyridinyl)methyl]-1-(1-methylethyl)-1H-indazole-4-carboxamide (100 mg, 0.24 mmol), 5-(4,4,5,5-tetramethyl-1,3,2-dioxaborolan-2-yl)-1,3-dihydro-2H-benzimidazol-2-one (93 mg, 0.36 mmol) in dioxane/water (3 mL:1 mL). PdCl$_2$(dppf)-CH$_2$Cl$_2$ (9.8 mg, 0.012 mmol) was added and the resulting mixture was degassed with nitrogen for 10 min. Sodium bicarbonate (60.4 mg, 0.72 mmol) was added, the vessel was sealed, and the insoluble mixture was heated in a microwave at 130° C. for 20 min. DCM/MeOH (1:1) was added, it was pre-absorbed on silica gel and purified by SiO$_2$ chromatography (eluent: gradient 100% DCM to 80:20:2 DCM/MeOH/NH$_4$OH). Fractions were evaporated. EtOH was added, it was sonicated and the solids that precipitated were filtered, washed with EtOH and DCM and dried to afford the title compound (43 mg, 37%) as a beige solid. $^1$H NMR (400 MHz, DMSO-d$_6$) δ ppm 11.53 (s, 1H) 10.78 (s, 1H) 10.74 (s, 1H) 8.64 (t, J=4.80 Hz, 1H) 8.35 (s, 1H) 8.02 (s, 1H) 7.81 (s, 1H) 7.44 (dd, J=8.08, 1.77 Hz, 1H) 7.36-7.39 (m, 1H) 7.03 (d, J=8.08 Hz, 1H) 5.89 (s, 1H) 5.16 (quin, J=6.57 Hz, 1H) 4.39 (d, J=4.80 Hz, 2H) 2.21 (s, 3H) 2.13 (s, 3H) 1.50 (s, 3H) 1.49 (s, 3H). MS (ES) [M+H]$^+$ 471.3

Example 108

6-[6-(Acetylamino)-3-pyridinyl]-N-[(4,6-dimethyl-2-oxo-1,2-dihydro-3-pyridinyl)methyl]-1-(1-methylethyl)-1H-indazole-4-carboxamide

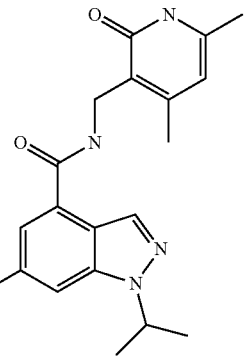

In a 25 mL sealable tube under nitrogen were combined 6-bromo-N-[(4,6-dimethyl-2-oxo-1,2-dihydro-3-pyridinyl)methyl]-1-(1-methylethyl)-1H-indazole-4-carboxamide (110 mg, 0.24 mmol), N-[5-(4,4,5,5-tetramethyl-1,3,2-dioxaborolan-2-yl)-2-pyridinyl]acetamide (104 mg, 0.4 mmol) in DME/water (3 mL:1 mL). PdCl$_2$(dppf)-CH$_2$Cl$_2$ (10.76 mg, 0.013 mmol) was added and the resulting mixture was degassed with nitrogen for 10 min. Sodium bicarbonate (66.4 mg, 0.79 mmol) was added, the vessel was sealed, and the insoluble mixture was heated in a microwave at 120° C. for 20 min. Water was added and the solids that precipitated were filtered off. DCM was added to the solids and it was purified by SiO$_2$ chromatography (eluent: gradient 100% DCM to 80:20:2 DCM/MeOH/NH$_4$OH). Fractions were evaporated. EtOAc was added, it was sonicated and the solids that precipitated were filtered, washed with hexanes and dried to afford the title compound (91 mg, 72%) as a light beige solid. $^1$H NMR (400 MHz, DMSO-d$_6$) δ ppm 11.54 (s, 1H) 10.65 (s, 1H) 8.84 (d, J=2.27 Hz, 1H) 8.64 (t, J=4.93 Hz, 1H) 8.39 (s, 1H) 8.25-8.30 (m, 1H) 8.15-8.24 (m, 2H) 7.89-7.93 (m, 1H) 5.89 (s, 1H) 5.18 (quin, J=6.63 Hz, 1H) 4.40 (d, J=4.80 Hz, 2H) 2.22 (s, 3H) 2.13 (s, 3H) 2.12 (s, 3H) 1.51 (s, 3H) 1.50 (s, 3H). MS (ES) [M+H]$^+$ 473.1.

Example 109

N-[(4,6-Dimethyl-2-oxo-1,2-dihydro-3-pyridinyl)methyl]-1-(1-methylethyl)-6-(3-pyridinyl)-1H-indazole-4-carboxamide

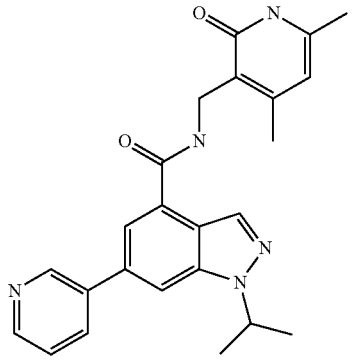 [SMILES: Cc1cc(C)c(CNC(=O)c2cc(-c3cccnc3)cc3c2cnn3C(C)C)c(=O)[nH]1]

In a 25 mL sealable tube under nitrogen were combined 6-bromo-N-[(4,6-dimethyl-2-oxo-1,2-dihydro-3-pyridinyl)

methyl]-1-(1-methylethyl)-1H-indazole-4-carboxamide (120 mg, 0.29 mmol) and 3-pyridinylboronic acid (53 mg, 0.43 mmol) in DME/water (3 mL:1 mL). PdCl$_2$(dppf)-CH$_2$Cl$_2$ (11.7 mg, 0.014 mmol) was added and the resulting mixture was degassed with nitrogen for 10 min.

Sodium bicarbonate (72.5 mg, 0.86 mmol) was added and the insoluble mixture was heated in a microwave at 120° C. for 20 min. It was evaporated and the residue was dissolved in DCM and purified by SiO$_2$ chromatography (eluent: gradient 100% DCM to 80:20:2 DCM/MeOH/NH$_4$OH). Fractions were evaporated. DMF was added along with some water and the solids that precipitated were filtered, washed with water and hexanes and dried to afford the title compound (74 mg, 61%) as a light grey solid. $^1$H NMR (400 MHz, DMSO-d$_6$) δ ppm 11.54 (s, 1H) 9.11 (d, J=2.02 Hz, 1H) 8.66 (t, J=4.80 Hz, 1H) 8.61 (dd, J=4.80, 1.26 Hz, 1H) 8.42 (s, 1H) 8.28 (dt, J=8.02, 1.93 Hz, 1H) 8.25 (s, 1H) 7.93 (s, 1H) 7.54 (dd, J=7.83, 4.80 Hz, 1H) 5.89 (s, 1H) 5.19 (dt, J=13.14, 6.57 Hz, 1H) 4.40 (d, J=4.80 Hz, 2H) 2.22 (s, 3H) 2.12 (s, 3H) 1.52 (s, 3H) 1.50 (s, 3H). MS (ES) [M+H]$^+$ 416.1.

Example 110

N-[(4,6-Dimethyl-2-oxo-1,2-dihydro-3-pyridinyl)methyl]-1-(1-methylethyl)-6-[6-(4-morpholinyl)-3-pyridinyl]-1H-indazole-4-carboxamide

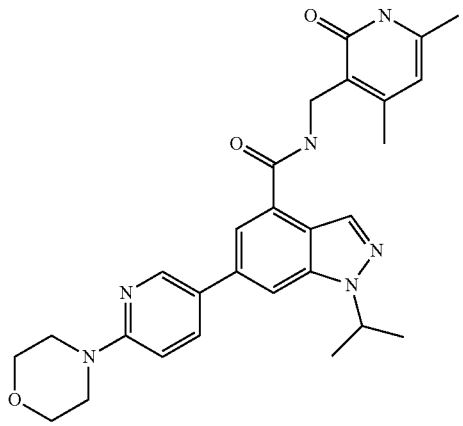 [SMILES: Cc1cc(C)c(CNC(=O)c2cc(-c3ccc(N4CCOCC4)nc3)cc3c2cnn3C(C)C)c(=O)[nH]1]

In a 25 mL sealable tube under nitrogen were combined 6-bromo-N-[(4,6-dimethyl-2-oxo-1,2-dihydro-3-pyridinyl)methyl]-1-(1-methylethyl)-1H-indazole-4-carboxamide (110 mg, 0.26 mmol) and [6-(4-morpholinyl)-3-pyridinyl]boronic acid (82 mg, 0.39 mmol) in DME/water (3 mL:1 mL). PdCl$_2$(dppf)-CH$_2$Cl$_2$ (10.76 mg, 0.013 mmol) was added and the resulting mixture was degassed with nitrogen for 10 min. Sodium bicarbonate (66.4 mg, 0.79 mmol) was added and the insoluble mixture was heated in a microwave at 110° C. for 20 min. It was evaporated, DCM/MeOH (1:1) was added, it was pre-absorbed on silica gel and purified by SiO$_2$ chromatography (eluent: gradient 100% DCM to 80:20:2 DCM/MeOH/NH$_4$OH). Fractions were evaporated. EtOH was added, it was sonicated and the solids that precipitated were filtered, washed with hexanes and dried to afford the title compound (123 mg, 89%) as a light beige solid. $^1$H NMR (400 MHz, DMSO-d$_6$) δ ppm 11.54 (s, 1H) 8.69 (d, J=2.27 Hz, 1H) 8.61 (t, J=4.93 Hz, 1H) 8.36 (s, 1H) 8.08-8.12 (m, 2H) 7.85 (d, J=1.01 Hz, 1H) 6.98 (d, J=8.84 Hz, 1H) 5.89 (s, 1H) 5.14 (quin, J=6.57 Hz, 1H) 4.39 (d, J=5.05 Hz, 2H) 3.71-3.75 (m, 4H) 3.50-3.55 (m, 4H) 2.22 (s, 3H) 2.13 (s, 3H) 1.50 (s, 3H) 1.49 (s, 3H). MS (ES) [M+H]$^+$ 501.1.

Example 111

N-[(4,6-Dimethyl-2-oxo-1,2-dihydro-3-pyridinyl)methyl]-1-(1-methylethyl)-6-[6-(methyloxy)-3-pyridinyl]-1H-indazole-4-carboxamide

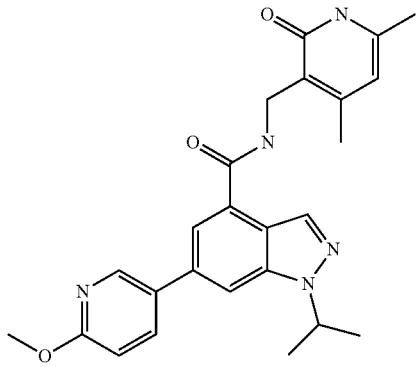

In a 25 mL sealable tube under nitrogen were combined 6-bromo-N-[(4,6-dimethyl-2-oxo-1,2-dihydro-3-pyridinyl)methyl]-1-(1-methylethyl)-1H-indazole-4-carboxamide (120 mg, 0.29 mmol) and [6-(methyloxy)-3-pyridinyl]boronic acid (66 mg, 0.43 mmol) in DME/water (3 mL:1 mL). PdCl$_2$(dppf)-CH$_2$Cl$_2$ (11.7 mg, 0.014 mmol) was added and the resulting mixture was degassed with nitrogen for 10 min. Sodium bicarbonate (72.5 mg, 0.86 mmol) was added and the insoluble mixture was heated in a microwave at 110° C. for 20 min. Water was added and the solids that precipitated were filtered. DCM was added and it was purified by SiO$_2$ chromatography (eluent: gradient 100% DCM to 80:20:2 DCM/MeOH/NH$_4$OH). Fractions were evaporated. EtOAc was added along with some hexanes, it was sonicated and the solids that precipitated were filtered. DMF was added along with some water and the solids that precipitated were filtered and dried to afford the title compound (57 mg, 43%) as an off-white solid. $^1$H NMR (400 MHz, DMSO-d$_6$) δ ppm 11.54 (s, 1H) 8.69 (d, J=2.27 Hz, 1H) 8.62 (t, J=4.80 Hz, 1H) 8.39 (s, 1H) 8.22 (dd, J=8.72, 2.65 Hz, 1H) 8.15 (s, 1H) 7.87 (s, 1H) 6.97 (d, J=8.59 Hz, 1H) 5.89 (s, 1H) 5.15 (dt, J=13.07, 6.47 Hz, 1H) 4.39 (d, J=4.80 Hz, 2H) 3.92 (s, 3H) 2.22 (s, 3H) 2.12 (s, 3H) 1.51 (s, 3H) 1.49 (s, 3H). MS (ES) [M+H]$^+$ 446.1.

Example 112

N-[(4,6-Dimethyl-2-oxo-1,2-dihydro-3-pyridinyl)methyl]-1-(1-methylethyl)-6-[2-(trifluoromethyl)phenyl]-1H-indazole-4-carboxamide

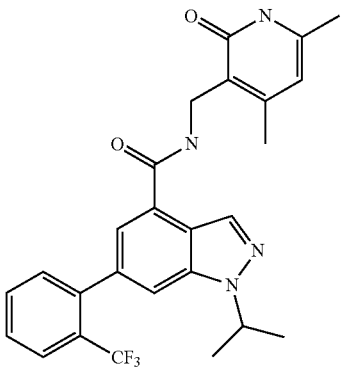 [SMILES: Cc1cc(C)c(CNC(=O)c2cc(-c3ccccc3C(F)(F)F)cc3c2cnn3C(C)C)c(=O)[nH]1]

In a 25 mL sealable tube under nitrogen were combined 6-bromo-N-[(4,6-dimethyl-2-oxo-1,2-dihydro-3-pyridinyl)methyl]-1-(1-methylethyl)-1H-indazole-4-carboxamide (100 mg, 0.24 mmol) and [2-(trifluoromethyl)phenyl]boronic acid (68.3 mg, 0.36 mmol) in dioxane/water (3 mL:1 mL). PdCl$_2$(dppf)-CH$_2$Cl$_2$ (9.78 mg, 0.012 mmol) was added and the resulting mixture was degassed with nitrogen for 10 min. Sodium bicarbonate (60.4 mg, 0.72 mmol) was added and the insoluble mixture was heated in a microwave at 110° C. for 15 min. Water was added and the solids that precipitated were filtered off. DCM/MeOH (1:1) was added, it was pre-absorbed on silica gel and purified by SiO$_2$ chromatography (eluent: gradient 100% DCM to 80:20:2 DCM/MeOH/NH$_4$OH). Fractions were evaporated. EtOAc was added along with some hexanes, it was sonicated and the solids that precipitated were filtered and dried to afford the title compound (87 mg, 74%) as an off-white solid. $^1$H NMR (400 MHz, DMSO-d$_6$) δ ppm 11.52 (s, 1H) 8.53 (t, J=4.80 Hz, 1H) 8.43 (s, 1H) 7.88 (d, J=7.83 Hz, 1H) 7.81 (s, 1H) 7.77 (t, J=7.45 Hz, 1H) 7.66 (t, J=7.71 Hz, 1H) 7.53-7.57 (m, 2H) 5.87 (s, 1H) 5.05 (dt, J=13.14, 6.57 Hz, 1H) 4.35 (d, J=4.80 Hz, 2H) 2.19 (s, 3H) 2.10 (s, 3H) 1.48 (s, 3H) 1.47 (s, 3H). MS (ES) [M+H]$^+$ 483.0.

Example 113

6-{4-[(Dimethylamino)sulfonyl]phenyl}-N-[(4,6-dimethyl-2-oxo-1,2-dihydro-3-pyridinyl)methyl]-1-(1-methylethyl)-1H-indazole-4-carboxamide

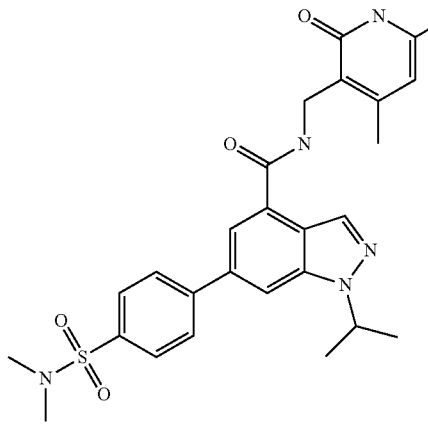

In a 25 mL sealable tube under nitrogen were combined 6-bromo-N-[(4,6-dimethyl-2-oxo-1,2-dihydro-3-pyridinyl)methyl]-1-(1-methylethyl)-1H-indazole-4-carboxamide (220 mg, 0.53 mmol) and {4-[(dimethylamino)sulfonyl]phenyl}boronic acid (181 mg, 0.79 mmol) in 3:1 dioxane/water (4 mL). PdCl$_2$(dppf)-CH$_2$Cl$_2$ (21.5 mg, 0.026 mmol) was added and the resulting mixture was degassed with nitrogen for 10 min. Sodium bicarbonate (133 mg, 1.58 mmol) was added and the insoluble mixture was heated in a microwave at 110° C. for 20 min. Water was added and the solids that precipitated were filtered. Purification by reversed-phase HPLC (C18, 15% to 80% CH$_3$CN in water with 0.1% TFA, 12 minute gradient) afforded the TFA salt. Acetonitrile was evaporated off and the resulting mixture was diluted with saturated sodium bicarbonate. The solids that precipitated were filtered off. EtOAc/EtOH (5:1) was added, along with some hexanes, and the mixture was sonicated. The solids that precipitated were filtered off and dried to afford the title compound (132 mg, 47%) as a white solid. $^1$H NMR (400 MHz, DMSO-d$_6$) δ ppm 11.49 (br. s., 1H) 8.71 (t, J=4.42 Hz, 1H) 8.43 (s, 1H) 8.27 (s, 1H) 8.15 (s, 1H) 8.13 (s, 1H) 7.94 (d, J=1.26 Hz, 1H) 7.88 (s, 1H) 7.86 (s, 1H) 5.89 (s, 1H) 5.21 (quin, J=6.57 Hz, 1H) 4.40 (d, J=4.80 Hz, 2H) 2.66 (s, 6H) 2.21 (s, 3H) 2.12 (s, 3H) 1.52 (s, 3H) 1.50 (s, 3H). MS (ES) [M+H]$^+$ 522.

Example 114

N-[(4,6-Dimethyl-2-oxo-1,2-dihydro-3-pyridinyl)methyl]-1-(1-methylethyl)-6-(2-methylphenyl)-1H-indazole-4-carboxamide

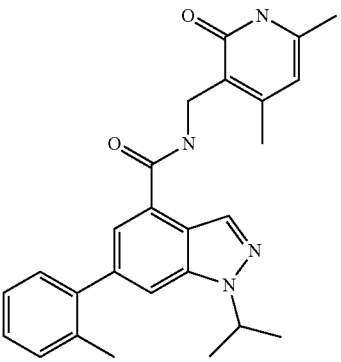 [SMILES: Cc1cc(C)c(CNC(=O)c2cc(-c3ccccc3C)cc3c2cnn3C(C)C)c(=O)[nH]1]

In a 25 mL sealable tube under nitrogen were combined 6-bromo-N-[(4,6-dimethyl-2-oxo-1,2-dihydro-3-pyridinyl)methyl]-1-(1-methylethyl)-1H-indazole-4-carboxamide (120 mg, 0.29 mmol) and [(2-methylphenyl)boronic acid (58.6 mg, 0.43 mmol) in dioxane/water (3 mL:1 mL). PdCl$_2$(dppf)-CH$_2$Cl$_2$ (11.74 mg, 0.014 mmol) was added and the resulting mixture was degassed with nitrogen for 10 min. Sodium bicarbonate (72.5 mg, 0.86 mmol) was added and the insoluble mixture was heated in a microwave at 100° C. for 15 min. DCM/MeOH (1:1) was added, it was pre-absorbed on silica gel and purified by SiO$_2$ chromatography (eluent: gradient 100% DCM to 80:20:2 DCM/MeOH/NH$_4$OH). Fractions were evaporated. EtOAc was added along with some hexanes, it was sonicated and the solids that precipitated were filtered and dried to afford the title compound (84 mg, 66%) as an off-white solid. $^1$H NMR (400 MHz, DMSO-d$_6$) δ ppm 11.51 (s, 1H) 8.55 (t, J=4.80 Hz, 1H) 8.41 (s, 1H) 7.80 (s, 1H) 7.55 (d, J=1.01 Hz, 1H) 7.27-7.35 (m, 4H) 5.87 (s, 1H) 5.09 (quin, J=6.57 Hz, 1H) 4.36 (d, J=5.05 Hz, 2H) 2.26 (s, 3H) 2.20 (s, 3H) 2.11 (s, 3H) 1.49 (s, 3H) 1.47 (s, 3H). MS (ES) [M+H]$^+$ 429.1.

Example 115

6-Bromo-N-[(4-cyclohexyl-6-methyl-2-oxo-1,2-dihydro-3-pyridinyl)methyl]-1-(1-methylethyl)-1H-indazole-4-carboxamide

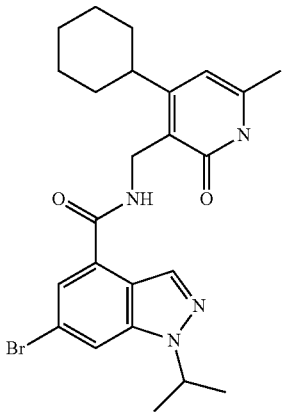 [SMILES: Cc1cc(C2CCCCC2)c(CNC(=O)c2cc(Br)cc3c2cnn3C(C)C)c(=O)[nH]1]

In a 25 mL sealable tube under nitrogen were combined 6-bromo-1-(1-methylethyl)-1H-indazole-4-carboxylic acid (237 mg, 0.84 mmol) and 3-(aminomethyl)-4-cyclohexyl-6-methyl-2(1H)-pyridinone.TFA (434 mg, 1.3 mmol) in DMSO (10 mL). 1-hydroxy-7-azabenzotriazole (194 mg, 1.42 mmol) was added and the resulting mixture was degassed with nitrogen for 10 minutes. N-methylmorpholine (0.39 mL, 3.52 mmol) and EDC (273 mg, 1.42 mmol) were added, the vessel was sealed, and the mixture was stirred at room temperature for 2 days. The mixture was poured into 10 mL of ice-water and beige solids crashed out. $K_2CO_3$ (10%) was added to adjust the pH~8-9 and the mixture stirred for 30 min and let stand for another 30 min. Solids were filtered off and air-dried. DMF was added, it was heated and sonicated and some water was added. Solids that precipitated were filtered, washed with water and dried to afford the title compound (307 mg, 73%) as a light beige solid. $^1$H NMR (400 MHz, DMSO-d$_6$) δ ppm 11.53 (s, 1H) 8.63 (t, J=4.80 Hz, 1H) 8.37 (s, 1H) 8.20 (s, 1H) 7.68 (d, J=1.26 Hz, 1H) 6.01 (s, 1H) 5.05 (dt, J=13.14, 6.57 Hz, 1H) 4.43 (d, J=4.80 Hz, 2H) 2.84 (t, J=11.24 Hz, 1H) 2.15 (s, 3H) 1.70 (d, J=13.39 Hz, 2H) 1.60 (d, J=12.13 Hz, 3H) 1.47 (s, 3H) 1.45 (s, 3H) 1.42 (br. s., 1H) 1.17-1.39 (m, 4H). MS (ES) [M+H]$^+$ 485.2, 487.2.

Example 116

1-(1-Methylethyl)-N-[(6-methyl-2-oxo-4-propyl-1,2-dihydro-3-pyridinyl)methyl]-1H-indazole-4-carboxamide

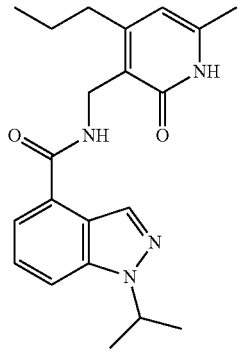 [SMILES: CCCc1cc(C)[nH]c(=O)c1CNC(=O)c1cccc2c1cnn2C(C)C]

6-Bromo-1-(1-methylethyl)-N-[(6-methyl-2-oxo-4-phenyl-1,2-dihydro-3-pyridinyl)methyl]-1H-indazole-4-carboxamide (70.3 mg, 0.15 mmol) in 3:1 EtOH/THF (4 mL) was hydrogenated using Pd/C (10% wet Degussa type) and a balloon of hydrogen. The reaction mixture was stirred at room temperature overnight. It was filtered through Celite, washed with EtOAc and EtOH and the solvent was evaporated. DMF was added with some water and white solids that crashed out were filtered off, air-dried for 15 min and dried in a vacuum oven for 3 h. The residue was purified by Gilson reversed-phase HPLC (30×100 Varian Polaris C18, 15-80% gradient of MeCN in water with 0.1% TFA over 12 minutes). Most of the solvent was removed and saturated NaHCO$_3$ was added. The solids that crashed out were filtered off, air-dried for 15 min and dried in vacuum oven overnight to give the title compound (19 mg, 37%). $^1$H NMR (400 MHz, DMSO-d$_6$) δ ppm 11.75 (br. s., 1H) 8.63 (br. s., 1H) 8.34 (s, 1H) 7.85 (d, J=8.34 Hz, 1H) 7.39-7.51 (m, 7H) 5.99 (s, 1H) 5.03 (quin, J=6.57 Hz, 1H) 4.22 (d, J=4.29 Hz, 2H) 2.21 (s, 3H) 1.49 (s, 3H) 1.47 (s, 3H). MS (ES) [M+H]$^+$ 367.2.

The following compounds were prepared using the general procedures outlined for Examples 103-116:

Example 117

6-Bromo-1-cyclopentyl-N-[(6-methyl-2-oxo-4-propyl-1,2-dihydro-3-pyridinyl)methyl]-1H-indazole-4-carboxamide

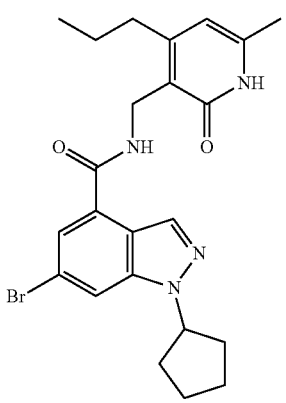 [SMILES: CCCc1cc(C)[nH]c(=O)c1CNC(=O)c1cc(Br)cc2c1cnn2C1CCCC1]

$^1$H NMR (400 MHz, DMSO-d$_6$) δ ppm 11.54 (s, 1H) 8.62 (t, J=4.80 Hz, 1H) 8.36 (s, 1H) 8.20 (s, 1H) 7.69 (d, J=1.26 Hz, 1H) 5.91 (s, 1H) 5.22 (quin, J=7.01 Hz, 1H) 4.36 (d, J=4.80 Hz, 2H) 2.07-2.15 (m, 5H) 1.93-2.01 (m, 2H) 1.83-1.91 (m, 2H) 1.65-1.73 (m, 2H) 1.47-1.56 (m, 2H) 0.89 (t, J=7.33 Hz, 3H). MS (ES) [M+H]$^+$ 471.2, 473.0.

Example 118

6-Bromo-N-[(4-cyclopropyl-6-methyl-2-oxo-1,2-dihydro-3-pyridinyl)methyl]-1-(1-methylethyl)-1H-indazole-4-carboxamide

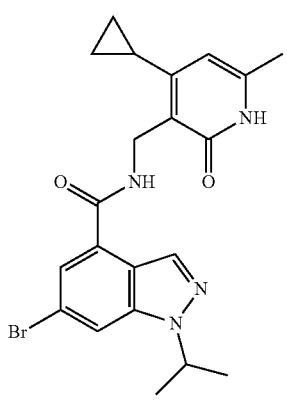 [SMILES: Cc1cc(C2CC2)c(CNC(=O)c2cc(Br)cc3c2cnn3C(C)C)c(=O)[nH]1]

$^1$H NMR (400 MHz, DMSO-d$_6$) δ ppm 11.48 (br. s., 1H) 8.66 (t, J=4.67 Hz, 1H) 8.32-8.38 (m, 1H) 8.20 (s, 1H) 7.71 (d, J=1.26 Hz, 1H) 5.52 (s, 1H) 5.06 (quin, J=6.57 Hz, 1H) 4.53 (d, J=4.80 Hz, 2H) 2.06-2.17 (m, 4H) 1.47 (s, 3H) 1.45 (s, 3H) 0.89-0.97 (m, 2H) 0.68-0.78 (m, 2H). MS (ES) [M+H]$^+$ 443.0, 445.1.

Example 119

1-cyclopentyl-N-[(4,6-dimethyl-2-oxo-1,2-dihydro-3-pyridinyl)methyl]-6-[2-(4-methyl-1-piperazinyl)-4-pyridinyl]-1H-indazole-4-carboxamide

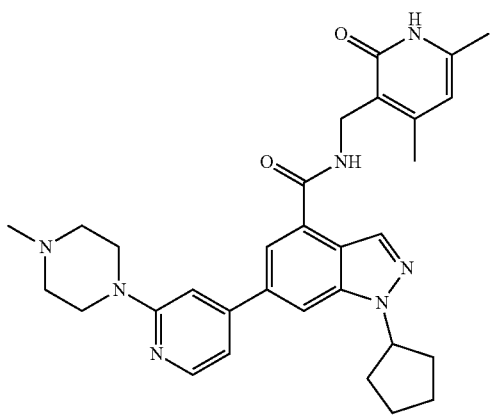

$^1$H NMR (400 MHz, DMSO-d$_6$) δ ppm 11.54 (s, 1H) 8.65 (t, J=4.80 Hz, 1H) 8.39 (s, 1H) 8.24 (s, 1H) 8.21 (d, J=5.05 Hz, 1H) 7.87 (s, 1H) 7.21 (s, 1H) 7.14 (d, J=5.31 Hz, 1H) 5.89 (s, 1H) 5.38 (quin, J=7.14 Hz, 1H) 4.39 (d, J=5.05 Hz, 2H) 3.56-3.63 (m, 4H) 2.44 (t, J=4.80 Hz, 4H) 2.24 (s, 3H) 2.22 (s, 3H) 2.14-2.20 (m, 2H) 2.12 (s, 3H) 1.98-2.05 (m, 2H) 1.91 (dd, J=8.84, 5.56 Hz, 2H) 1.68-1.75 (m, 2H). MS (ES) [M+H]$^+$ 540.3.

Example 120

1-Cyclopentyl-N-[(4,6-dimethyl-2-oxo-1,2-dihydro-3-pyridinyl)methyl]-1H-indazole-4-carboxamide

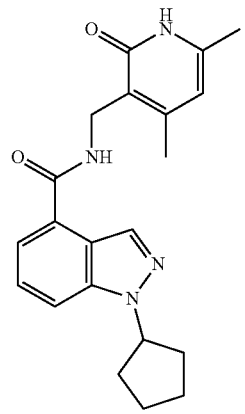 [SMILES: Cc1cc(C)c(CNC(=O)c2cccc3c2cnn3C2CCCC2)c(=O)[nH]1]

$^1$H NMR (400 MHz, DMSO-d$_6$) δ ppm 11.39 (br. s., 1H) 8.50 (br. s., 1H) 8.35 (s, 1H) 7.85 (d, J=8.59 Hz, 1H) 7.54 (d, J=7.07 Hz, 1H) 7.40 (dd, J=8.46, 7.20 Hz, 1H) 5.88 (s, 1H) 5.21 (quin, J=7.01 Hz, 1H) 4.36 (d, J=4.80 Hz, 2H) 2.22 (s, 3H) 2.09-2.16 (m, 6H) 1.96-2.04 (m, 2H) 1.84-1.92 (m, 2H) 1.66-1.74 (m, 2H). MS (ES) [M+H]$^+$ 365.3.

Example 121

6-Bromo-1-(1-methylethyl)-N-[(6-methyl-2-oxo-4-phenyl-1,2-dihydro-3-pyridinyl)methyl]-1H-indazole-4-carboxamide

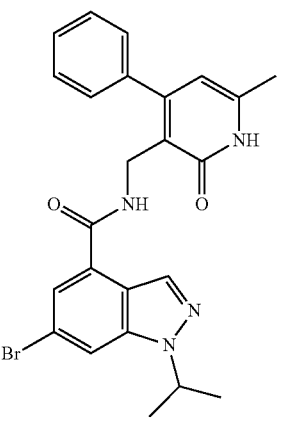 [SMILES: Cc1cc(-c2ccccc2)c(CNC(=O)c2cc(Br)cc3c2cnn3C(C)C)c(=O)[nH]1]

$^1$H NMR (400 MHz, DMSO-d$_6$) δ ppm 11.86 (br. s., 1H) 8.60 (t, J=4.04 Hz, 1H) 8.34 (s, 1H) 8.21 (s, 1H) 7.64 (d, J=1.26 Hz, 1H) 7.39-7.47 (m, 5H) 6.00 (s, 1H) 5.06 (dt, J=13.14, 6.57 Hz, 1H) 4.17 (d, J=4.04 Hz, 2H) 2.22 (s, 3H) 1.47 (s, 3H) 1.45 (s, 3H). MS (ES) [M+H]$^+$ 478.9, 480.8.

Example 122

1-Cyclopentyl-N-[(4,6-dimethyl-2-oxo-1,2-dihydro-3-pyridinyl)methyl]-6-(2-oxo-2,3-dihydro-1H-benzimidazol-5-yl)-1H-indazole-4-carboxamide

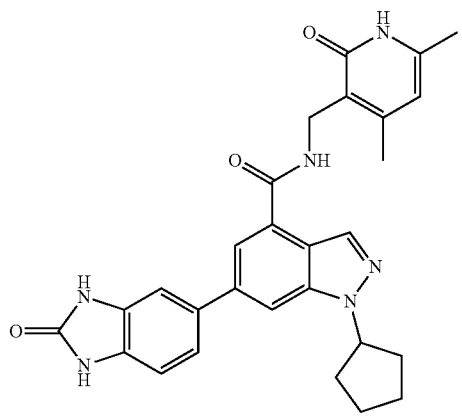 [SMILES: Cc1cc(C)c(CNC(=O)c2cc(-c3ccc4[nH]c(=O)[nH]c4c3)cc3c2cnn3C2CCCC2)c(=O)[nH]1]

$^1$H NMR (400 MHz, DMSO-d$_6$) δ ppm 11.53 (s, 1H) 10.78 (s, 1H) 10.74 (s, 1H) 8.64 (t, J=4.80 Hz, 1H) 8.34 (s, 1H) 8.03 (s, 1H) 7.79-7.84 (m, 1H) 7.44 (dd, J=8.21, 1.64 Hz, 1H) 7.37 (s, 1H) 7.03 (d, J=8.08 Hz, 1H) 5.89 (s, 1H) 5.34 (quin, J=7.14 Hz, 1H) 4.39 (d, J=4.80 Hz, 2H) 2.21 (s, 3H) 2.15-2.19 (m, 1H) 2.13 (s, 4H) 1.98-2.06 (m, 2H) 1.85-1.94 (m, 2H) 1.67-1.76 (m, 2H). MS (ES) [M+H]$^+$ 497.3.

Example 123

1-(1-methylethyl)-N-{[6-methyl-4-(1-methylethyl)-2-oxo-1,2-dihydro-3-pyridinyl]methyl}-6-[2-(4-methyl-1-piperazinyl)-4-pyridinyl]-1H-indazole-4-carboxamide

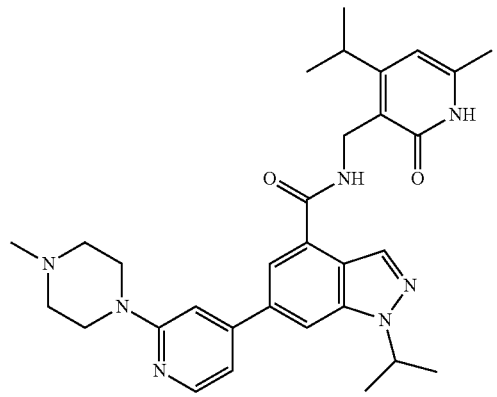

$^1$H NMR (400 MHz, DMSO-d$_6$) δ ppm 11.51 (br. s., 1H) 8.67 (t, J=4.55 Hz, 1H) 8.39 (s, 1H) 8.24 (s, 1H) 8.20 (d, J=5.31 Hz, 1H) 7.85 (d, J=1.01 Hz, 1H) 7.21 (s, 1H) 7.14 (dd, J=5.31, 1.26 Hz, 1H) 6.03 (s, 1H) 5.21 (quin, J=6.63 Hz, 1H) 4.48 (br. s., 1H) 4.46 (br. s., 1H) 3.54-3.64 (m, 4H) 3.25 (dt, J=13.64, 6.82 Hz, 1H) 2.41-2.46 (m, 4H) 2.24 (s, 3H) 2.16 (s, 3H) 1.52 (s, 3H) 1.50 (s, 3H) 1.12 (s, 3H) 1.10 (s, 3H). MS (ES) [M+H]$^+$ 542.3.

Example 124

1-(1-Methylethyl)-N-[(6-methyl-2-oxo-4-propyl-1,2-dihydro-3-pyridinyl)methyl]-6-(2-oxo-2,3-dihydro-1H-benzimidazol-5-yl)-1H-indazole-4-carboxamide

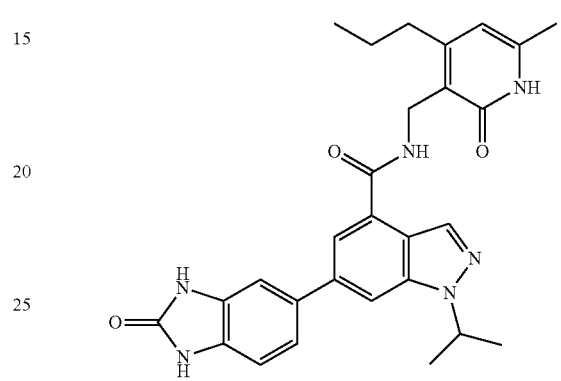

$^1$H NMR (400 MHz, DMSO-d$_6$) δ ppm 11.54 (s, 1H) 10.79 (s, 1H) 10.74 (s, 1H) 8.65 (t, J=4.93 Hz, 1H) 8.35 (s, 1H) 8.02 (s, 1H) 7.80 (s, 1H) 7.43 (dd, J=8.08, 1.77 Hz, 1H) 7.37 (s, 1H) 7.03 (d, J=8.08 Hz, 1H) 5.91 (s, 1H) 5.16 (quin, J=6.63 Hz, 1H) 4.42 (d, J=4.80 Hz, 2H) 2.52-2.57 (m, 1H) 2.14 (s, 3H) 1.51-1.59 (m, 2H) 1.50 (s, 3H) 1.49 (s, 3H) 0.89 (t, J=7.33 Hz, 3H). MS (ES) [M+H]$^+$ 499.3.

Example 125

1-Cyclopentyl-N-[(4,6-dimethyl-2-oxo-1,2-dihydro-3-pyridinyl)methyl]-6-(6-methyl-3-pyridinyl)-1H-indazole-4-carboxamide

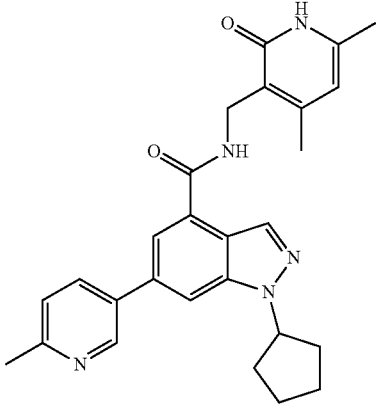

$^1$H NMR (400 MHz, DMSO-d$_6$) δ ppm 11.45 (br. s., 1H) 8.97 (d, J=2.27 Hz, 1H) 8.69 (br. s., 1H) 8.39 (s, 1H) 8.21 (s, 1H) 8.17 (dd, J=8.08, 2.53 Hz, 1H) 7.90 (s, 1H) 7.40 (d, J=8.08 Hz, 1H) 5.89 (s, 1H) 5.35 (quin, J=7.14 Hz, 1H) 4.39 (d, J=4.80 Hz, 2H) 2.54 (s, 3H) 2.22 (s, 3H) 2.16 (d, J=7.58

Hz, 2H) 2.12 (s, 3H) 1.98-2.06 (m, 2H) 1.86-1.94 (m, 2H) 1.68-1.76 (m, 2H). MS (ES) [M+H]+ 456.0.

Example 126

1-(1-methylethyl)-N-[(6-methyl-2-oxo-4-propyl-1,2-dihydro-3-pyridinyl)methyl]-6-[2-(4-methyl-1-piperazinyl)-4-pyridinyl]-1H-indazole-4-carboxamide

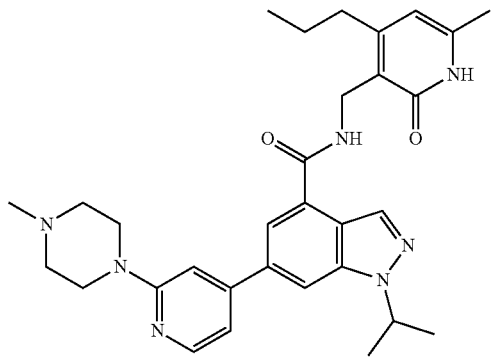

¹H NMR (400 MHz, DMSO-d₆) δ ppm 11.54 (s, 1H) 8.65 (t, J=4.80 Hz, 1H) 8.40 (s, 1H) 8.24 (s, 1H) 8.21 (d, J=5.30 Hz, 1H) 7.86 (s, 1H) 7.21 (s, 1H) 7.14 (d, J=5.31 Hz, 1H) 5.91 (s, 1H) 5.21 (dt, J=13.14, 6.57 Hz, 1H) 4.42 (d, J=4.80 Hz, 2H) 3.56-3.63 (m, 4H) 2.53-2.56 (m, 2H) 2.44 (t, J=4.93 Hz, 4H) 2.24 (s, 3H) 2.13 (s, 3H) 1.52-1.61 (m, 2H) 1.52 (s, 3H) 1.50 (s, 3H) 0.89 (t, J=7.33 Hz, 3H). MS (ES) [M+H]+ 542.2.

Example 127

1-Cyclopentyl-N-[(6-methyl-2-oxo-4-propyl-1,2-dihydro-3-pyridinyl)methyl]-6-(6-methyl-3-pyridinyl)-1H-indazole-4-carboxamide

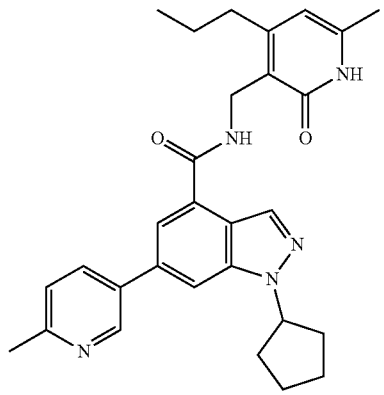

¹H NMR (400 MHz, DMSO-d₆) δ ppm 11.46 (br. s., 1H) 8.96 (d, J=2.02 Hz, 1H) 8.70 (br. s., 1H) 8.40 (s, 1H) 8.21 (s, 1H) 8.17 (dd, J=8.08, 2.53 Hz, 1H) 7.89 (s, 1H) 7.40 (d, J=8.08 Hz, 1H) 5.91 (s, 1H) 5.31-5.39 (m, 1H) 4.42 (d, J=4.55 Hz, 2H) 2.54 (s, 5H) 2.12-2.20 (m, 5H) 2.05 (br. s., 2H) 1.90 (dd, J=8.97, 5.68 Hz, 2H) 1.67-1.76 (m, 2H) 1.48-1.57 (m, 2H) 0.88 (t, J=7.33 Hz, 3H). MS (ES) [M+H]+ 484.2.

Example 128

1-Cyclopentyl-N-[(6-methyl-2-oxo-4-propyl-1,2-dihydro-3-pyridinyl)methyl]-6-(3-pyridinyl)-1H-indazole-4-carboxamide

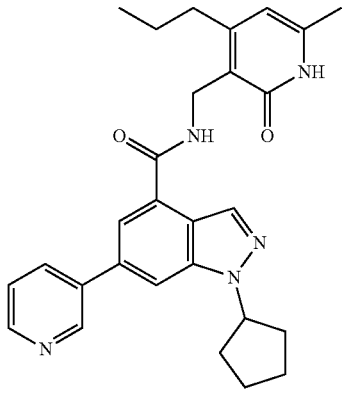 [SMILES: CCCc1cc(C)[nH]c(=O)c1CNC(=O)c1cc(-c2cccnc2)cc2c1cnn2C1CCCC1]

¹H NMR (400 MHz, DMSO-d₆) δ ppm 11.55 (br. s., 1H) 9.14 (s, 1H) 8.60-8.70 (m, 2H) 8.42 (s, 1H) 8.35 (d, J=8.08 Hz, 1H) 8.28 (s, 1H) 7.93 (d, J=1.01 Hz, 1H) 7.61 (dd, J=7.83, 4.80 Hz, 1H) 5.92 (s, 1H) 5.36 (quin, J=7.14 Hz, 1H) 4.43 (d, J=4.80 Hz, 2H) 2.54 (d, J=6.82 Hz, 2H) 2.12-2.21 (m, 5H) 1.99-2.07 (m, 2H) 1.86-1.95 (m, 2H) 1.67-1.77 (m, 2H) 1.48-1.57 (m, 2H) 0.88 (t, J=7.33 Hz, 3H). MS (ES) [M+H]+ 470.2.

Example 129

1-(1-Methylethyl)-N-[(6-methyl-2-oxo-4-propyl-1,2-dihydro-3-pyridinyl)methyl]-6-(3-pyridinyl)-1H-indazole-4-carboxamide

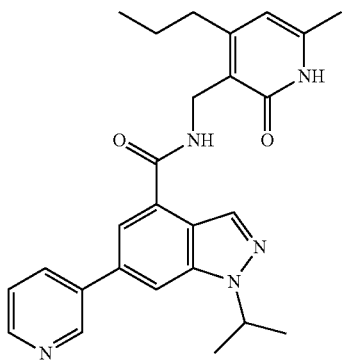 [SMILES: CCCc1cc(C)[nH]c(=O)c1CNC(=O)c1cc(-c2cccnc2)cc2c1cnn2C(C)C]

¹H NMR (400 MHz, DMSO-d₆) δ ppm 11.54 (s, 1H) 9.11 (br. s., 1H) 8.66 (t, J=4.80 Hz, 1H) 8.62 (d, J=4.04 Hz, 1H) 8.42 (s, 1H) 8.28 (dt, J=8.21, 1.83 Hz, 1H) 8.25 (s, 1H) 7.92 (d, J=1.01 Hz, 1H) 7.55 (dd, J=7.96, 4.67 Hz, 1H) 5.92 (s, 1H) 5.19 (quin, J=6.63 Hz, 1H) 4.43 (d, J=4.80 Hz, 2H) 2.54 (d, J=7.07 Hz, 2H) 2.13 (s, 3H) 1.52-1.59 (m, 2H) 1.52 (s, 3H) 1.50 (s, 3H) 0.88 (t, J=7.33 Hz, 3H). MS (ES) [M+H]+ 444.3.

Example 130

1-Cyclopentyl-N-[(4,6-dimethyl-2-oxo-1,2-dihydro-3-pyridinyl)methyl]-6-[6-(4-morpholinyl)-3-pyridinyl]-1H-indazole-4-carboxamide

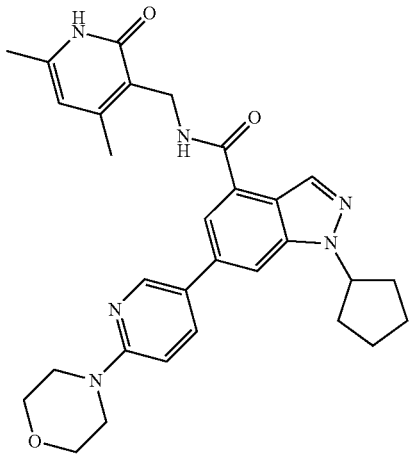 [SMILES: Cc1cc(C)c(CNC(=O)c2cc(-c3ccc(N4CCOCC4)nc3)cc3c2cnn3C2CCCC2)c(=O)[nH]1]

$^1$H NMR (400 MHz, DMSO-d$_6$) δ ppm 11.54 (s, 1H), 8.69 (d, J=2.27 Hz, 1H), 8.60 (t, J=5.05 Hz, 1H), 8.35 (s, 1H), 8.10 (ddd, J=2.78, 2.91, 5.94 Hz, 2H), 7.85 (d, J=1.01 Hz, 1H), 6.98 (d, J=8.84 Hz, 1H), 5.89 (s, 1H), 5.31 (t, J=7.07 Hz, 1H), 4.39 (d, J=4.80 Hz, 2H), 3.70-3.76 (m, 4H), 3.50-3.55 (m, 4H), 2.22 (s, 3H), 2.09-2.18 (m, 5H), 1.96-2.07 (m, 2H), 1.89 (dd, J=5.68, 9.22 Hz, 2H), 1.66-1.77 (m, 2H). MS (ES) [M+H]+ 527.1.

Example 131

1-Cyclopentyl-N-[(4,6-dimethyl-2-oxo-1,2-dihydro-3-pyridinyl)methyl]-6-(5-pyrimidinyl)-1H-indazole-4-carboxamide

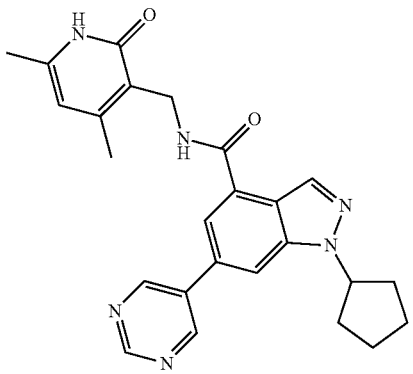 [SMILES: Cc1cc(C)c(CNC(=O)c2cc(-c3cncnc3)cc3c2cnn3C2CCCC2)c(=O)[nH]1]

$^1$H NMR (400 MHz, DMSO-d$_6$) δ ppm 11.54 (s, 1H), 9.35 (s, 2H), 9.23 (s, 1H), 8.63 (t, J=4.93 Hz, 1H), 8.44 (s, 1H), 8.39 (s, 1H), 8.01 (d, J=1.26 Hz, 1H), 5.90 (s, 1H), 5.35 (dq, J=7.07, 7.33 Hz, 1H), 4.40 (d, J=4.80 Hz, 2H), 2.22 (s, 3H), 2.13 (s, 5H), 1.98-2.08 (m, 2H), 1.85-1.96 (m, 2H), 1.67-1.77 (m, 2H). MS (ES) [M+H]+ 443.0.

INTERMEDIATES

Intermediate 1

3-(Aminomethyl)-4,6-dimethyl-2(1H)-pyridinone hydrochloride

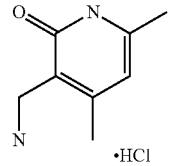

Palladium on carbon (10%) (3.24 g) was charged into a 2 L dry Parr bottle and a small amount of acetic acid was added. Next added 4,6-dimethyl-2-oxo-1,2-dihydro-pyridine-3-carbonitrile (30 g, 202.7 mmol), sodium acetate (30.75 g, 375.0 mmol), platinum oxide (0.218 g), and acetic acid (1 L). The bottle was capped, placed on Parr apparatus, and shaken under an atmosphere of H$_2$ (100 psi) for 2 days. The reaction mixture was filtered. The solvent was removed to give a residue, which was treated with 150 mL of conc. HCl, and the formed solids were filtered. The yellow filtrate was concentrated. To the crude compound was added 30 mL of conc. HCl and 150 mL EtOH, the contents cooled to 0° C., and stirred at 0° C. for 2 h. The formed solids were filtered, washed with cold EtOH, ether, and dried. The product was collected as 36 g. This batch was combined with other batches prepared on smaller scales and triturated with ether to give 51 g of pure compound. $^1$H NMR (400 MHz, DMSO-d$_6$) δ ppm 11.85 (br s, 1H) 8.13 (br s, 3H) 5.93-6.01 (m, 1H) 3.72-3.80 (m, 2H) 2.22 (s, 3H) 2.16 (s, 3H).

Intermediate 2

3-(aminomethyl)-6-methyl-4-propyl-2 (1H)-pyridinone

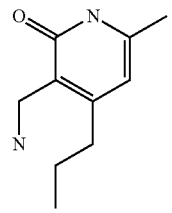

Step 1

To a stirred solution of t-BuOK (20 g, 178.5 mmol) and cyanoacetamide (16.5 g, 196 mmol) in DMSO (300 mL) was added (3E)-3-hepten-2-one (20 g, 178.3 mmol) under argon atmosphere at room temperature. The reaction mixture was stirred at room temperature for 30 min and then additional t-BuOK (60 g, 535.7 mmol) was added to the reaction mixture. The argon was then displaced by oxygen gas and stirred for 48 hrs at room temperature under oxygen. Reaction mixture was cooled to 0° C. and diluted with water (80 mL) followed by 4N HCl (120 mL). The mixture was stirred for 15 min and the solid was filtered. The solid was washed with water (1 L) and dried to afford 1,2-dihydro-6-methyl-2-oxo-4-propylpyridine-3-carbonitrile as an off white solid (12 g, 38%). $^1$H NMR (CDCl$_3$, 400 MHz): δ 1.030 (t, 3H, J=7.2 Hz), 1.728 (m, 2H), 2.429 (s, 3H), 2.701 (t, 2H, J=7.6 Hz), 6.083 (s, 1H). LCMS E-S (M–H)=175.11.

Step 2

To a suspension of Raney Ni (2 g) in methanol (250 mL) was added 1,2-dihydro-6-methyl-2-oxo-4-propylpyridine-3-carbonitrile (5 g, 28.4 mmol) and methanolic ammonia (750 mL). The reaction mixture was stirred at room temperature under hydrogen pressure (60 psi) for 48 hrs. The reaction mixture was filtered through celite pad and washed with methanol (250 mL). The filtrate was concentrated under reduced pressure to afford the crude product (5.1 g). The crude product was purified by column chromatography by using a short column of silica gel (60-120 mesh) treated with methanolic $NH_3$, (eluant: 0-25% methanol in DCM) and isolated to afford the desired product 3-(amino methyl)-6-methyl-4-propylpyridin-2(1H)-one as an off white solid (2 g, 39% yield). $^1$H NMR (DMSO, 400 MHz): δ 0.921 (t, 3H, J=7.2 Hz), 1.518 (m, 2H), 2.09 (s, 3H), 2.418 (t, 2H, J=7.6 Hz), 3.451 (s, 2H), 4-5.6 (br s, 2H, exchangeable), 5.822 (s, 1H). LCMS E-S (M+H)=181.22.

Intermediate 3

3-(Aminomethyl)-6-methyl-4-(1-methylethyl)-2(1H)-pyridinone

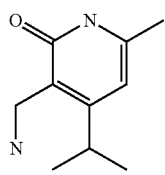

The title compound was prepared in the same manner as described for 3-(aminomethyl)-6-methyl-4-propyl-2(11H)-pyridinone (Intermediate 2, steps 1 and 2) from (3E)-5-methyl-3-hexen-2-one (20 g, 137 mmol). LCMS E-S (M+H)= 181.1. $^1$H NMR (400 MHz, DMSO-$d_6$) δ ppm 11.8-11.9 (br s, 1H), 7.86-7.96 (br s, 3H), 6.10 (s, 1H), 3.82-3.86 (m, 2H), 3.02-3.09 (m, 1H), 2.17 (s, 3H), 1.08 (d, 6H).

Intermediate 4

3-(Aminomethyl)-4-cyclohexyl-6-methyl-2(1H)-pyridinone

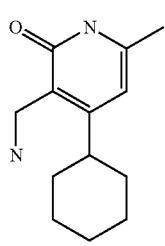 [SMILES: Cc1cc(C2CCCCC2)c(CN)c(=O)[nH]1]

Step 1

To a stirred suspension of $CrCl_2$ (58 g, 472.8 mmol in THF (1500 mL) was added a THF solution (500 mL) of 1,1-dichloro-2-propanone (10 g, 78.8 mmol) and cyclohexanecarbaldehyde (8.84 g, 78.8 mmol). The reaction mixture was heated at reflux for 2 h, and then quenched by the addition of 1.0 M HCl. The reaction mixture was filtered through a pad of Celite and concentrated in vacuo. The crude residue (10 g) was added to a solution of DMSO (150 mL) containing t-BuOK (7.5 g, 65.7 mmol) and cyanoacetamide (6.1 g, 72.3 mmol) and stirred at room temperature for 30 min. Additional t-BuOK (22.5 g, 197.1 mmol) was added and the reaction mixture was stirred under an atmosphere of oxygen for an additional 1 h. The contents were purged with argon, diluted with 4 volumes of $H_2O$, and then 5 volumes of 4 N HCl, which were added slowly. The reaction mixture was filtered, washed with water and dried to give 4-cyclohexyl-6-methyl-2-oxo-1,2-dihydro-3-pyridinecarbonitrile (4.5 g, 32%). $^1$H NMR (400 MHz, DMSO-$d_6$) δ ppm 6.25 (s, 1H), 2.61-2.65 (m, 1H), 2.22 (s, 3H), 1.66-1.79 (m, 4H), 1.24-1.46 (m, 6H).

Step 2

To an ice-bath cooled THF (100 mL) solution of the product from step 1 (2 g, 9.26 mmol) were added $NaBH_4$ (0.81 g, 21.3 mmol), and $I_2$ (2.3 g, 9.26 mmol), and the mixture stirred for 30 min. The reaction mixture was then heated at reflux for 3 h, and then allowed to cool to room temperature. After cooling to 0° C., the reaction mixture was acidified by slow addition of 3 N HCl (1 mL). The reaction mixture was concentrated in vacuo and the crude product purified by reverse phase HPLC to give the title compound as a solid (0.5 g, 25%). LCMS E-S (M+H)=221.1. $^1$H NMR (400 MHz, DMSO-$d_6$) δ ppm 11.8-11.9 (br s, 1H), 7.80-7.93 (br s, 3H), 6.07 (s, 1H), 3.69 (s, 2H), 2.67-2.75 (m, 1H), 2.17 (s, 3H), 1.58-1.72 (m, 5H), 1.19-1.41 (m, 5H).

Intermediate 5

3-(Aminomethyl)-4-ethyl-6-methyl-2(1H)-pyridinone hydrochloride

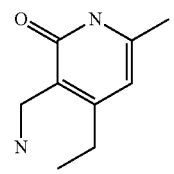

Step 1

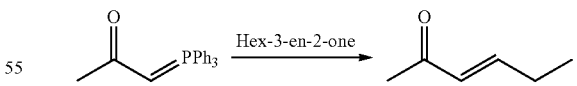

To a stirred solution of 1-(triphenylphosphoranylidene)-2-propanone (100 g, 307 mmol) in DCM (500 mL) was added propionaldehyde (140 mL, 1929 mmol) at room temperature. The reaction mixture was then stirred at room temperature for 18 hours. The reaction was monitored by TLC. The solvent (DCM) was distilled off using ordinary distillation. The residue was then distilled using fractional distillation under vacuum (~450 mbar) and the desired product was isolated. The title compound, hex-3-en-2-one (20 g, 66%), was collected at 110° C. $^1$H NMR (CDCl$_3$, 400 MHz) δ ppm 1.071-

1.121 (t, 3H, J=7.4 Hz), 2.250-2.299 (m, 5H), 6.054-6.094 (d, 1H, J=16 Hz), 6.823-6.895 (m, 1H).

Step 2

4-Ethyl-1,2-dihydro-6-methyl-2-oxopyridine-3-carbonitrile

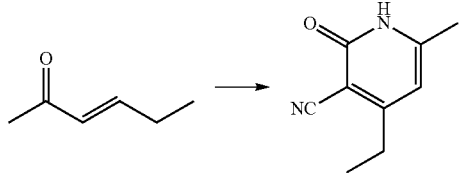

To a stirred solution of t-BuOK (22.85 g, 204.08 mmol) and cyanoacetamide (18.8 g, 224.1 mmol) in DMSO (300 mL) was added hex-3-en-2-one (20 g, 204.08 mmol) under argon atmosphere at room temperature. The reaction mixture was then stirred at room temperature for 30 min and then added additional t-BuOK (68.5 g, 612.05 mmol) was added. Argon gas was displaced by oxygen gas and the mixture stirred for 48 hrs at room temperature in presence of oxygen. Reaction was monitored by TLC. The reaction mixture was cooled to 0° C. and diluted with water (100 mL) followed by 4 N HCl (120 mL). The mixture was stirred for 15 min and the resulting solid was filtered. The solid was washed with water (1 L) and dried to afford the title compound, 4-ethyl-1,2-dihydro-6-methyl-2-oxopyridine-3-carbonitrile (10.5 g, 31%), as an off white solid. $^1$H NMR (CDCl$_3$, 400 MHz): δ ppm 1.148-1.185 (t, 3H, J=7.4 Hz), 2.237 (s, 3H), 2.557-2.614 (m, 2H), 6.211 (s, 1H), 12.330 (broad s, 1H). MS (ES) [M+H]$^+$ 161.06.

Step 3

3-(Amino methyl)-4-ethyl-6-methylpyridin-2(1H)-one

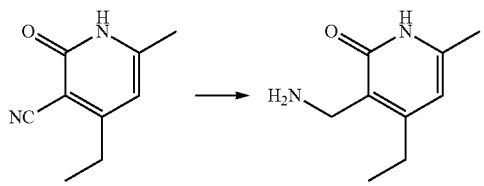

To a suspension of Raney Nickel (6 g) in methanol (200 mL) was added 4-ethyl-1,2-dihydro-6-methyl-2-oxopyridine-3-carbonitrile (10 g, 61.7 mmol) and methanolic ammonia (750 mL). The reaction mixture was stirred at room temperature under hydrogen pressure (80 psi) for 48 hrs. The reaction mixture was filtered through Celite and washed with methanol (250 mL). The filtrate was concentrated under reduced pressure and the residue purified by filter column using silica gel (60-120 mesh), eluted with 10% MeOH in CHCl$_3$, to afford 3-(amino methyl)-4-ethyl-6-methylpyridin-2(1H)-one (5.6 g, 54%) as an off white solid. $^1$H NMR (DMSO-D$_6$, 400 MHz) (free amine): δ ppm 1.063-1.101 (t, 3H, J=7.6 Hz), 2.101 (s, 3H), 2.412-2.449 (m, 2H), 3.448 (s, 2H), 5.835 (s, 1H). MS (ES) [M+H]$^+$ 167.06.

Step 4

3-(Aminomethyl)-4-ethyl-6-methylpyridin-2(1H)-one hydrochloride

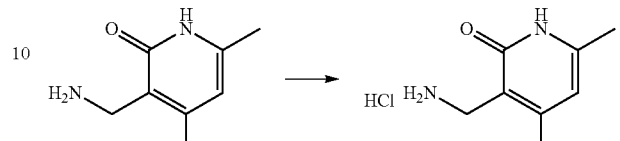

3-(Amino methyl)-4-ethyl-6-methylpyridin-2(1H)-one, (5.6 g, 33 mmol) was suspended in DCM (560 mL) and the insoluble contents/particles were filtered. The filtrate was concentrated and dried. The residue was dissolved in DCM (10 mL) and 4 M HCl in 1,4-dioxane (16 mL, 66 mmol) was added at 0° C. and stirred for 10 min, at which time the reaction mixture was concentrated under high-vacuum and dried. The resulting crude solid was triturated with hexane (150 mL) and filtered. The solid was dried under vacuum. Collected 3-(amino methyl)-4-ethyl-6-methylpyridin-2(1H)-one hydrochloride (5.9 g, 86%). $^1$H NMR (400 MHz, DMSO-d$_6$) δ ppm 1.082-1.120 (t, 3H, J=7.6 Hz), 2.179 (s, 3H), 2.503-2.544 (m, 2H), 3.785-3.798 (d, 2H, J=5.2 Hz), 6.024 (s, 1H), 7.985 (broad s, 2H), 11.858 (broad s, 1H). MS (ES) [M+H]$^+$ 167.2.

Intermediate 6

3-(aminomethyl)-6-methyl-4,4'-bipyridin-2(1H)-one

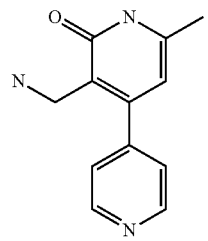 [SMILES: Cc1cc(-c2ccncc2)c(CN)c(=O)[nH]1]

Step 1

(Z)-3-hydroxy-1-(pyridin-4-yl)but-2-en-1-one

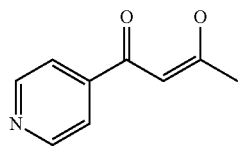

To a solution of ethyl 4-pyridinecarboxylate (30 g, 198 mmol) and acetone (34.58 g, 595 mmol) in THF (150 mL) was slowly added NaOMe (12.87 g, 238 mmol) at 35-40° C. The mixture was stirred at room temperature for 0.5 h, and then heated at reflux for 3 h. The mixture was cooled to room temperature and filtered to give a solid, which was washed with t-BuOMe, and dissolved in H$_2$O. The solution was acidified with acetic acid and the resulting oily product was extracted with CHCl$_3$. The solvent was removed in vacuo, and the crude product was obtained (12 g, 37%) and used without further purification. $^1$H NMR (400 MHz, DMSO-$d_6$) δ 8.73 (d, 2H), 7.76 (d, 2H), 6.63 (s, 1H), 2.21 (s, 3H); note: enolic OH does not appear.

Step 2

6-methyl-2-oxo-1,2-dihydro-[4,4'-bipyridine]-3-carbonitrile

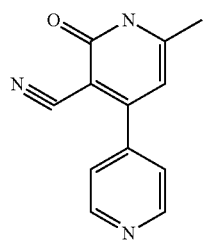 [SMILES: Cc1cc(-c2ccncc2)c(C#N)c(=O)[nH]1]

To a solution of (2Z)-3-hydroxy-1-(4-pyridinyl)-2-buten-1-one (8 g, crude, 49 mmol) and cyanoacetamide (4.12 g, 49 mmol) in anhydrous EtOH (100 mL) was added piperidine (4.17 g, 49 mmol) under $N_2$ at 75° C. The mixture was heated at reflux for 1 h, and then cooled to room temperature. After filtration, the solid was collected and washed with $H_2O$ to give the crude product (4 g) as two isomers. After separation by HPLC, 1.8 g of 6-methyl-2-oxo-1,2-dihydro-4,4'-bipyridine-3-carbonitrile and 1.2 g of 4-methyl-6-oxo-1,6-dihydro-2,4'-bipyridine-5-carbonitrile were obtained. The identity of 6-methyl-2-oxo-1,2-dihydro-4,4'-bipyridine-3-carbonitrile was established by nOE analysis. $^1$H NMR (400 MHz, DMSO-$d_6$) δ 12.79 (br. s., 1H), 8.75 (d, 2H), 7.58 (d, 2H), 6.37 (s, 1H), 2.31 (s, 3H).

Step 3

3-(aminomethyl)-6-methyl-4,4'-bipyridin-2(1H)-one

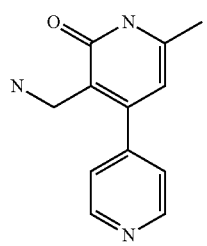 [SMILES: Cc1cc(-c2ccncc2)c(CN)c(=O)[nH]1]

To an ice bath cooled THF (100 mL) solution of 6-methyl-2-oxo-1,2-dihydro-4,4'-bipyridine-3-carbonitrile (4 g, 18.9 mmol) was added NaBH$_4$ (1.43 g, 37.9 mmol), and I$_2$ (4.81 g, 18.9 mmol), and the mixture was stirred for 0.5 h. The reaction mixture was then heated at reflux for 4 h. After cooling to 0° C., the reaction mixture was adjusted to pH 5 with 4 N HCl. The mixture was concentrated in vacuo to give the crude compound, which was purified by HPLC to give 3-(aminomethyl)-6-methyl-4,4'-bipyridin-2(1H)-one (1.9 g, 31%) as a TFA salt. LCMS MH+=216.0 $^1$H NMR (400 MHz, DMSO-$d_6$ in $D_2O$) δ 8.87 (d, 2H), 7.87 (d, 2H), 6.13 (s, 1H), 3.65 (br s, 2H), 2.17 (s, 3H).

Intermediate 7

3-(aminomethyl)-6-methyl-4-(phenylmethyl)-2(1H)-pyridinone and 3-(aminomethyl)-4-methyl-6-(phenylmethyl)-2(1H)-pyridinone

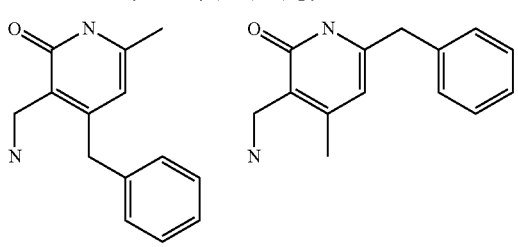

Step 1

1-phenylpentane-2,4-dione

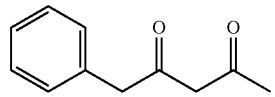

To a solution of NaNH$_2$ (19.02 g, 480 mmol) in anhydrous ether (400 mL) under N$_2$ at −5° C. was added dropwise ethyl phenylacetate (19.2 g, 150 mmol) and then acetone (21.23 g, 370 mmol) with vigorous stirring. After addition, the reaction mixture was stirred at room temperature overnight. The mixture was then acidified to pH 4.0-5.0 with 1N HCl. The organic layer was separated and concentrated in vacuo. The crude product was purified by silica gel chromatography to give 1-phenyl-2,4-pentanedione (18.32 g, 44%). $^1$H NMR (400 MHz, CDCl3-$d_3$) δ 15.49 (br s, 1H), 7.33-7.45 (m, 5H), 5.53 (s, 1H), 3.66 (s, 2H), 2.10 (s, 3H).

Step 2

4-benzyl-6-methyl-2-oxo-1,2-dihydropyridine-3-carbonitrile and 6-benzyl-4-methyl-2-oxo-1,2-dihydropyridine-3-carbonitrile

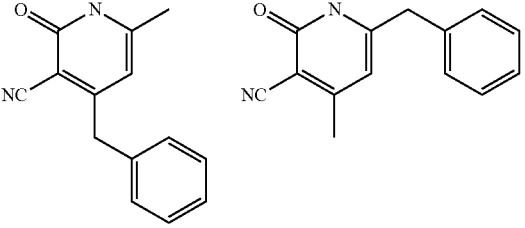 [SMILES: Cc1cc(Cc2ccccc2)c(C#N)c(=O)[nH]1 ; Cc1cc(Cc2ccccc2)[nH]c(=O)c1C#N]

1-phenyl-2,4-pentanedione (18.32 g, 104 mmol) and cyanoacetamide (8.74 g, 104 mmol) were dissolved in EtOH (104 mL) and heated until homogenous (ca. 75° C.). Piperidine (8.86 g, 104 mmol) was added and the reaction mixture heated at reflux for 15-30 min. followed by cooling to room temperature, during which time precipitation occurred. The heterogenous contents were filtered to give a solid which was suspended in 200 mL water and stirred vigorously for 20 min. The heterogenous mixture was filtered to afford 6-methyl-2-oxo-4-(phenylmethyl)-1,2-dihydro-3-pyridinecarbonitrile and 4-methyl-2-oxo-6-(phenylmethyl)-1,2-dihydro-3-pyridinecarbonitrile (12.06 g, 52%). LCMS MH+=225.1 ¹H NMR (400 MHz, DMSO-d₆) δ 7.21-7.31 (m, 10H), 6.06 (s, 2H), 3.89 (s, 2H), 3.79 (s, 2H), 2.24 (s, 3H), 2.15 (s, 3H).

Step 3 tert-butyl ((4-benzyl-6-methyl-2-oxo-1,2-dihydropyridin-3-yl)methyl)carbamate compound and tert-butyl ((6-benzyl-4-methyl-2-oxo-1,2-dihydropyridin-3-yl)methyl)carbamate

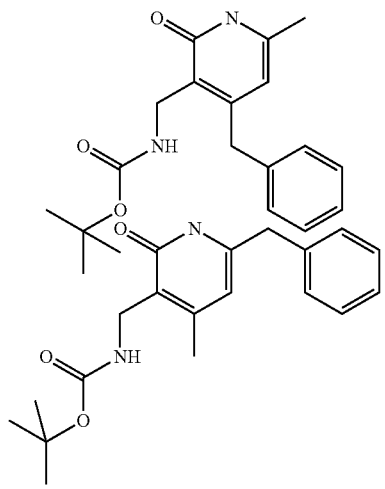

Sodium acetate (6.14 g, 74.8 mmol), Pd/C (0.65 g, 1 mmol), and platinum (II) oxide (45 mg, 1 mmol) were placed in a dried Parr bottle equipped with nitrogen inlet. A small amount of acetic acid was added to wet the catalysts. A solution of 6-methyl-2-oxo-4-(phenylmethyl)-1,2-dihydro-3-pyridinecarbonitrile and 4-methyl-2-oxo-6-(phenylmethyl)-1,2-dihydro-3-pyridinecarbonitrile (6 g, 26.7 mmol) in acetic acid (300 mL) was added to the vessel. The contents were sealed and hydrogenated on Parr shaker at 45 psi for 12 h. The reaction mixture was filtered and washed with acetic acid. The filtrate was removed under reduced pressure. The residue was washed with methanol and filtered to afford a crude mixture of 3-(aminomethyl)-6-methyl-4-(phenylmethyl)-2(1H)-pyridinone and 3-(aminomethyl)-4-methyl-6-(phenylmethyl)-2(1H)-pyridinone. The reaction was run in duplicate to afford a total crude recovery of 14.5 g. To a solution of the above crude product mixture (4.0 g, 17.5 mmol) in THF (10 mL) and DMF (10 mL) was added di-tert-butoxycarbonyl anhydride (5.0 g, 23.4 mmoL) and triethylamine (5.2 g, 52.5 mmol) at 0° C. The reaction mixture was stirred with warming to room temperature and then stirred for an additional 4 h. The contents were diluted with ice water and then filtered. The collected solid was dried and the products separated by HPLC to furnish 1.2 g of 1,1-dimethylethyl {[4-methyl-2-oxo-6-(phenylmethyl)-1,2-dihydro-3-pyridinyl]methyl}carbamate (¹H NMR (400 MHz, DMSO-d₆) δ 11.55-1.60 (br s, 1H), 7.20-7.29 (m, 5H), 5.85 (s, 1H), 3.92 (s, 2H), 3.90 (s, 2H), 2.10 (s, 3H), 1.32 (s, 9H) and 1.0 g of 1,1-dimethylethyl {[6-methyl-2-oxo-4-(phenylmethyl)-1,2-dihydro-3-pyridinyl]methyl}carbamate (¹H NMR (400 MHz, DMSO-d₆) δ 11.50-11.55 (br s, 1H), 7.18-7.25 (m, 5H), 5.75 (s, 1H), 4.02 (s, 2H), 3.85 (s, 2H), 2.05 (s, 3H), 1.32 (s, 9H).

Step 4

3-(aminomethyl)-6-benzyl-4-methylpyridin-2(1H)-one

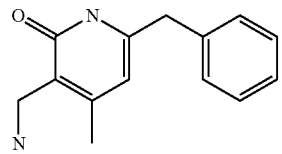 [SMILES: Cc1cc(Cc2ccccc2)[nH]c(=O)c1CN]

A solution of 1,1-dimethylethyl {[4-methyl-2-oxo-6-(phenylmethyl)-1,2-dihydro-3-pyridinyl]methyl}carbamate (1.2 g, 3.66 mmol) in 4N HCl (in 15 mL 1,4 dioxane) was heated to 60° C. for 1 h. The mixture was cooled to room temperature. The mixture was filtered and dried to give 3-(aminomethyl)-4-methyl-6-(phenylmethyl)-2(1H)-pyridinone as an HCl salt (0.725 g, 87%). LCMS MH+=229.1 ¹H NMR (400 MHz, DMSO-d₆) δ 11.9-12.0 (br s, 1H), 7.99 (br s, 3H), 7.20 (s, 5H), 5.97 (s, 1H), 3.72-3.75 (m, 4H), 2.17 (s, 3H).

3-(aminomethyl)-4-benzyl-4-methylpyridin-2(1H)-one

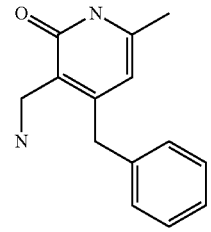 [SMILES: Cc1cc(Cc2ccccc2)c(CN)c(=O)[nH]1]

A solution of 1,1-dimethylethyl {[6-methyl-2-oxo-4-(phenylmethyl)-1,2-dihydro-3-pyridinyl]methyl}carbamate (1.0 g, 3.0 mmol) in 4N HCl (in 15 mL 1,4 dioxane) was heated to 60° C. for 1 h. The mixture was cooled to room temperature. The mixture was filtered and dried to give 3-(aminomethyl)-6-methyl-4-(phenylmethyl)-2(1H)-pyridinone as an HCl salt (0.600 g, 86%). LCMS MH+=229.1 ¹H NMR (400 MHz, DMSO-d₆) δ 11.9-12.0 (br s, 1H), 8.03 (br s, 3H), 7.16-7.30 (m, 5H), 5.84 (s, 1H), 3.91 (s, 2H), 3.81 (s, 2H), 2.10 (s, 3H).

Intermediate 8

3-(aminomethyl)-4-(sec-butyl)-6-methylpyridin-2(1H)-one

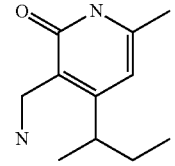

a) (E)-5-methylhept-3-en-2-one

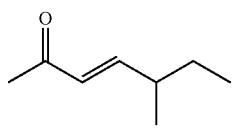

To a stirred solution of 1-(triphenylphosphoranylidene)-2-propanone (73.9 g, 232.55 mmol) in DCM (150 mL) was added 2-methyl butanal (20 g, 232.55 mmol) and the resulting reaction mixture was stirred at room temperature for 16 h. DCM was distilled off from the reaction mixture using short path condenser and after that, the desired product (E)-5-methylhept-3-en-2-one, 2 (12 g, 41%) was collected as colorless liquid by fractional distillation. $^1$H NMR (CDCl$_3$, 400 MHz): δ 0.909-0.891 (t, 3H, J=7.2 Hz), 1.085-0.976 (m, 3H), 1.46-1.103 (m, 2H), 1.632-1.606 (d, 1H), 2.252-2.205 (m, 3H), 6.061-6.018 (dd, 1H), 6.716-6.657 (m, 1H). GCMS=126.2 (M)-Purity 87%.

b) 4-sec-butyl-1,2-dihydro-6-methyl-2-oxopyridine-3-carbonitrile

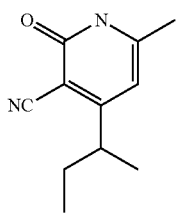

To a stirred solution of t-BuOK (8 g, 71.42 mmol) and cyanoacetamide (6.6 g, 78.57 mmol) in DMSO (80 mL) was added (E)-5-methylhept-3-en-2-one, 2 (9 g, 71.42 mmol) under argon atmosphere at room temperature. The reaction mixture was stirred at room temperature for 1 h and then added additional t-BuOK (24 g, 214.28 mmol) was added. Then argon was displaced by oxygen and stirred at RT for 48 h. The reaction mixture was cooled to 0° C., diluted with water (36 mL) followed by 4N HCl (up to pH~4) and the resulting reaction mixture was stirred for 15 min. The separated solid was collected by filtration, washed with water (10 mL), pet ether (100 mL) and dried to afford the title compound as yellow solid (7 g, 53%). $^1$H NMR (DMSO-d$_6$, 400 MHz): δ 0.816-0.779 (t, 3H, J=7.6 Hz), 1.178-1.161 (d, 3H, J=6.8 Hz), 1637-1.505 (m, 2H), 2.24 (s, 3H), 2.814-2.760 (m, 1H), 6.239 (s, 1H), 12.324 (bs, 1H); LCMS (ES−) m/z=189.20 (M−H)

c) 4-sec-butyl-3-(aminomethyl)-6-methylpyridin-2(1H)-one

To a suspension of Raney Ni (10 g) in methanol (50 mL) was added 4-sec-butyl-1,2-dihydro-6-methyl-2-oxopyridine-3-carbonitrile (7 g, 36.8 mmol) followed by methanolic ammonia (200 mL) and the resulting reaction mixture was stirred at room temperature under hydrogen pressure (80 psi) for 18 h. The reaction mixture was filtered through Celite pad and washed with methanol (250 mL). The filtrate was concentrated under reduced pressure to afford the crude product (7 g). The reaction was repeated again under same condition. The crude products were combined and purified by silica gel chromatography (eluent: 8% MeOH in CHCl$_3$, spiked with NH$_3$) and the obtained solid was triturated with diethyl ether (50 mL) and dried under vacuum to afford the title compound as yellow solid (3.5 g, 28%). $^1$H NMR (DMSO-d$_6$, 400 MHz): δ 0.809-0.774 (t, 3H, J=6.8 Hz), 1.113-1.097 (d, 3H, J=6.4 Hz), 1.504-1.468 (t, 2H, J=7.2 Hz), 2.184 (s, 3H), 2.839-2.822 (d, 1H, J=6.8 Hz), 3.822 (s, 2H), 6.059 (s, 1H), 8.315 (bs, 2H); LCMS (ES+) m/z=195.22 (M+H)

Assay Protocol

Compounds contained herein were evaluated for their ability to inhibit the methyltransferase activity of EZH2 within the PRC2 complex. Human PRC2 complex was prepared by co-expressing each of the 5 member proteins (FLAG-EZH2, EED, SUZ12, RbAp48, AEBP2) in Sf9 cells followed by co-purification. Enzyme activity was measured in a scintillation proximity assay (SPA) where a tritiated methyl group is transferred from 3H-SAM to a lysine residue on Histone H3 of a mononucleosome, purified from HeLa cells. Mononucleosomes were captured on SPA beads and the resulting signal is read on a ViewLux plate reader.

Part A. Compound Preparation
1. Prepare 10 mM stock of compounds from solid in 100% DMSO.
2. Set up an 11-point serial dilution (1:3 dilution, top concentration 10 mM) in 100% DMSO for each test compound in a 384 well plate leaving columns 6 and 18 for DMSO controls.
3. Dispense 100 nL of compound from the dilution plate into reaction plates (Grenier Bio-One, 384-well, Cat #784075).

Part B. Reagent Preparation
Prepare the following solutions:
1. 50 mM Tris-HCl, pH 8: Per 1 L of base buffer, combine 1 M Tris-HCl, pH 8 (50 mL) and distilled water (950 mL).
2. 1× Assay Buffer: Per 10 mL of 1× Assay Buffer, combine 50 mM Tris-HCl, pH 8 (9958 uL), 1 M MgCl$_2$ (20 uL), 2 M DTT (20 uL), and 10% Tween-20 (2 uL) to provide a final concentration of 50 mM Tris-HCl, pH 8, 2 mM MgCl$_2$, 4 mM DTT, 0.002% Tween-20.
3. 2× Enzyme Solution: Per 10 mL of 2× Enzyme Solution, combine 1× Assay Buffer and PRC2 complex to provide a final enzyme concentration of 10 nM.
4. SPA Bead Suspension: Per 1 mL of SPA Bead Suspension, combine PS-PEI coated LEADSeeker beads (40 mg) and ddH2O (1 mL) to provide a final concentration of 40 mg/mL.
5. 2× Substrate Solution: Per 10 mL of 2× Substrate Solution, combine 1× Assay Buffer (9728.55 uL), 800 ug/mL mononucleosomes (125 uL), 1 mM cold SAM (4 uL), and 7.02 uM 3H-SAM (142.45 uL; 0.55 mCi/mL) to provide a final concentration of 5 ug/mL nucleosomes, 0.2 uM cold SAM, and 0.05 uM 3H-SAM.
6. 2.67× Quench/Bead Mixture: Per 10 mL of 2.67× Quench/Bead Mixture, combine ddH$_2$O (9358 uL), 10 mM cold SAM (267 uL), 40 mg/mL Bead Suspension (375 uL) to provide a final concentration of 100 uM cold SAM and 0.5 mg/mL SPA beads.

Part C. Assay Reaction in 384-well Grenier Bio-One Plates
Compound Addition
1. Dispense 100 nL/well of 100× Compound to test wells (as noted above).
2. Dispense 100 nL/well of 100% DMSO to columns 6 & 18 for high and low controls, respectively.

Assay
1. Dispense 5 uL/well of 1× Assay Buffer to column 18 (low control reactions).

2. Dispense 5 uL/well of 2× Enzyme Solution to columns 1-17, 19-24.
3. Spin assay plates for ~1 minute at 500 rpm.
4. Stack the assay plates, covering the top plate.
5. Incubate the compound/DMSO with the enzyme for 30 minutes at room temperature.
6. Dispense 5 uL/well of 2× Substrate Solution to columns 1-24.
7. Spin assay plates for ~1 minute at 500 rpm.
8. Stack the assay plates, covering the top plate.
9. Incubate the assay plates at room temperature for 1 hour.

Quench/Bead Addition
1. Dispense 5 uL/well of the 3× Quench/Bead Mixture to columns 1-24.
2. Seal the top of each assay plate with adhesive TopSeal.
3. Spin assay plates for ~1 minute at 500 rpm.
4. Equilibrate the plates for >20 min.

Read Plates
1. Read the assay plates on the Viewlux Plate Reader utilizing the 613 nm emission filter with a 300 s read time.

Reagent addition can be done manually or with automated liquid handler.
*The final DMSO concentration in this assay is 1%.
*The positive control is in column 6; negative control is in column 18.
*Final starting concentration of compounds is 100 μM.

Part D. Data Analysis

Percent inhibition was calculated relative to the DMSO control for each compound concentration and the resulting values were fit using standard $IC_{50}$ fitting parameters within the ABASE data fitting software package.

Exemplified compounds of the present invention were generally tested according to the above or an analogous assay and were found to be inhibitors of EZH2. The $IC_{50}$ values ranged from about 1 nM to about 10 M; The $IC_{50}$ values of the more active compounds range from about 1 nM to about 500 nM; The most active compounds are under 50 nM. As tested in the foregoing assay or an analogous assay, compounds of the various Examples gave the $IC_{50}$ data (nM) in the paragraph below. Repeating the assay run(s) may result in a somewhat different.

Ex 1, 32; Ex 3, 158; Ex 4, 25; Ex 5, 8; Ex 7, 40; Ex 8, 10; Ex 9, 16; Ex 10, 13; Ex 12, 4; Ex 13, 126; Ex 14, 5; Ex 15, 2; Ex 16, 3; Ex 17, 8; Ex 18, 10; Ex 19, 6; Ex 20, 10; Ex 21, 5; Ex 22, 20; Ex 23, 8; Ex 24, 5; Ex 25, 13; Ex 27, 32; Ex 29, 40; Ex 30, 32; Ex 31, 20; Ex 32, 25; Ex 33, 5.

What is claimed is:
1. A compound of formula (I):

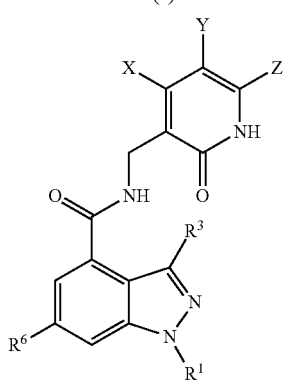

(I)

wherein
X and Z are selected independently from the group consisting of hydrogen, $(C_1-C_8)$alkyl, $(C_2-C_8)$alkenyl, $(C_2-C_8)$alkynyl, unsubstituted or substituted $(C_3-C_8)$cycloalkyl, unsubstituted or substituted $(C_3-C_8)$cycloalkyl-$(C_1-C_8)$alkyl or -$(C_2-C_8)$alkenyl, unsubstituted or substituted $(C_5-C_8)$cycloalkenyl, unsubstituted or substituted $(C_5-C_8)$cycloalkenyl-$(C_1-C_8)$alkyl or -$(C_2-C_8)$alkenyl, $(C_6-C_{10})$bicycloalkyl, unsubstituted or substituted aryl, unsubstituted or substituted aryl-$(C_1-C_8)$alkyl or -$(C_2-C_8)$alkenyl, halo, cyano, —$COR^a$, —$CO_2R^a$, —$CONR^aR^b$, —$CONR^aNR^aR^b$, —$SR^a$, —$SOR^a$, —$SO_2R^a$, —$SO_2NR^aR^b$, nitro, —$NR^aR^b$, —$NR^aC(O)R^b$, —$NR^aC(O)NR^aR^b$, —$NR^aC(O)OR^a$, —$NR^aSO_2R^b$, —$NR^aSO_2NR^aR^b$, —$NR^aNR^aR^b$, —$NR^aNR^aC(O)R^b$, —$NR^aNR^aC(O)NR^aR^b$, —$NR^aNR^aC(O)OR^a$, —$OR^a$, —$OC(O)R^a$, and —$OC(O)NR^aR^b$;

Y is H or halo;

$R^1$ is $(C_1-C_8)$alkyl, $(C_2-C_8)$alkenyl, $(C_2-C_8)$alkynyl, unsubstituted or substituted $(C_3-C_8)$cycloalkyl, unsubstituted or substituted $(C_3-C_8)$cycloalkyl-$(C_1-C_8)$alkyl or -$(C_2-C_8)$alkenyl, unsubstituted or substituted $(C_5-C_8)$cycloalkenyl, unsubstituted or substituted $(C_5-C_8)$cycloalkenyl-$(C_1-C_8)$alkyl or -$(C_2-C_8)$alkenyl, unsubstituted or substituted $(C_6-C_{10})$bicycloalkyl, unsubstituted or substituted aryl, unsubstituted or substituted aryl-$(C_1-C_8)$alkyl or -$(C_2-C_8)$alkenyl, —$COR^a$, —$CO_2R^a$, —$CONR^aR^b$, or —$CONR^aNR^aR^b$;

$R^3$ is hydrogen, $(C_1-C_8)$alkyl, cyano, trifluoromethyl, —$NR^aR^b$, or halo;

$R^6$ is selected from the group consisting of hydrogen, halo, $(C_1-C_8)$alkyl, $(C_2-C_8)$alkenyl, —$B(OH)_2$, substituted or unsubstituted $(C_2-C_8)$alkynyl, unsubstituted or substituted $(C_3-C_8)$cycloalkyl, unsubstituted or substituted $(C_3-C_8)$cycloalkyl-$(C_1-C_8)$alkyl, or substituted $(C_5-C_8)$cycloalkenyl, unsubstituted or substituted $(C_5-C_8)$cycloalkenyl-$(C_1-C_8)$alkyl, $(C_6-C_{10})$bicycloalkyl, unsubstituted or substituted aryl, unsubstituted or substituted aryl-$(C_1-C_8)$alkyl, cyano, —$COR^a$, —$CO_2R^a$, —$CONR^aR^b$, —$CONR^aNR^aR^b$, —$SR^a$, —$SOR^a$, —$SO_2R^a$, —$SO_2NR^aR^b$, nitro, —$NR^aR^b$, —$NR^aC(O)R^b$, —$NR^aC(O)NR^aR^b$, —$NR^aC(O)OR^a$, —$NR^aSO_2R^b$, —$NR^aSO_2NR^aR^b$, —$NR^aNR^aR^b$, —$NR^aNR^aC(O)R^b$, —$NR^aNR^aC(O)NR^aR^b$, —$NR^aNR^aC(O)OR^a$, —$OR^a$, —$OC(O)R^a$, and —$OC(O)NR^aR^b$;

wherein any $(C_1-C_8)$alkyl, $(C_2-C_8)$alkenyl, $(C_2-C_8)$alkynyl, cycloalkyl, cycloalkenyl, bicycloalkyl, or aryl group is optionally substituted by 1, 2, or 3 groups independently selected from the group consisting of —$O(C_1-C_6)$alkyl$(R^c)_{1-2}$, —$S(C_1-C_6)$alkyl$(R^c)_{1-2}$, —$(C_1-C_6)$alkyl$(R^c)_{1-2}$, halo, $(C_1-C_6)$alkyl, $(C_3-C_8)$cycloalkyl, $(C_5-C_8)$cycloalkenyl, $(C_1-C_6)$haloalkyl, cyano, —$COR^a$, —$CO_2R^a$, —$CONR^aR^b$, —$SR^a$, —$SOR^a$, —$SO_2R^a$, —$SO_2NR^aR^b$, nitro, —$NR^aR^b$, —$NR^aC(O)R^b$, —$NR^aC(O)NR^aR^b$, —$NR^aC(O)OR^a$, —$NR^aSO_2R^b$, —$NR^aSO_2NR^aR^b$, —$OR^a$, —$OC(O)R^a$, —$OC(O)NR^aR^b$, aryl, and aryl$(C_1-C_4)$alkyl;

wherein any aryl moiety of said aryl or aryl$(C_1-C_4)$alkyl is optionally substituted by 1, 2, or 3 groups independently selected from the group consisting of halo, $(C_1-C_6)$alkyl, $(C_3-C_8)$cycloalkyl, $(C_5-C_8)$cycloalkenyl, $(C_1-C_6)$haloalkyl, cyano, —$COR^a$, —$CO_2R^a$, —$CONR^aR^b$, —$SR^a$, —$SOR^a$, —$SO_2R^a$, —$SO_2NR^aR^b$, nitro, —$NR^aR^b$, —$NR^aC(O)R^b$, —$NR^aC(O)NR^aR^b$, —$NR^aC(O)OR^a$, —$NR^aSO_2R^b$, —$NR^aSO_2NR^aR^b$, —$OR^a$, —$OC(O)R^a$, and —$OC(O)NR^aR^b$;

$R^a$ and $R^b$ are each independently hydrogen, $(C_1-C_8)$alkyl, $(C_2-C_8)$alkenyl, $(C_2-C_8)$alkynyl, $(C_3-C_8)$cycloalkyl, $(C_5-C_8)$cycloalkenyl, $(C_6-C_{10})$bicycloalkyl, or aryl, wherein said $(C_1-C_8)$alkyl, $(C_2-C_8)$alkenyl, $(C_2-C_8)$alkynyl, cycloalkyl, cycloalkenyl, bicycloalkyl, or aryl group is optionally substituted by 1, 2, or 3 groups independently selected from halo, hydroxyl, $(C_1-C_4)$alkoxy, amino, $(C_1-C_4)$alkylamino, $((C_1-C_4)$alkyl$)((C_1-C_4)$alkyl$)$amino, —CO$_2$H, —CO$_2(C_1-C_4)$alkyl, —CONH$_2$, —CONH$(C_1-C_4)$alkyl, —CON$((C_1-C_4)$alkyl$)((C_1-C_4)$alkyl$)$, —SO$_2(C_1-C_4)$alkyl, —SO$_2$NH$_2$, —SO$_2$NH$(C_1-C_4)$alkyl, and —SO$_2$N$((C_1-C_4)$alkyl$)((C_1-C_4)$alkyl$)$;

or $R^a$ and $R^b$ taken together with the nitrogen to which they are attached represent a 5-8 membered saturated or unsaturated ring, optionally containing an additional heteroatom selected from oxygen, nitrogen, and sulfur, wherein said ring is optionally substituted by 1, 2, or 3 groups independently selected from $(C_1-C_4)$alkyl, $(C_1-C_4)$haloalkyl, amino, $(C_1-C_4)$alkylamino, $((C_1-C_4)$alkyl$)((C_1-C_4)$alkyl$)$amino, hydroxyl, oxo, $(C_1-C_4)$alkoxy, and $(C_1-C_4)$alkoxy$(C_1-C_4)$alkyl, wherein said ring is optionally fused to a $(C_3-C_8)$cycloalkyl or aryl ring;

or $R^a$ and $R^b$ taken together with the nitrogen to which they are attached represent a 6- to 10-membered bridged bicyclic ring system optionally fused to a $(C_3-C_8)$cycloalkyl or aryl ring; and each $R^c$ is independently —NR$^a$SO$_2$R$^b$, —SOR$^a$, —SO$_2$R$^a$, —NR$^a$C(O)OR$^a$, —NR$^a$R$^b$, or —CO$_2$R$^a$;

or a pharmaceutically acceptable salt thereof.

2. The compound according to claim 1 wherein:

X and Z are selected independently from the group consisting of $(C_1-C_8)$alkyl, $(C_3-C_8)$cycloalkyl, aryl, —NR$^a$R$^b$, and —OR$^a$;

Y is H;

$R^1$ is $(C_1-C_8)$alkyl or $(C_3-C_8)$cycloalkyl;

$R^3$ is hydrogen, $(C_1-C_8)$alkyl, or halo;

$R^6$ is hydrogen, halo, cyano, trifluoromethyl, amino, $(C_1-C_8)$alkyl, $(C_3-C_8)$cycloalkyl, aryl, acylamino, $(C_2-C_8)$alkynyl, aryl$(C_2-C_8)$alkynyl, —SO$_2$R$^a$, —SO$_2$NR$^a$R$^b$, or —NR$^a$SO$_2$R$^b$;

wherein any $(C_1-C_8)$alkyl, $(C_3-C_8)$cycloalkyl, $(C_2-C_8)$alkynyl, or aryl$(C_2-C_8)$alkynyl group is optionally substituted by 1, 2, or 3 groups independently selected from halo, $(C_1-C_6)$alkyl, $(C_3-C_8)$cycloalkyl, $(C_5-C_8)$cycloalkenyl, $(C_1-C_6)$haloalkyl, cyano, —COR$^a$, —CO$_2$R$^a$, —CONR$^a$R$^b$, —SR$^a$, —SOR$^a$, —SO$_2$R$^a$, —SO$_2$NR$^a$R$^b$, nitro, —NR$^a$R$^b$, —NR$^a$C(O)R$^b$, —NR$^a$C(O)NR$^a$R$^b$, —NR$^a$C(O)OR$^a$, —NR$^a$SO$_2$R$^b$, —NR$^a$SO$_2$NR$^a$R$^b$, —OR$^a$, —OC(O)R$^a$, —OC(O)NR$^a$R$^b$, aryl, and aryl$(C_1-C_4)$alkyl; and $R^a$ and $R^b$ are each independently hydrogen, $(C_1-C_8)$alkyl, $(C_2-C_8)$alkenyl, $(C_2-C_8)$alkynyl, $(C_3-C_8)$cycloalkyl, $(C_5-C_8)$cycloalkenyl, $(C_6-C_{10})$bicycloalkyl, or aryl, wherein said $(C_1-C_8)$alkyl, $(C_2-C_8)$alkenyl, $(C_2-C_8)$alkynyl, cycloalkyl, cycloalkenyl, bicycloalkyl, or aryl group is optionally substituted by 1, 2, or 3 groups independently selected from halo, hydroxyl, $(C_1-C_4)$alkoxy, amino, $(C_1-C_4)$alkylamino, $((C_1-C_4)$alkyl$)((C_1-C_4)$alkyl$)$amino, —CO$_2$H, —CO$_2(C_1-C_4)$alkyl, —CONH$_2$, —CONH$(C_1-C_4)$alkyl, —CON$((C_1-C_4)$alkyl$)((C_1-C_4)$alkyl$)$, —SO$_2(C_1-C_4)$alkyl, —SO$_2$NH$_2$, —SO$_2$NH$(C_1-C_4)$alkyl, and —SO$_2$N$((C_1-C_4)$alkyl$)((C_1-C_4)$alkyl$)$;

or $R^a$ and $R^b$ taken together with the nitrogen to which they are attached represent a 5-8 membered saturated or unsaturated ring, optionally containing an additional heteroatom selected from oxygen, nitrogen, and sulfur, wherein said ring is optionally substituted by 1, 2, or 3 groups independently selected from $(C_1-C_4)$alkyl, $(C_1-C_4)$haloalkyl, amino, $(C_1-C_4)$alkylamino, $((C_1-C_4)$alkyl$)((C_1-C_4)$alkyl$)$amino, hydroxyl, oxo, $(C_1-C_4)$alkoxy, and $(C_1-C_4)$alkoxy$(C_1-C_4)$alkyl, wherein said ring is optionally fused to a $(C_3-C_8)$cycloalkyl or aryl ring;

or $R^a$ and $R^b$ taken together with the nitrogen to which they are attached represent a 6- to 10-membered bridged bicyclic ring system optionally fused to a $(C_3-C_8)$cycloalkyl or aryl ring;

wherein any aryl is selected from the group consisting of phenyl and naphthyridine;

or a pharmaceutically acceptable salt thereof.

3. The compound according to claim 1 wherein:

X is methyl, ethyl, n-propyl, isopropyl, cyclopropyl, cyclobutyl, cyclopentyl, cyclohexyl, phenyl, trifluoromethyl, tetrahydropyran, hydroxymethyl, methoxymethyl, or benzyl;

Y is H;

Z is methyl, ethyl, n-propyl, isopropyl, trifluoromethyl, or benzyl;

$R^1$ is isopropyl, tert-butyl, cyclobutyl, cyclopentyl, cyclohexyl, or benzyl;

$R^3$ is H, methyl, or Br; and $R^6$ is methyl, cyclopropyl, propyl, dimethylamino, ethylamino, (2-hydroxyethyl)amino, 2-propen-1-ylamino, phenylamino, (phenylmethyl)amino, (4-pyridinylmethyl)amino, 2-(dimethylamino)ethyl]amino, [4-(aminocarbonyl)phenyl]amino, 3-hydroxy-3-methyl-1-butyn-1-yl, phenylethynyl, 7-oxo-1,5,6,7-tetrahydro-1,8-naphthyridin-3-yl, phenyl, 2-methylphenyl, 2-nitrophenyl, 2-phenylethyl, 3-aminophenyl, 4-aminophenyl, 4-chlorophenyl, 4-fluorophenyl, 4-(methyloxy)phenyl, 3-(acetylamino)phenyl, 4-(acetylamino)phenyl, 4-(aminocarbonyl)phenyl, 4-(aminosulfonyl)phenyl, 4-(methylsulfonyl)phenyl, 4-[(dimethylamino)sulfonyl]phenyl, 4-[(methylamino)carbonyl]phenyl, 4-[(methylamino)sulfonyl]phenyl, or 4-[(methylsulfonyl)amino]phenyl;

or a pharmaceutically acceptable salt thereof.

4. The compound according to claim 1 wherein:

X is $(C_1-C_8)$alkyl or $(C_3-C_8)$cycloalkyl;

Y is H;

Z is $(C_1-C_3)$alkyl;

$R^1$ is $(C_3-C_8)$alkyl or $(C_3-C_8)$cycloalkyl;

$R^3$ is hydrogen, $(C_1-C_3)$alkyl, or halo;

$R^6$ is selected from the group consisting of hydrogen, halo, cyano, trifluoromethyl, amino, $(C_1-C_8)$alkyl, $(C_3-C_8)$cycloalkyl, aryl, acylamino, $(C_2-C_8)$alkynyl, aryl$(C_2-C_8)$alkynyl, —SO$_2$R$^a$, —SO$_2$NR$^a$R$^b$, and —NR$^a$SO$_2$R$^b$;

wherein any $(C_1-C_8)$alkyl, $(C_3-C_8)$cycloalkyl, $(C_2-C_8)$alkynyl, or aryl$(C_2-C_8)$alkynyl group is optionally substituted by 1, 2, or 3 groups independently selected from —O$(C_1-C_6)$alkyl$(R^c)_{1-2}$, —S$(C_1-C_6)$alkyl$(R^c)_{1-2}$, —$(C_1-C_6)$alkyl$(R^c)_{1-2}$, halo, $(C_1-C_6)$alkyl, $(C_3-C_8)$cycloalkyl, $(C_5-C_8)$cycloalkenyl, $(C_1-C_6)$haloalkyl, cyano, —COR$^a$, —CO$_2$R$^a$, —CONR$^a$R$^b$, —SR$^a$, —SOR$^a$, —SO$_2$R$^a$, —SO$_2$NR$^a$R$^b$, nitro, —NR$^a$R$^b$, —NR$^a$C(O)R$^b$, —NR$^a$C(O)NR$^a$R$^b$, —NR$^a$C(O)OR$^a$, —NR$^a$SO$_2$R$^b$, —NR$^a$SO$_2$NR$^a$R$^b$, —OR$^a$, —OC(O)R$^a$, —OC(O)NR$^a$R$^b$, aryl, and aryl$(C_1-C_4)$alkyl;

$R^a$ and $R^b$ are each independently hydrogen, $(C_1-C_8)$alkyl, $(C_2-C_8)$alkenyl, $(C_2-C_8)$alkynyl, $(C_3-C_8)$cycloalkyl, $(C_5-C_8)$cycloalkenyl, $(C_6-C_{10})$bicycloalkyl, or aryl, wherein said $(C_1-C_8)$alkyl, $(C_2-C_8)$alkenyl, $(C_2-C_8)$alkynyl, cycloalkyl, cycloalkenyl, bicycloalkyl, or aryl group is optionally substituted by 1, 2, or 3 groups independently selected from halo, hydroxyl, ($C_1$-$C_4$)alkoxy, amino, ($C_1$-$C_4$)alkylamino, (($C_1$-$C_4$)alkyl)(($C_1$-$C_4$)alkyl)amino, —$CO_2$H, —$CO_2$($C_1$-$C_4$)alkyl, —$CONH_2$, —CONH($C_1$-$C_4$)alkyl, —CON(($C_1$-$C_4$)alkyl)(($C_1$-$C_4$)alkyl), —$SO_2$($C_1$-$C_4$)alkyl, —$SO_2NH_2$, —$SO_2$NH($C_1$-$C_4$)alkyl, and —$SO_2$N(($C_1$-$C_4$)alkyl)(($C_1$-$C_4$)alkyl);

or $R^a$ and $R^b$ taken together with the nitrogen to which they are attached represent a 5-8 membered saturated or unsaturated ring, optionally containing an additional heteroatom selected from oxygen, nitrogen, and sulfur, wherein said ring is optionally substituted by 1, 2, or 3 groups independently selected from ($C_1$-$C_4$)alkyl, ($C_1$-$C_4$)haloalkyl, amino, ($C_1$-$C_4$)alkylamino, (($C_1$-$C_4$)alkyl)(($C_1$-$C_4$)alkyl)amino, hydroxyl, oxo, ($C_1$-$C_4$)alkoxy, and ($C_1$-$C_4$)alkoxy($C_1$-$C_4$)alkyl; and each $R^c$ is independently —$NR^aSO_2R^b$, —$SOR^a$, —$SO_2R^a$, —$NR^aC(O)OR^a$, —$NR^aR^b$, or —$CO_2R^a$;

or a pharmaceutically acceptable salt thereof.

5. The compound according to claim 1 wherein $R^6$ is selected from the group consisting of: halo, cyano, trifluoromethyl, amino, ($C_1$-$C_8$)alkyl, ($C_3$-$C_8$)cycloalkyl, acylamino, ($C_2$-$C_8$)alkynyl, aryl($C_2$-$C_8$)alkynyl, —$SO_2R^a$, —$SO_2NR^aR^b$, and —$NR^aSO_2R^b$; or a pharmaceutically acceptable salt thereof.

6. The compound according to claim 1 wherein $R^6$ is aryl, wherein said aryl is optionally substituted by 1, 2, or 3 groups independently selected from —O($C_1$-$C_6$)alkyl($R^c$)$_{1-2}$, —S($C_1$-$C_6$)alkyl($R^c$)$_{1-2}$, —($C_1$-$C_6$)alkyl($R^c$)$_{1-2}$, halo, ($C_1$-$C_6$)alkyl, ($C_3$-$C_8$)cycloalkyl, ($C_5$-$C_8$)cycloalkenyl, ($C_1$-$C_6$)haloalkyl, cyano, —$COR^a$, —$CO_2R^a$, —$CONR^aR^b$, —$SR^a$, —$SOR^a$, —$SO_2R^a$, —$SO_2NR^aR^b$, nitro, —$NR^aR^b$, —$NR^aC(O)R^b$, —$NR^aC(O)NR^aR^b$, —$NR^aC(O)OR^a$, —$NR^aSO_2R^b$, —$NR^aSO_2NR^aR^b$, —$OR^a$, —$OC(O)R^a$, —$OC(O)NR^aR^b$, aryl, and aryl($C_1$-$C_4$)alkyl;

$R^a$ and $R^b$ are each independently hydrogen, ($C_1$-$C_8$)alkyl, ($C_2$-$C_8$)alkenyl, ($C_2$-$C_8$)alkynyl, ($C_3$-$C_8$)cycloalkyl, ($C_5$-$C_8$)cycloalkenyl, ($C_6$-$C_{10}$)bicycloalkyl, or aryl, wherein said ($C_1$-$C_8$)alkyl, ($C_2$-$C_8$)alkenyl, ($C_2$-$C_8$)alkynyl, cycloalkyl, cycloalkenyl, bicycloalkyl, or aryl group is optionally substituted by 1, 2, or 3 groups independently selected from halo, hydroxyl, ($C_1$-$C_4$)alkoxy, amino, ($C_1$-$C_4$)alkylamino, (($C_1$-$C_4$)alkyl)(($C_1$-$C_4$)alkyl)amino, —$CO_2$H, —$CO_2$($C_1$-$C_4$)alkyl, —$CONH_2$, —CONH($C_1$-$C_4$)alkyl, —CON(($C_1$-$C_4$)alkyl)(($C_1$-$C_4$)alkyl), —$SO_2$($C_1$-$C_4$)alkyl, —$SO_2NH_2$, —$SO_2$NH($C_1$-$C_4$)alkyl, and —$SO_2$N(($C_1$-$C_4$)alkyl)(($C_1$-$C_4$)alkyl); and each $R^c$ is independently —$NR^aSO_2R^b$, —$SOR^a$, —$SO_2R^a$, —$NR^aC(O)OR^a$, —$NR^aR^b$, or —$CO_2R^a$;

or a pharmaceutically acceptable salt thereof.

7. The compound according to claim 1 which is:

6-chloro-1-(1-methylethyl)-N-[(6-methyl-2-oxo-4-propyl-1,2-dihydro-3-pyridinyl)methyl]-1H-indazole-4-carboxamide;

N-[(4,6-dimethyl-2-oxo-1,2-dihydro-3-pyridinyl)methyl]-6-fluoro-1-(1-methylethyl)-1H-indazole-4-carboxamide;

6-Bromo-N-[(4,6-dimethyl-2-oxo-1,2-dihydro-3-pyridinyl)methyl]-1-(1-methylethyl)-1H-indazole-4-carboxamide;

6-bromo-N-((4-ethyl-6-methyl-2-oxo-1,2-dihydropyridin-3-yl)methyl)-1-isopropyl-1H-indazole-4-carboxamide;

6-bromo-1-(1-methylethyl)-N-{[6-methyl-2-oxo-4-(phenylmethyl)-1,2-dihydro-3-pyridinyl]methyl}-1H-indazole-4-carboxamide;

6-bromo-1-(1-methylethyl)-N-[(6-methyl-2-oxo-1,2-dihydro-4,4'-bipyridin-3-yl)methyl]-1H-indazole-4-carboxamide;

1-(1-methylethyl)-N-{[6-methyl-2-oxo-4-(phenylmethyl)-1,2-dihydro-3-pyridinyl]methyl}-1H-indazole-4-carboxamide;

N-((4,6-dimethyl-2-oxo-1,2-dihydropyridin-3-yl)methyl)-6-(4-(2-(dimethylamino)ethoxy)phenyl)-1-isopropyl-1H-indazole-4-carboxamide;

N-[(4,6-dimethyl-2-oxo-1,2-dihydro-3-pyridinyl)methyl]-1-(1-methylethyl)-6-[4-(1-piperazinyl)phenyl]-1H-indazole-4-carboxamide;

6-{4-[(dimethylamino)methyl]phenyl}-1-(1-methylethyl)-N-{[6-methyl-4-(1-methylethyl)-2-oxo-1,2-dihydro-3-pyridinyl]methyl}-1H-indazole-4-carboxamide;

6-(4-((dimethylamino)methyl)phenyl)-N-((4-ethyl-6-methyl-2-oxo-1,2-dihydropyridin-3-yl)methyl)-1-isopropyl-1H-indazole-4-carboxamide;

6-{3-[(dimethylamino)methyl]phenyl}-N-[(4,6-dimethyl-2-oxo-1,2-dihydro-3-pyridinyl)methyl]-1-(1-methylethyl)-1H-indazole-4-carboxamide;

6-{4-[(dimethylamino)methyl]phenyl}-N-[(4,6-dimethyl-2-oxo-1,2-dihydro-3-pyridinyl)methyl]-1-(1-methylethyl)-1H-indazole-4-carboxamide;

6-{4-[(dimethylamino)methyl]phenyl}-1-(1-methylethyl)-N-[(6-methyl-2-oxo-4-propyl-1,2-dihydro-3-pyridinyl)methyl]-1H-indazole-4-carboxamide;

6-{3-[(dimethylamino)methyl]phenyl}-1-(1-methylethyl)-N-[(6-methyl-2-oxo-4-propyl-1,2-dihydro-3-pyridinyl)methyl]-1H-indazole-4-carboxamide;

N-((4-cyclohexyl-6-methyl-2-oxo-1,2-dihydropyridin-3-yl)methyl)-6-cyclopropyl-1-isopropyl-1H-indazole-4-carboxamide;

6-bromo-1-ethyl-1H-indazole-4-carboxylic acid (6-methyl-2-oxo-4-propyl-1,2-dihydro-pyridin-3-ylmethyl)-amide;

6-bromo-N-((6-methyl-2-oxo-4-propyl-1,2-dihydropyridin-3-yl)methyl)-1-propyl-1H-indazole-4-carboxamide;

6-bromo-1-cyclopentyl-N-((4,6-dimethyl-2-oxo-1,2-dihydropyridin-3-yl)methyl)-1H-indazole-4-carboxamide;

6-bromo-1-cyclopentyl-N-((4-ethyl-6-methyl-2-oxo-1,2-dihydropyridin-3-yl)methyl)-1H-indazole-4-carboxamide;

1-cyclopentyl-N-((4,6-dimethyl-2-oxo-1,2-dihydropyridin-3-yl)methyl)-6-(3-(pyrrolidin-1-yl)phenyl)-1H-indazole-4-carboxamide;

1-cyclopentyl-N-((4,6-dimethyl-2-oxo-1,2-dihydropyridin-3-yl)methyl)-6-(3-(3-hydroxypropyl)phenyl)-1H-indazole-4-carboxamide;

1-cyclopentyl-N-((4,6-dimethyl-2-oxo-1,2-dihydropyridin-3-yl)methyl)-6-(3-(trifluoromethoxy)phenyl)-1H-indazole-4-carboxamide;

1-cyclopentyl-N-((4,6-dimethyl-2-oxo-1,2-dihydropyridin-3-yl)methyl)-6-(4-fluorophenyl)-1H-indazole-4-carboxamide;

1-cyclopentyl-N-((4,6-dimethyl-2-oxo-1,2-dihydropyridin-3-yl)methyl)-6-(4-((dimethylamino)methyl)phenyl)-1H-indazole-4-carboxamide;

6-chloro-1-cyclopentyl-N-[(4,6-dimethyl-2-oxo-1,2-dihydro-3-pyridinyl)methyl]-1H-indazole-4-carboxamide;

6-chloro-1-cyclopentyl-N-[(6-methyl-2-oxo-4-propyl-1,2-dihydro-3-pyridinyl)methyl]-1H-indazole-4-carboxamide;

6-cyano-1-cyclopentyl-N-[(4,6-dimethyl-2-oxo-1,2-dihydro-3-pyridinyl)methyl]-1H-indazole-4-carboxamide;

6-(aminomethyl)-1-cyclopentyl-N-[(4,6-dimethyl-2-oxo-1,2-dihydro-3-pyridinyl)methyl]-1H-indazole-4-carboxamide;

6-amino-1-cyclopentyl-N-[(4,6-dimethyl-2-oxo-1,2-dihydro-3-pyridinyl)methyl]-1H-indazole-4-carboxamide;

1-cyclopentyl-N-[(4,6-dimethyl-2-oxo-1,2-dihydro-3-pyridinyl)methyl]-6-[(phenylsulfonyl)amino]-1H-indazole-4-carboxamide;

1-cyclopentyl-N-[(4,6-dimethyl-2-oxo-1,2-dihydro-3-pyridinyl)methyl]-6-(3-hydroxy-3-methyl-1-butyn-1-yl)-1H-indazole-4-carboxamide;

6-bromo-1-cyclopropyl-N-[(4,6-dimethyl-2-oxo-1,2-dihydro-3-pyridinyl)methyl]-1H-indazole-4-carboxamide;

6-bromo-1-cyclopropyl-N-[(6-methyl-2-oxo-4-propyl-1,2-dihydro-3-pyridinyl)methyl]-1H-indazole-4-carboxamide;

1-cyclopropyl-6-{4-[(dimethylamino)methyl]phenyl}-N-[(4,6-dimethyl-2-oxo-1,2-dihydro-3-pyridinyl)methyl]-1H-indazole-4-carboxamide;

1-cyclopropyl-6-{4-[(dimethylamino)methyl]phenyl}-N-[(6-methyl-2-oxo-4-propyl-1,2-dihydro-3-pyridinyl)methyl]-1H-indazole-4-carboxamide;

6-bromo-N-((1,2-dihydro-4,6-dimethyl-2-oxopyridin-3-yl)methyl)-1-isopropyl-3-methyl-1H-indazole-4-carboxamide;

6-bromo-1-isopropyl-3-methyl-N-((6-methyl-2-oxo-4-propyl-1,2-dihydropyridin-3-yl)methyl)-1H-indazole-4-carboxamide;

6-(3-((dimethylamino)methyl)phenyl)-N-((1,2-dihydro-4,6-dimethyl-2-oxopyridin-3-yl)methyl)-1-isopropyl-1H-indazole-4-carboxamide;

N-((4,6-dimethyl-2-oxo-1,2-dihydropyridin-3-yl)methyl)-6-(4-fluorophenyl)-1-isopropyl-3-methyl-1H-indazole-4-carboxamide;

6-(4-((dimethylamino)methyl)phenyl)-N-((1,2-dihydro-4,6-dimethyl-2-oxopyridin-3-yl)methyl)-1-isopropyl-3-methyl-1H-indazole-4-carboxamide;

6-{3-[(dimethylamino)methyl]phenyl}-3-methyl-1-(1-methylethyl)-N-[(6-methyl-2-oxo-4-propyl-1,2-dihydro-3-pyridinyl)methyl]-1H-indazole-4-carboxamide;

6-{4-[(dimethylamino)methyl]phenyl}-3-methyl-1-(1-methylethyl)-N-[(6-methyl-2-oxo-4-propyl-1,2-dihydro-3-pyridinyl)methyl]-1H-indazole-4-carboxamide;

6-cyano-N-((4,6-dimethyl-2-oxo-1,2-dihydropyridin-3-yl)methyl)-1-isopropyl-3-methyl-1H-indazole-4-carboxamide;

1-cyclopentyl-6-(cyclopropylsulfonyl)-N-((4,6-dimethyl-2-oxo-1,2-dihydropyridin-3-yl)methyl)-1H-indazole-4-carboxamide;

6-(cyclopropylsulfonyl)-N-((4-ethyl-6-methyl-2-oxo-1,2-dihydropyridin-3-yl)methyl)-1-isopropyl-1H-indazole-4-carboxamide;

N-((4-ethyl-6-methyl-2-oxo-1,2-dihydropyridin-3-yl)methyl)-1-isopropyl-6-(methylsulfonyl)-1H-indazole-4-carboxamide;

N-[(4,6-dimethyl-2-oxo-1,2-dihydro-3-pyridinyl)methyl]-1-(1-methylethyl)-6-(methylsulfonyl)-1H-indazole-4-carboxamide;

N-[(4,6-dimethyl-2-oxo-1,2-dihydro-3-pyridinyl)methyl]-1-(1-methylethyl)-6-(4-morpholinylsulfonyl)-1H-indazole-4-carboxamide;

6-[(cyclopropylamino)sulfonyl]-N-[(4,6-dimethyl-2-oxo-1,2-dihydro-3-pyridinyl)methyl]-1-(1-methylethyl)-1H-indazole-4-carboxamide;

N-[(4,6-dimethyl-2-oxo-1,2-dihydro-3-pyridinyl)methyl]-1-(1-methylethyl)-6-(1-pyrrolidinylsulfonyl)-1H-indazole-4-carboxamide;

6-({[3-(dimethylamino)propyl]amino}sulfonyl)-N-[(4,6-dimethyl-2-oxo-1,2-dihydro-3-pyridinyl)methyl]-1-(1-methylethyl)-1H-indazole-4-carboxamide;

N-((4,6-dimethyl-2-oxo-1,2-dihydropyridin-3-yl)methyl)-1-isopropyl-6-((4-methylpiperazin-1-yl)sulfonyl)-1H-indazole-4-carboxamide;

6-bromo-N-((4-(sec-butyl)-6-methyl-2-oxo-1,2-dihydropyridin-3-yl)methyl)-1-isopropyl-1H-indazole-4-carboxamide;

6-Bromo-1-(1-methylethyl)-N-[(6-methyl-2-oxo-4-propyl-1,2-dihydro-3-pyridinyl)methyl]-1H-indazole-4-carboxamide; or 6-Bromo-1-(1-methylethyl)-N-{[6-methyl-4-(1-methylethyl)-2-oxo-1,2-dihydro-3-pyridinyl]methyl}-1H-indazole-4-carboxamide;

or a pharmaceutically acceptable salt thereof.

8. The compound according to claim 1 which is:

6-bromo-N-[(4,6-dimethyl-2-oxo-1,2-dihydro-3-pyridinyl)methyl]-1-(1-methylethyl)-1H-indazole-4-carboxamide;

N-[(4,6-dimethyl-2-oxo-1,2-dihydro-3-pyridinyl)methyl]-1-(1-methylethyl)-6-phenyl-1H-indazole-4-carboxamide;

N-[(4,6-dimethyl-2-oxo-1,2-dihydro-3-pyridinyl)methyl]-6-{4-[(methylamino)sulfonyl]phenyl}-1-(1-methylethyl)-1H-indazole-4-carboxamide;

N-[(4,6-dimethyl-2-oxo-1,2-dihydro-3-pyridinyl)methyl]-1-(1-methylethyl)-6-[2-(trifluoromethyl)phenyl]-1H-indazole-4-carboxamide;

6-{4-[(dimethylamino)sulfonyl]phenyl}-N-[(4,6-dimethyl-2-oxo-1,2-dihydro-3-pyridinyl)methyl]-1-(1-methylethyl)-1H-indazole-4-carboxamide;

N-[(4,6-dimethyl-2-oxo-1,2-dihydro-3-pyridinyl)methyl]-1-(1-methylethyl)-6-(2-methylphenyl)-1H-indazole-4-carboxamide;

6-bromo-N-[(4-cyclohexyl-6-methyl-2-oxo-1,2-dihydro-3-pyridinyl)methyl]-1-(1-methylethyl)-1H-indazole-4-carboxamide;

6-bromo-1-(1-methylethyl)-N-[(6-methyl-2-oxo-4-propyl-1,2-dihydro-3-pyridinyl)methyl]-1H-indazole-4-carboxamide;

1-(1-methylethyl)-N-[(6-methyl-2-oxo-4-propyl-1,2-dihydro-3-pyridinyl)methyl]-1H-indazole-4-carboxamide;

6-bromo-1-cyclopentyl-N-[(6-methyl-2-oxo-4-propyl-1,2-dihydro-3-pyridinyl)methyl]-1H-indazole-4-carboxamide;

6-bromo-N-[(4-cyclopropyl-6-methyl-2-oxo-1,2-dihydro-3-pyridinyl)methyl]-1-(1-methylethyl)-1H-indazole-4-carboxamide;

6-bromo-1-cyclopentyl-N-[(4,6-dimethyl-2-oxo-1,2-dihydro-3-pyridinyl)methyl]-1H-indazole-4-carboxamide;

6-bromo-1-(1-methylethyl)-N-{[6-methyl-4-(1-methylethyl)-2-oxo-1,2-dihydro-3-pyridinyl]methyl}-1H-indazole-4-carboxamide;

1-cyclopentyl-N-[(4,6-dimethyl-2-oxo-1,2-dihydro-3-pyridinyl)methyl]-1H-indazole-4-carboxamide; or 6-bromo-1-(1-methylethyl)-N-[(6-methyl-2-oxo-4-phenyl-1,2-dihydro-3-pyridinyl)methyl]-1H-indazole-4-carboxamide;

or a pharmaceutically acceptable salt thereof.

9. A pharmaceutical composition comprising the compound or pharmaceutically acceptable salt thereof according to claim 1 and a pharmaceutically acceptable excipient.

\* \* \* \* \*